(12) United States Patent
McKinnell et al.

(10) Patent No.: US 8,921,372 B2
(45) Date of Patent: Dec. 30, 2014

(54) INHIBITORS OF HEPATITIS C VIRUS

(75) Inventors: Robert Murray McKinnell, Millbrae, CA (US); Daniel D. Long, San Francisco, CA (US); Lori Jean Van Orden, San Francisco, CA (US); Lan Jiang, Fjoster City, CA (US); Mandy Loo, San Jose, CA (US); Daisuke Roland Saito, San Mateo, CA (US); Sheila Zipfel, San Mateo, CA (US); Eric L. Stangeland, Pacifica, CA (US); Kassandra Lepack, San Mateo, CA (US); Gavin Ogawa, San Francisco, CA (US); Xiaojun Huang, Sunnyvale, CA (US); Weijiang Zhang, Concord, CA (US)

(73) Assignee: Theravance Biopharma R&D IP, LLC, South San Francisco, CA (US)

( * ) Notice: Subject to any disclaimer, the term of this patent is extended or adjusted under 35 U.S.C. 154(b) by 89 days.

(21) Appl. No.: 13/288,216

(22) Filed: Nov. 3, 2011

(65) Prior Publication Data

US 2012/0114600 A1    May 10, 2012

Related U.S. Application Data

(60) Provisional application No. 61/410,267, filed on Nov. 4, 2010, provisional application No. 61/444,046, filed on Feb. 17, 2011, provisional application No. 61/492,267, filed on Jun. 1, 2011.

(51) Int. Cl.
*A61K 31/497* (2006.01)
*C07D 401/14* (2006.01)
*C07D 403/14* (2006.01)
*A61P 1/16* (2006.01)

(52) U.S. Cl.
CPC ................................. *C07D 403/14* (2013.01)
USPC .................................... 514/253.09; 544/364

(58) Field of Classification Search
USPC ...................................... 544/364; 514/253.09
See application file for complete search history.

(56) References Cited

U.S. PATENT DOCUMENTS

| | | | |
|---|---|---|---|
| 7,659,270 B2 | 2/2010 | Bachand et al. | |
| 7,745,636 B2 | 6/2010 | Bachand et al. | |
| 8,318,925 B2 * | 11/2012 | Tang | 536/24.5 |
| 2008/0050336 A1 | 2/2008 | Bachand et al. | |
| 2009/0068140 A1 | 3/2009 | Bachand et al. | |
| 2010/0215618 A1 | 8/2010 | Carter et al. | |
| 2011/0064695 A1 | 3/2011 | Qiu et al. | |
| 2011/0142798 A1 | 6/2011 | Qiu et al. | |
| 2011/0237579 A1 | 9/2011 | Li et al. | |
| 2011/0286961 A1 | 11/2011 | Belema et al. | |
| 2011/0300104 A1 | 12/2011 | Qiu et al. | |

FOREIGN PATENT DOCUMENTS

| | | |
|---|---|---|
| WO | 2008/021927 A2 | 2/2008 |
| WO | 2009/102318 A1 | 8/2009 |
| WO | 2010/094977 A1 | 8/2010 |
| WO | 2010/096777 A1 | 8/2010 |
| WO | 2011/031934 A1 | 3/2011 |

OTHER PUBLICATIONS

Conte et al., "Synthesis and SAR of piperazinyl-N-phenylbenzamides as inhibitors of hepatitis C virus RNA replication in cell culture", Bioorganic & Medicinal Chemistry Letters, 19 (2009) 1779-1783.
Cordek et al., "Targeting the NS5A protein of HCV: An emerging option", Drugs of the Future, 36(9): 691-711 (2011).
International Search Report for PCT/US2011/059061 dated Jan. 26, 2012.

* cited by examiner

*Primary Examiner* — James O Wilson
*Assistant Examiner* — Cecilia M Jaisle
(74) *Attorney, Agent, or Firm* — Jeffrey A. Hagenah; Roberta P. Saxon

(57) ABSTRACT

The invention provides compounds of formula (I):

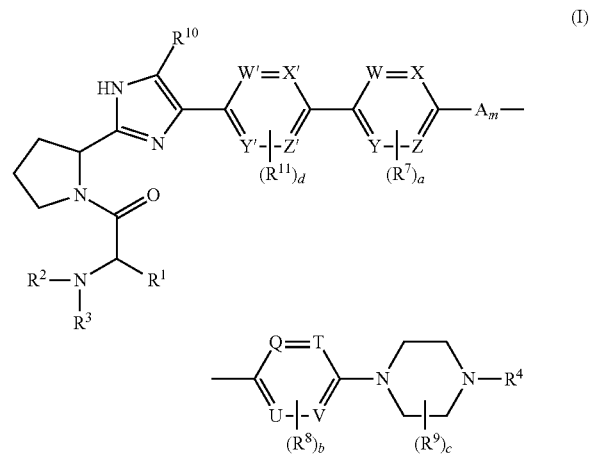

(I)

wherein the variables are defined in the specification, or a pharmaceutically-acceptable salt thereof, that are inhibitors of replication of the hepatitis C virus. The invention also provides pharmaceutical compositions comprising such compounds, methods of using such compounds to treat hepatitis C viral infections, and processes and intermediates useful for preparing such compounds.

18 Claims, No Drawings

INHIBITORS OF HEPATITIS C VIRUS

CROSS-REFERENCE TO RELATED APPLICATIONS

This application claims the benefit of U.S. Provisional Application Nos. 61/410,267, filed on Nov. 4, 2010, 61/444,046, filed on Feb. 17, 2011, and 61/492,267, filed on Jun. 1, 2011, the disclosures of which are incorporated herein by reference in their entirety.

BACKGROUND OF THE INVENTION

1. Field Of The Invention

The invention is directed to compounds useful as inhibitors of replication of the hepatitis C virus (HCV). The invention is also directed to pharmaceutical compositions comprising such compounds, methods of using such compounds to treat HCV infection, and processes and intermediates useful for preparing such compounds.

2. State Of The Art

Recent estimates place the number of people infected with the hepatitis C virus (HCV) worldwide at more than 170 million, including 3 million people in the United States. The infection rate is thought to be roughly 4 to 5 times that of the human immunodeficiency virus (HIV). While in some individuals, the natural immune response is able to overcome the virus, in the majority of cases, a chronic infection is established, leading to increased risk of developing cirrhosis of the liver and hepatocellular carcinomas. Infection with hepatitis C, therefore, presents a serious public health problem.

Prior to mid-2011, the accepted standard of care for HCV involved the use of a pegylated interferon which is believed to act by boosting the body's immune response, together with ribavirin. Unfortunately, the course of treatment is lengthy, typically 48 weeks, often accompanied by serious adverse side effects, including depression, flu-like symptoms, fatigue, and hemolytic anemia, and ineffective in up to 50% of patients. In mid-2011, two HCV protease inhibitors were approved in the United States to be used in combination with interferon and ribavirin. Although better cure rates have been reported, the course of therapy is still lengthy and accompanied by undesirable side effects. Accordingly, there remains a serious unmet need in HCV treatment.

The virus responsible for HCV infection has been identified as a positive-strand RNA virus belonging to the family Flaviviridae. The HCV genome encodes a polyprotein that during the viral lifecycle is cleaved into ten individual proteins, including both structural and non-structural proteins. The six non-structural proteins, denoted as NS2, NS3, NS4A, NS4B, NS5A, and NS5B have been shown to be required for RNA replication. In particular, the NS5A protein appears to play a significant role in viral replication, as well as in modulation of the physiology of the host cell. Effects of NS5A on interferon signaling, regulation of cell growth and apoptosis have also been identified. (Macdonald et al., *Journal of General Virology* (2004), 85, 2485-2502.) Compounds which inhibit the function of the NS5A protein are expected to provide a new approach to HCV therapy.

SUMMARY OF THE INVENTION

In one aspect, the invention provides novel compounds which inhibit replication of the HCV virus.

Accordingly, the invention provides a compound of formula (I):

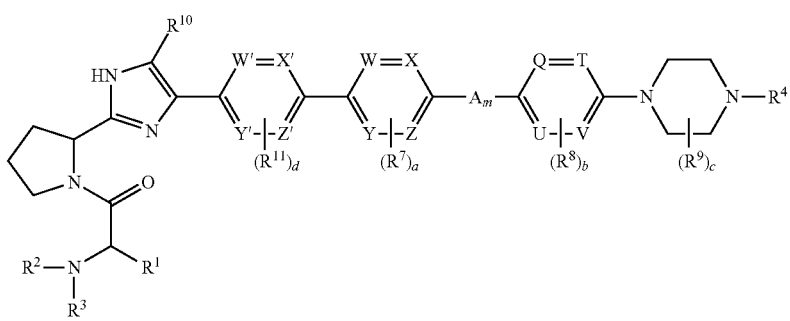

wherein:

$R^1$ is selected from $C_{1-6}$alkyl, phenyl, $C_{3-6}$cycloalkyl, heteroaryl, and heterocycle;

wherein $C_{1-6}$alkyl is optionally substituted with $-OR^q$, wherein $R^q$ is hydrogen or $C_{1-3}$alkyl;

$R^2$ is selected from hydrogen and $C_{1-6}$alkyl;

$R^3$ is selected from hydrogen, $C_{1-6}$alkyl, $-C(O)OC_{1-6}$alkyl, $-C(O)OC_{3-6}$cycloalkyl, $-C(O)NR^aR^b$, $-C(O)C_{1-6}$alkyl, $-C(O)C_{3-6}$cycloalkyl, and $-S(O)_2C_{1-3}$alkyl;

wherein $R^a$ and $R^b$ are independently hydrogen or $C_{1-6}$alkyl;

$R^4$ is $-C(O)R^5$ or $-S(O)_2R^6$;

$R^5$ is selected from $C_{1-6}$alkyl, $C_{3-6}$cycloalkyl, $C_{1-6}$alkoxy, $-C(R^kR^d)NR^eR^f$, $-NR^gR^h$, heteroaryl, heterocycle, $-CH_2$-heteroaryl, and phenyl;

wherein $C_{1-6}$alkyl is optionally substituted with one or two substituents independently selected from $-OR^e$, $-S(O)_2C_{1-3}$alkyl, $-NHC(O)C_{1-3}$alkyl, and $-NHC(O)OC_{1-3}$alkyl;

$C_{1-6}$alkoxy is optionally substituted with $-OR^d$;

$C_{3-6}$cycloalkyl is optionally substituted with one, two, or three substituents independently selected from $C_{1-3}$alkyl, $NR^jR^m$, $-OR^n$, and halo;

any heterocycle is optionally substituted with one, two, or three substituents independently selected from $C_{1-3}$alkyl, halo, $-C(O)OC_{1-3}$alkyl, $-C(O)C_{1-6}$alkyl, $-C(O)C_{3-6}$cycloalkyl, $-C(O)NHC_{1-6}$alkyl, $-C(O)NHC_{3-6}$cycloalkyl, and $-S(O)_2C_{1-3}$alkyl;

wherein any $-C(O)C_{1-6}$alkyl is optionally substituted with $-NHC(O)OC_{1-3}$alkyl, $-OR^n$, $-NR^dR^e$, or heterocycle, any $-C(O)C_{3-6}$cycloalkyl is optionally substituted with one or two $C_{1-3}$alkyl, and any —C(O)NHC$_{1-6}$alkyl is optionally substituted with —OR$^n$ or C$_{3-6}$cycloalkyl;

any heteroaryl is optionally substituted with C$_{1-6}$alkyl;

R$^c$ is independently selected from hydrogen, C$_{1-6}$alkyl, and phenyl;

R$^d$ is independently hydrogen or C$_{1-6}$alkyl;

R$^e$ is independently hydrogen or C$_{1-6}$alkyl;

R$^f$ is independently selected from hydrogen, C$_{1-6}$alkyl, —C(O)OC$_{1-6}$alkyl, and —C(O)C$_{1-6}$alkyl;

R$^n$ is independently hydrogen or C$_{1-3}$alkyl;

R$^k$ is independently selected from hydrogen, C$_{1-6}$alkyl, C$_{3-6}$cycloalkyl, phenyl, and —CH$_2$OR$^6$;

R$^g$ is independently hydrogen or C$_{1-6}$alkyl;

R$^h$ is independently selected from hydrogen, C$_{1-6}$alkyl, C$_{3-6}$cycloalkyl, and —S(O)$_2$C$_{1-3}$alkyl, wherein C$_{1-6}$alkyl is optionally substituted with —OR$^d$;

R$^j$ is independently hydrogen or C$_{1-6}$alkyl;

R$^m$ is independently selected from hydrogen, C$_{1-6}$alkyl, —C(O)OC$_{1-6}$alkyl, and —C(O)C$_{1-6}$alkyl;

R$^6$ is selected from C$_{1-6}$alkyl, C$_{3-6}$cycloalkyl, phenyl, and a heteroaryl ring;

R$^7$, R$^8$, and R$^{11}$ are independently selected from halo, C$_{1-6}$alkyl, C$_{1-6}$alkoxy, —C(O)OR$^n$, —CH$_2$NR$^a$R$^b$, and —CN, wherein C$_{1-6}$alkyl and C$_{1-6}$alkoxy are optionally substituted with one, two, three, four, or five halo, and wherein C$_{1-6}$alkoxy is optionally substituted with —OR$^d$;

R$^9$ is independently selected from C$_{1-6}$alkyl, —CH$_2$OR$^n$, —C(O)NR$^n$R$^p$, and C(O)OR$^n$, wherein C$_{1-6}$alkyl is optionally substituted with —S(O)$_2$C$_{1-3}$alkyl or with —SC$_{1-3}$alkyl;

R$^p$ is independently hydrogen or C$_{1-3}$alkyl;

R$^{10}$ is selected from hydrogen, halo, C$_{1-6}$alkyl, —C(O)OR$^c$, —C(O)NR$^a$R$^b$, —CH$_2$NR$^a$R$^b$, C$_{3-6}$cycloalkyl, and —CN;

W', X', Y', and Z' are independently carbon or nitrogen wherein any carbon atom is bonded to hydrogen or to R$^{11}$, provided that at least two of W', X', Y', and Z' are carbon;

W, X, Y, and Z are independently carbon or nitrogen wherein any carbon atom is bonded to hydrogen or to R$^7$, provided that at least two of W, X, Y, and Z are carbon;

A$_m$ is —NHC(O)— or —C(O)NH—;

Q, T, U, and V are independently carbon or nitrogen wherein any carbon atom is bonded to hydrogen or to R$^8$, provided that at least two of Q, T, U, and V are carbon; and a, b, c, and d are independently 0, 1, or 2;

or a pharmaceutically-acceptable salt or stereoisomer thereof.

As used hereinafter, the phrase "compound of formula (I)" means a compound of formula (I) or a pharmaceutically acceptable salt thereof; i.e., this phrase means a compound of formula (I) in free base form or in a pharmaceutically acceptable salt form unless otherwise indicated.

The invention also provides a pharmaceutical composition comprising a compound of the invention and a pharmaceutically-acceptable carrier. In addition, the invention provides a pharmaceutical composition comprising a compound of the invention, a pharmaceutically-acceptable carrier and one or more other therapeutic agents useful for treating hepatitis C viral infections.

The invention also provides a method of treating a hepatitis C viral infection in a mammal, the method comprising administering to the mammal a therapeutically effective amount of a compound or of a pharmaceutical composition of the invention. In addition, the invention provides a method of treating a hepatitis C viral infection in a mammal, the method comprising administering to the mammal a compound or a pharmaceutical composition of the invention and one or more other therapeutic agents useful for treating hepatitis C viral infections. Further, the invention provides a method of inhibiting replication of the hepatitis C virus in a mammal, the method comprising administering a compound or a pharmaceutical composition of the invention.

In separate and distinct aspects, the invention also provides synthetic processes and intermediates described herein, which are useful for preparing compounds of the invention.

The invention also provides a compound of the invention as described herein for use in medical therapy, as well as the use of a compound of the invention in the manufacture of a formulation or medicament for treating a hepatitis C viral infection in a mammal.

DETAILED DESCRIPTION OF THE INVENTION

Among other aspects, the invention provides inhibitors of HCV replication of formula (I), pharmaceutically-acceptable salts thereof, and intermediates for the preparation thereof. The following substituents and values are intended to provide representative examples of various aspects of this invention. These representative values are intended to further define such aspects and are not intended to exclude other values or limit the scope of the invention.

In a specific aspect, R$^1$ is selected from C$_{1-6}$alkyl, phenyl, C$_{3-6}$cycloalkyl, heteroaryl, and heterocycle; wherein C$_{1-6}$alkyl is optionally substituted with —OR$^q$; wherein R$^q$ is hydrogen or C$_{1-3}$alkyl.

In another specific aspect of the invention, R$^1$ is selected from C$_{1-6}$alkyl, phenyl, C$_{3-6}$cycloalkyl, heteroaryl, and heterocycle.

In another specific aspect, R$^1$ is selected from C$_{1-6}$alkyl, phenyl, and C$_{3-6}$cycloalkyl, wherein C$_{1-6}$alkyl is optionally substituted with —OR$^q$; wherein R$^q$ is hydrogen or C$_{1-3}$alkyl.

In another specific aspect, R$^1$ is selected from C$_{1-6}$alkyl and phenyl.

In a specific aspect, R$^1$ is C$_{1-3}$ alkyl.

In another specific aspect, R$^1$ is isopropyl.

In a specific aspect, R$^2$ is hydrogen or C$_{1-6}$alkyl.

In other specific aspects, R$^2$ is hydrogen or C$_{1-3}$alkyl; or R$^2$ is hydrogen.

In a specific aspect, R$^3$ is selected from hydrogen, C$_{1-6}$alkyl, —C(O)OC$_{1-6}$alkyl, —C(O)OC$_{3-6}$cycloalkyl, —C(O)NR$^a$R$^b$, —C(O)C$_{1-6}$alkyl, —C(O)C$_{3-6}$cycloalkyl, and —S(O)$_2$C$_{1-3}$alkyl, wherein R$^a$ and R$^b$ are independently hydrogen or C$_{1-6}$alkyl.

In another specific aspect, R$^3$ is selected from hydrogen, C$_{1-6}$alkyl, —C(O)OC$_{1-6}$alkyl, —C(O)NR$^a$R$^b$, —C(O)C$_{3-6}$cycloalkyl, and —S(O)$_2$C$_{1-3}$alkyl, wherein R$^a$ and R$^b$ are independently hydrogen or C$_{1-6}$alkyl.

In yet other specific aspects, R$^3$ is selected from hydrogen, C$_{1-6}$alkyl, and —C(O)OC$_{1-6}$alkyl; and R$^3$ is —C(O)OC$_{1-3}$alkyl.

In a specific aspect, R$^1$ is C$_{1-6}$alkyl, R$^2$ is hydrogen, and R$^3$ is —C(O)OC$_{1-6}$alkyl.

In another specific aspect, R$^1$ is isopropyl, R$^2$ is hydrogen, and R$^3$ is —C(O)OCH$_3$.

In yet other specific aspects, R$^1$ is phenyl and R$^2$ and R$^3$ are each C$_{1-3}$alkyl, or R$^1$ is phenyl and R$^2$ and R$^3$ are each ethyl; or R$^1$ is phenyl, R$^2$ is hydrogen, and R$^3$ is —C(O)OC$_{1-3}$alkyl.

In a specific aspect, R$^4$ is —C(O)R$^5$ wherein R$^5$ is defined as in formula (I).

In another specific aspect, R$^4$ is —C(O)R$^5$ wherein R$^5$ is selected from C$_{1-6}$alkyl, C$_{3-6}$cycloalkyl, C$_{1-6}$alkoxy, —C(R$^k$R$^d$)NR$^e$R$^f$, —NR$^g$R$^h$, heteroaryl, heterocycle, —CH$_2$-heteroaryl, and phenyl; wherein C$_{1-6}$alkyl is optionally substituted with —OR$^c$ or —S(O)$_2$C$_{1-3}$alkyl; C$_{3-6}$cycloalkyl is optionally substituted with one or two C$_{1-3}$alkyl, or with NR$^j$R$^m$ or —OR$^n$; any heterocycle is optionally substituted with one or two substituents selected from C$_{1-3}$alkyl, halo, —C(O)OC$_{1-3}$alkyl, —C(O)C$_{1-6}$alkyl optionally substituted with —NHC(O)OC$_{1-3}$alkyl, and —C(O)C$_{3-6}$cycloalkyl optionally substituted with one or two C$_{1-3}$alkyl; and any heteroaryl is optionally substituted with C$_{1-6}$alkyl, wherein R$^h$ is selected from hydrogen, C$_{1-6}$alkyl, C$_{3-6}$cycloalkyl, and —S(O)$_2$C$_{1-3}$alkyl, and R$^c$, R$^k$, R$^d$, R$^e$, R$^f$, R$^g$, R$^j$, R$^m$, and R$^n$ are defined as in formula (I).

In another specific aspect, R$^4$ is —C(O)R$^5$ wherein R$^5$ is selected from C$_{1-6}$alkyl, C$_{3-6}$cycloalkyl, C$_{1-6}$alkoxy, —C(R$^k$R$^d$)NR$^e$R$^f$, —NR$^g$R$^h$, heteroaryl, heterocycle, and —CH$_2$-heteroaryl, wherein any heteroaryl or heterocycle has five or six ring atoms; C$_{3-6}$cycloalkyl is optionally substituted with one or two C$_{1-3}$alkyl; any heterocycle is optionally substituted with one or two substituents selected from C$_{1-3}$alkyl halo, —C(O)OC$_{1-3}$alkyl, —C(O)C$_{1-6}$alkyl optionally substituted with —NHC(O)OC$_{1-3}$alkyl, and —C(O)C$_{3-6}$cycloalkyl optionally substituted with one or two C$_{1-3}$alkyl; R$^k$, R$^d$, R$^e$, R$^g$, and R$^h$ are each independently hydrogen or C$_{1-3}$alkyl; and R$^f$ is selected from hydrogen and —C(O)C$_{1-3}$alkyl.

In another specific aspect, R$^4$ is —C(O)R$^5$ wherein R$^5$ is selected from C$_{3-4}$cycloalkyl, —CH$_2$NR$^e$R$^f$, —NR$^g$R$^h$, imidazolyl, pyrazolyl, pyrimidinyl, and pyrrolidinyl; wherein: C$_{3-4}$cycloalkyl is optionally substituted with one or two C$_{1-3}$alkyl; pyrrolidinyl is substituted with methyl and a substituent selected from —C(O)OC$_{1-3}$alkyl, —C(O)C$_{1-6}$alkyl, and —C(O)NHC$_{1-6}$alkyl, wherein—C(O)C$_{1-6}$alkyl is substituted with —NHC(O)OC$_{1-3}$alkyl, —OR$^n$, —NR$^d$R$^e$, or heterocycle.

In yet another specific aspect, R$^4$ is —C(O)R$^5$ wherein R$^5$ is selected from, —O-tert-butyl, cyclopropyl, tert-butyl, —NHCH$_3$, 2,2-dimethylcyclopropyl, pyrimidinyl, pyrazolyl, imidazolyl, —CH$_2$-pyrazolyl, 1-acetylpyrrolidinyl, 2-methylpyrrolidine-1-carboxylic acid methyl ester, 1-cyclopropyl-2-methylpyrrolidine, 1--(2,2-dimethylcyclopropyl)-2-methylpyrrolidine, and [-2-methyl-1-(2-methyl-pyrrolidine-1-carbonyl)-propyl]-carbamic acid methyl ester.

In yet another specific aspect, R$^4$ is —C(O)R$^5$ wherein R$^5$ is selected from, —O-tert-butyl, cyclopropyl, tert-butyl, —NHCH$_3$, 2,2-dimethylcyclopropyl, pyrimidinyl, pyrazolyl, imidazolyl, —CH$_2$-pyrazolyl, and 1-acetylpyrrolidinyl.

In another aspect, R$^4$ is —C(O)R$^5$ wherein R$^5$ is a five- or six-membered heteroaryl ring;

In yet another aspect R$^4$ is —C(O)R$^5$ wherein R$^5$ is cyclopropyl or 2,2-dimethylcyclopropyl.

In another aspect, R$^4$ is —C(O)R$^5$ wherein R$^5$ is selected from —NHCH$_3$, 2,2-dimethylcyclopropyl,

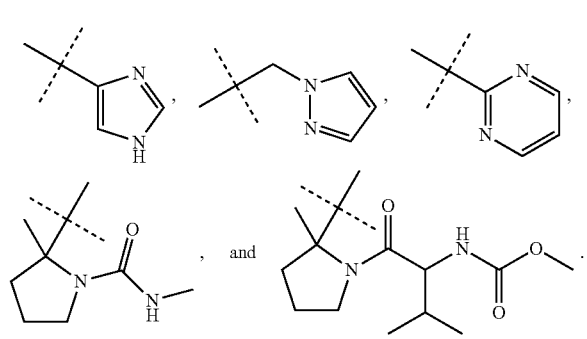

In another aspect, R$^4$ is —C(O)R$^5$ wherein R$^5$ is selected from —NHCH$_3$, 2,2-dimethylcyclopropyl, and

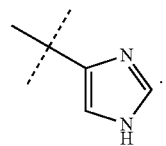

In yet another aspect, R$^4$ is —C(O)R$^5$ wherein R$^5$ is —NHCH$_3$

In a specific aspect, R$^4$ is —S(O)$_2$R$^6$ wherein R$^6$ is selected from C$_{1-6}$alkyl, C$_{3-6}$cycloalkyl, and heteroaryl.

In another specific aspect, R$^4$ is —S(O)$_2$R$^6$ wherein R$^6$ is selected from C$_{1-6}$alkyl, C$_{3-6}$cycloalkyl, and a five- or six-membered heteroaryl.

In another specific aspect, R$^4$ is —S(O)$_2$R$^6$ wherein R$^6$ is C$_{1-6}$alkyl.

In yet another specific aspect, R$^4$ is —S(O)$_2$R$^6$ wherein R$^6$ is methyl.

In a specific aspect, R$^7$, R$^8$, and R$^{11}$ are independently selected from halo, C$_{1-6}$alkyl, C$_{1-6}$alkoxy, —C(O)OR$^n$, —CH$_2$NR$^a$R$^b$, and —CN, wherein C$_{1-6}$alkyl and C$_{1-6}$alkoxy are optionally substituted with one, two, or three halo and wherein C$_{1-6}$alkoxy is optionally substituted with —OR$^d$.

In another specific aspect, R$^7$, R$^8$, and R$^{11}$ are independently selected from halo, C$_{1-6}$alkyl, C$_{1-6}$alkoxy, —C(O)OR$^6$, —CH$_2$NR$^a$R$^b$, and —CN, wherein C$_{1-6}$alkyl and C$_{1-6}$alkoxy are optionally substituted with one, two, or three halo In a specific aspect, R$^7$ is independently selected from halo, C$_{1-6}$alkyl, and C$_{1-6}$alkoxy wherein C$_{1-6}$alkyl and C$_{1-6}$alkoxy are optionally substituted with one, two, or three halo.

In another specific aspect, R$^7$ is halo.

In yet another specific aspect, R$^7$ is chloro or fluoro.

In still another specific aspect, R$^7$ is selected from methyl, —CF$_3$, —OCH$_3$, —OCF$_3$, and fluoro.

In yet another specific aspect, R$^7$ is selected from fluoro, chloro, —CF$_3$, and —OCF$_3$.

In a specific aspect, R$^9$ is selected from C$_{1-6}$alkyl, —CH$_2$OR$^n$, —C(O)NR$^n$R$^p$, and C(O)OR$^n$, wherein C$_{1-6}$alkyl is optionally substituted with —S(O)$_2$C$_{1-3}$alkyl or with —SC$_{1-3}$alkyl.

In another specific aspect, R$^9$ is selected from C$_{1-6}$alkyl, —CH$_2$OR$^n$, —C(O)NR$^n$R$^p$, and C(O)OR$^n$.

In another specific aspect, R$^9$ is C$_{1-6}$alkyl or —CH$_2$OR$^n$.

In another specific aspect, R$^9$ is C$_{1-6}$alkyl.

In yet another specific aspect, R$^9$ is methyl.

In a specific aspect, R$^{10}$ is selected from hydrogen, halo, C$_{1-6}$alkyl, —C(O)OR$^c$, —C(O)NR$^a$R$^b$, —CH$_2$NR$^a$R$^b$, C$_{3-6}$cycloalkyl, and —CN.

In a specific aspect, R$^{10}$ is selected from hydrogen, halo, and C$_{1-6}$alkyl.

In other specific aspects, R$^{10}$ is halo; or R$^{10}$ is chloro.

In yet another specific aspect, R$^{10}$ is hydrogen.

In a specific aspect W', X', Y', and Z' are each CH.

In a specific aspect, W, X, Y, and Z are independently carbon or nitrogen wherein any carbon atom is bonded to hydrogen or to R$^7$, provided that at least two of W, X, Y, and Z are carbon.

In another specific aspect, W, X, Y, and Z are independently carbon or nitrogen wherein any carbon atom is bonded to hydrogen or R$^7$, provided that at least three of W, X, Y, and Z are carbon.

In another specific aspect, W, X, Y, and Z are each carbon and two of W, X, Y, and Z are CH and two of W, X, Y, and Z are bonded to R$^7$.

In yet another specific aspect, W and Z are independently carbon bonded to $R^7$ and X and Y are CH.

In a specific aspect, Q, T, U, and V are independently selected from CH and N.

In a specific aspect, Q, U, and V are each CH and T is N.

In a specific aspect, a is 1 or 2.

In another specific aspect, a is 1.

In another specific aspect a is 0.

In a specific aspect, b is 0.

In a specific aspect, c is 1 or 2.

In another specific aspect, c is 2.

In another specific aspect, c is 1.

In another specific aspect, c is 0.

In a specific aspect, d is 1.

In a specific aspect, d is 0.

In one aspect, the invention provides compounds of formula (I) disclosed in U.S. Provisional Application No. 61/492,267, filed on Jun. 1, 2011.

In another aspect, the invention provides compounds of formula (II):

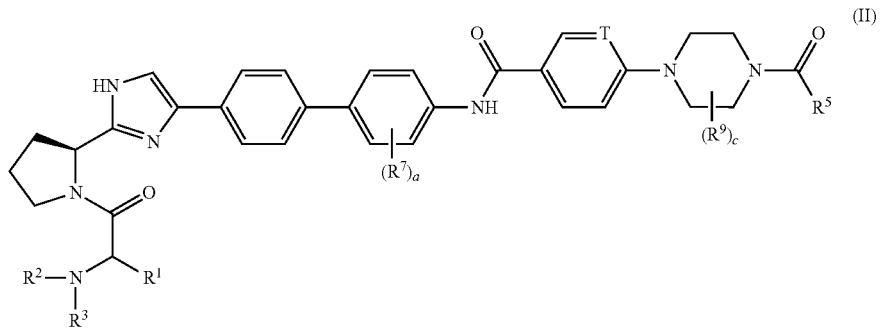

wherein the variables of formula (II) are as defined herein.

In another aspect, the invention provides compounds of formula (III)

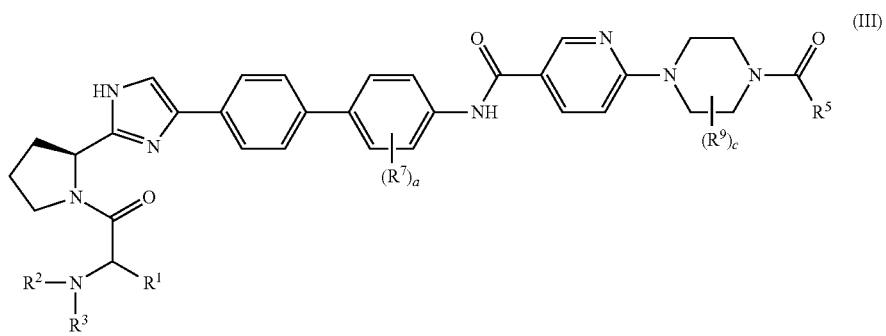

wherein the variables of formula (III) are as defined herein.

A particular group of compounds of formula (III) is a group wherein:

$R^1$ is selected from $C_{1-6}$alkyl, phenyl, and $C_{3-6}$cycloalkyl, wherein $C_{1-6}$alkyl is optionally substituted with —$OR^q$;

$R^3$ is selected from hydrogen, $C_{1-6}$alkyl, —C(O)OC$_{1-6}$alkyl, —C(O)NR$^a$R$^b$, —C(O)C$_{3-6}$cycloalkyl, and —S(O)$_2$ C$_{1-3}$alkyl;

$R^5$ is selected from $C_{1-6}$alkyl, $C_{3-6}$cycloalkyl, $C_{1-6}$alkoxy, —C(R$^k$R$^d$)NR$^e$R$^f$, —NR$^g$R$^h$, heteroaryl, heterocycle, and —CH$_2$-heteroaryl;

wherein:

any heteroaryl or heterocycle has 5 or 6 ring atoms;

$C_{1-6}$alkyl is optionally substituted with one or two substituents independently selected from —OR$^c$, —NHC(O)C$_{1-3}$alkyl, and —NHC(O)OC$_{1-3}$alkyl;

$C_{1-6}$alkoxy is optionally substituted with —OR$^d$;

$C_{3-6}$cycloalkyl is optionally substituted with one or two substituents independently selected from $C_{1-3}$alkyl and halo;

any heterocycle is optionally substituted with one, two, or three substituents independently selected from $C_{1-3}$alkyl, halo, —C(O)OC$_{1-3}$alkyl, —C(O)C$_{1-6}$alkyl, —C(O)C$_{3-6}$cycloalkyl, —C(O)NHC$_{1-6}$alkyl, and —C(O)NHC$_{3-6}$cycloalkyl;

wherein any —C(O)C$_{1-6}$alkyl is optionally substituted with —NHC(O)OC$_{1-3}$alkyl, —OR$^n$, —NR$^d$R$^e$, or heterocycle, any —C(O)C$_{3-6}$cycloalkyl is optionally substituted with one or two C$_{1-3}$alkyl, and any —C(O)NHC$_{1-6}$alkyl is optionally substituted with —OR$^n$ or C$_{3-6}$cycloalkyl;

any heteroaryl is optionally substituted with C$_{1-3}$alkyl;

$R^k$, $R^d$, $R^e$, $R^g$, and $R^h$ are each independently hydrogen or C$_{1-3}$alkyl;

$R^f$ is selected from hydrogen and —C(O)C$_{1-3}$alkyl;

$R^7$ is selected from halo, C$_{1-3}$alkyl, and C$_{1-3}$alkoxy wherein C$_{1-6}$alkyl and C$_{1-6}$alkoxy are optionally substituted with one, two, or three halo;

$R^9$ is C$_{1-3}$alkyl;

a is 1 or 2; and c is 1 or 2; and all other variables are as defined in formula (I).

Another group of compounds of formula (III) is a group wherein:

$R^5$ is selected from C$_{3-4}$cycloalkyl, —CH$_2$NR$^e$R$^f$, —NR$^g$ R$^h$, imidazolyl, pyrazolyl, pyrimidinyl, and pyrrolidinyl;

wherein:
C$_{3-4}$cycloalkyl is optionally substituted with one or two C$_{1-3}$alkyl; pyrrolidinyl is substituted with methyl and a substituent selected from —C(O)OC$_{1-3}$alkyl, —C(O)C$_{1-6}$alkyl, —C(O)NHC$_{1-6}$alkyl, wherein —C(O)C$_{1-6}$alkyl is substituted with —NHC(O)OC$_{1-3}$alkyl, —OR$^n$, —NR$^d$R$^e$, or heterocycle;
wherein R$^e$, R$^g$, and R$^h$ are each independently hydrogen or C$_{1-3}$alkyl; and
R$^f$ is selected from hydrogen and —C(O)C$_{1-3}$alkyl.

Yet another group of compounds of formula (III) is a group wherein:
R$^1$ is isopropyl, R$^2$ is hydrogen; R$^3$ is —C(O)OCH$_3$;
R$^7$ is selected from fluoro, chloro, —CF$_3$, and —OCF$_3$, R$^9$ is methyl; and R$^5$ is selected from —NHCH$_3$, 2,2-dimethylcyclopropyl, and

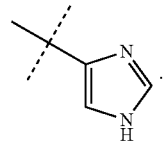

In another aspect, the invention additionally provides compounds of formula (IV):

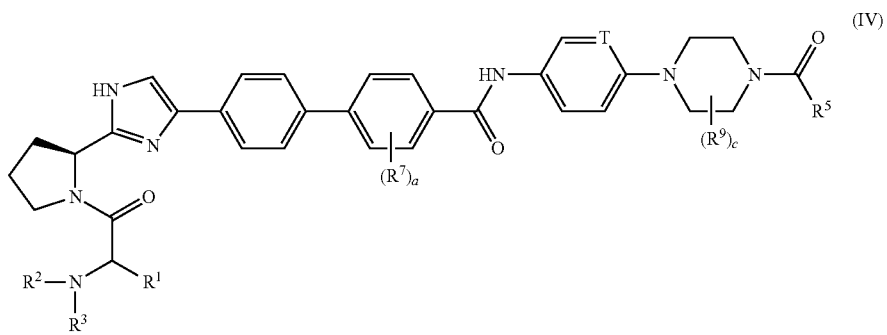

wherein the variables of formula (IV) are as defined herein.

In still another aspect, the invention provides compounds of formula (V):

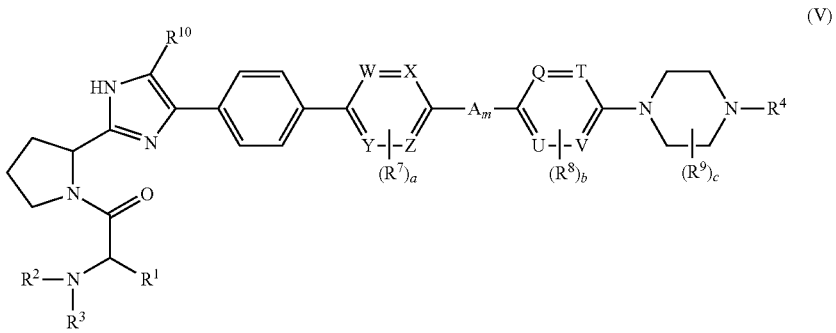

wherein the variables are as defined herein.

In one aspect, the invention provides the compounds of Examples 1-77 and Tables 1-34 below.

In yet another aspect, the invention provides a compound selected from the compounds depicted below

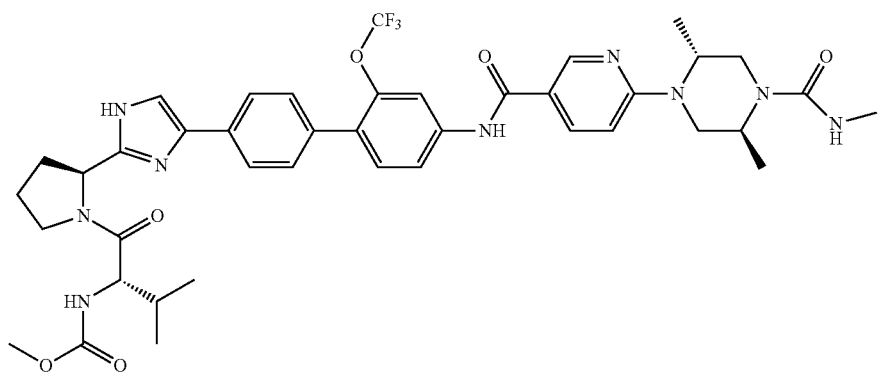
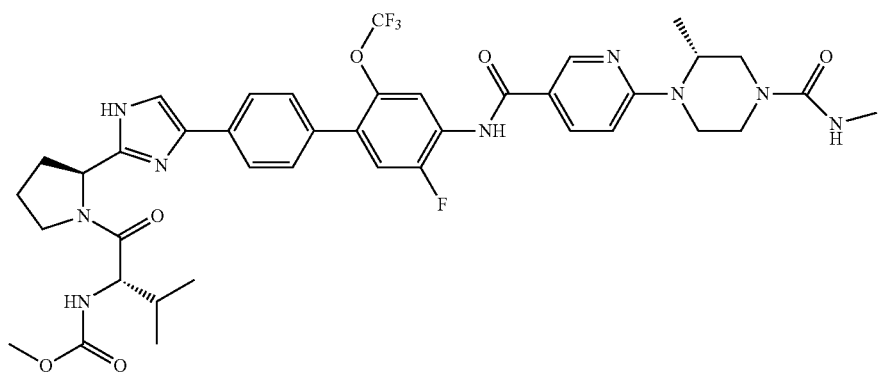
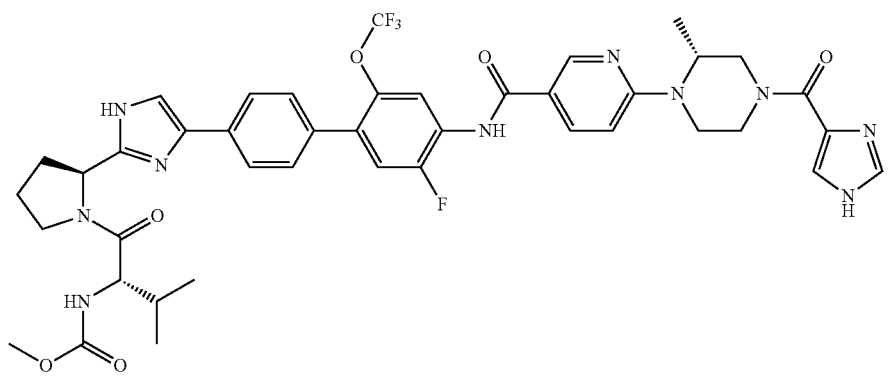
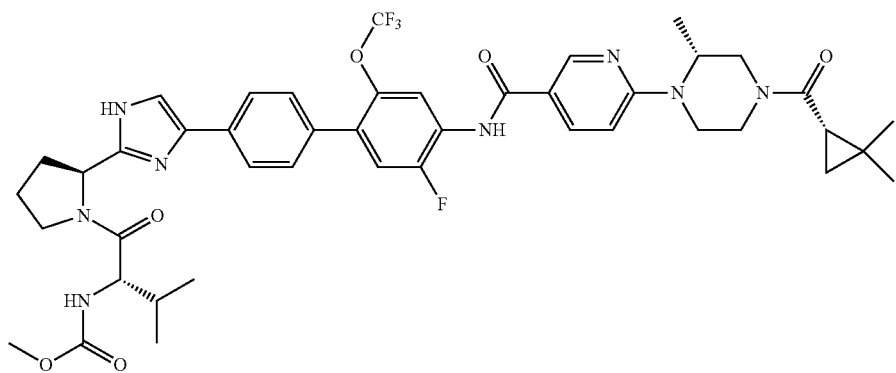

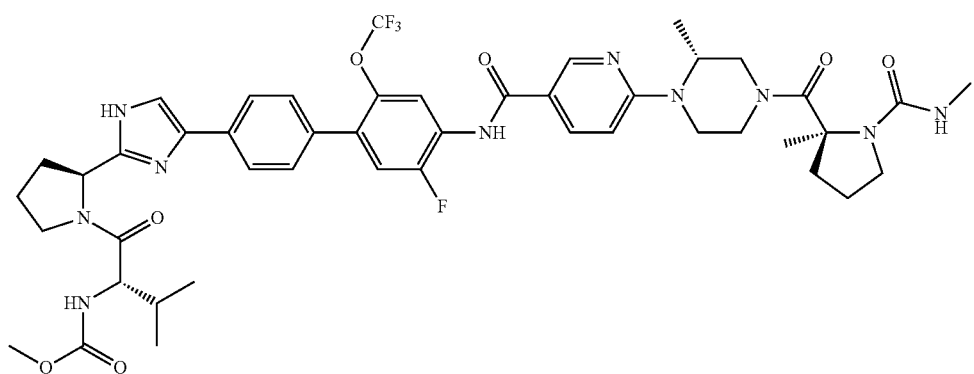
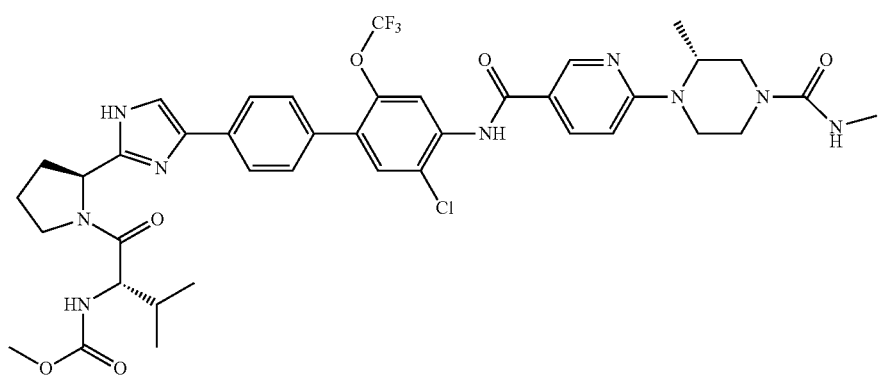
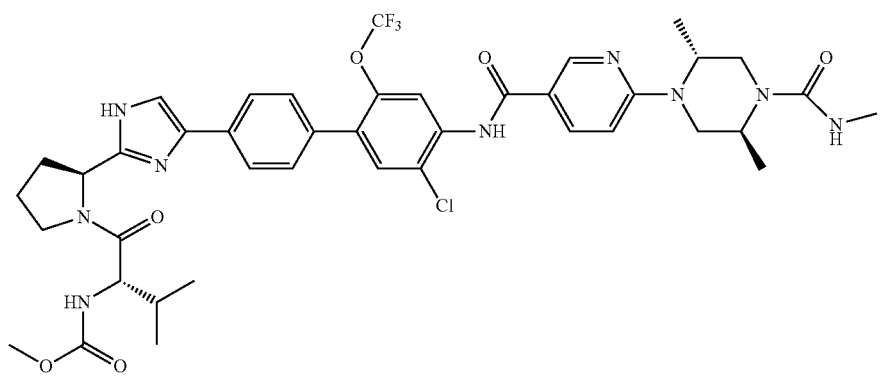
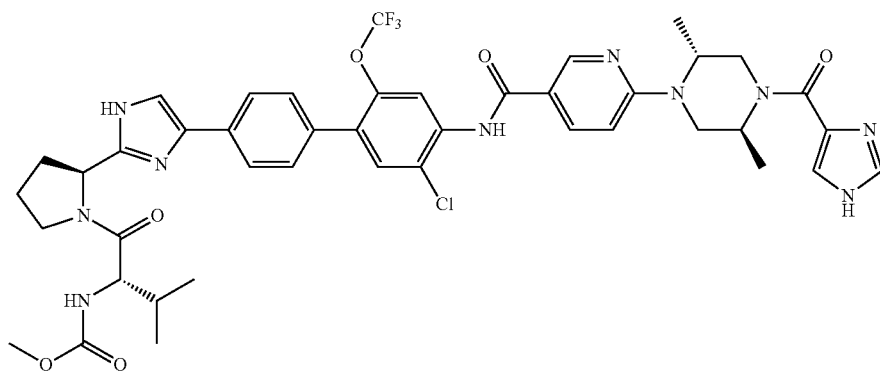

-continued
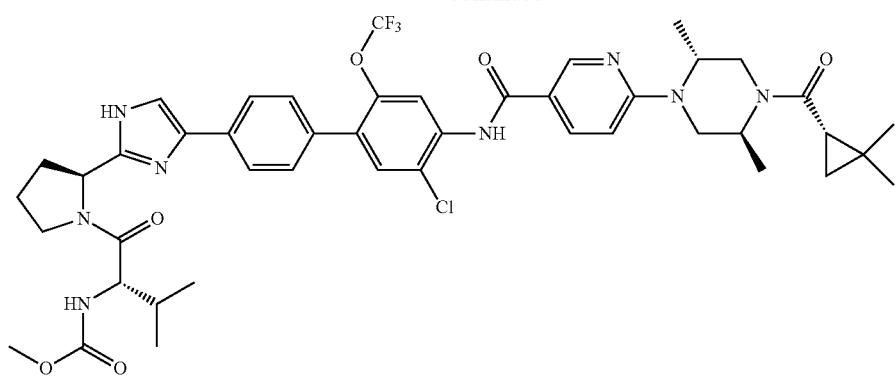
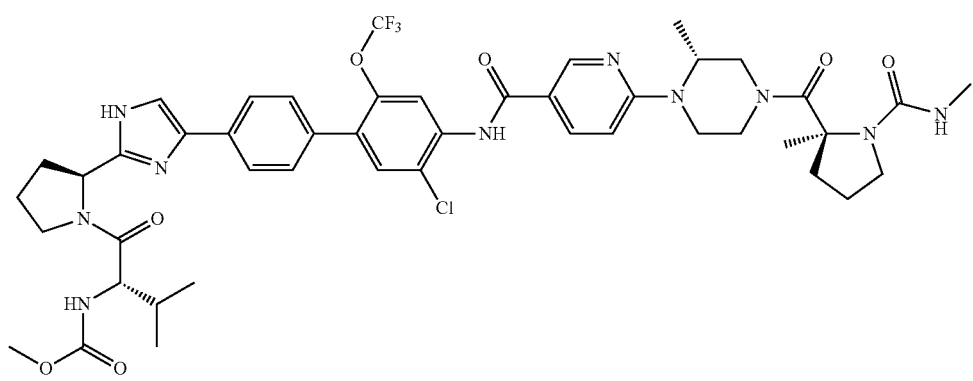
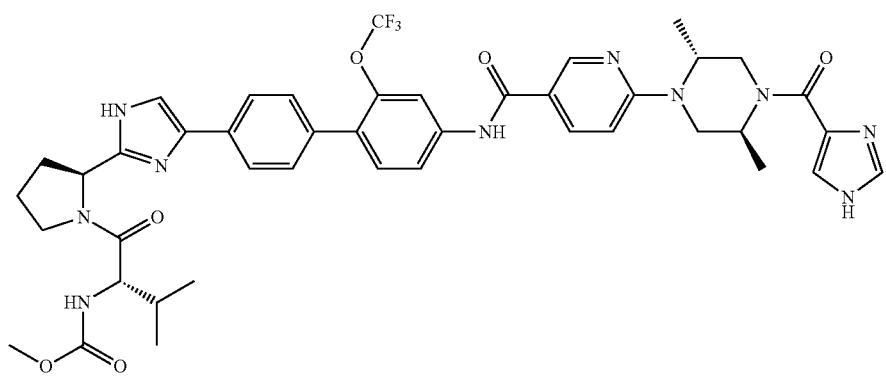
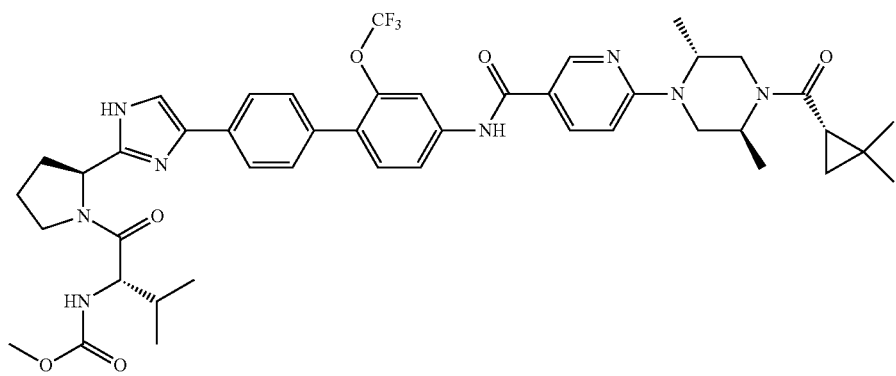

-continued
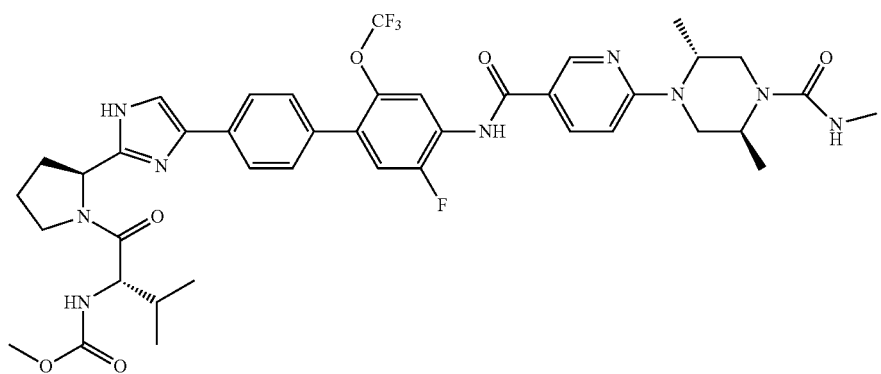
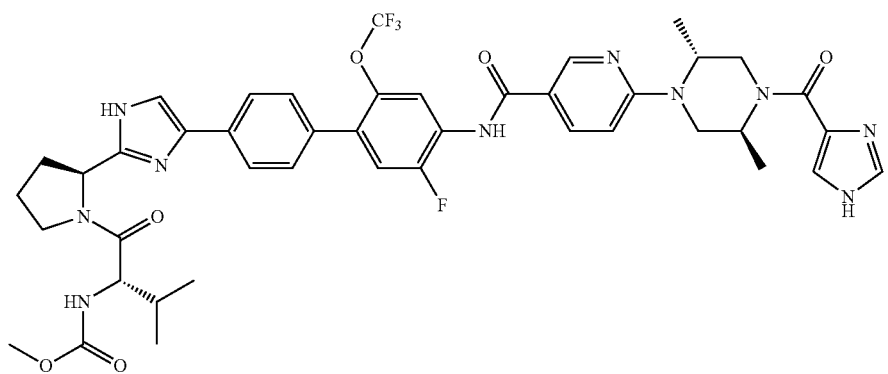
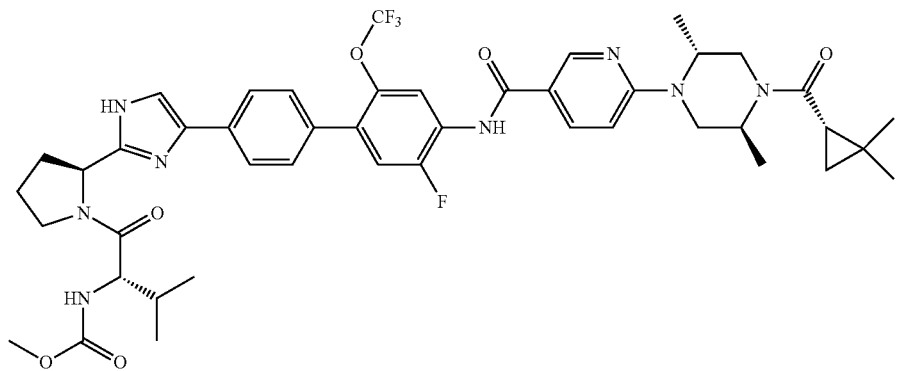
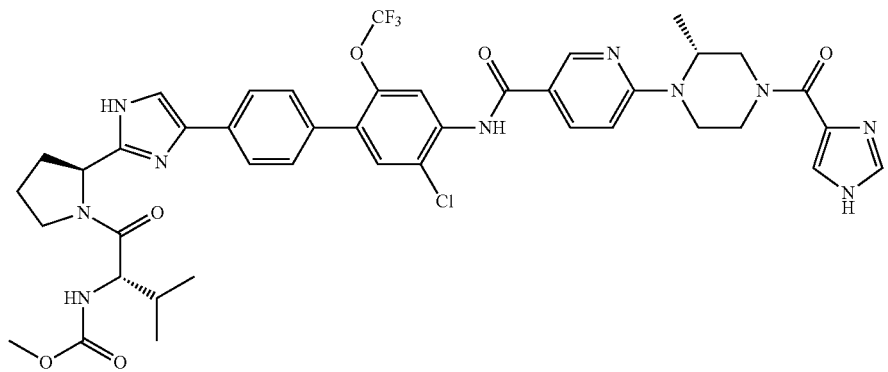

-continued
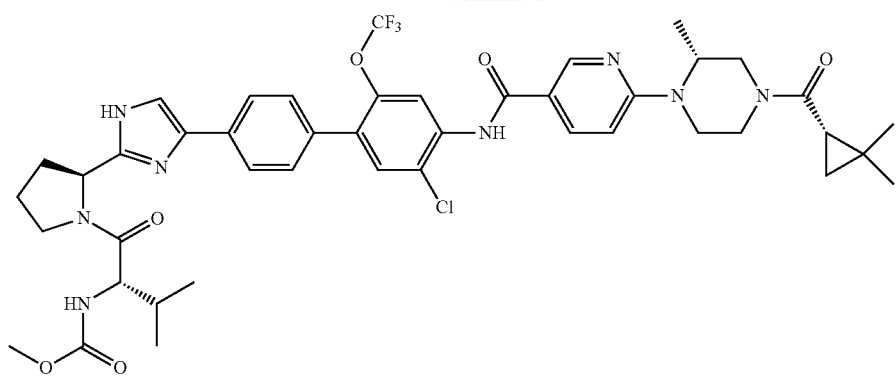
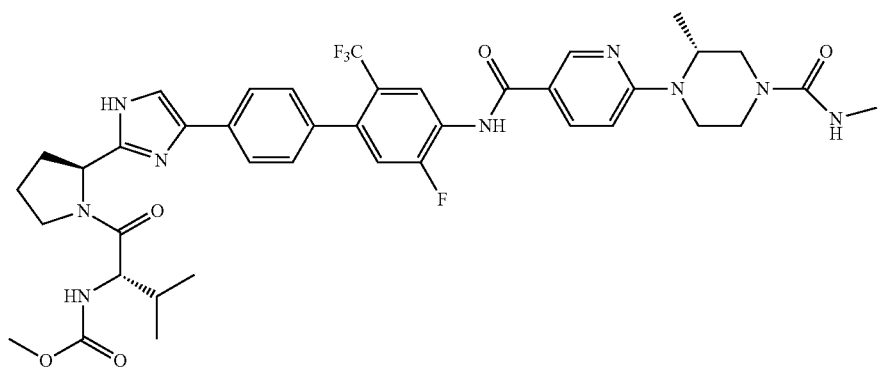
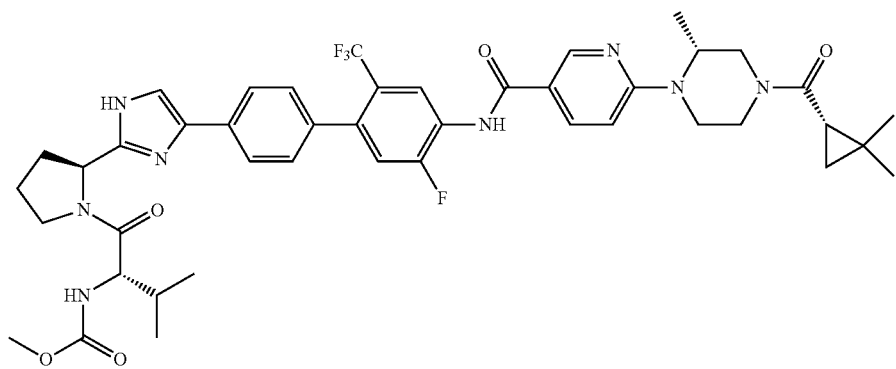
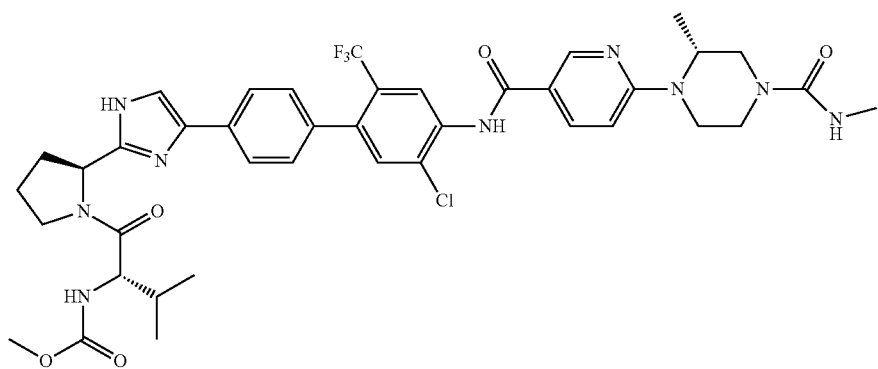

-continued
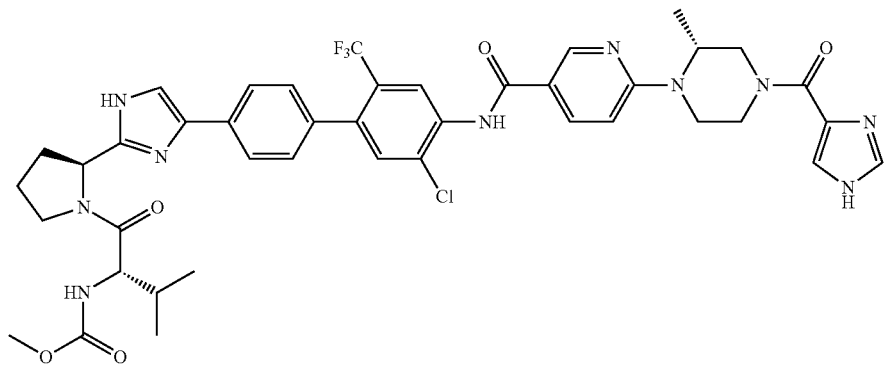 [SMILES: COC(=O)N[C@H](C(=O)N1CCC[C@H]1c1nc(-c2ccc(-c3cc(Cl)c(NC(=O)c4ccc(N5CCN(C(=O)c6c[nH]cn6)C[C@H]5C)nc4)cc3C(F)(F)F)cc2)c[nH]1)C(C)C]
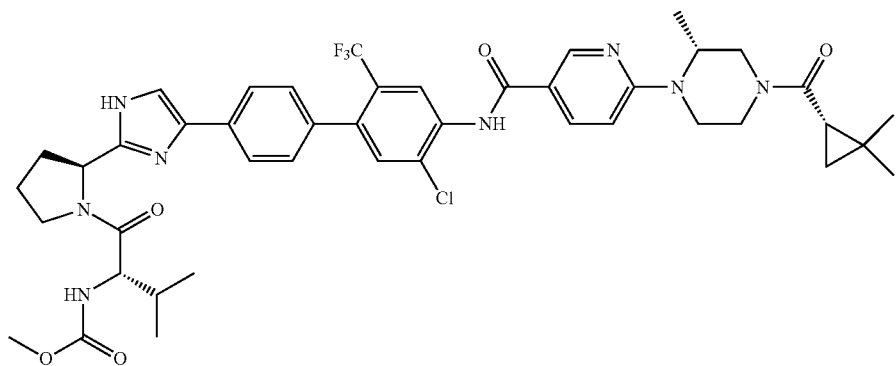
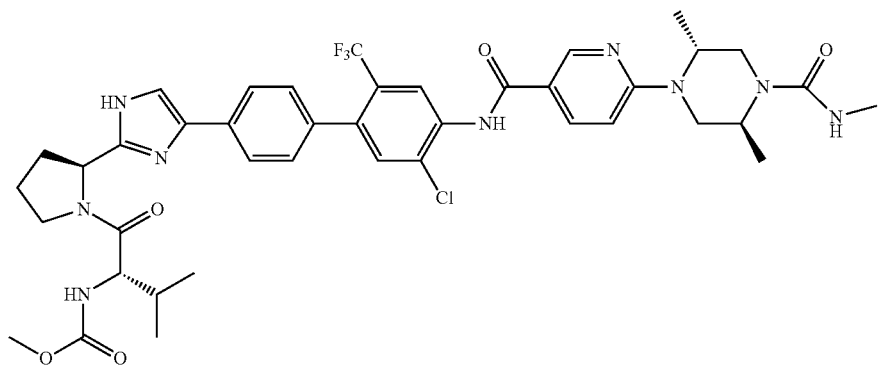
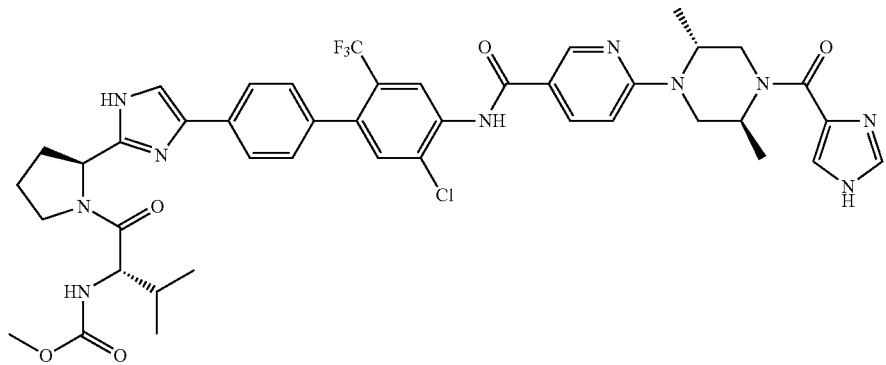

-continued
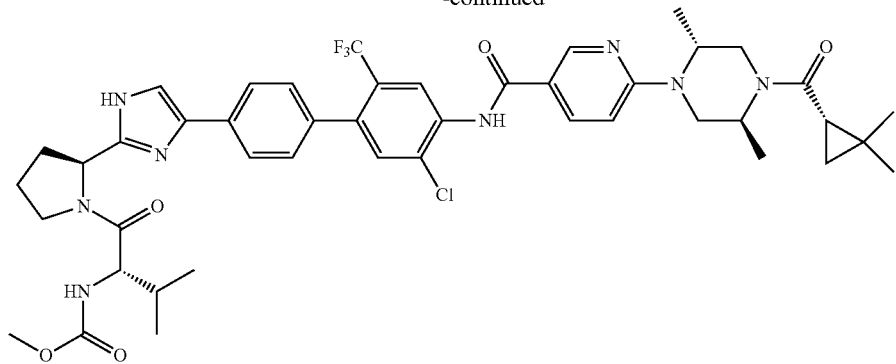
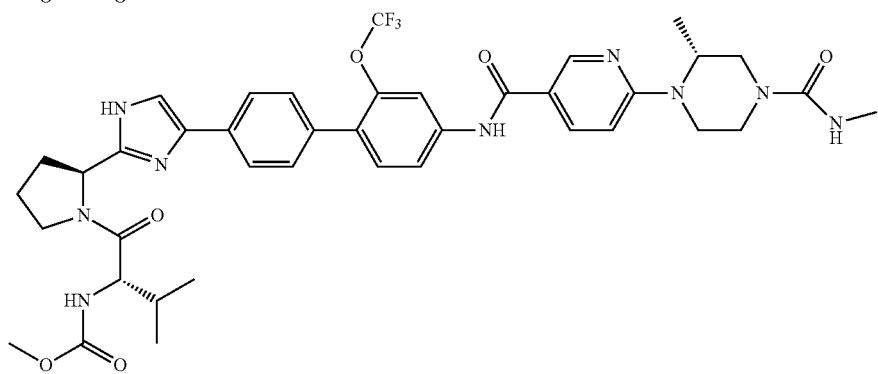
and pharmaceutically-acceptable salts thereof.
In a still further aspect, the invention provides a compound selected from the following compounds
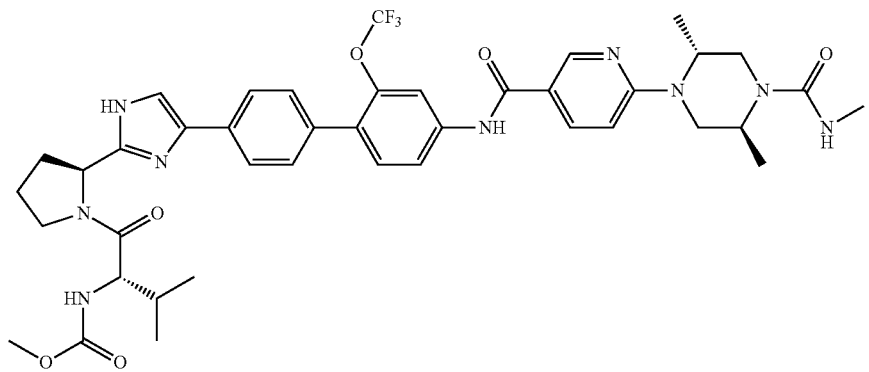
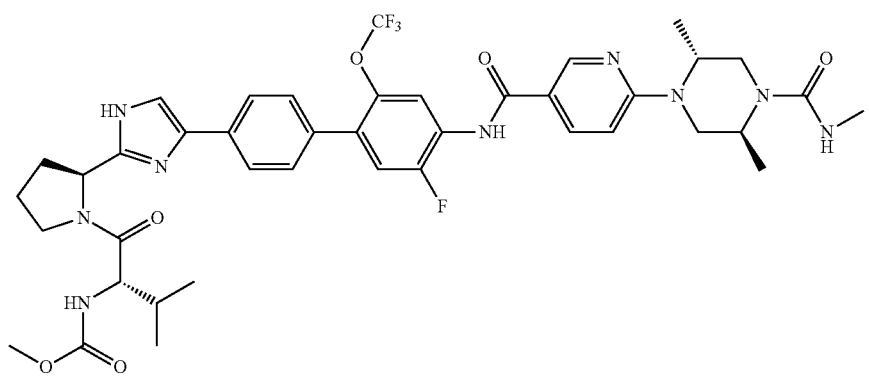

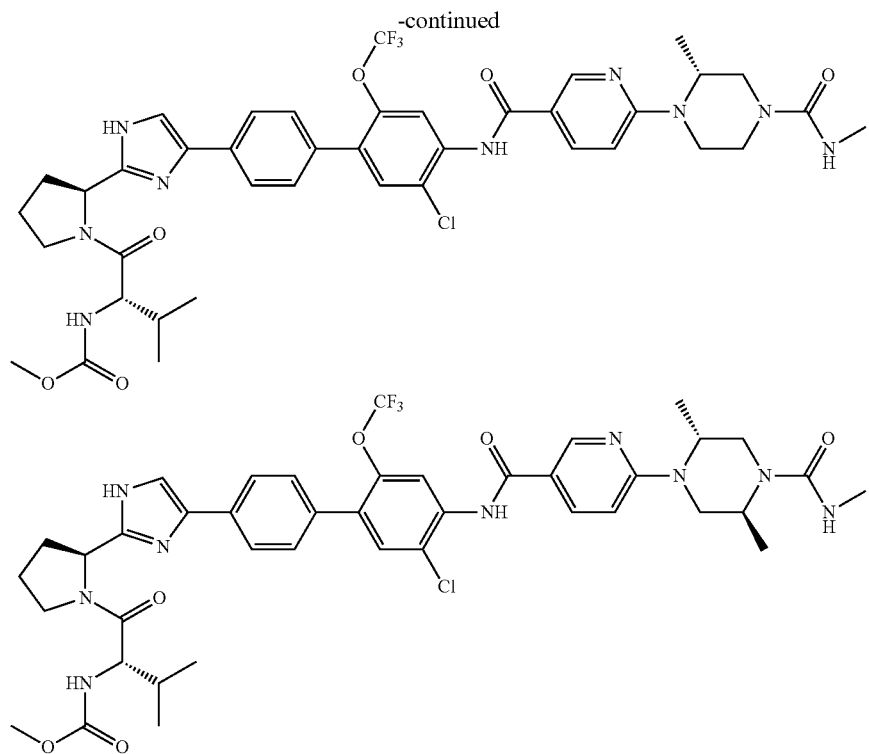

and pharmaceutically-acceptable salts thereof.

The chemical naming convention used herein is illustrated for the compound of Example 1:

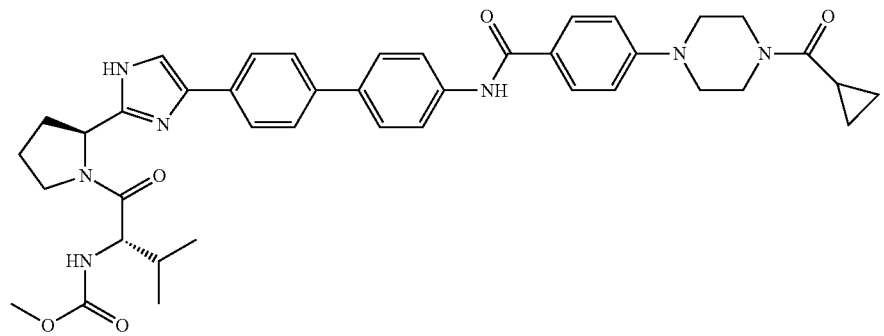 [SMILES: COC(=O)N[C@H](C(=O)N1CCC[C@H]1c1nc(-c2ccc(-c3ccc(NC(=O)c4ccc(N5CCN(C(=O)C6CC6)CC5)cc4)cc3)cc2)c[nH]1)C(C)C]

which is {(S)-1-[(S)-2-(4-{4'-[4-(4-cyclopropanecarbonyl-piperazin-1-yl)-benzoylamino]-biphenyl-4-yl}-1H-imidazol-2-yl)-pyrrolidine-1-carbonyl]-2-methyl-propyl}-carbamic acid methyl ester according to the IUPAC conventions as implemented in AutoNom software, (MDL Information Systems, GmbH, Frankfurt, Germany).

The compounds of the invention contain one or more chiral centers and therefore, such compounds (and intermediates thereof) can exist as racemic mixtures; pure stereoisomers (i.e., enantiomers or diastereomers); stereoisomer-enriched mixtures and the like. Chiral compounds shown or named herein without a defined stereochemistry at a chiral center are intended to include any or all possible stereoisomer variations at the undefined stereocenter unless otherwise indicated. The depiction or naming of a particular stereoisomer means the indicated stereocenter has the designated stereochemistry with the understanding that minor amounts of other stereoisomers may also be present unless otherwise indicated, provided that the utility of the depicted or named compound is not eliminated by the presence of another stereoisomer.

Compounds of formula (I) also contain several basic groups (e.g., amino groups) and therefore, such compounds can exist as the free base or in various salt forms, such a mono-protonated salt form, a di-protonated salt form, a tri-protonated salt form, or mixtures thereof. All such forms are included within the scope of this invention, unless otherwise indicated.

This invention also includes isotopically-labeled compounds of formula (I), i.e., compounds of formula (I) where an atom has been replaced or enriched with an atom having the same atomic number but an atomic mass different from the atomic mass that predominates in nature. Examples of isotopes that may be incorporated into a compound of formula (I) include, but are not limited to, $^{2}H$, $^{3}H$, $^{11}C$, $^{13}C$, $^{14}C$, $^{13}N$, $^{15}N$, $15O$, $^{17}O$, $^{18}O$, $^{35}S$, $^{36}Cl$, and $^{18}F$. Of particular interest are compounds of formula (I) enriched in tritium or carbon-14, which compounds can be used, for example, in tissue distribution studies. Also of particular interest are compounds of formula (I) enriched in deuterium especially at a site of metabolism, which compounds are expected to have greater metabolic stability. Additionally of particular interest are compounds of formula (I) enriched in a positron emitting isotope, such as $^{11}C$, $^{18}F$, $^{15}O$ and $^{13}N$, which compounds can be used, for example, in Positron Emission Tomography (PET) studies.

Definitions

When describing this invention including its various aspects and embodiments, the following terms have the following meanings, unless otherwise indicated.

The term "alkyl" means a monovalent saturated hydrocarbon group which may be linear or branched or combinations thereof. Unless otherwise defined, such alkyl groups typically contain from 1 to 10 carbon atoms. Representative alkyl groups include, by way of example, methyl (Me), ethyl (Et), n-propyl (n-Pr) or (nPr), isopropyl (i-Pr) or (iPr), n-butyl (n-Bu) or (nBu), sec-butyl, isobutyl, tert-butyl (t-Bu) or (tBu), n-pentyl, n-hexyl, 2,2-dimethylpropyl, 2-methylbutyl, 3-methylbutyl, 2-ethylbutyl, 2,2-dimethylpentyl, 2-propylpentyl, and the like When a specific number of carbon atoms are intended for a particular term, the number of carbon atoms is shown preceding the term. For example, the term "$C_{1-3}$ alkyl" means an alkyl group having from 1 to 3 carbon atoms wherein the carbon atoms are in any chemically-acceptable configuration, including linear or branched configurations.

The term "alkoxy" means the monovalent group —O-alkyl, where alkyl is defined as above. Representative alkoxy groups include, by way of example, methoxy, ethoxy, propoxy, butoxy, and the like.

The term "cycloalkyl" means a monovalent saturated carbocyclic group which may be monocyclic or multicyclic. Unless otherwise defined, such cycloalkyl groups typically contain from 3 to 10 carbon atoms. Representative cycloalkyl groups include, by way of example, cyclopropyl (cPr), cyclobutyl, cyclopentyl, cyclohexyl, cycloheptyl, cyclooctyl, adamantyl, and the like.

The term "heterocycle", "heterocyclic", or "heterocyclic ring" means a monovalent saturated or partially unsaturated cyclic non-aromatic group, having from 3 to 10 total ring atoms, wherein the ring contains from 2 to 9 carbon ring atoms and from 1 to 4 ring heteroatoms selected from nitrogen, oxygen, and sulfur. Heterocyclic groups may be monocyclic or multicyclic (i.e., fused or bridged). Representative heterocyclic groups include, by way of example, pyrrolidinyl, piperidinyl, piperazinyl, imidazolidinyl, morpholinyl, thiomorpholyl, indolin-3-yl, 2-imidazolinyl, 1,2,3,4-tetrahydroisoquinolin-2-yl, quinuclidinyl, 7-azanorbornanyl, nortropanyl, and the like, where the point of attachment is at any available carbon or nitrogen ring atom. Where the context makes the point of attachment of the heterocyclic group evident, such groups may alternatively be referred to as a non-valent species, i.e. pyrrolidine, piperidine, piperazine, imidazole, etc.

The term "heteroaryl" or "heteroaryl ring" means a monovalent aromatic group having from 5 to 10 total ring atoms, wherein the ring contains from 1 to 9 carbon ring atoms and from 1 to 4 ring heteroatoms selected from nitrogen, oxygen, and sulfur. Heteroaryl groups may be monocyclic or multicyclic. Representative heteroaryl groups include, by way of example, pyrroyl, isoxazolyl, isothiazolyl, pyrazolyl, oxazolyl, oxadiazolyl, thiadiazolyl, thiazolyl, imidazolyl, triazolyl, tetrazolyl, furanyl, triazinyl, thienyl, pyridyl (or, equivalently, pyridinyl), pyrimidyl, pyridazinyl, pyrazinyl, indolyl, benzofuranyl, benzothienyl, benzimidazolyl, benzthiazolyl, and the like, where the point of attachment is at any available carbon or nitrogen ring atom. Where the context makes the point of attachment of the heteroaryl group evident, such groups may alternatively be referred to as a non-valent species, i.e. pyrrole, isoxazole, isothiazole, pyrazole, imidazole, etc.

The term "halo" means fluoro, chloro, bromo or iodo.

The term "therapeutically effective amount" means an amount sufficient to effect treatment when administered to a patient in need of treatment.

The term "treatment" as used herein means the treatment of a disease, disorder, or medical condition in a patient (such as hepatitis C viral infection), such as a mammal (particularly a human) which includes one or more of the following:

(a) preventing the disease, disorder, or medical condition from occurring, i.e., preventing the reoccurrence of the disease or medical condition or prophylactic treatment of a patient that is pre-disposed to the disease or medical condition;

(b) ameliorating the disease, disorder, or medical condition, i.e., eliminating or causing regression of the disease, disorder, or medical condition in a patient, including counteracting the effects of other therapeutic agents;

(c) suppressing the disease, disorder, or medical condition, i.e., slowing or arresting the development of the disease, disorder, or medical condition in a patient; or (d) alleviating the symptoms of the disease, disorder, or medical condition in a patient.

The term "pharmaceutically acceptable salt" means a salt that is acceptable for administration to a patient or a mammal, such as a human (e.g., salts having acceptable mammalian safety for a given dosage regime). Representative pharmaceutically acceptable salts include salts of acetic, ascorbic, benzenesulfonic, benzoic, camphorsulfonic, citric, ethanesulfonic, edisylic, fumaric, gentisic, gluconic, glucoronic, glutamic, hippuric, hydrobromic, hydrochloric, isethionic, lactic, lactobionic, maleic, malic, mandelic, methanesulfonic, mucic, naphthalenesulfonic, naphthalene-1,5-disulfonic, naphthalene-2,6-disulfonic, nicotinic, nitric, orotic, pamoic, pantothenic, phosphoric, succinic, sulfuric, tartaric, p-toluenesulfonic and xinafoic acid, and the like.

The term "salt thereof" means a compound formed when the hydrogen of an acid is replaced by a cation, such as a metal cation or an organic cation and the like. For example, the cation can be a protonated form of a compound of formula (I), i.e. a form where one or more amino groups have been protonated by an acid. Typically, the salt is a pharmaceutically acceptable salt, although this is not required for salts of intermediate compounds that are not intended for administration to a patient.

The term "amino-protecting group" means a protecting group suitable for preventing undesired reactions at an amino nitrogen. Representative amino-protecting groups include, but are not limited to, formyl; acyl groups, for example alkanoyl groups, such as acetyl and tri-fluoroacetyl; alkoxycarbonyl groups, such as tert butoxycarbonyl (Boc); arylmethoxycarbonyl groups, such as benzyloxycarbonyl (Cbz) and 9-fluorenylmethoxycarbonyl (Fmoc); arylmethyl groups, such as benzyl (Bn), trityl (Tr), and 1,1-di-(4'-methoxyphenyl)methyl; silyl groups, such as trimethylsilyl (TMS), tert-butyldimethylsilyl (TBDMS), [2-(trimethylsilyl)ethoxy]methyl (SEM); and the like. Numerous protecting groups, and their introduction and removal, are described in T. W. Greene and G. M. Wuts, *Protecting Groups in Organic Synthesis*, Third Edition, Wiley, New York General Synthetic Procedures Compounds of this invention, and intermediates thereof, can be prepared according to the following general methods and procedures using commercially-available or routinely-prepared starting materials and reagents. The substituents and variables (e.g., $R^1$, $R^2$, $R^3$, $R^4$, etc.) used in the following schemes have the same meanings as those defined elsewhere herein unless otherwise indicated. Additionally, compounds having an acidic or basic atom or functional group may be used or may be produced as a salt unless otherwise indicated (in some cases, the use of a salt in a particular reaction will require conversion of the salt to a non-salt form, e.g., a free base, using routine procedures before conducting the reaction).

Although a particular embodiment of the present invention may be shown or described in the following procedures, those skilled in the art will recognize that other embodiments or aspects of the present invention can also be prepared using such procedures or by using other methods, reagents, and starting materials know to those skilled in the art. In particular, it will be appreciated that compounds of the invention may be prepared by a variety of process routes in which reactants are combined in different orders to provide different intermediates en route to producing final products.

In one exemplary method of synthesis, compounds of formula (1-3) in which $A_m$ is defined as —NHC(O)— are prepared as shown in Scheme 1:

where $R^1$, $R^2$, and $R^3$ are defined as in formula (I), or as an amino-protecting group Pg. Aniline intermediate 1-1 is reacted with carboxylic acid 1-2 according to typical amide bond formation conditions to provide a compound of formula 1-3 In some instances, the carboxylic acid 1-2 is first converted to an acid chloride and then reacted with aniline intermediate 1-1 to provide a compound of formula 1-3. As shown in the examples below, the amide bond formation reaction may utilize coupling agents, such as N,N,N',N'-tetramethyl-O-(7-azabenzotriazol-1-yOuronium hexafluorophosphate (HATU), or as 1,3 dicyclohexylcarbodiimide (DCC), 1-(3-dimethylaminopropyl)-3-ethylcarbodiimide (EDC), or benzotriazol-1-yloxytripyrrolidino-phosphonium hexafluorophosphate (PyBop), optionally combined with 1-hydroxy-7-azabenzotriazole (HOAt). Preferably, the process of Scheme 1 is used to prepare compounds of formula 1-3 in which $R^7$ is absent (a is 0) or $R^7$ is an electron rich substituent such as an unsubstituted-alkyl or unsubstituted-alkoxy, and the reaction is performed in the presence of coupling agents EDC and HOAt at a temperature of about 50 to about 60° C. Preferably, only one of G and $R^{4a}$ is a protecting group, or, if two protecting groups are present, groups removable under different conditions are used.

Scheme 1

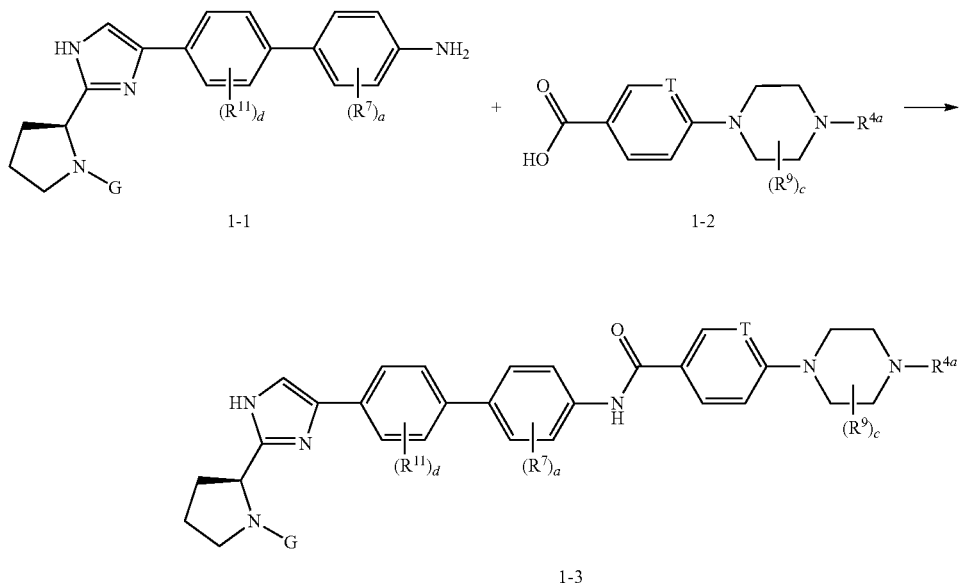

where $R^{4a}$ is an amino-protecting group Pg or $R^{4a}$ is $R^4$ as defined in formula (I), and G represents the group $G_1$

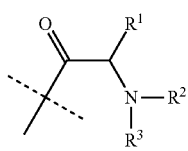

When the variable $R^{4a}$ is defined as $R^4$ and the variable G is defined as $G_1$, then the product 1-3 of the reaction of Scheme 1 is a final compound of formula (I).

Alternatively, when $R^{4a}$ is defined as $R^4$ and G is defined as protecting group Pg, for example Boc, the product 1-3 of the reaction of Scheme 1 is a protected intermediate which is then deprotected, for example, by treatment with an acid, and reacted with a reagent X-$G_1$, where X is a halogen leaving group, or with a carboxylic acid of formula HO-$G_1$, the latter under amide bond formation conditions as described above, to provide the desired product.

In another exemplary method of synthesis, compounds of formulas 2-2 and 2-3 are prepared as shown in Scheme 2:

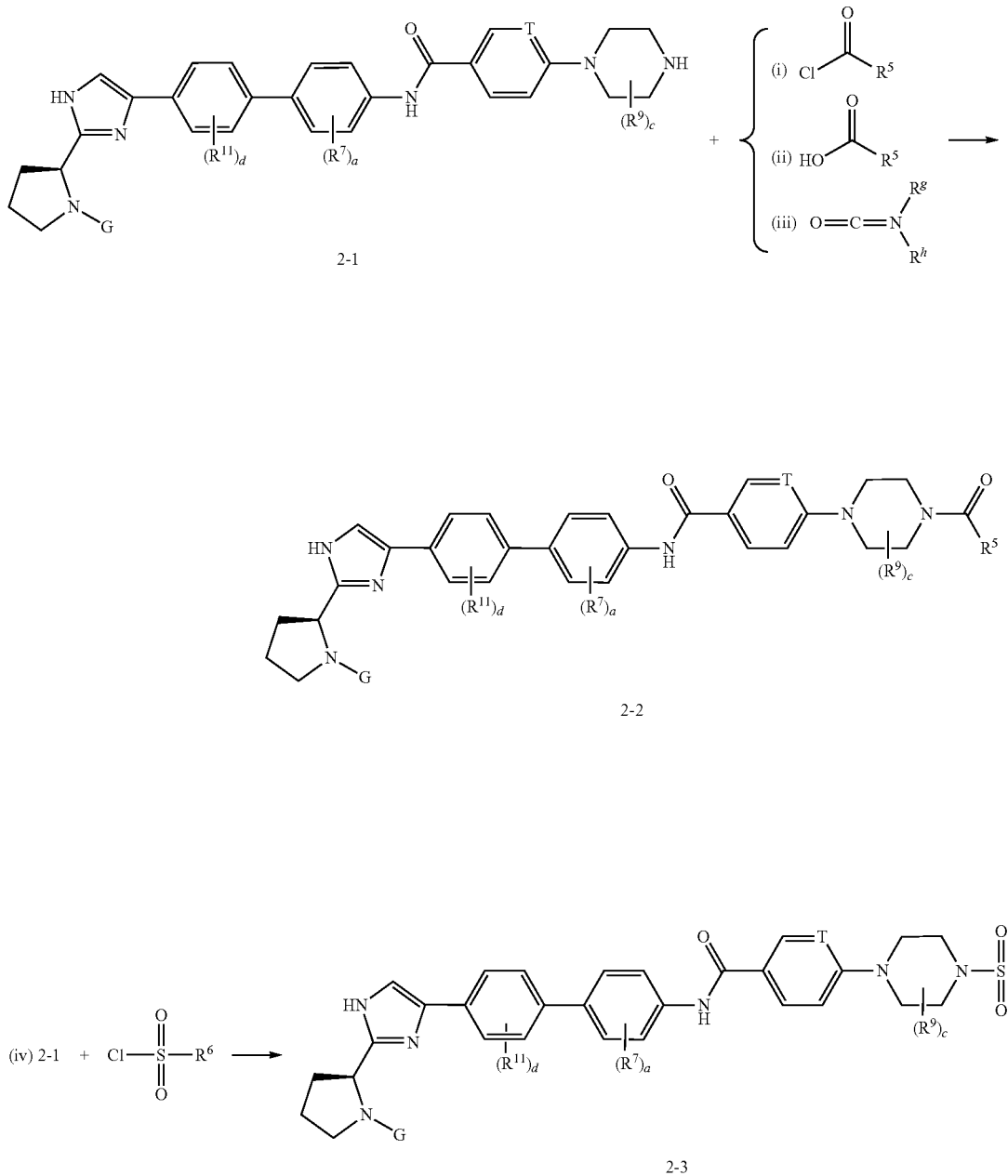

When G represents $G_1$ in intermediate 2-1, then the reaction of Scheme 2, directly provides compounds of the invention. To prepare a compound of formula 2-2 where $R^4$ is defined as —C(O)$R^5$, intermediate 2-1 is reacted with an acid chloride (reaction (i)) or, where $R^5$ is defined as —NR$^g$R$^h$, with an isocyanate (reaction (iii)) in the presence of base. Alternatively, intermediate 2-1 is reacted with a carboxylic acid (reaction (ii)) under amide bond formation conditions to prepare a compound of formula 2-2. Similarly, to prepare a compound of formula 2-3 where $R^4$ is defined as —S(O)$_2$R$^6$, intermediate 2-1 is typically reacted with a sulfonyl chloride in the presence of base (reaction (iv)).

As described above, when G represents a protecting group a subsequent deprotection step, and coupling with an intermediate X-$G_1$ or HO-$G_1$ provides the final product.

The intermediates of the above Schemes may be prepared by conventional synthetic reactions. For example, the biaryl aniline intermediate 1-1 may be prepared by the Suzuki coupling reaction in the presence of a palladium catalyst (Miyaura and Suzuki, *Chem. Rev.* 1995, 95, 2457-2483). As shown in Scheme 3 below, either coupling partner may bear the boronate moiety. Alternatively, a boronic acid reagent may be used in place of a boronate reagent, such as the pinacol boronate depicted below.

Scheme 3

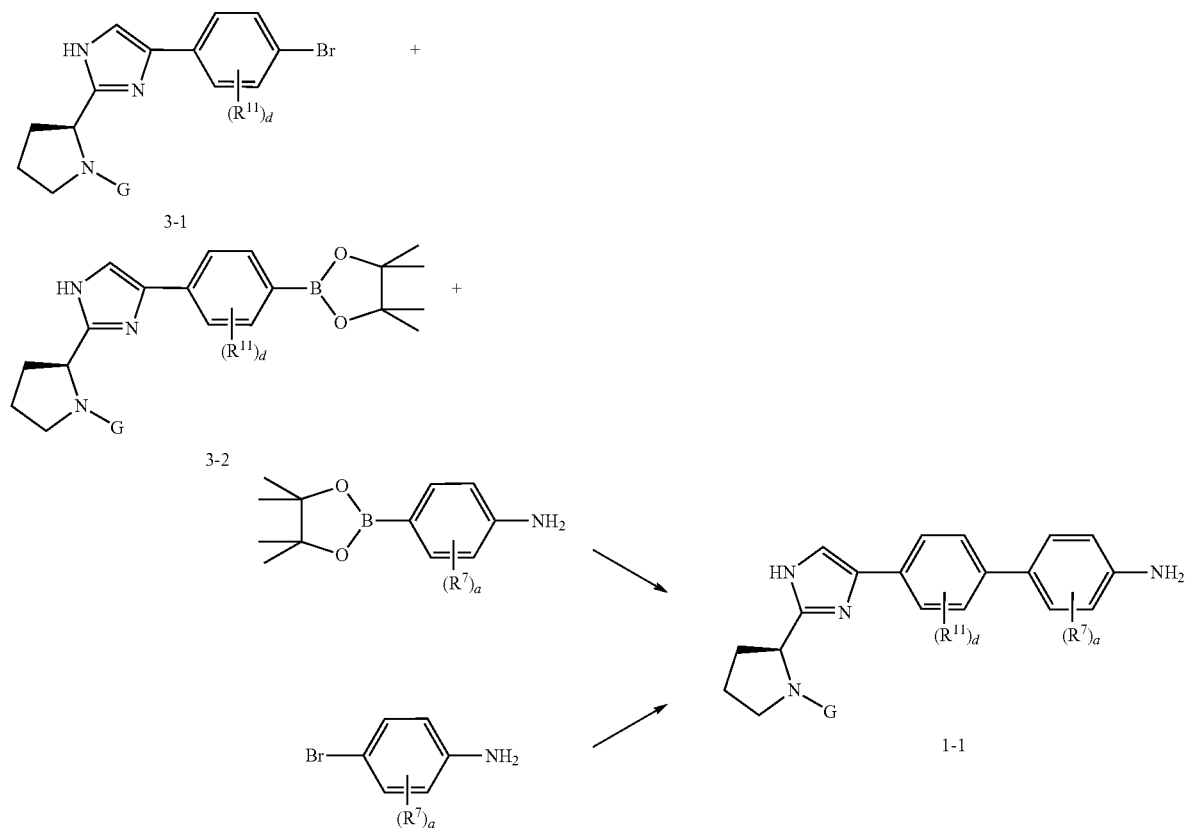

An exemplary process for the preparation of intermediate 1-2 in which $R^{4a}$ represents Pg (compound 1-2") or $R^{4a}$ represents, for example, —C(O)$R^5$ (compound 1-2') is shown in Scheme 4.

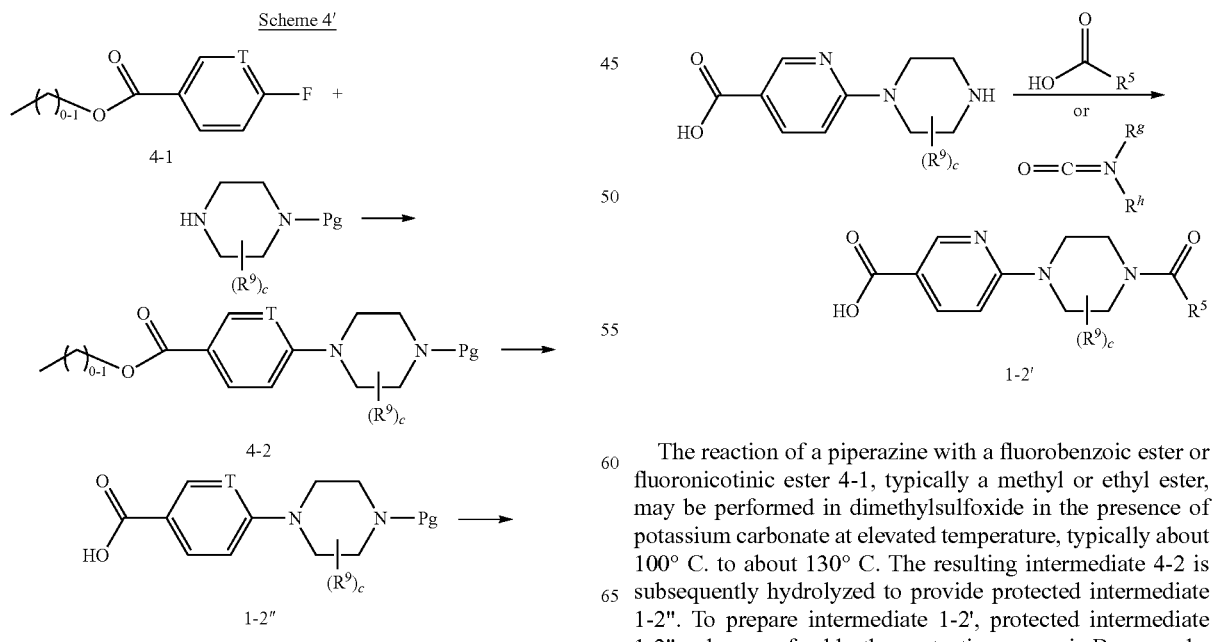

The reaction of a piperazine with a fluorobenzoic ester or fluoronicotinic ester 4-1, typically a methyl or ethyl ester, may be performed in dimethylsulfoxide in the presence of potassium carbonate at elevated temperature, typically about 100° C. to about 130° C. The resulting intermediate 4-2 is subsequently hydrolyzed to provide protected intermediate 1-2". To prepare intermediate 1-2', protected intermediate 1-2", where preferably the protecting group is Boc, can be deprotected and then reacted with an acid chloride, carboxylic acid, or isocyanate as in Scheme 2 to provide intermediate 1-2'.

An alternative process for the preparation of intermediate 1-2 in which T represents nitrogen and $R^{4a}$ represents Pg (compound 1-2a") or $R^{4a}$ represents —C(O)$R^5$ (compound 1-2a') is shown in Scheme 5.

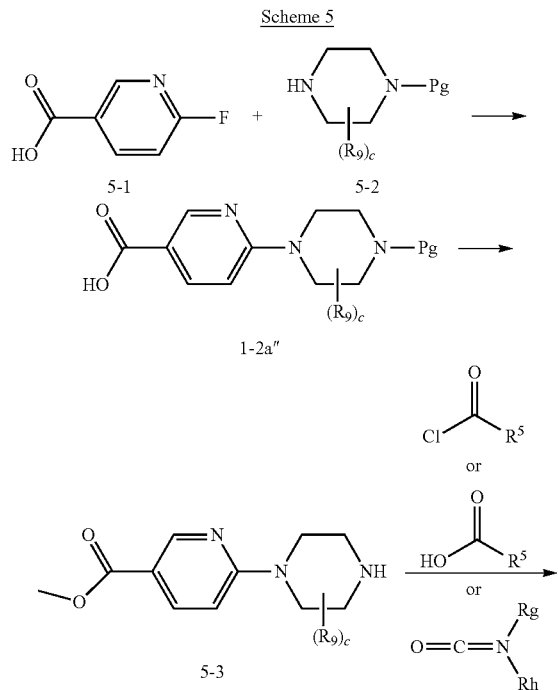

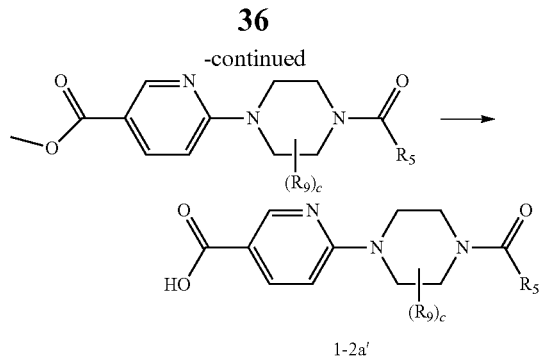

The reaction of a fluoronicotinic acid 5-1 with the protected piperazine 5-2 to provide intermediate 1-2a" is typically performed using isopropylmagnesium chloride at a temperature below about −20° C.

To prepare intermediate 1-2a', protected intermediate 1-2a", where preferably the protecting group is Boc, can be deprotected and esterified by reaction with sulfuric acid in methanol to provide an ester intermediate 5-3, which is reacted with an acid chloride, carboxylic acid, or isocyanate as in Scheme 2 and subsequently hydrolyzed to provide intermediate 1-2a'.

Intermediate 2-1 where G represents $G_1$ may be prepared by the process of Scheme 1 where the variable $R^{4a}$ is defined as protecting group Pg. In this instance, formula 1-3 describes a protected intermediate, which is deprotected to provide intermediate 2-1.

An alternative process for the preparation of intermediate 2-1 in which T represents nitrogen (compound 2-1a) is shown in Scheme 6.

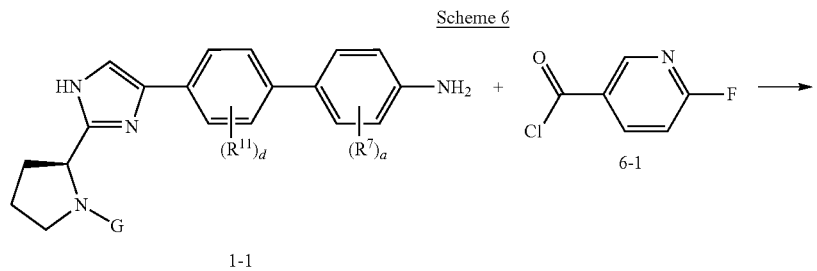

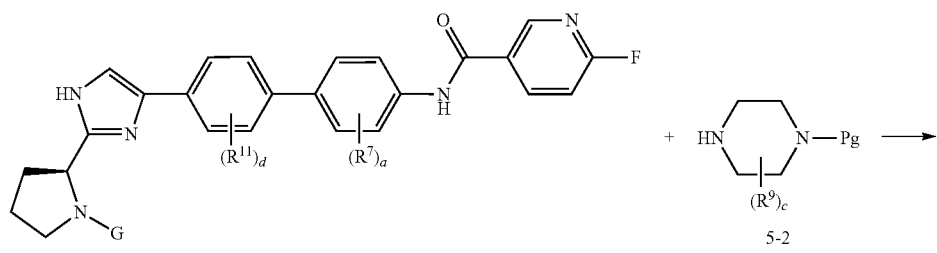

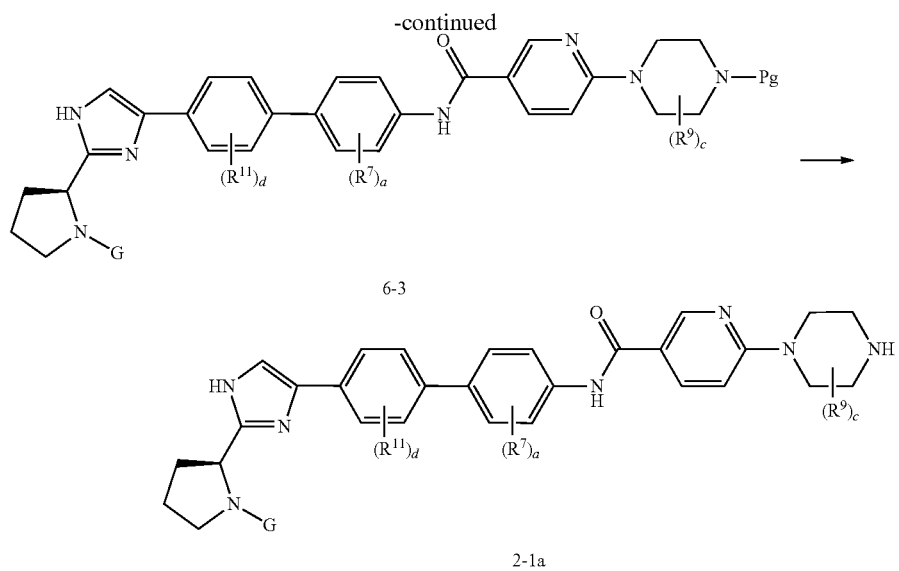

In a first step, biphenyl aniline 1-1 is reacted with a fluoropyridine carbonyl chloride 6-1 in the presence of base to provide fluoro intermediate 6-2, which is reacted with an excess of protected piperidine 5-2 to provide protected intermediate 6-3. The reaction typically is performed in the presence of base with heating to a temperature of about 80° C. to about 120° C. for a period of about 4 to about 48 hours. Finally, intermediate 6-3 is deprotected, for example, by treatment with hydrochloric acid in an organic solvent to provide intermediate 2-1a as the HCl salt.

Yet another alternative process for the preparation of intermediate 2-1a utilizes a Suzuki coupling reaction of the boronate reagent 3-2 with intermediate 7-1, followed by a deprotection step, under conditions described above, as shown in Scheme 7.

Scheme 7

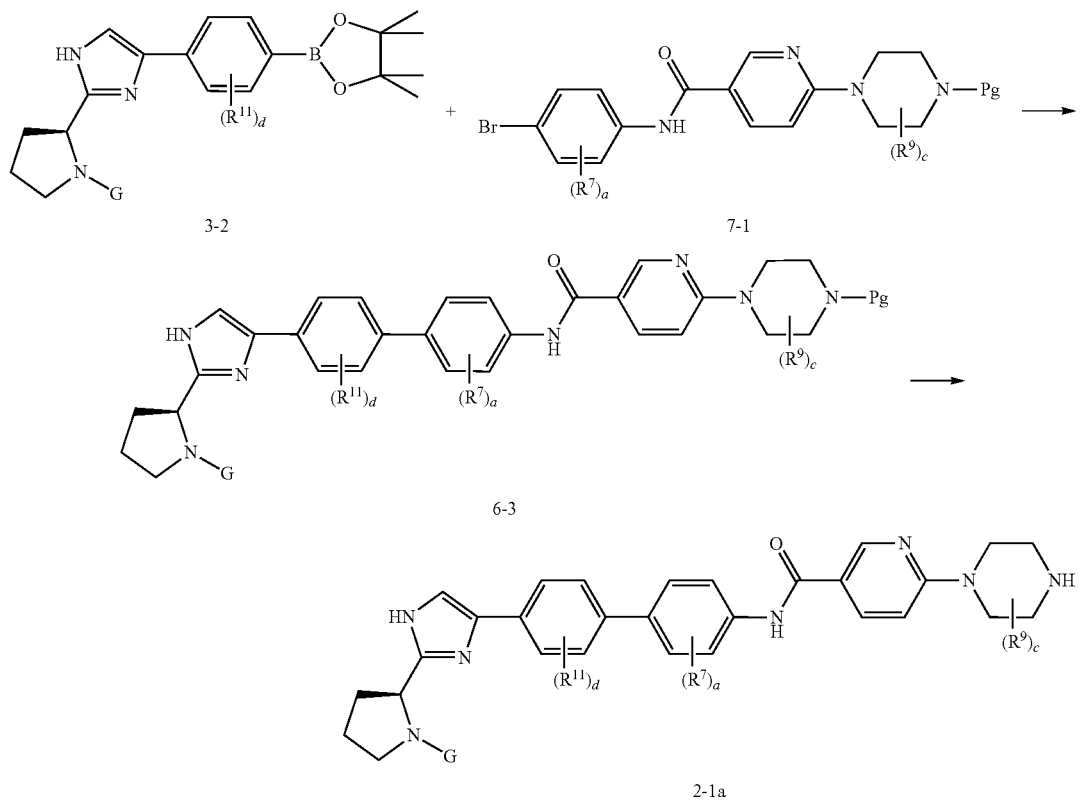

If protected intermediate 7-1 were replaced by an intermediate 7-1' bearing the substituent $R^4$

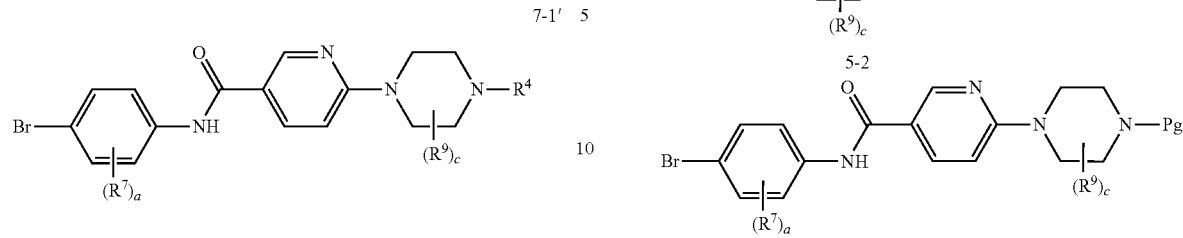

7-1' then the Suzuki coupling of the boronate 3-2 in the first step of Scheme 7 would directly provide a final compound of the invention.

In the Suzuki coupling reaction of Scheme 7, alternatively, the opposite coupling partner could bear the boronate moiety, as shown in Scheme 3.

The bromo intermediate 7-1 may be prepared, for example, by amide coupling of arylamine 8-1 with a fluoropyridine carbonyl chloride 6-1, followed by reaction with a protected piperazine 5-2 as shown in Scheme 8.

Scheme 8

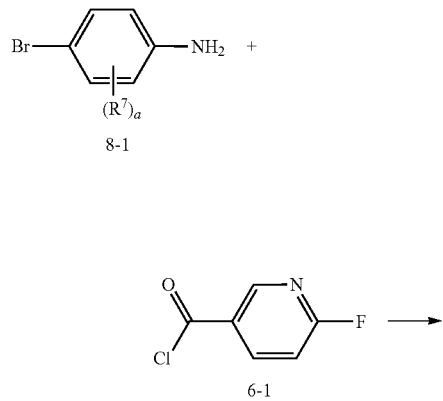

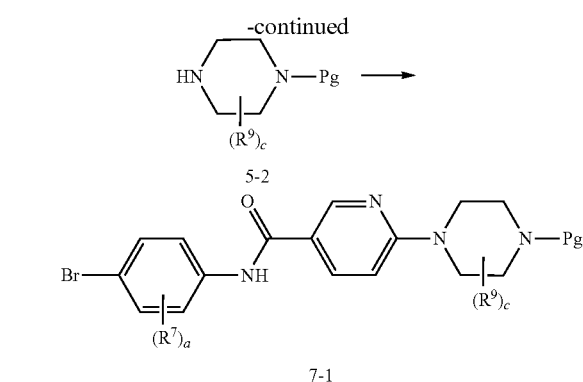

Alternatively, intermediate 7-1 may be prepared by the reaction of 8-1 with the carboxylic acid intermediate 1-2" as given in Scheme 9.

Scheme 9

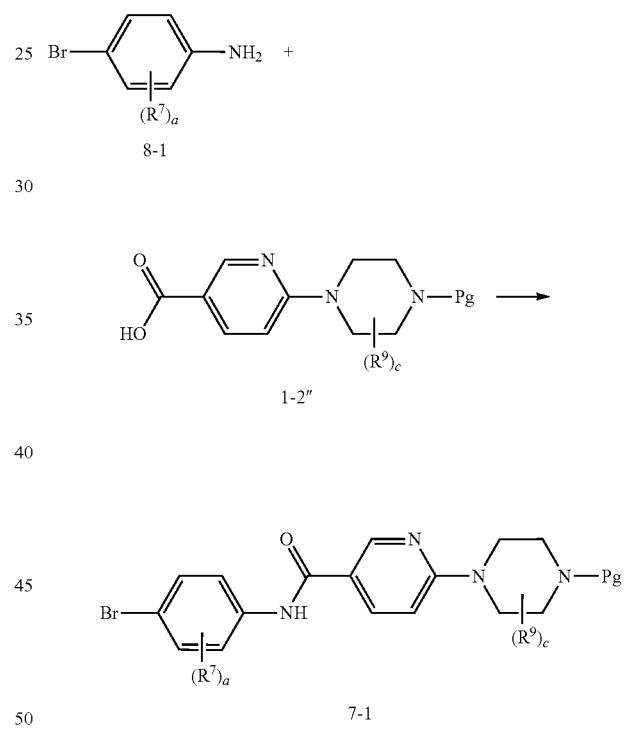

Intermediates 3-1 and 3-2 used in the Suzuki reaction of Scheme 3 may be prepared, for example, as shown in Schemes 10 and 11.

Scheme 10

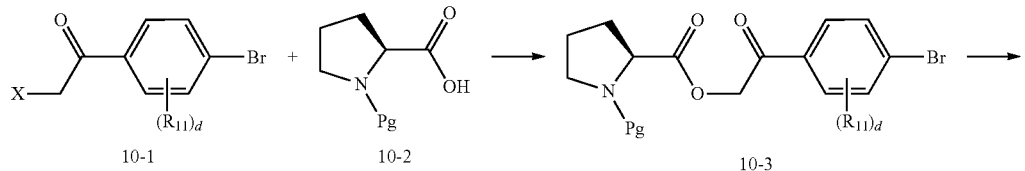

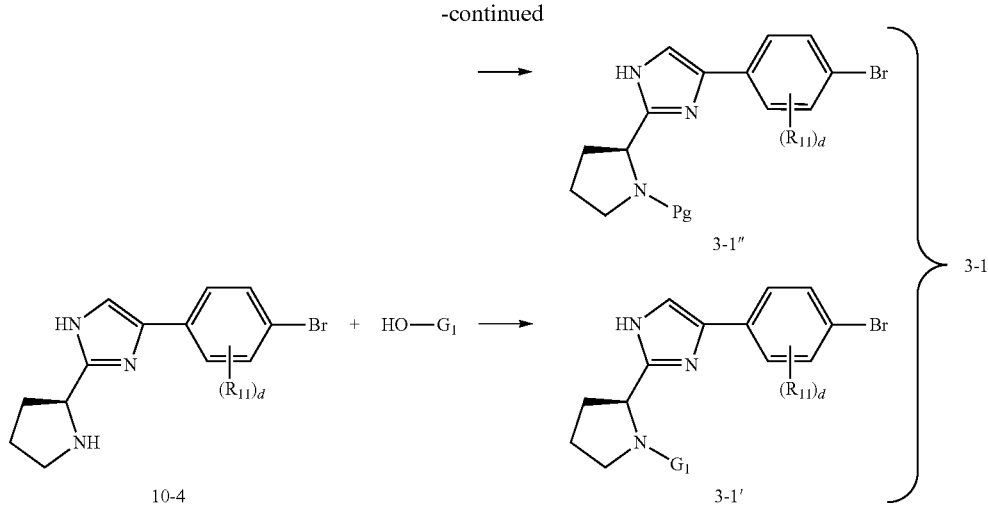

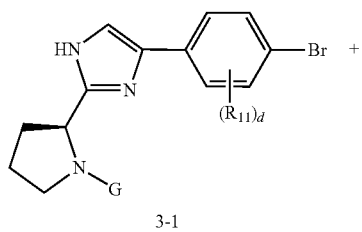

Reagent 10-1, where X represents bromo or chloro is reacted with a protected proline carboxylic acid 10-2 to provide intermediate 10-3 which is converted to intermediate 3-1″, where the variable G represents a protecting group, in the presence of an excess of ammonium acetate. The ring closure reaction typically is performed at a temperature between about 100° C. and about 120° C. for a period of about 4 to about 24 hours. To provide compound 3-1′ where the variable G represents $G_1$, intermediate 3-1″ is typically deprotected to provide intermediate 10-4, which is then coupled with a reagent HO-$G_1$ to provide compound 3-1′.

Finally, to provide boronate intermediate 3-2, intermediate 3-1 is reacted with 11-1 in the presence of a palladium catalyst as shown in Scheme 11.

Scheme 11

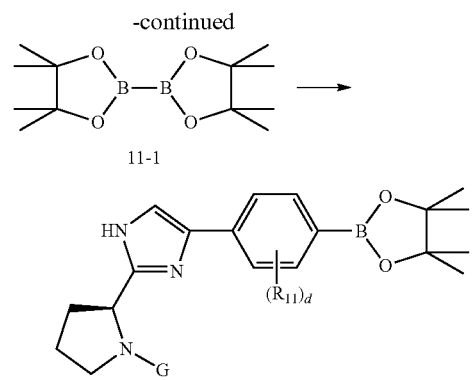

For the preparation of intermediate 2-1a in Scheme 7, boronate intermediate 3-2 may be prepared in situ according to the process of Scheme 11 and then reacted with intermediate 7-1 to provide intermediate 6-3 in a single pot process.

Compounds of Formula 12-3 in which the variable $A_m$ is defined as —C(O)NH— are prepared by processes analogous to those described above. One exemplary process for the preparation of compounds of Formula 12-3 is shown in Scheme 12.

Scheme 12

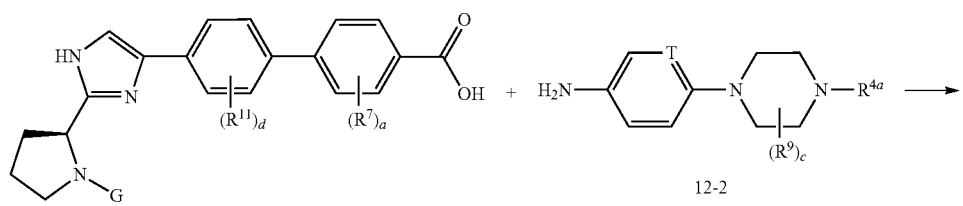

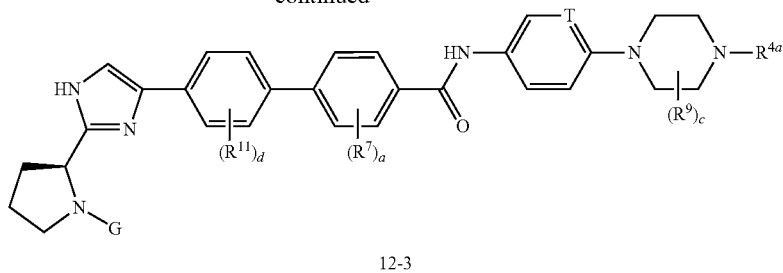

12-3

The acid 12-1 and aniline or aminopyridine 12-2 are reacted under amide bond formation conditions. As above, when the variable $R^{4a}$ represents $R^4$ and the variable G represents $G_1$, then the reaction of Scheme 12 directly provides final compounds of formula (I).

Alternatively, when $R^{4a}$ represents $R^4$ and G represents protecting group Pg, for example Boc, the reaction provides a protected intermediate of formula 12-3 which is then deprotected and reacted with a reagent X-$G_1$, where X is a halogen leaving group, or with a carboxylic acid of formula HO-$G_1$, to provide the desired product.

In yet another alternative route, a compound of formula 12-3 in which G is defined as $G_1$ and $R^{4a}$ is a protecting group Pg, provides a useful intermediate, which is deprotected and reacted, for example, with an acid chloride, carboxylic acid, or isocyanate, as in Scheme 2 to provide final compounds of formula (I).

The intermediates of Scheme 12 may be prepared by conventional synthetic reactions. For example, the biaryl acid intermediate 12-1 may be prepared by the Suzuki coupling reaction of Scheme 13

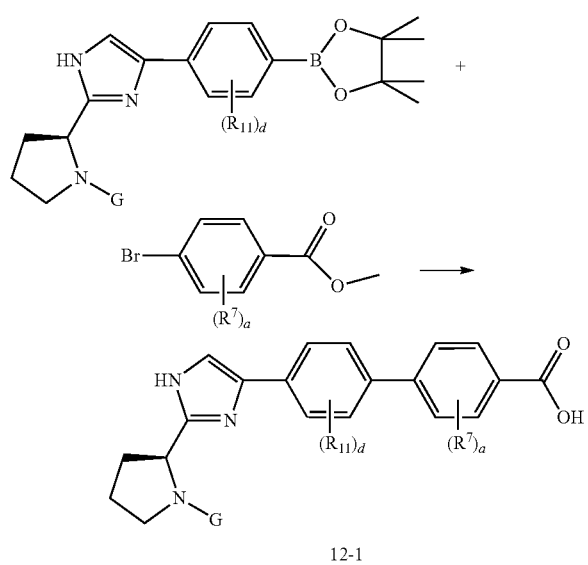

Scheme 13

12-1

A useful process for the preparation of the aminopyridine intermediate 12-2 of Scheme 12 utilizes a nitro substituted-chloropyridine or chlorophenyl 14-1 which is reacted with a protected piperazine 5-2 to provide a protected intermediate 14-2 as shown in Scheme 14.

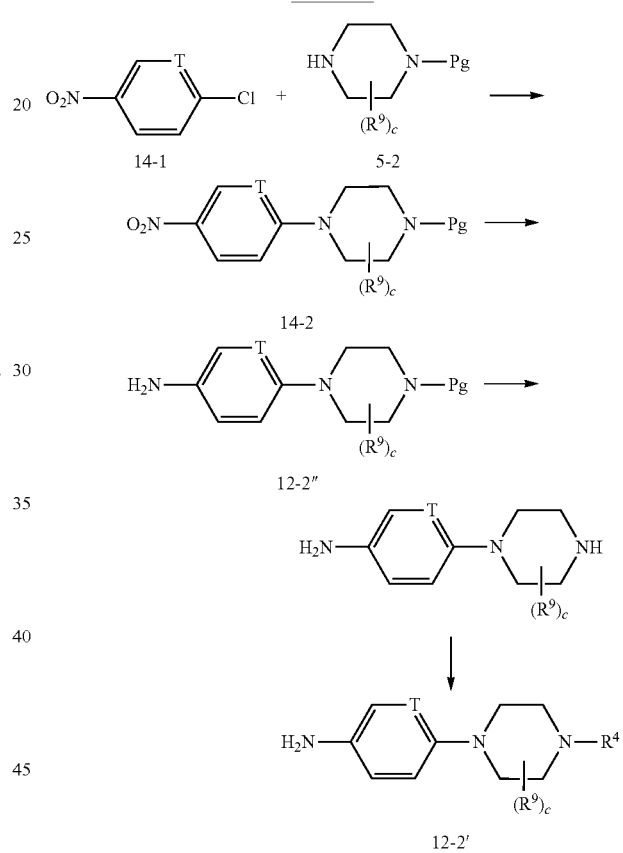

Scheme 14

Reduction of the nitro group to the amine provides intermediate 12-2″ where $R^{4a}$ represents a protecting group. Deprotection of compound 12-2″ and reaction, for example, with an acid chloride, carboxylic acid, or isocyanate, as in schemes above provides intermediate 12-2′, in which $R^{4a}$ represents $R^4$.

It will be understood by those of skill in the art, that other compounds of the invention having heterocyclic rings in place of the phenyl rings of the structures in the above schemes may be prepared by similar methods starting with appropriate starting materials. Details regarding specific reaction conditions and other procedures for preparing representative compounds of the invention or intermediates thereto are described in the examples below.

It will further be understood, this disclosure encompasses compounds of formula (I) when prepared by synthetic processes such as those described above and below or by metabolic processes including those occurring in vivo in human or animal body or in vitro.

Pharmaceutical Compositions

The compounds of the invention and pharmaceutically-acceptable salts thereof are typically used in the form of a pharmaceutical composition or formulation. Such pharmaceutical compositions may be administered to a patient by any acceptable route of administration including, but not limited to, oral, rectal, vaginal, nasal, inhaled, topical (including transdermal) and parenteral modes of administration.

Accordingly, in one of its compositions aspects, the invention is directed to a pharmaceutical composition comprising a pharmaceutically-acceptable carrier or excipient and a compound of formula (I), where, as defined above, "compound of formula (I)" means a compound of formula (I) or a pharmaceutically-acceptable salt thereof. Optionally, such pharmaceutical compositions may contain other therapeutic and/or formulating agents if desired. When discussing compositions and uses thereof, the "compound of the invention" may also be referred to herein as the "active agent". As used herein, the term "compound of the invention" is intended to include all compounds encompassed by formula (I) as well as the species embodied in formulas (II), (III), (IV), and (V), and pharmaceutically-acceptable salts thereof.

The pharmaceutical compositions of the invention typically contain a therapeutically effective amount of a compound of the present invention. Those skilled in the art will recognize, however, that a pharmaceutical composition may contain more than a therapeutically effective amount, i.e., bulk compositions, or less than a therapeutically effective amount, i.e., individual unit doses designed for multiple administration to achieve a therapeutically effective amount.

Typically, such pharmaceutical compositions will contain from about 0.1 to about 95% by weight of the active agent; preferably, from about 5 to about 70% by weight; and more preferably from about 10 to about 60% by weight of the active agent.

Any conventional carrier or excipient may be used in the pharmaceutical compositions of the invention. The choice of a particular carrier or excipient, or combinations of carriers or excipients, will depend on the mode of administration being used to treat a particular patient or type of medical condition or disease state. In this regard, the preparation of a suitable pharmaceutical composition for a particular mode of administration is well within the scope of those skilled in the pharmaceutical arts. Additionally, the carriers or excipients used in the pharmaceutical compositions of this invention are commercially-available. By way of further illustration, conventional formulation techniques are described in Remington: The Science and Practice of Pharmacy, 20th Edition, Lippincott Williams & White, Baltimore, Md. (2000); and H. C. Ansel et al., Pharmaceutical Dosage Forms and Drug Delivery Systems, 7th Edition, Lippincott Williams & White, Baltimore, Md. (1999).

Representative examples of materials which can serve as pharmaceutically acceptable carriers include, but are not limited to, the following: sugars, such as lactose, glucose and sucrose; starches, such as corn starch and potato starch; cellulose, such as microcrystalline cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical compositions.

Pharmaceutical compositions are typically prepared by thoroughly and intimately mixing or blending the active agent with a pharmaceutically-acceptable carrier and one or more optional ingredients. The resulting uniformly blended mixture can then be shaped or loaded into tablets, capsules, pills and the like using conventional procedures and equipment.

The pharmaceutical compositions of the invention are preferably packaged in a unit dosage form. The term "unit dosage form" refers to a physically discrete unit suitable for dosing a patient, i.e., each unit containing a predetermined quantity of active agent calculated to produce the desired therapeutic effect either alone or in combination with one or more additional units. For example, such unit dosage forms may be capsules, tablets, pills, and the like, or unit packages suitable for parenteral administration.

In one embodiment, the pharmaceutical compositions of the invention are suitable for oral administration. Suitable pharmaceutical compositions for oral administration may be in the form of capsules, tablets, pills, lozenges, cachets, dragees, powders, granules; or as a solution or a suspension in an aqueous or non-aqueous liquid; or as an oil-in-water or water-in-oil liquid emulsion; or as an elixir or syrup; and the like; each containing a predetermined amount of a compound of the present invention as an active ingredient.

When intended for oral administration in a solid dosage form (i.e., as capsules, tablets, pills and the like), the pharmaceutical compositions of the invention will typically comprise the active agent and one or more pharmaceutically-acceptable carriers, such as sodium citrate or dicalcium phosphate. Optionally or alternatively, such solid dosage forms may also comprise: fillers or extenders, such as starches, microcrystalline cellulose, lactose, sucrose, glucose, mannitol, and/or silicic acid; binders, such as carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and/or sodium carbonate; solution retarding agents, such as paraffin; absorption accelerators, such as quaternary ammonium compounds; wetting agents, such as cetyl alcohol and/or glycerol monostearate; absorbents, such as kaolin and/or bentonite clay; lubricants, such as talc, calcium stearate, magnesium stearate, solid polyethylene glycols, sodium lauryl sulfate, and/or mixtures thereof; coloring agents; and buffering agents.

Release agents, wetting agents, coating agents, sweetening, flavoring and perfuming agents, preservatives and antioxidants can also be present in the pharmaceutical compositions of the invention. Examples of pharmaceutically-acceptable antioxidants include: water-soluble antioxidants, such as ascorbic acid, cysteine hydrochloride, sodium bisulfate, sodium metabisulfate, sodium sulfite and the like; oil-soluble antioxidants, such as ascorbyl palmitate, butylated hydroxyanisole, butylated hydroxytoluene, lecithin, propyl gallate, alpha-tocopherol, and the like; and metal-chelating agents, such as citric acid, ethylenediamine tetraacetic acid, sorbitol, tartaric acid, phosphoric acid, and the like. Coating agents for tablets, capsules, pills and like, include those used for enteric coatings, such as cellulose acetate phthalate, polyvinyl acetate phthalate, hydroxypropyl methylcellulose phthalate, methacrylic acidmethacrylic acid ester copolymers, cellulose acetate trimellitate, carboxymethyl ethyl cellulose, hydroxypropyl methyl cellulose acetate succinate, and the like.

Pharmaceutical compositions of the invention may also be formulated to provide slow or controlled release of the active agent using, by way of example, hydroxypropyl methyl cellulose in varying proportions; or other polymer matrices, liposomes and/or microspheres. In addition, the pharmaceutical compositions of the invention may optionally contain opacifying agents and may be formulated so that they release the active ingredient only, or preferentially, in a certain portion of the gastrointestinal tract, optionally, in a delayed manner. Examples of embedding compositions which can be used include polymeric substances and waxes. The active agent can also be in micro-encapsulated form, if appropriate, with one or more of the above-described excipients.

Suitable liquid dosage forms for oral administration include, by way of illustration, pharmaceutically-acceptable emulsions, microemulsions, solutions, suspensions, syrups and elixirs. Liquid dosage forms typically comprise the active agent and an inert diluent, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (esp., cottonseed, groundnut, corn, germ, olive, castor and sesame oils), glycerol, tetrahydrofuryl alcohol, polyethylene glycols and fatty acid esters of sorbitan, and mixtures thereof. Suspensions, in addition to the active ingredient, may contain suspending agents such as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

The compounds of this invention can also be administered parenterally (e.g. by intravenous, subcutaneous, intramuscular or intraperitoneal injection). For parenteral administration, the active agent is typically admixed with a suitable vehicle for parenteral administration including, by way of example, sterile aqueous solutions, saline, low molecular weight alcohols such as propylene glycol, polyethylene glycol, vegetable oils, gelatin, fatty acid esters such as ethyl oleate, and the like. Parenteral formulations may also contain one or more anti-oxidants, solubilizers, stabilizers, preservatives, wetting agents, emulsifiers, buffering agents, or dispersing agents. These formulations may be rendered sterile by use of a sterile injectable medium, a sterilizing agent, filtration, irradiation, or heat.

Alternatively, the pharmaceutical compositions of the invention are formulated for administration by inhalation. Suitable pharmaceutical compositions for administration by inhalation will typically be in the form of an aerosol or a powder. Such compositions are generally administered using well-known delivery devices, such as a metered-dose inhaler, a dry powder inhaler, a nebulizer or a similar delivery device.

When administered by inhalation using a pressurized container, the pharmaceutical compositions of the invention will typically comprise the active ingredient and a suitable propellant, such as dichlorodifluoromethane, trichlorofluoromethane, dichlorotetrafluoroethane, carbon dioxide or other suitable gas. Additionally, the pharmaceutical composition may be in the form of a capsule or cartridge (made, for example, from gelatin) comprising a compound of the invention and a powder suitable for use in a powder inhaler. Suitable powder bases include, by way of example, lactose or starch.

The compounds of the invention can also be administered transdermally using known transdermal delivery systems and excipients. For example, the active agent can be admixed with permeation enhancers, such as propylene glycol, polyethylene glycol monolaurate, azacycloalkan-2-ones and the like, and incorporated into a patch or similar delivery system. Additional excipients including gelling agents, emulsifiers and buffers, may be used in such transdermal compositions if desired.

Utility

The compounds of the invention have been shown to inhibit viral replication in HCV replicon assays and therefore are expected to be useful for the treatment of hepatitis C viral infections.

In one aspect, therefore, the invention provides a method of inhibiting replication of the hepatitis C virus in a mammal (e.g., a human), the method comprising administering to the mammal a therapeutically-effective amount of a compound of the invention or of a pharmaceutical composition comprising a pharmaceutically-acceptable carrier and a compound of the invention.

The invention further provides a method of treating hepatitis C viral infections in a mammal (e.g., a human), the method comprising administering to the mammal a therapeutically-effective amount of compound of the invention or of a pharmaceutical composition comprising a pharmaceutically-acceptable carrier and a compound of the invention.

The compounds of the invention may inhibit viral replication by inhibiting the function of the NS5A protein encoded by the HCV genome. In one aspect, therefore, the invention provides a method of inhibiting the NS5A protein of HCV in a mammal, the method comprising administering to the mammal, a compound or a composition of the invention.

When used to treat HCV infections, the compounds of the invention will typically be administered orally in a single daily dose or in multiple doses per day, although other forms of administration may be used. The amount of active agent administered per dose or the total amount administered per day will typically be determined by a physician, in the light of the relevant circumstances, including the condition to be treated, the chosen route of administration, the actual compound administered and its relative activity, the age, weight, and response of the individual patient, the severity of the patient's symptoms, and the like.

Suitable doses for treating HCV infections will range from about 1 to about 2000 mg/day of active agent, including from about 5 to about 200 mg/day and from about 10 to about 130 mg per day of active agent for an average 70 kg human.

Combination Therapy

Compounds of the invention may also be used in combination with one or more agents which act by the same mechanism or by different mechanisms to effect treatment of HCV. Useful classes of agents for combination therapy include, but are not limited to, HCV NS3 protease inhibitors, HCV NS5B nucleoside and non-nucleoside polymerase inhibitors, helicase inhibitors, NS4B protein inhibitors, HCV viral entry inhibitors, cyclophyllin inhibitors, toll-like receptor agonists, inhibitors of heat shock proteins, interfering RNA, antisense RNA, HCV internal ribosome entry site (IRES) inhibitors, thiazolides, nucleoside analogs such as ribavirin and related compounds, interferons and other immunomodulatory agents, inosine 5'-monophosphate dehydrogenase (IMPDH) inhibitors, and other NS5A protein inhibitors. Agents which act to inhibit HCV replication by any other mechanism may also be used in combination with the present compounds.

HCV NS3 protease inhibitors which may be used in combination therapy include, but are not limited to, telaprevir (VX-950), boceprevir (SCH-503034), TMC-435, narlaprevir (SCH-900518), vaniprevir (MK-7009), danoprevir (ITMN- 191, R-7227), BI-201335, ABT-450, BMS-650032, GS-9256, ACH-1625, ACH-2684, BMS-605339, VX-985, PHX-1766, BMS-791325, and IDX-320.

Examples of HCV NS5B nucleoside polymerase inhibitors include, but are not limited to, RG7128, IDX-184, PSI-7977, PSI-7851, PSI-938, INX-189 (INX-08189), RG7348, MK-0608, TMC-649128, and HCV-796, while, non-nucleoside HCV NS5B polymerase inhibitors, include but are not limited to, filibuvir (PF-8685540), tegobuvir (GS-9190), VX-222, VX-759, ANA-598 (setrobuvir), ABT-072, ABT-333, BI-207127, BMS-791325, MK-3281, IDX-37, and BMS-824393.

A wide variety of interferons and pegylated interferons, including alpha, beta, omega, and gamma interferons, having antiviral, antiproliferative or immunomodulatory effects, can be combined with the present compounds. Representative examples include, but are not limited to, Intron® A (interferon-alpha2b), Actimmune® (interferon-gamma-1b), Alferon N, Advaferon®, Roferon-A (interferon alpha-2a) Pegln-tron® (peginterferon-alpha 2b), Alfaferone, Pegasys® (peginterferon alpha-2a), Alfanative (interferon alpha), Zalbin™ (albinterferon alpha-2b), Infergon® (interferon alfacon-1), Omega DUROS® (omega interferon), Locteron™ (interferon alpha), PEG-rIL-29 (pegylated interferon lambda), and Rebif® (interferon beta-1a).

Nucleoside analog antiviral agents include, but are not limited to, ribavirin (Copegus®, Rebetol®, Virazole®) and Viramidine (taribavirin). Interferons and ribavirin are also provided in in the form of kits which include, for example, but are not limited to, Rebetron® (interferon alpha-2b/ribavirin) and Pegetron® (Peginterferon alpha-2b/ribavirin)

Useful compounds acting by other mechanisms include, but are not limited to: cyclophilin inhibitors, such as DEB-025, SCY-635, NIM-811, and cyclosporine and derivatives; toll-like receptor agonists, such as resiquimod, IMO-2125, and ANA-773, HCV viral entry inhibitors, such as civacir, thiazolides, such as nitazoxanide, and broad-spectrum viral inhibitors, such as, inosine-5'-monophosphate dehydrogenase (IMPDH) inhibitors.

In addition, compounds of the invention may be combined with an NS5A inhibitor, for example, BMS-790052, AZD-7295, PPI-461, PPI-1301, GS-5885, or GSK2336805.

In another aspect, therefore, the invention provides a therapeutic combination for use in the treatment of hepatitis C viral infections, the combination comprising a compound of the invention and one or more other therapeutic agents useful for treating HCV. For example, the invention provides a combination comprising a compound of the invention and one or more agents selected from HCV NS3 protease inhibitors, HCV NS5B nucleoside and non-nucleoside polymerase inhibitors, interferons and pegylated interferons, and ribavirin and related nucleoside analogs. Also provided, therefore, is a pharmaceutical composition comprising a compound of the invention and one or more other therapeutic agents useful for treating HCV.

Further, in a method aspect, the invention provides a method of treating a hepatitis C viral infection in a mammal, the method comprising administering to the mammal a compound of the invention and one or more other therapeutic agents useful for treating HCV.

In another method aspect, the invention provides a method of inhibiting replication of the hepatitis C virus in a mammal, the method comprising administering to the mammal a compound of the invention and one or more other therapeutic agents useful for inhibiting replication of the hepatitis C virus.

For example, in one method aspect, the invention provides a method of treating a hepatitis C viral infection in a mammal, the method comprising administering to the mammal a compound of the invention, an interferon or pegylated interferon, and ribavirin.

In another exemplary method aspect, the invention provides a method of treating a hepatitis C viral infection in a mammal, the method comprising administering to the mammal a compound of the invention, an interferon or pegylated interferon, ribavirin, and an HCV NS3 protease inhibitor.

In still another method aspect, the invention provides a method of treating a hepatitis C viral infection in a mammal, the method comprising administering to the mammal a compound of the invention, ribavirin, and an HCV NS3 protease inhibitor.

Still other combination therapies, include, for example, a compound of the invention, an HCV NS3 protease inhibitor, an HCV NS5B nucleoside polymerase inhibitor, and an HCV NS5B non-nucleoside polymerase inhibitor; and a compound of the invention, an HCV NS5B nucleoside polymerase inhibitor, and an HCV NS5B non-nucleoside polymerase inhibitor.

In another method aspect, the invention provides a method of inhibiting replication of the hepatitis C virus in a mammal, using a compound of the invention in combination with other agents, as described above.

When used in combination therapy, the agents may be formulated in a single pharmaceutical composition, as disclosed above, or the agents may be provided in separate compositions that are administered simultaneously or at separate times, by the same or by different routes of administration. When administered separately, the agents are administered sufficiently close in time so as to provide a desired therapeutic effect.

Such compositions can be packaged separately or may be packaged together as a kit. The two or more therapeutic agents in the kit may be administered by the same route of administration or by different routes of administration.

Finally, the compounds of the invention may also find utility as research tools, for example, for discovering new HCV NS5A protein inhibitors or explicating mechanisms of HCV replication.

Compounds of the invention have been demonstrated to be potent inhibitors of HCV replication in HCV replicon assays, as described in the following examples.

EXAMPLES

The following synthetic and biological examples are offered to illustrate the invention, and are not to be construed in any way as limiting the scope of the invention. In the examples below, the following abbreviations have the following meanings unless otherwise indicated. Abbreviations not defined below have their generally accepted meanings.

ACN=acetonitrile
DCM=dichloromethane
DMA=N,N-dimethylacetamide
DMF=N,N-dimethylformamide
DMSO=dimethyl sulfoxide
EDC=N-(3-dimethylaminopropyl)-N-ethylcarbodiimide hydrochloride
EtOAc=ethyl acetate
h=hour(s)
HATU=N,N,N',N'-tetramethyl-O-(7-azabenzotriazol-1-yl)uronium hexafluorophosphate
HCTU=2-(6-chloro-1H-benzotriazole-1-yl)-1,1,3,3-tetramethylaminium hexafluorophosphate HOAt=1-hydroxy-7-azabenzotriazole
min=minute(s)
Pd(dppf)Cl$_2$=dichloro(1,1'-bis(diphenylphosphino)-ferrocene)dipalladium(II)
MTBE=methyl tert-butyl ether
RT=room temperature
TFA=trifluoroacetic acid
THF=tetrahydrofuran Reagents and solvents were purchased from commercial suppliers (Aldrich, Fluka, Sigma, etc.), and used without further purification. Reactions were run under nitrogen atmosphere, unless noted otherwise. Progress of reaction mixtures was monitored by thin layer chromatography (TLC), analytical high performance liquid chromatography (anal. HPLC), and mass spectrometry. Reaction mixtures were worked up as described specifically in each reaction; commonly they were purified by extraction and other purification methods such as temperature-, and solvent-dependent crystallization, and precipitation. In addition, reaction mixtures were routinely purified by preparative HPLC, typically using C18 or BDS column packings and conventional eluents. Typical preparative HPLC conditions are described below.

Characterization of reaction products was routinely carried out by mass and $^1$H-NMR spectrometry. For NMR analysis, samples were dissolved in deuterated solvent (such as CD$_3$OD, CDCl$_3$, or d$_6$-DMSO), and $^1$H-NMR spectra were acquired with a Varian Gemini 2000 instrument (400 MHz) under standard observation conditions. Mass spectrometric identification of compounds was performed by an electrospray ionization method (ESMS) with an Applied Biosystems (Foster City, Calif.) model API 150 EX instrument or an Agilent (Palo Alto, Calif.) model 1200 LC/MSD instrument.

General Preparative HPLC Conditions
Column: C18, 5 µm. 21.2×150 mm or C18, 5 µm 21×250 or C14 21×150
Column temperature: Room Temperature
Flow rate: 20.0 mL/min
Mobile Phases: A=Water+0.05% TFA
B=ACN+0.05% TFA,
Injection volume: (100-1500 µL)
Detector wavelength: 214 nm Crude compounds were dissolved in 1:1 water:acetic acid at about 50 mg/mL. A 4 minute analytical scale test run was carried out using a 2.1×50 mm C18 column followed by a 15 or 20 minute preparative scale run using 100 µL injection with the gradient based on the % B retention of the analytical scale test run. Exact gradients were sample dependent. Samples with close running impurities were checked with a 21×250 mm C18 column and/or a 21×150 mm C14 column for best separation. Fractions containing desired product were identified by mass spectrometric analysis.

Analytical HPLC Methods A, B, C
Column: Zorbax Bonus-RP 3.5 µm. 4.6×150 mm
Column temperature: 35° C.
Flow rate: 1.0 mL/min
Mobile Phases: A=Water/ACN (98:2)+0.1% TFA
B=Water/ACN (10:90)+0.1% TFA,
Injection volume: 100-1500 µL
Detector wavelength: 254 nm (Methods A and B) 214 nm (Method C)
Sample preparation: Dissolve in 1:1 ACN:water Gradient Method A
21 min total (time (min)/% B): 0.5/10, 15/60, 16.5/80, 17/80, 18/10, 21/10.

Gradient Method B
40 min total (time (min)/% B): 0.5/15, 28/40, 30/80, 33/80, 35/15, 40/15.

Gradient Method C
29 min total (time (min)/% B): 0.5/10, 24/90, 25/90, 26/10, 29/10

Preparation 1: 4-(4-bromo-phenyl)-2-(S)-pyrrolidin-2-yl-1H-imidazole

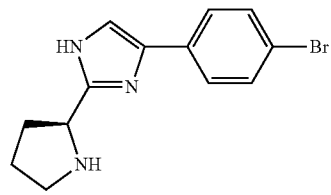 [SMILES: Brc1ccc(-c2c[nH]c([C@@H]3CCCN3)n2)cc1]

(a) 2-Bromo-1-(4-bromo-phenyl)-ethanone

Bromine (80 g, 500 mmol) was added dropwise to a solution of 1-(4-bromo-phenyl)-ethanone (100 g, 500 mmol) in dichloromethane (1500 mL) at ambient temperature. The reaction mixture was stirred for 3 h and then concentrated. The residue was washed with dichloromethane (100 mL) to give the crude title compound (120 g, 86% yield) as a white solid. $^1$H NMR (CDCl$_3$, 400 MHz) δ (ppm): 7.78 (d, J=8.4 Hz, 2H), 7.57 (d, J=8.4 Hz, 2H), 4.32 (s, 2H).

(b) (S)-pyrrolidine-1,2-dicarboxylic acid 2-[2-(4-bromo-phenyl)-2-oxo-ethyl]ester 1-tert-butyl ester Diisopropylethylamine (67 g, 518 mmol) was added dropwise to a solution of the product of the previous step (120 g, 432 mmol) and (S)-pyrrolidine-1,2-dicarboxylic acid 1-tert-butyl ester (L-Boc proline) (102 g, 475 mmol) in acetonitrile (2 L) at room temperature. The reaction mixture was stirred overnight and concentrated to dryness. The residue was dissolved in ethyl acetate (2 L) and washed with water (2 L). The organic layer was dried over sodium sulfate and concentrated to give crude title compound (178 g, 100% yield).

(c) (S)-2-[4-(4-bromo-phenyl)-1H-imidazol-2-yl]-pyrrolidine-1-carboxylic acid tert-butyl ester A solution of the product of the previous step (178 g, 432 mmol) and ammonium acetate (500 g, 6.5 mol) in toluene (2 L) was heated at reflux overnight. The solvent was removed and the residue was dissolved in ethyl acetate (2 L) and washed with water (2 L). The organic layer was dried over sodium sulfate and concentrated. The residue was purified by silica gel column chromatography in 1:3 petroleum ether: ethyl acetate to give the title compound (120 g, 71% yield) as a yellow solid. $^1$H NMR (CDCl$_3$, 400 MHz) δ (ppm): 7.56 (s, 1H), 7.39 (d, J=8.0 Hz, 2H), 7.24 (m, 1H), 7.14 (s, 1H), 4.88 (m, 1H), 3.33 (m, 2H), 2.94 (s, 1H), 2.07 (m, 2H), 1.88 (m, 1H), 1.42 (s, 9H).

(d) 4-(4-bromo-phenyl)-2-(S)-pyrrolidin-2-yl-1H-imidazole

To a solution of (S)-2-[4-(4-bromo-phenyl)-1H-imidazol-2-yl]-pyrrolidine-1-carboxylic acid tert-butyl ester (3 g, 7.6 mmol) in methanol (3 mL) was added 4N HCl in methanol (60 mL) at 0° C. The reaction mixture was stirred for 2 h and then concentrated to give crude hydrochloride salt of the title compound (2.51 g 100% yield) as a yellow solid.

Preparation 2:
(S)-2-Methoxycarbonylamino-3-methyl-butyric acid

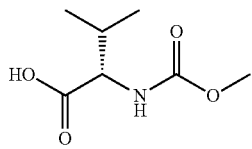

A mixture of (S)-2-amino-3-methyl-butyric acid (10 g, 85 mmol), NaOH (10.3 g, 255 mmol) in water (100 mL) was treated with methylchloridocarbonate (8 g, 85 mmol) at 0° C. The reaction mixture was stirred for 24 h at room temperature and then 5 N aqueous HCl was added to the reaction mixture to adjust pH to 4. The mixture was filtered through a pad of Celite to give the product (10 g, 67% yield) as a white solid. $^1$H NMR (CH$_3$OD, 400 MHz) δ (ppm) 4.05 (d, 1H), 3.65 (s, 3H), 2.14 (m, 1H), 0.95 (m, 6H).

Preparation 3: ((S)-1-{(S)-2-[4-(4-bromo-phenyl)-1H-imidazol-2-yl]-pyrrolidine-1-carbonyl}-2-methyl-propyl)-carbamic acid methyl ester

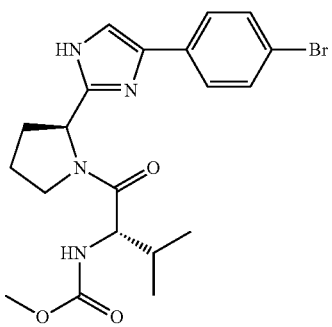 [SMILES: COC(=O)N[C@H](C(=O)N1CCC[C@H]1c1nc(-c2ccc(Br)cc2)c[nH]1)C(C)C]

Triethylamine (2.3 g, 11.4 mmol) was added to a solution of 4-(4-bromo-phenyl)-2-(S)-pyrrolidin-2-yl-1H-imidazole hydrochloride (2 g, 11.4 mol), (S)-2-methoxycarbonylamino-3-methyl-butyric acid (2.5 g, 7.6 mmol), and HATU (4.3 g, 11.4 mmol) in dimethylformamide (50 mL) at 0° C. under nitrogen. The reaction mixture was stirred at room temperature overnight and treated with ethyl acetate (100 mL) and water (1000 mL). The organic layer was washed with water (2×100 mL) and brine (100 mL), dried over anhydrous sodium sulfate and concentrated. The residue was purified by silica gel column chromatography in 1:1 petroleum ether: ethyl acetate to give the title compound (2.5 g 74% yield) as a yellow solid. $^1$H NMR (d$_6$-DMSO, 400 MHz) δ (ppm) 7.63 (d, J=8.8 Hz, 2H), 7.54 (m, 1H), 7.47 (m, 2H), 7.26 (d, J=8.4 Hz, 1H), 5.03 (m, 1H), 4.02 (t, J=8.4 Hz, 1H), 3.76 (m, 2H), 3.51 (s, 3H), 2.10 (m, 2H), 1.93 (m, 3H), 0.85 (d, J=6.8 Hz, 3H), 0.81 (d, J=6.8 Hz, 3H).

Preparation 4: ((S)-1-{(S)-2-[4-(4'-Amino-biphenyl-4-yl)-1H-imidazol-2-yl]-pyrrolidine-1-carbonyl}-2-methyl-propyl)-carbamic acid methyl ester

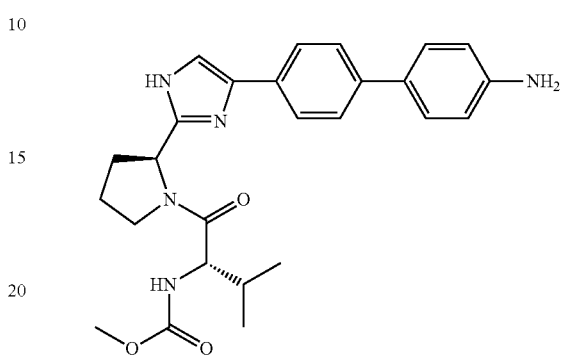

To a mixture of 4-(benzyloxycarbonylamino)phenylboronic acid (1.57 g, 5.79 mmol) and ((S)-1-{(S)-2-[4-(4-bromo-phenyl)-1H-imidazol-2-yl]-pyrrolidine-1-carbonyl}-2-methyl-propyl)-carbamic acid methyl ester (1.74 g, 3.86 mmol) in N,N-dimethylformamide (30 mL, 400 mmol) was added water (21.91 mL, 1216 mmol) and sodium bicarbonate (2.43 g, 28.96 mmol). The resulting mixture was purged with nitrogen. Tetrakis(triphenylphosphine)palladium(0) (468 mg, 0.41 mmol) was added. The reaction mixture was purged with nitrogen and then heated at 90° C. overnight. The reaction mixture was cooled to RT, diluted with methanol (10 mL), then filtered. The filtrate was concentrated and the crude product was purified by preparative HPLC to give a white solid. (1.28 g) The crude material was dissolved in methanol (40 mL) and then pumped through a continuous flow hydrogenator at 70° C. using a palladium hydroxide on carbon (20% w/w) cartridge. The resulting solution was concentrated to ~10 mL, treated with Stratospheres™ PL-CO3 resin and stirred at room temperature for 30 min. The reaction mixture was filtered and the filtrate was concentrated to give the title compound (680 mg).

Preparation 5: ((S)-1-{(S)-2-[4-(4'-amino-biphenyl-4-yl)-1H-imidazol-2-yl]-pyrrolidine-1-carbonyl}-2-methyl-propyl)-carbamic acid methyl ester To a solution of ((S)-1-{(S)-2[4-(4-bromo-phenyl)-1H-imidazol-2-A-pyrrolidine-1-carbonyl}-2-methyl-propyl)-carbamic acid methyl ester (9.10 g, 20.34 mmol) in dioxane: water (3:1) (200 mL), was added 4-(4,4,5,5-tetramethyl-1,3,2-dioxaborolan-2-yl)aniline (4.9 g, 22.37 mmol), sodium carbonate (4.3 g, 40.68 mmol) and Pd(dppf)$_2$Cl$_2$ (0.83 g, 5%). The reaction mixture was warmed to reflux under nitrogen, stirred for 4 h, cooled to RT, filtered, and concentrated. The residue was extracted with ethyl acetate and water, dried with sodium sulfate and concentrated. The crude product was purified by silica gel chromatography eluting with 1:1 hexane: ethyl acetate, to provide the title compound (7 g, 75% yield) as a yellow solid. $^1$H NMR (CDCl$_3$, 400 MHz) δ (ppm) 7.62-7.55 (m, 1H), 7.50 (d, J=8.0 Hz, 2 H), 7.40 (m, 3H), 7.18 (s, 1H), 6.75 (d, J=8.4 Hz, 2H), 5.50 (d, J=9.2 Hz, 1H), 5.25-5.23 (m, 1H), 4.31 (t, J=2.4 Hz, 1H), 3.83-3.80 (m, 1H), 3.67 (s, 3H), 3.59-3.53 (m, 1H), 3.05-2.95 (m, 1H), 2.40-2.30

(m, 1H), 2.19-2.11 (m, 1H), 2.08-2.03 (m, 1H), 1.98-1.93 (m, 1H), 1.07-1.01 (m, 1H), 0.85 (d, J=6.8 Hz, 6 H).

Preparation 6:
4-(4-(tert-butoxycarbonyl)piperazin-1-yl)benzoic acid

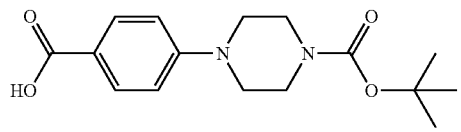

(a) 4-(4-Ethoxycarbonyl-phenyl)-piperazine-1-carboxylic acid tert-butyl ester A mixture of piperazine-1-carboxylic acid tert-butyl ester (18.6 g, 0.1 mol), 4-fluoro-benzoic acid ethyl ester (16.8 g, 1 mol) and potassium carbonate (0.15 mol) in dimethylsulfoxide (100 mL) was stirred at 120° C. for 24 h. The reaction mixture was cooled to room temperature and poured into water (1 L). The solid precipitate was filtered, washed with water, and concentrated to dryness to provide the title compound (20 g, 60% yield) as a white solid. $^1$H NMR (CDCl$_3$, 400 MHz) δ (ppm) 7.91 (d, 2H), 6.83 (d, 2H), 4.30 (q, 2H), 3.55 (m, 4H), 3.26 (m, 4H), 1.46 (s, 9H), 1.32 (t, 3H).

(b) 4-(4-(tert-butoxycarbonyl)piperazin-1-yl)benzoic acid

To a mixture of 4-(4-ethoxycarbonyl-phenyl)-piperazine-1-carboxylic acid tert-butyl ester (10 g, 29.9 mmol) in ethanol (200 mL was added 1 N sodium hydroxide (100 mL). The reaction mixture was stirred at 70° C. overnight. The solvent was removed under vacuum and the residue washed twice with ethyl acetate, acidified to pH 6 with 5 N HCl, filtered, and concentrated to dryness to provide the title compound (8 g, 87% yield) as a white solid. $^1$H NMR (d$_6$-DMSO, 400 MHz) δ (ppm) 7.74 (m, 2H), 6.92 (m, 2H), 3.90 (m, 2H), 3.42 (m, 2H), 3.25 (m, 4H), 1.38 (s, 9H).

Preparation 7:
4-(4-cyclopropanecarbonyl-piperazin-1-yl)-benzoic acid

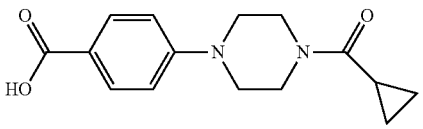 [SMILES: O=C(O)c1ccc(N2CCN(C(=O)C3CC3)CC2)cc1]

(a) 4-piperazin-1-yl-benzoic acid

A mixture of 4-(4-(tert-butoxycarbonyl)piperazin-1-yl) benzoic acid (28 g, 91 mmol) in hydrochloric acid in methanol (300 mL) was stirred at room temperature for 4 h. The resulting precipitate was collected by filtration and concentrated to dryness to provide the title compound (17 g, 61% yield) as a white solid.

(b) 4-(4-cyclopropanecarbonyl-piperazin-1-yl)-benzoic acid

To a mixture of 4-piperazin-1-yl-benzoic acid (20 g, 71.6 mmol) and triethylamine (58 g, 573 mmol) in dichloromethane (500 mL) was added cyclopropanecarbonyl chloride dropwise at 0° C. The reaction mixture was stirred at RT overnight. The solvent was removed by rotary evaporation. The residue was diluted with water, treated with sodium hydroxide, and washed with ethyl acetate and dichloromethane. The aqueous phase was acidified to pH 6 with 5 N HCl. The resulting precipitate was collected by filtration and concentrated to dryness to provide the title compound (10 g, 51% yield) as a white solid. $^1$H NMR(CH$_3$OD, 400 MHz) δ (ppm) 7.87 (m, 2H), 6.95 (m, 2H), 3.90 (s, 2H), 3.73 (s, 2H), 3.29 (m, 4H), 1.99 (m, 1H), 0.86 (m, 4H).

Preparation 8: [(S)-2-Methyl-1-((S)-2-{4-[4'-(4-piperazin-1-yl-benzoylamino)-biphenyl-4-yl]-1H-imidazol-2-yl}-pyrrolidine-1-carbonyl)-propyl]-carbamic acid methyl ester

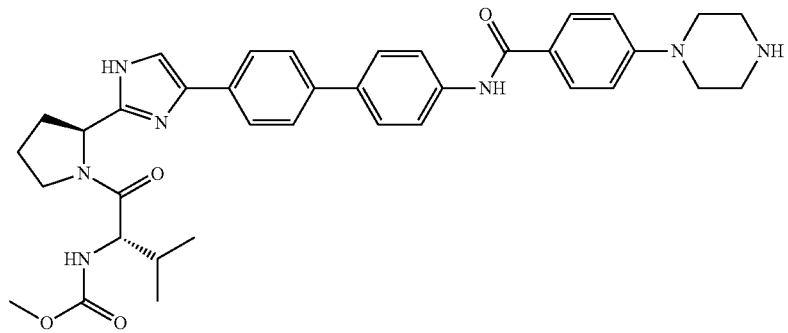 [SMILES: COC(=O)N[C@H](C(=O)N1CCC[C@H]1c1nc(-c2ccc(-c3ccc(NC(=O)c4ccc(N5CCNCC5)cc4)cc3)cc2)c[nH]1)C(C)C]

To a solution of 4-(4-(tert-butoxycarbonyl)piperazin-1-yl) benzoic acid (365 mg, 1.19 mmol) in dichloromethane (18 mL, 280 mmol) and N,N-dimethylformamide (92.3 uL, 1.19 mmol) was added oxalyl chloride (101 uL, 1.19 mmol). The reaction mixture was stirred for 20 min at room temperature and then N,N-diisopropylethylamine (1.42 mL, 8.14 mmol) was added followed by ((S)-1-{(S)-2-[4-(4'-amino-biphenyl-4-yl)-1H-imidazol-2-yl]-pyrrolidine-1-carbonyl}-2-methyl-propyl)-carbamic acid methyl ester (500.0 mg, 1.083 mmol) and the mixture was allowed to react overnight with stirring.

A second solution of 4-(4-(tert-butoxycarbonyl)piperazin-1-yl)benzoic acid (365 mg, 1.19 mmol) and oxalyl chloride (101 uL, 1.19 mmol) in dichloromethane (18 mL, 280 mmol) and N,N-dimethylformamide (92.3 uL, 1.19 mmol) was prepared and added to the reaction mixture which was stirred for 1 h. Methanol (10 mL) was added. The mixture was concentrated under vacuum and then dissolved in DCM (25 mL) and washed with saturated aqueous sodium bicarbonate (10 mL). The organic layer was concentrated, dissolved in 2.0 M hydrogen chloride in 1,4-dioxane (16.2 mL, 16.2 mmol) and ethanol (1.0 mL, 0.17 mmol) and stirred at room temperature overnight. The reaction mixture was dissolved in 1:1 acetic acid:water (8.0 mL), and purified by preparative HPLC using a BDS column to provide the trifluoroacetic acid salt of the title compound. $^1$H NMR (d$_6$-DMSO, 400 MHz) δ (ppm) 10.11 (s, 1H), 8.99-8.77 (m, 2H), 7.92 (dd, J=15.0, 8.9 Hz, 4H), 7.84 (m, 4H), 7.76 (t, J=9.3 Hz, 2H), 7.37-7.25 (m, 2H), 7.09 (d, J=9.1 Hz, 2H), 7.02 (d, J=8.9 Hz, 1H), 6.96 (d, J=9.1 Hz, 1H), 5.12 (t, J=7.1 Hz, 1H), 4.15-4.06 (m, 1H), 3.90-3.81 (m, 1H), 3.66-3.56 (m, 1H), 3.55-3.46 (m, 6H), 3.46-3.39 (m, 2H), 3.39-3.29 (m, 2H), 2.43-2.32 (m, 1H), 2.22-1.91 (m, 4H), 0.82 (d, J=6.7 Hz, 3H), 0.77 (d, J=6.6 Hz, 3H).

The TFA salt was dissolved in methanol (10 mL) and treated with Stratospheres™ PL-CO3 resin and stirred at room temperature for 30 min. The reaction mixture was filtered and the filtrate was concentrated to provide the title compound (0.354 g).

Preparation 9: [(S)-2-Methyl-1-((S)-2-{4-[4-(4,4,5,5-tetramethyl-[1,3,2]dioxaborolan-2-yl)-phenyl]-1H-imidazol-2-yl}-pyrrolidine-1-carbonyl)-propyl]-carbamic acid methyl ester

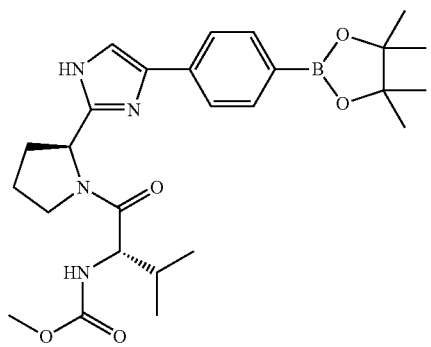

To a solution of ((S)-1-{(S)-2-[4-(4-bromo-phenyl)-1H-imidazol-2-yl]-pyrrolidine-1-carbonyl}-2-methyl-propyl)-carbamic acid methyl ester (50 g, 0.11 mol), 4,4,5,5,4',4',5',5'-octamethyl-[2,2']bi[[1,3,2]dioxaborolanyl] (57 g, 0.22 mol) and potassium acetate (108 g, 1.1 mol) in dioxane (1000 mL) was added Pd(dppf)Cl$_2$·CH$_2$Cl$_2$ (4.5 g, 5.5 mmol) under nitrogen. The reaction mixture was stirred at 85° C. overnight and then ethyl acetate (100 mL) and water (1000 mL) were added. The organic layer was washed with water (2×1000 mL) and brine (1000 mL), dried over anhydrous Na$_2$SO$_4$ and concentrated. The residue was purified by silica gel column chromatography (1:1 petroleum ether:ethyl acetate) to give the title compound (22.5 g) as a yellow solid. $^1$H NMR (CDCl$_3$, 400 MHz) δ (ppm) 7.71 (m, 3H), 7.32 (m, 1H), 7.19 (m, 1H), 5.56 (m, 1H), 5.18 (m, 1H), 4.23 (m, 1H), 3.73 (m, 1H), 3.61 (s, 3H), 3.55 (m, 1H), 2.95 (m, 1H), 2.38 (s, 1H), 2.13 (m, 1H), 2.02 (m, 1H), 1.89 (m, 2H), 1.22 (s, 12H), 0.79 (d, 6H).

Preparation 10: ((S)-1-{(S)-2-[4-(4'-Amino-2'-fluoro-biphenyl-4-yl)-1H-imidazol-2-yl]-pyrrolidine-1-carbonyl}-2-methyl-propyl)-carbamic acid methyl ester

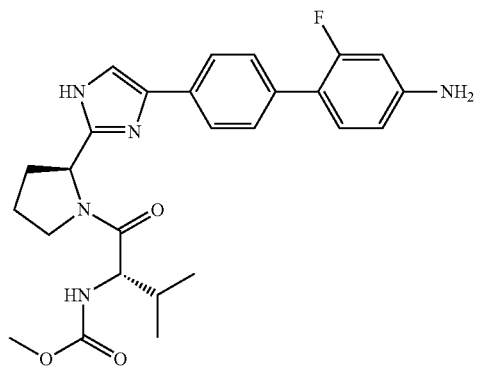 [SMILES: COC(=O)N[C@H](C(=O)N1CCC[C@H]1c1nc(-c2ccc(-c3ccc(N)cc3F)cc2)c[nH]1)C(C)C]

[(S)-2-Methyl-1-((S)-2-{4-[4-(4,4,5,5-tetramethyl-[1,3,2] dioxaborolan-2-yl)-phenyl]-1H-imidazol-2-yl}-pyrrolidine-1-carbonyl)-propyl]-carbamic acid methyl ester (60 mg, 0.12 mmol) and 4-bromo-3-fluoroaniline (23 mg, 0.12 mmol) were dissolved in 1,2-dimethoxyethane (1.2 mL, 12 mmol) and water (0.44 mL, 24 mmol). The reaction mixture was purged with nitrogen. Sodium carbonate (41.6 mg, 0.39 mmol) was added, followed by tetrakis(triphenylphosphine) palladium(0) (21 mg, 0.018 mmol) and the mixture was purged with nitrogen, sealed and heated at 85° C. overnight. The reaction mixture was cooled to room temperature, diluted with ethyl acetate (5 mL), and washed with water (5 mL). The organic layer was concentrated, dissolved in 1:1 acetic acid: water (8 mL) and purified by preparative HPLC to produce the TFA salt which was passed through StratoSpheres™ PL- CO3 resin (0.36 mmol) to provide the title compound (15 mg). (m/z): [M+H]+ calcd for $C_{26}H_{30}FN_5O_3$ 480.23 found 480.4.

Preparation 11: 4'-{2-[(S)-1-((S)-2-Methoxycarbonylamino-3-methyl-butyryl)-pyrrolidin-2-yl]-1H-imidazol-4-yl}-biphenyl-4-carboxylic acid

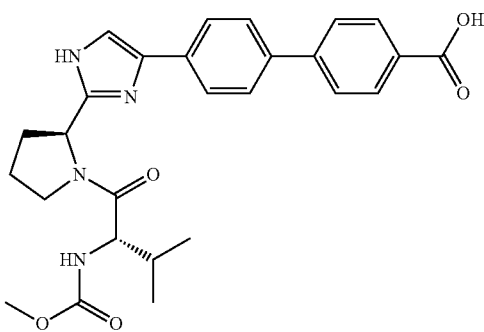 [SMILES: COC(=O)N[C@H](C(=O)N1CCC[C@H]1c1nc(-c2ccc(-c3ccc(C(=O)O)cc3)cc2)c[nH]1)C(C)C]

To a mixture of [(S)-2-methyl-1-((S)-2-{4-[4-(4,4,5,5-tetramethyl-[1,3,2]dioxaborolan-2-yl)-phenyl]-1H-imidazol-2-yl}-pyrrolidine-1-carbonyl)-propyl]-carbamic acid methyl ester (1.05 g, 2.12 mmol) and 4-iodo-benzoic acid methyl ester (665 mg, 2.54 mmol) in N,N-dimethylformamide (9.0 mL, 120 mmol) at RT was added water (2.0 mL, 110 mmol) and sodium bicarbonate (711 mg, 8.46 mmol). The reaction mixture was flushed with nitrogen, and tetrakis(triphenylphosphine)palladium(0) (122 mg, 0.106 mmol) was added under nitrogen. The reaction mixture was flushed with nitrogen and then heated at 90° C. overnight under an atmosphere of nitrogen.

The reaction mixture was cooled to RT and partitioned between EtOAc (60.0 mL) and water (20.0 mL). The organic layer was washed with water (2×20.0 mL), dried over sodium sulfate, filtered and concentrated to give a black oil, which was purified by silica gel chromatography (24 g silica gel, 0-100% EtOAc:hexanes). Desired fractions were combined and concentrated to give a yellowish oil and further dried under vacuum to give a yellowish foam. (956.9 mg).

The product from the previous step was combined with the corresponding product of a previous run (total 1.13 g), dissolved in methanol (10.0 mL) and water (2.1 mL) and treated with lithium hydroxide monohydrate (564.5 mg) at 60° C. for 3 h. The reaction mixture was concentrated and the residue was treated with 1:1 acetic acid:water (8.0 mL), and sonicated. Additional TFA (3.0 mL) was and the reaction mixture was sonicated, resulting in a greyish solid precipitate. The reaction mixture was stirred at RT for 10 min and then filtered. The filtrate was extracted with EtOAc (20.0 mL). The organic layer was dried over sodium sulfate, filtered and concentrated to give a yellowish oil which was dissolved in 1:1 acetic acid:water (6.0 mL), and purified by reverse phase preparative HPLC. Desired fractions were combined and freeze dried to give a white solid (107.6 mg). The solid from the filtration was taken up into EtOAc (60.0 mL) and washed with water (2×15.0 mL), aqueous saturated sodium bicarbonate (20.0 mL), and brine (15.0 mL), dried over sodium sulfate, filtered and concentrated to give the title compound as a yellowish solid (490 mg) (m/z): [M+H]+ calcd for $C_{27}H_{30}N_4O_5$ 491.22 found 491.6.

Preparation 12: N-(4-Bromo-phenyl)-4-(4-cyclopropanecarbonyl-piperazin-1-yl)-benzamide

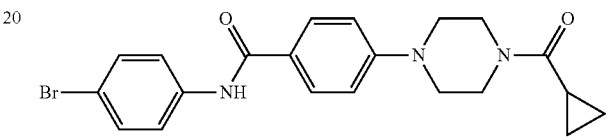

A solution of 4-(4-cyclopropanecarbonyl-piperazin-1-yl)-benzoic acid (1.0 g, 3.6 mmol) and N-(3-dimethylaminopropyl)-N-ethylcarbodiimide hydrochloride (0.70 g, 3.6 mmol) and 1-hydroxy-7-azabenzotriazole (0.50 g, 3.6 mmol) in dichloromethane (39 mL, 610 mmol) was stirred for 20 min at room temperature and then p-bromoaniline (0.52 g, 3.0 mmol) and N,N-diisopropylethylamine (2.6 mL, 15 mmol) were added and the reaction mixture was stirred for 2 days. The reaction mixture was filtered; the filtrate was dissolved in 1:1 acetic acid:water (8 mL). A precipitate formed. This material was filtered to provide the title product as the acetic acid salt (225 mg). (m/z): [M+H]+ calcd for $C_{21}H_{22}BrN_3O_2$ 428.09 found 428.0.

Preparation 13: 4-(4-Cyclopropanecarbonyl-piperazin-1-yl)-N-[4'-((S)-2-pyrrolidin-2-yl-1H-imidazol-4-yl)-biphenyl-4-yl]-benzamide

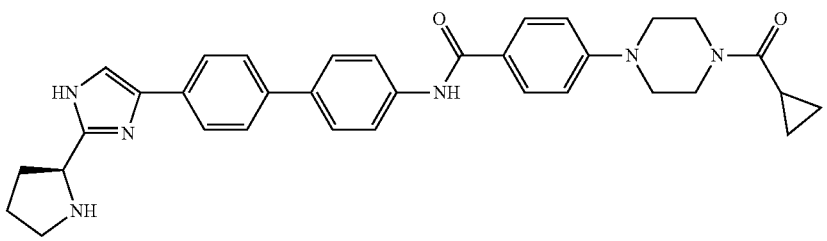 [SMILES: O=C(Nc1ccc(-c2ccc(-c3c[nH]c([C@@H]4CCCN4)n3)cc2)cc1)c1ccc(N2CCN(C(=O)C3CC3)CC2)cc1]

(a) (S)-2-(4-{4'-[4-(4-Cyclopropanecarbonyl-piperazin-1-yl)-benzoylamino]-biphenyl-4-yl}-1H-imidazol-2-yl)-pyrrolidine-1-carboxylic acid tert-butyl ester To a mixture of (S)-2-{4-[4-(4,4,5,5-tetramethyl-[1,3,2]dioxaborolan-2-yl)-phenyl]-1H-imidazol-2-yl}-pyrrolidine-1-carboxylic acid tert-butyl ester (1.40 g, 3.19 mmol) and N-(4-bromo-phenyl)-4-(4-cyclopropanecarbonyl-piperazin-1-yl)-benzamide (0.910 g, 2.12 mmol) in N,N-dimethylformamide (16.53 mL, 213.5 mmol) at RT was added sodium bicarbonate (1.338 g, 15.93 mmol). Water (12.06 mL, 669.2 mmol) was then added. Nitrogen was bubbled through the resulting mixture for 5 min and then tetrakis(triphenylphosphine)palladium(0) (0.258 g, 0.223 mmol) was added. The reaction mixture was heated at 90° C. under nitrogen overnight, cooled to RT, diluted with methanol (30.0 mL), and filtered. The filtrate was concentrated and dissolved in ethyl acetate (~3 mL) and hexanes (2 mL) was slowly added to give a precipitate of crude product. This material was filtered to provide 150 mg of the product. The filtrate was concentrated and subjected to the same precipitation conditions to provide an additional 50 mg of product. This material was combined with the first precipitation crop and was used without further purification in the next step.

(b) 4-(4-Cyclopropanecarbonyl-piperazin-1-yl)-N-[4'-((S)-2-pyrrolidin-2-yl1H-imidazol-4-yl)-biphenyl-4-yl]-benzamide The product of the previous step (200 mg, 0.3 mmol) was dissolved in 4 M HCl in 1,4-dioxane (0.6 mL, 2 mmol). The reaction mixture was stirred for 4 h, and concentrated under vacuum to provide the title compound as the HCl salt. (176 mg). (m/z): [M+H]$^+$ calcd for $C_{34}H_{36}N_6O_2$ 561.29 found 561.4.

Preparation 14: (R)-Diethylamino-phenyl-acetic acid

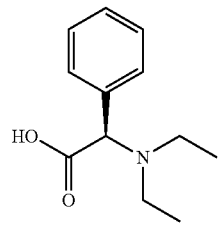

Sodium cyanoborohydride (15 g, 238 mmol) was added in portions over a few minutes to a cooled (ice/water) mixture of (R)-amino-phenyl-acetic acid (6.00 g, 39.7 mmol) and methanol (150 mL), and stirred for 5 min. Acetaldehyde (40 mL) was added drop-wise over 10 min. The reaction mixture was stirred at the cooled temperature for 45 min and at ambient temperature for 6.5 hr. The reaction mixture was again cooled to 0° C. Additional acetaldehyde (60 mL) was then added drop-wise over 10 min. The reaction mixture was stirred at 0° C. for 45 min and at ambient temperature overnight. The reaction mixture was cooled with an ice-water bath and treated with water (3 mL). Concentrated HCl was added dropwise over 45 min until the pH of the mixture was 1.5-2.0. The cooling bath was removed and stirring was continued while adding concentrated HCl to maintain the pH of the mixture ~1.5-2.0. The reaction mixture was stirred overnight, filtered, and the filtrate was concentrated under vacuum. The crude material was purified by preparative HPLC and washed with ethyl acetate to afford the title compound as a shiny white solid (5 g, 61% yield). $^1$H NMR (d$_6$-DMSO, 400 MHz) δ (ppm) 7.47 (m, 2H), 7.36 (m, 3H), 4.34 (s, 1H), 2.90 (m, 2H), 2.86 (m, 2H), 1.03 (t, 6H).

Preparation 15: {(S)-1-[(S)-2-(5-{4'-[(6-Fluoro-pyridine-3-carbonyl)-amino]-biphenyl-4-yl}-1H-imidazol-2-yl)-pyrrolidine-1-carbonyl]-2-methyl-propyl}-carbamic acid methyl ester

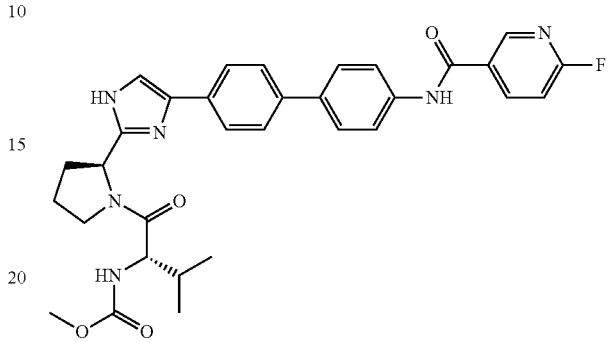

To a solution of ((S)-1-{(S)-2-[5-(4'-amino-biphenyl-4-yl)-1H-imidazol-2-yl]-pyrrolidine-1-carbonyl}-2-methyl-propyl)-carbamic acid methyl ester (2000 mg, 4 mmol) dissolved in dichloromethane (27.8 mL) and N,N-dimethylacetamide (2.82 mL, 30.3 mmol) was added a solution of 2-fluoropyridine-5-carbonyl chloride (691 mg, 4.33 mmol) dissolved in dichloromethane (6.0 mL) and the reaction mixture was stirred at room temperature for 30 min. The reaction mixture was concentrated, dissolved in a minimal amount of dichloromethane and ethyl ether was slowly added until a white precipitate formed. The mixture was sonicated and filtered to produce the HCl salt of the desired product. The solid was dissolved in ethyl acetate (20 mL), stirred at room temperature for 30 min, and filtered to produce the HCl salt of the title product as a free flowing yellow solid (2.5 g). (m/z): [M+H]$^+$ calcd for $C_{32}H_{33}FN_6O_4$ 585.26 found 585.5.

Preparation 16: ((S)-2-Methyl-1-{(S)-2-[4-(4'-{[6-((S)-2-methyl-piperazin-1-yl)-pyridine-3-carbonyl]-amino}-biphenyl-4-yl)-1H-imidazol-2-yl]-pyrrolidine-1-carbonyl}-propyl)-carbamic acid methyl ester

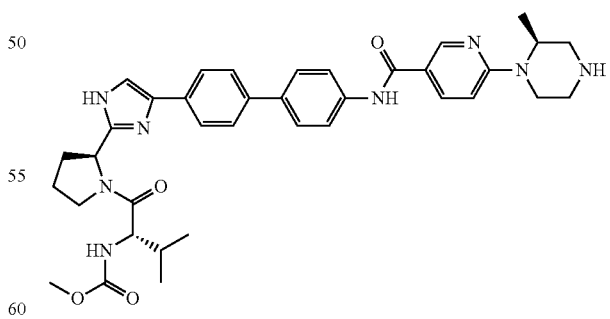

A mixture of the hydrochloride salt of {(S)-1-[(S)-2-(5-{4'-[(6-fluoro-pyridine-3-carbonyl)-amino]-biphenyl-4-yl}-1H-imidazol-2-yl)-pyrrolidine-1-carbonyl]-2-methyl-propyl}-carbamic acid methyl ester (600.0 mg, 0.966 mmol) and (S)-3-methyl-piperazine-1-carboxylic acid tert-butyl ester (0.290 g, 1.449 mmol) in dimethyl sulfoxide (1.5 mL) and N,N-diisopropylethylamine (1.01 mL, 5.80 mmol) was heated at 120° C. overnight. The reaction mixture was cooled to RT and water (5.0 mL) was added. The resulting mixture was centrifuged and filtered. To the solid was added 4.0 M hydrogen chloride in 1,4-dioxane (4.9 mL, 20 mmol) and the reaction mixture was stirred at RT for 30 min, and then concentrated. The residue was coevaporated with ethyl acetate (3×5.0 mL), dissolved in 1:1 acetic acid:water (8 mL), filtered, and purified by reverse phase preparative HPLC. Desired fractions were combined and freeze dried to give the title compound as the trifluoroacetic acid salt (320 mg). (m/z): $[M+H]^+$ calcd for $C_{37}H_{44}N_8O_4$ 665.36 found 665.4.

Preparation 17: (R)-4-[5-(4-Bromo-3-methyl-phenylcarbamoyl)-pyridin-2-yl]-3-methyl-piperazine-1-carboxylic acid tert-butyl ester

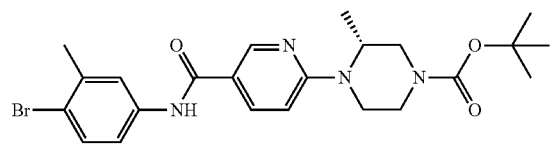 [SMILES: Cc1cc(NC(=O)c2ccc(N3CCN(C(=O)OC(C)(C)C)C[C@H]3C)nc2)ccc1Br]

(a) N-(4-Bromo-3-methyl-phenyl)-6-fluoro-nicotinamide

To a solution of 4-bromo-3-methylaniline (200 mg, 1 mmol) dissolved in DCM (4 mL) was slowly added a solution of 2-fluoropyridine-5-carbonyl chloride (170 mg, 1.1 mmol) dissolved in DCM (1 mL). A white precipitate was observed. The reaction mixture was concentrated to produce the HCl salt of the desired product.

(b) (R)-4-[5-(4-Bromo-3-methyl-phenylcarbamoyl)-pyridin-2-yl]-3-methyl-piperazine-1-carboxylic acid tert-butyl ester The white solid from the previous step was dissolved in dimethyl sulfoxide (2 mL, 30 mmol), (R)-3-methyl-piperazine-1-carboxylic acid tert-butyl ester (220 mg, 1.1 mmol) was added, followed by N,N-diisopropylethylamine (2 mL, 10 mmol. The reaction mixture was heated at 120° C. overnight, cooled to RT, and extracted with ethyl acetate/water. The organic layer was dried over sodium sulfate, filtered, concentrated, and purified by silica gel chromatography (0-40% ethyl acetate:hexanes) to produce the title compound as a light yellow solid (200 mg, 40% yield). (m/z): $[M+H]^+$ calcd for $C_{23}H_{29}BrN_4O_3$ 489.15 found 489.4.

Preparation 18: ((S)-2-Methyl-1-{(S)-2-[4-(2'-methyl-4'-{[6-((R)-2-methyl-piperazin-1-yl)-pyridine-3-carbonyl]-amino}-biphenyl-4-yl)-1H-imidazol-2-yl]-pyrrolidine-1-carbonyl}-propyl)-carbamic acid methyl ester

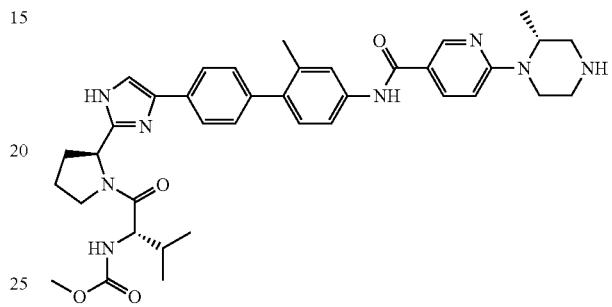

(a) (R)-4-[5-(4'-{2-[(S)-1-((S)-2-Methoxycarbonylamino-3-methyl-butyryl)-pyrrolidin-2-yl]-1H-imidazol-4-yl}-2-methyl-biphenyl-4-ylcarbamoyl)-pyridin-2-yl]-3-methyl-piperazine-1-carboxylic acid tert-butyl ester A mixture of [(S)-2-methyl-1-((S)-2-{4-[4-(4,4,5,5-tetramethyl-[1,3,2]dioxaborolan-2-yl)-phenyl]-1H-imidazol-2-yl}-pyrrolidine-1-carbonyl)-propyl]-carbamic acid methyl ester (200 mg, 0.41 mmol) and (R)-4-[5-(4-bromo-3-methyl-phenylcarbamoyl)-pyridin-2-yl]-3-methyl-piperazine-1-carboxylic acid tert-butyl ester (200 mg, 0.4 mmol; Preparation 17) was dissolved in 1,2-dimethoxyethane (4.25 mL, 40.9 mmol) and water (0.74 mL, 40.9 mmol) and the mixture was sparged under nitrogen. Sodium bicarbonate (129 mg, 1.53 mmol) was added, followed by tetrakis(triphenylphosphine)palladium(0) (70.8 mg, 0.0613 mmol). The reaction mixture was further sparged with nitrogen, sealed under nitrogen and heated at 90° C. overnight. The reaction mixture was extracted with ethyl acetate (5 mL) and water (3 mL); the organic layer was dried over sodium sulfate, filtered and concentrated to produce a brown oil, which was purified by reverse phase HPLC to produce the di-TFA salt of the title intermediate. (m/z): $[M+H]^+$ calcd for $C_{43}H_{54}N_8O_6$ 779.43 found 779.5.

(b) ((S)-2-Methyl-1-{(S)-2-[4-(2'-methyl-4'-{[6-((R)-2-methyl-piperazin-1-yl)-pyridine-3-carbonyl]-amino}-biphenyl-4-yl)-1H-imidazol-2-yl]-pyrrolidine-1-carbonyl}-propyl)-carbamic acid methyl ester The TFA salt of the previous step was treated with 4 M HCl in 1,4-dioxane (3 mL, 10 mmol) and stirred at room temperature for 1 h. The reaction mixture was concentrated and evaporated with ethyl acetate (2×) to produce the tri-HCl salt of the title compound as a yellow solid (180 mg, 60% total yield). (m/z): [M+H]+ calcd for $C_{38}H_{46}N_8O_4$ 679.37 found 679.7.

Preparation 19: (S)-1-Acetyl-2-methyl-pyrrolidine-2-carboxylic acid

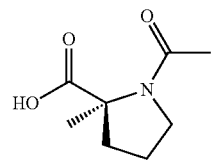

To a solution of (S)-2-methyl-pyrrolidine-2-carboxylic acid (50.0 mg, 0.387 mmol) dissolved in N,N-dimethylacetamide (1.5 mL, 16 mmol) was added a solution of acetyl chloride (31.9 mg, 0.406 mmol) dissolved in N,N-dimethylacetamide (0.5 mL), and then N,N-diisopropylethylamine (1 mL, 6 mmol) was added and the reaction mixture stirred at room temperature for 30 minutes. The reaction mixture was concentrated to produce the title compound as a light brown oil (30 mg, 40% yield). (m/z): [M+H]+ calcd for $C_8H_{13}NO_3$ 172.10 found 172.2.

Preparation 20: (S)-1-((S)-2-Methoxycarbonylamino-3-methyl-butyryl)-2-methyl-pyrrolidine-2-carboxylic acid

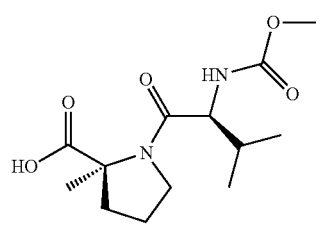 [SMILES: COC(=O)N[C@H](C(=O)N1CCC[C@@]1(C)C(=O)O)C(C)C]

To a solution of (S)-2-methoxycarbonylamino-3-butyric acid (543 mg, 3.10 mmol) dissolved in N,N-dimethylacetamide (10 mL, 11 mmol) was added HATU (1413 mg, 3.72 mmol) followed by N,N-diisopropylethylamine (1.62 mL, 9.29 mmol). The reaction mixture stirred for 10 min and then (S)-2-methyl-pyrrolidine-2-carboxylic acid (400 mg, 3.10 mmol) was added. The reaction mixture was stirred at room temperature overnight, concentrated by rotary evaporation, dissolved in 1:1 acetic acid:water (5 mL), filtered, and purified by preparative HPLC. Fractions with desired molecular weight were combined and lyophilized to give the title compound (604 mg 68% yield). [M+H]+ calcd for $C_{13}H_{22}N_2O_5$ 287.15 found 287.0

Preparation 21 (R)-4-[5-(4-Bromo-3-ethoxy-phenylcarbamoyl)-pyridin-2-yl]-3-methyl-piperazine-1-carboxylic acid tert-butyl ester

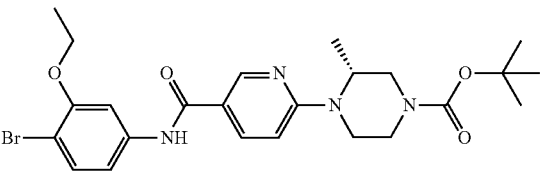 [SMILES: CCOc1cc(NC(=O)c2ccc(N3CCN(C(=O)OC(C)(C)C)C[C@H]3C)nc2)ccc1Br]

(a) N-(4-Bromo-3-ethoxy-phenyl)-6-fluoro-nicotinamide

To a solution of 4-bromo-3-ethoxyaniline hydrochloride (500 mg, 2 mmol) dissolved in DCM (7 mL) was slowly added a solution of 2-fluoropyridine-5-carbonyl chloride (240 mg, 1.5 mmol) dissolved in DCM (1.2 mL). A white precipitate was observed. The reaction mixture was stirred for 1 h, and concentrated to produce the HCl salt of the title intermediate.

(m/z): [M+H]+ calcd for $C_{14}H_{12}BrFN_2O_2$ 339.01 found 339.0.

(b) (R)-4-[5-(4-Bromo-3-ethoxy-phenylcarbamoyl)-pyridin-2-yl]-3-methyl-piperazine-1-carboxylic acid tert-butyl ester The white solid from the previous step was dissolved in DMSO (3.2 mL, 44 mmol), (R)-3-methyl-piperazine-1-carboxylic acid tert-butyl ester (300 mg, 1.5 mmol) was added, followed by N,N-diisopropylethylamine (2.6 mL, 14.8 mmol). The reaction mixture was heated at 120° C. overnight, cooled to room temperature, and extracted with ethyl acetate/water. The organic layer was dried over sodium sulfate, filtered, concentrated, and purified by silica gel chromatography (0-40% ethyl acetate:hexanes) to produce the title compound as a light yellow solid (324 mg, 42% yield). (m/z): [M+H]+ calcd for $C_{24}H_{31}BrN_4O_4$ 519.15 found 519.5.

Preparation 22: ((S)-1-{(S)-2-[4-(2'-Ethoxy-4'-{[6-((R)-2-methyl-piperazin-1-yl)-pyridine-3-carbonyl]-amino}-biphenyl-4-yl)-1H-imidazol-2-yl]-pyrrolidine-1-carbonyl}-2-methyl-propyl)-carbamic acid methyl ester

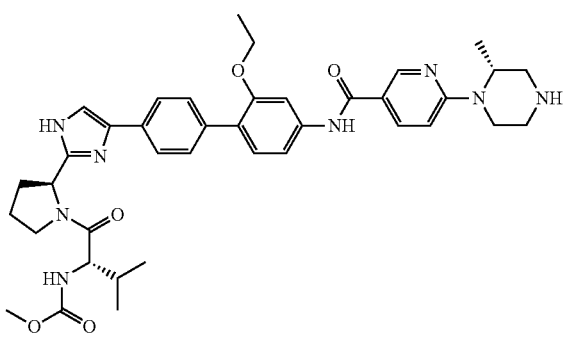 [SMILES: CCOc1cc(NC(=O)c2ccc(N3CCNC[C@H]3C)nc2)ccc1-c1ccc(-c2c[nH]c([C@@H]3CCCN3C(=O)[C@@H](NC(=O)OC)C(C)C)n2)cc1]

(a) (R)-4-[5-(2-Ethoxy-4'-{2-[(S)-1-((S)-2-methoxy-carbonylamino-3-methyl-butyryl)-pyrrolidin-2-yl]-1H-imidazol-4-yl}-biphenyl-4-ylcarbamoyl)-pyridin-2-yl]-3-methyl-piperazine-1-carboxylic acid tert-butyl ester A mixture of [(S)-2-methyl-1-((S)-2-{4-[4-(4,4,5,5-tetramethyl-[1,3,2]dioxaborolan-2-yl)-phenyl]-1H-imidazol-2-yl}-pyrrolidine-1-carbonyl)-propyl]-carbamic acid methyl ester (253 mg, 0.52 mmol) and the TFA salt of (R)-4-[5-(4-bromo-3-ethoxy-phenylcarbamoyl)-pyridin-2-yl]-3-methyl-piperazine-1-carboxylic acid ten-butyl ester (324 mg, 0.52 mmol; Preparation 21) was dissolved in 1,2-dimethoxy-ethane (5.32 mL, 51.2 mmol) and water (0.92 mL, 51.2 mmol) and the mixture was sparged under nitrogen. Sodium bicarbonate (161 mg, 1.92 mmol) was added, followed by tetrakis(triphenylphosphine)palladium(0) (89 mg, 0.077 mmol). The reaction mixture was further sparged with nitrogen, sealed under nitrogen and heated at 90° C. overnight. The reaction mixture was extracted with ethyl acetate and water. The organic layer was dried over sodium sulfate, filtered and concentrated to produce the title intermediate as a brown oil. (m/z): [M+H]+ calcd for $C_{44}H_{56}N_8O_7$ 809.43 found 809.6.

(b) ((S)-1-{(S)-2-[4-(2'-Ethoxy-4'-{[6-((R)-2-methyl-piperazin-1-yl)-pyridine-3-carbonyl]-amino}-biphenyl-4-yl)-1H-imidazol-2-yl]-pyrrolidine-1-carbonyl}-2-methyl-propyl)-carbamic acid methyl ester The brown oil of the previous step was treated with 4 M HCl in 1,4-dioxane (3.8 mL, 15.3 mmol) and stirred at room temperature for 1 h. The reaction mixture was concentrated and evaporated with ethyl acetate (2×) to produce to produce a brown solid. The solid was dissolved in 1:1 acetic acid:water solution (4 mL), filtered, and purified by reverse phase HPLC to produce the tri-TFA salt of the title compound as a yellow solid. (m/z): [M+H]+ calcd for $C_{39}H_{48}N_8O_5$ 709.37 found 709.9.

Preparation 23-1: (R)-4-[5-(4-Bromo-3-trifluoromethoxy-phenylcarbamoyl)-pyridin-2-yl]-3-methyl-piperazine-1-carboxylic acid tert-butyl ester

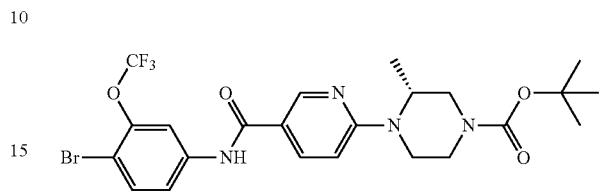

(a) N-(4-Bromo-3-trifluoromethoxy-phenyl)-6-fluoro-nicotinamide

To a solution of 4-bromo-3-trifluoromethoxy-phenylamine (300 mg, 1 mmol) dissolved in DCM (5 mL) was slowly added a solution of 2-fluoropyridine-5-carbonyl chloride (190 mg, 1.2 mmol) dissolved in DCM (1 mL). A white precipitate was observed. The reaction mixture was concentrated to produce the HCl salt of the title intermediate. (m/z): [M+H]+ calcd for $C_{13}H_7BrF_4N_2O_2$ 378.96 found 379.0.

(b) (R)-4-[5-(4-Bromo-3-trifluoromethoxy-phenylcarbamoyl)-pyridin-2-yl]-3-methyl-piperazine-1-carboxylic acid tert-butyl ester The white solid from the previous step was dissolved in DMSO (2 mL) and (R)-3-methyl-piperazine-1-carboxylic acid tert-butyl ester (230 mg, 1.2 mmol) was added, followed by N,N-diisopropylethylamine (2 mL, 10 mmol). The reaction mixture was heated at 120° C. overnight, cooled to room temperature, and extracted with ethyl acetate/water. The organic layer was dried over sodium sulfate, filtered, concentrated, and purified by silica gel chromatography (0-40% ethyl acetate:hexanes) to produce the title compound as a light yellow solid (200 mg, 40% yield). (m/z): [M+H]+ calcd for $C_{23}H_{26}BrF_3N_4O_4$ 559.11, 561.11 found 561.0.

Preparation 23-2: (R)-4-[5-(4-Bromo-3-trifluoromethyl-phenylcarbamoyl)-pyridin-2-yl]-3-methyl-piperazine-1-carboxylic acid tert-butyl ester

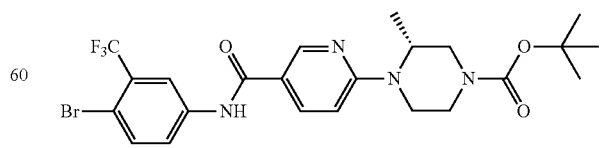

Following the procedure of Preparation 23-1 substituting 5-amino-2-bromobenzotrifluoride (300 mg, 1 mmol) for 4-bromo-3-trifluoromethoxy-phenylamine (300 mg, 1 mmol), the title intermediate was prepared (m/z): [M+H]+ calcd for $C_{23}H_{26}BrF_3N_4O_3$ 543.11, 545.11 found 545.4.

Preparation 24: ((S)-2-Methyl-1-{(S)-2-[4-(4'-{[6-((R)-2-methyl-piperazin-1-yl)-pyridine-3-carbonyl]-amino}-2'-trifluoromethoxy-biphenyl-4-yl)-1H-imidazol-2-yl]pyrrolidine-1-carbonyl}-propyl)-carbamic acid methyl ester

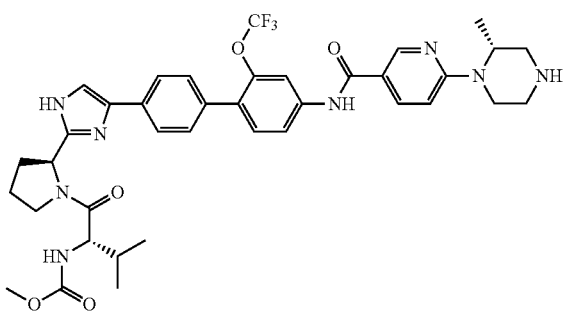 [SMILES: COC(=O)N[C@H](C(=O)N1CCC[C@H]1c1nc(-c2ccc(-c3ccc(NC(=O)c4ccc(N5CCNC[C@H]5C)nc4)cc3OC(F)(F)F)cc2)c[nH]1)C(C)C]

A mixture of [(S)-2-methyl-1-((S)-2-{4-[4-(4,4,5,5-tetramethyl-[1,3,2]dioxaborolan-2-yl)-phenyl]-1H-imidazol-2-yl}-pyrrolidine-1-carbonyl)-propyl]-carbamic acid methyl ester (360 mg, 0.64 mmol) and (R)-4-[5-(4-bromo-3-trifluoromethoxy-phenylcarbamoyl)-pyridin-2-yl]-3-methyl-piperazine-1-carboxylic acid tert-butyl ester (360 mg, 0.64 mmol; Preparation 23-1) was dissolved in 1,2-dimethoxyethane (6.69 mL, 64.4 mmol) and water (1.16 mL, 64.4 mmol) and the mixture was sparged under nitrogen. Sodium bicarbonate (203 mg, 2.41 mmol) was added, followed by tetrakis(triphenylphosphine)palladium(0) (112 mg, 0.097 mmol). The reaction mixture was further sparged with nitrogen, sealed under nitrogen and heated at 90° C. overnight. The reaction mixture was extracted with ethyl acetate (5 mL) and water (3 mL); the organic layer was dried over sodium sulfate, filtered and concentrated to produce a brown oil.

The oil from the previous step was treated with 4 M HCl in 1,4-dioxane (4 mL, 20 mmol) and stirred at room temperature for 1 h. The reaction mixture was concentrated and evaporated with ethyl acetate (2x) to produce the HCl salt of the title compound as a yellow solid which was purified by preparative HPLC to provide the tri-TFA salt of the title compound (150 mg, 21% overall yield). (m/z): [M+H]+ calcd for $C_{38}H_{43}F_3N_8O_5$ 749.33 found 749.5.

Preparation 25: ((S)-2-Methyl-1-{(S)-2-[4-(4'-{[6-((R)-2-methyl-piperazin-1-yl)-pyridine-3-carbonyl]-amino}-2'-trifluoromethyl-biphenyl-4-yl)-1H-imidazol-2-yl]-pyrrolidine-1-carbonyl}-propyl)-carbamic acid methyl ester

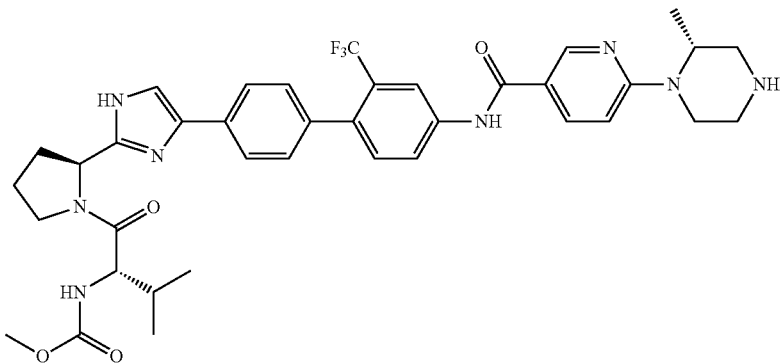 [SMILES: COC(=O)N[C@H](C(=O)N1CCC[C@H]1c1nc(-c2ccc(-c3ccc(NC(=O)c4ccc(N5CCNC[C@H]5C)nc4)cc3C(F)(F)F)cc2)c[nH]1)C(C)C]

A mixture of [(S)-2-methyl-1-((S)-2-{4-[4-(4,4,5,5-tetramethyl-[1,3,2]dioxaborolan-2-yl)-phenyl]-1H-imidazol-2-yl}-pyrrolidine-1-carbonyl)-propyl]-carbamic acid methyl ester (280 mg, 0.57 mmol) and (R)-4-[5-(4-bromo-3-trifluoromethyl-phenylcarbamoyl)-pyridin-2-yl]-3-methyl-piperazine-1-carboxylic acid tert-butyl ester (300 mg, 0.72 mmol; Preparation 23-2) was dissolved in 1,4-dioxane (5.8 mL, 75 mmol) and water (0.83 mL, 46 mmol). Cesium carbonate (560 mg, 1.7 mmol) was added, the reaction mixture was sparged with nitrogen and then chloro(2-dicyclohexylphosphino-2',4',6'-tri-isopropyl-1,1'-biphenyl)[2-(2-aminoethyl)phenyl]palladium(II) methyl-t-butylether adduct (28 mg, 0.034 mmol) was added. The reaction mixture was sealed with nitrogen and heated at 95° C. for 3 h. The reaction mixture was extracted with ethyl acetate and water; the organic layer was dried over sodium sulfate, filtered and concentrated to produce an orange oil.

The oil from the previous step was treated with 4 M HCl in 1,4-dioxane (4 mL, 20 mmol) and stirred at room temperature for 1 h. The reaction mixture was concentrated and evaporated with ethyl acetate (2x) to produce the HCl salt of the title compound as a yellow solid which was purified by preparative HPLC to provide the tri-TFA salt of the title compound (150 mg, 24% overall yield). (m/z): [M+H]+ calcd for $C_{38}H_{43}F_3N_8O_4$ 733.34 found 733.5.

Preparation 26: (2S,5R)-4-(5-Carboxy-pyridin-2-yl)-2,5-dimethyl-piperazine-1-carboxylic acid tert-butyl ester

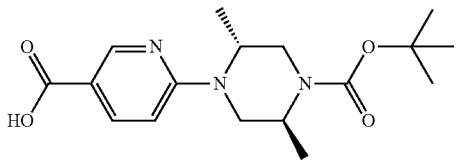 [SMILES: C[C@@H]1CN(C(=O)OC(C)(C)C)[C@@H](C)CN1c1ccc(C(=O)O)cn1]

(a) (2S,5R)-4-(5-Methoxycarbonyl-pyridin-2-yl)-2,5-dimethyl-piperazine-1-carboxylic acid tert-butyl ester A mixture of 6-fluoronicotinic acid methyl ester (200 mg, 1.29 mmol) and (2S,5R)-2,5-dimethyl-piperazine-1-carboxylic acid tert-butyl ester was heated at 120° C. in DMSO (2.0 mL) with potassium carbonate (178 mg, 1.29 mmol) for 2 h. The reaction mixture was partitioned between ethyl acetate (20.0 mL) and water (5.0 mL). The organic layer was washed with water (2×5.0 mL), dried over sodium sulfate, filtered and concentrated to give the title intermediate as a yellowish oil.

(b) (2S,5R)-4-(5-Carboxy-pyridin-2-yl)-2,5-dimethyl-piperazine-1-carboxylic acid tert-butyl ester The oil of the previous step was dissolved in methanol (10.0 mL, 247 mmol) and water (2.5 mL, 140 mmol) and treated with lithium hydroxide monohydrate (108 mg, 2.58 mmol) at 40° C. overnight. The reaction mixture was concentrated; the residue was dissolved in 1:1 acetic acid:water solution (6 mL), filtered, and purified by reverse phase HPLC. Desired fractions were combined and freeze dried to give the tri-TFA salt of the title compound as a white solid (327 mg, yield 56%). (m/z): [M+H]+ calcd for $C_{17}H_{25}N_3O_4$ 336.18 found 336.5.

Preparation 27: (2S,5R)-4-[5-(4-Bromo-3-trifluoromethoxy-phenylcarbamoyl)-pyridin-2-yl]-2,5-dimethyl-piperazine-1-carboxylic acid tert-butyl ester

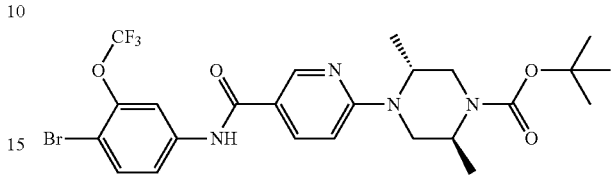

To a solution of 4-bromo-3-trifluoromethoxy-phenylamine (190 mg, 0.74 mmol) and N,N-diisopropylethylamine (0.65 mL, 3.73 mmol; in N,N-dimethylacetamide (3 mL) was added a solution of (2S,5R)-4-(5-carboxy-pyridin-2-yl)-2,5-dimethyl-piperazine-1-carboxylic acid tert-butyl ester TFA (330 mg, 0.74 mmol; Preparation 26) and HCTU (401 mg, 0.97 mmol) in N,N-dimethylacetamide (3 mL). The reaction mixture was heated at 50° C. overnight. The reaction mixture was concentrated by rotary evaporation, extracted with ethyl acetate/sat. sodium carbonate, dried over sodium sulfate, filtered, concentrated and purified by silica gel chromatography (0-50% ethyl acetate:hexanes) to provide the title compound (155 mg, yield 36%). (m/z): [M+H]+ calcd for $C_{24}H_{28}BrF_3N_4O_4$ 573.12, 575.12 found 575.5.

Preparation 28: ((S)-1-{(S)-2-[4-(4'-{[6-((2R,5S)-2,5-Dimethyl-piperazin-1-yl)-pyridine-3-carbonyl]-amino}-2'-trifluoromethoxy-biphenyl-4-yl)-1H-imidazol-2-yl]-pyrrolidine-1-carbonyl}-2-methyl-propyl)-carbamic acid methyl ester

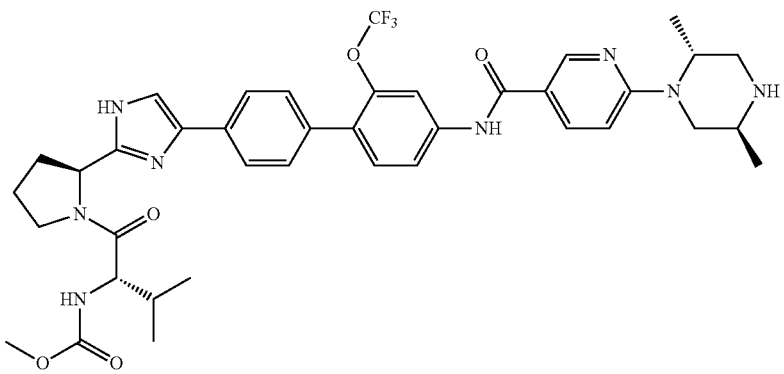

A mixture of [(S)-2-methyl-1-((S)-2-{4-[4-(4,4,5,5-tetramethyl-[1,3,2]dioxaborolan-2-yl)-phenyl]-1H-imidazol-2-yl}-pyrrolidine-1-carbonyl)-propyl]-carbamic acid methyl ester (86 mg, 0.17 mmol) and (2S,5R)-4-[5-(4-bromo-3-trifluoromethoxy-phenylcarbamoyl)-pyridin-2-yl]-2,5-dimethyl-piperazine-1-carboxylic acid tert-butyl ester (100 mg, 0.2 mmol, Preparation 27) was dissolved in 1,4-dioxane (1.8 mL, 23 mmol) and water (0.25 mL, 14 mmol). Cesium carbonate (170 mg, 0.52 mmol) was added. The reaction mixture was sparged with nitrogen and then tetrakis(triphenylphosphine)palladium(0) (12.1 mg, 0.011 mmol) was added. The reaction mixture was sealed under nitrogen and heated at 95° C. overnight. The reaction mixture was extracted with ethyl acetate/water, the organic layer was dried over sodium sulfate and concentrated to produce an orange oil.

The oil from the previous step was treated with 4 M HCl in 1,4-dioxane (2 mL, 7 mmol) and stirred at room temperature for 1 h. The reaction mixture was concentrated and evaporated with ethyl acetate (2×) to produce the HCl salt of the title compound as a yellow solid which was purified by preparative HPLC to provide the tri-TFA salt of the title compound (150 mg, 30% overall yield). (m/z): [M+H]$^+$ calcd for $C_{39}H_{45}F_3N_8O_5$ 763.35 found 763.7.

Preparation 29-A: ((S)-1-{(S)-2-[4-(4-Bromo-3-methyl-phenyl)-1H-imidazol-2-yl]-pyrrolidine-1-carbonyl}-2-methyl-propyl)-carbamic acid methyl ester

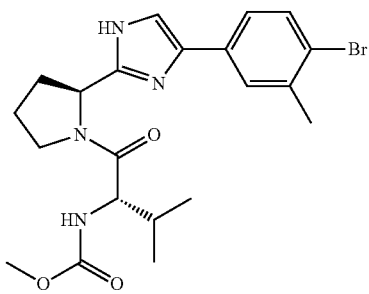 [SMILES: COC(=O)N[C@H](C(=O)N1CCC[C@H]1c1nc(-c2ccc(Br)c(C)c2)c[nH]1)C(C)C]

(a) 4-Bromo-N-methoxy-3,N-dimethyl-benzamide

A mixture of 4-bromo-3-methyl-benzoic acid (15 g, 0.069 mol), O,N-dimethyl hydroxylamine (6.5 g, 0.1 mol) HATU (38 g, 0.1 mol), and triethylamine (20 g, 0.2 mol) dissolved in DMF (50 mL) was stirred at RT for 12 h, concentrated, and purified by silica gel chromatography (1:1 EtOAc:petroleum ether) to provide the title intermediate (11 g, 61% yield) $^1$H NMR (CDCl$_3$, 400 MHz) δ (ppm): 7.52 (m, 2H), 7.32 (m, 1H), 3.50 (s, 3H), 3.29 (m, 3H), 2.38 (s, 3H).

(b) 1-(4-Bromo-3-methyl-phenyl)-ethanone

Methyl lithium (24 mL, 0.038 mol) was added to a solution of the product of the previous step (9 g, 0.035 mol) in THF (20 mL) at −78° C. and the reaction mixture was stirred at RT for 12 h. The organic layer was washed with aqueous ammonium chloride (20 mL), dried over sodium sulfate, filtered, concentrated and purified by silica gel chromatography (1:5 EtOAc: petroleum ether) to provide the title intermediate (6 g, 81% yield) $^1$H NMR (CDCl$_3$, 400 MHz) δ (ppm): 7.79 (m, 1H), 7.59 (m, 2H), 2.55 (d, J=2.8 Hz, 3H), 2.43 (d, J=0.4 Hz, 3H)

(c) 2-Bromo-1-(4-bromo-3-methyl-phenyl)-ethanone

Trimethyl phenylammonium tribromide (13 g, 0.036 mol) was added to a solution of 1-(4-bromo-3-methyl-phenyl)-ethanone (6.3 g, 0.030 mol) in THF (30 mL) and the reaction mixture was stirred at RT for 12 h, filtered, and concentrated to provide the title intermediate (8.6 g, 100% yield). $^1$H NMR (CDCl$_3$, 400 MHz) δ (ppm): 7.82 (m, 1H), 7.66 (m, 2H), 4.38 (s, 2H), 2.56 (s, 3H)

(d) (S)-Pyrrolidine-1,2-dicarboxylic acid 2-[2-(4-bromo-3-methyl-phenyl)-2-oxo-ethyl]ester 1-tert-butyl ester A mixture of the product of the previous step (8.6 g, 0.03 mol), (S)-pyrrolidine-1,2-dicarboxylic acid 1-tert-butyl ester (9.5 g, 0.044 mol), and potassium carbonate (12.4 g, 0.09 mol) was dissolved in ACN (50 mL) and the reaction mixture was stirred at RT for 12 h and concentrated to provide the title intermediate (13 g, 100% yield) (m/z): [M+H-Boc]$^+$ calcd for $C_{19}H_{24}BrNO_5$ 326.04 found 326.0.

(e) (S)-2-[4-(4-Bromo-3-methyl-phenyl)-1H-imidazol-2-yl]-pyrrolidine-1-carboxylic acid tert-butyl ester A mixture of the product of the previous step (13 g, 0.029 mol) and ammonium acetate (47 g, 0.61 mol) dissolved in toluene (100 mL) was stirred at 110° C. for 12 h, concentrated, and purified by silica gel chromatography (1:1 EtOAc: petroleum ether) to provide the title intermediate (8 g, 68% yield). $^1$H NMR (CDCl$_3$, 400 MHz) δ (ppm): 7.40 (m, 3H), 7.13 (m, 1H), 4.89 (m, 1H), 3.34 (m, 2H), 2.94 (m, 1H), 2.34 (s, 3H), 2.10 (m, 2H), 1.88 (m, 1H), 1.58 (m, 10H).

(f) 4-(4-Bromo-3-methyl-phenyl)-2-(S)-pyrrolidin-2-yl-1H-imidazole

To a solution of the product of the previous step (8 g, 0.020 mol) in methanol (3 mL) was added 4 N HCl in methanol (50 mL) at 0° C. The reaction mixture was stirred at RT for 4 h, and concentrated to give the title intermediate (6 g, 100% yield) as a yellow solid. (m/z): [M+H]$^+$ calcd for $C_{14}H_{16}BrN_3$ 306.06 found 307.7.

(g) ((S)-1-{(S)-2-[4-(4-Bromo-3-methyl-phenyl)-1H-imidazol-2-yl]-pyrrolidine-1-carbonyl}-2-methyl-propyl)-carbamic acid methyl ester A mixture of the product of the previous step (6 g, 0.018 mol), (S)-2-methoxycarbonylamino-3-methyl-butyric acid (4.6 g, 0.026 mol), HATU (10 g, 0.026 mol), and triethylamine (5.3 g, 0.078 mol) dissolved in DCM (50 mL) was stirred at RT for 12 h, concentrated and purified by silica gel chromatography (1:1 EtOAc:petroleum ether) to provide the title intermediate (5.5 g, 69% yield). $^1$H NMR (CDCl$_3$, 400 MHz) δ (ppm): 10.4 (s, 1H), 7.64 (m, 1H), 7.46 (m, 2H), 7.17 (m, 1H), 5.50 (m, 1H), 5.39 (m, 1H), 4.34 (m, 1H), 3.86 (m, 1H), 3.69 (s, 3H), 3.60 (m, 1H), 2.45-2.01 (m, 6H), 1.07 (m, 1H), 0.851 (m, 6H).

Preparation 29-B: ((S)-1-{(S)-2-[4-(4'-Amino-2,2'-dimethyl-biphenyl-4-yl)-1H-imidazol-2-yl]-pyrrolidine-1-carbonyl}-2-methyl-propyl)-carbamic acid methyl ester

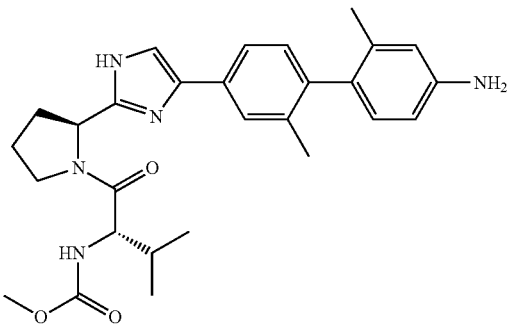 [SMILES: COC(=O)N[C@H](C(=O)N1CCC[C@H]1c1nc(-c2ccc(-c3ccc(N)cc3C)c(C)c2)c[nH]1)C(C)C]

Potassium carbonate (224 mg, 1.619 mmol) was added to a mixture of ((S)-1-{(S)-2-[4-(4-bromo-3-methyl-phenyl)-1H- imidazol-2-yl]-pyrrolidine-1-carbonyl}-2-methyl-propyl)-carbamic acid methyl ester (150 mg, 0.324 mmol) and 3-methyl-4-(4,4,5,5-tetramethyl-[1,3,2]dioxaborolan-2-yl)-phenylamine (90.6 mg, 0.389 mmol) in toluene (0.6 mL, 6 mmol) and water (0.3 mL, 20 mmol). The reaction mixture was degassed and flushed with nitrogen. Tetrakis(triphenylphosphine)palladium(0) (44.9 mg, 0.039 mmol) was added under nitrogen and then the reaction mixture was capped and heated at 100° C. overnight, cooled to RT and partitioned between ethyl acetate (10 mL) and water (2 mL). The organic layer was dried over sodium sulfate, filtered and concentrated to give a brownish oil, which was purified by silica gel chromatography (12 g silica gel, 0-100% EtOAc/hexanes). Desired fractions were combined and concentrated to give the title compound as a light yellowish foam (135 mg, 85% yield). (m/z): [M+H]$^+$ calcd for $C_{28}H_{35}N_5O_3$ 490.27 found 490.6.

Preparation 30: ((S)-1-{(S)-2-[4-(4'-{[6-((2R,5S)-2,5-Dimethyl-piperazin-1-yl)-pyridine-3-carbonyl]-amino}-2,2'-dimethyl-biphenyl-4-yl)-1H-imidazol-2-yl]-pyrrolidine-1-carbonyl}-2-methyl-propyl)-carbamic acid methyl ester 0.817 mmol). The resulting mixture was heated at 50° C. overnight. The reaction mixture was partitioned between EtOAc (10 mL) and water (2 mL). The organic layer was washed with water (2 mL), dried over sodium sulfate, filtered and concentrated to give a yellowish oil. (m/z): [M+H]$^+$ calcd for $C_{45}H_{58}N_8O_6$ 807.45 found 807.6.

(b) ((S)-1-{(S)-2-[4-(4'-{[6-((2R,5S)-2,5-Dimethyl-piperazin-1-yl)-pyridine-3-carbonyl]-amino}-2,2'-dimethyl-biphenyl-4-yl)-1H-imidazol-2-yl]-pyrrolidine-1-carbonyl}-2-methyl-propyl)-carbamic acid methyl ester The oily residue from the previous step was treated with 4 M HCl in 1,4-dioxane (1.5 mL, 6.0 mmol) at RT for 30 min. The reaction mixture was concentrated, the residue was dissolved in 1:1 acetic acid:water solution (8 mL), filtered, and purified by reverse phase HPLC. Desired fractions were combined and freeze dried to give the tri-TFA salt of the title

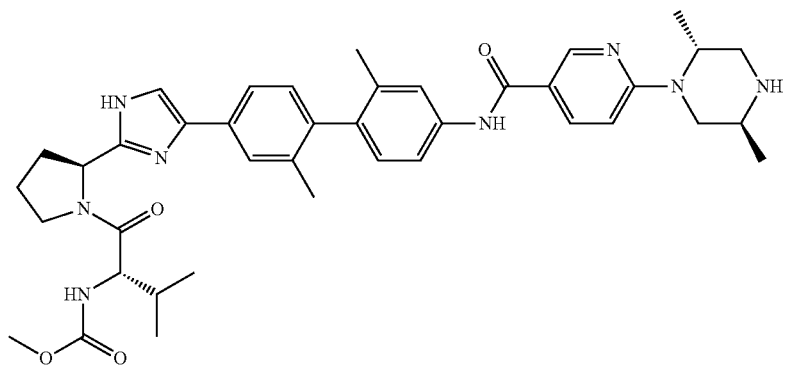

(a) (2S,5R)-4-[5-(4'-{2-[(S)-1-((S)-2-Methoxycarbonylamino-3-methyl-butyryl)-pyrrolidin-2-yl]-1H-imidazol-4-yl}-2,2'-dimethyl-biphenyl-4-ylcarbamoyl)-pyridin-2-yl]-2,5-dimethyl-piperazine-1-carboxylic acid tert-butyl ester A mixture of (2S,5R)-4-(5-carboxy-pyridin-2-yl)-2,5-dimethyl-piperazine-1-carboxylic acid tert-butyl ester TFA (80.8 mg, 0.180 mmol), EDC (34.4 mg, 0.180 mmol), and HOAt (24.5 mg, 0.180 mmol) in DMA (2.0 mL, 22 mmol)) was stirred at RT for 20 min and then ((S)-1-{(S)-2-[4-(4'-amino-2,2'-dimethyl-biphenyl-4-yl)-1H-imidazol-2-yl]-pyrrolidine-1-carbonyl}-2-methyl-propyl)-carbamic acid methyl ester (80.0 mg, 0.163 mmol; Preparation 29-B) was added followed by N,N-diisopropylethylamine (0.142 mL, compound as a white solid (66 mg, yield 39%). (m/z): [M+H]$^+$ calcd for $C_{40}H_{50}N_8O_4$ 707.40 found 707.8.

Preparation 31: (R)-4-[5-(4-Bromo-3,5-difluoro-phenylcarbamoyl)-pyridin-2-yl]-3-methyl-piperazine-1-carboxylic acid tert-butyl ester

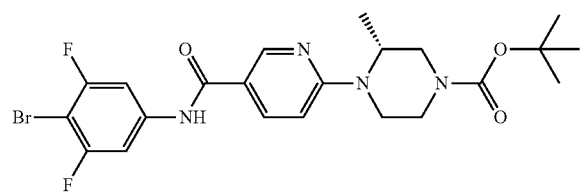 [SMILES: C[C@@H]1CN(C(=O)OC(C)(C)C)CCN1c1ccc(C(=O)Nc2cc(F)c(Br)c(F)c2)cn1]

To a solution of 4-bromo-3,5-difluoroaniline (250 mg, 1.2 mmol) dissolved in DCM (5 mL) was added a solution of 2-fluoropyridine-5-carbonyl chloride (190 mg, 1.2 mmol) dissolved in DCM (2 mL) followed by addition of N,N-diisopropylethylamine (100 uL, 0.60 mmol). The reaction mixture was stirred at RT for 1 h, and concentrated to produce a clear oil.

The oil from the previous step was dissolved in DMSO (2.6 mL, 36 mmol) and (R)-3-methyl-piperazine-1-carboxylic acid tert-butyl ester (240 mg, 1.2 mmol) and N,N-diisopropylethylamine (2.1 mL, 12 mmol) was added. The reaction mixture was heated at 120° C. overnight and extracted with ethyl acetate/water. The organic layer was dried over sodium sulfate, filtered, concentrated and purified by silica gel chromatography (0-40% ethyl acetate:hexanes) to produce the title product as a white solid (yield 62%). (m/z): [M+H]$^+$ calcd for $C_{22}H_{25}BrF_2N_4O_3$ 511.11. 513.11 found 513.4.

Preparation 32: ((S)-1-{(S)-2-[4-(2',6'-Difluoro-4'-{[6-((R)-2-methyl-piperazin-1-yl)-pyridine-3-carbonyl]-amino}-biphenyl-4-yl)-1H-imidazol-2-yl]-pyrrolidine-1-carbonyl}-2-methyl-propyl)-carbamic acid methyl ester A mixture of 6-fluoronicotinic acid (150 g, 1.063 mol) and (R)-3-methyl-piperazine-1-carboxylic acid tert-butyl ester (234.2 g, 1.169 mol) in tetrahydrofuran (1.75 L) was cooled to −40° C. and then 2 M isopropylmagnesium chloride in tetrahydrofuran (1.196 L, 2.39 mol) was added slowly maintaining the temperature less than −20° C. The reaction mixture was slowly warmed to RT, stirred at RT for 4 h and then 1 N HCl (1.75 L) and water (1.175 L) were added. The reaction mixture was extracted with ethyl acetate (4 L). The organic phase was evaporated to provide crude solid (534 g). To the crude solid was added acetone (2 L) and water (200 mL). The resulting reaction mixture was heated to 50° C. and then water (2.8 L) was added slowly. Seed crystals from a previous run at smaller scale were added after ~1 L of water. The reaction mixture was cooled to 20° C. over 3 h, stirred at 20° C. overnight and filtered. The solid was washed with 2:3 acetone:water (2×500 mL) and dried under vacuum to pro-

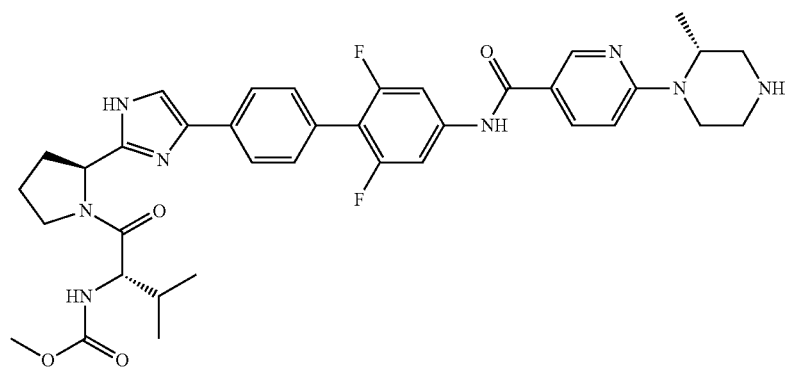 [SMILES: COC(=O)N[C@H](C(=O)N1CCC[C@H]1c1nc(-c2ccc(-c3c(F)cc(NC(=O)c4ccc(N5CCNC[C@H]5C)nc4)cc3F)cc2)c[nH]1)C(C)C]

Following the procedure of Preparation 24 at the 0.4 mmol scale substituting the product of Preparation 31 for the product of Preparation 23-1, the tri-TFA salt of the title compound was prepared. (m/z): [M+H]$^+$ calcd for $C_{37}H_{42}F_2N_8O_4$ 701.33 found 701.4.

Preparation 33: (R)-4-(5-Carboxy-pyridin-2-yl)-3-methyl-piperazine-1-carboxylic acid tert-butyl ester

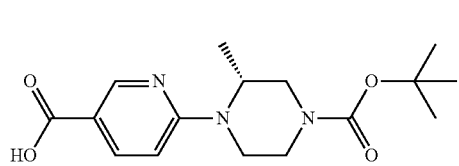

vide the title compound (329 g, 96% yield) as an off-white solid. HPLC Method A: Retention time 9.73 min.

Preparation 34: (R)-4-[5-(4-Bromo-3-fluoro-phenylcarbamoyl)-pyridin-2-yl]-3-methyl-piperazine-1-carboxylic acid tert-butyl ester

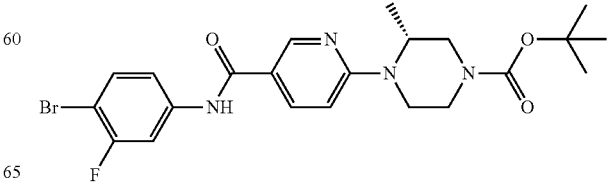

A solution of (R)-4-(5-carboxy-pyridin-2-yl)-3-methyl-piperazine-1-carboxylic acid tert-butyl ester (150 mg, 0.47 mmol, Preparation 33), EDC (130 mg, 0.70 mmol), and HOAt (95 mg, 0.70 mmol) dissolved in DMA (4.3 mL, 47 mmol) was stirred at RT for 30 min and then 4-bromo-3-fluoroaniline (89 mg, 0.47 mmol) was added, followed by N,N-diisopropylethylamine (0.2 mL, 1.2 mmol). The reaction mixture was stirred at RT overnight and extracted with ethyl acetate/water. The organic layer was dried over sodium sulfate, filtered, concentrated, and purified by silica gel chromatography (eluted: 0-40% EtOAc:hexanes) to provide the title compound as a light yellow oil (100 mg, 40% yield). (m/z): [M+H]$^+$ calcd for $C_{22}H_{26}BrFN_4O_3$ 493.12 found 493.2.

Preparation 35: ((S)-1-{(S)-2-[4-(2'-Fluoro-4'-{[6-((R)-2-methyl-piperazin-1-yl)-pyridine-3-carbonyl]-amino}-biphenyl-4-yl)-1H-imidazol-2-yl]-pyrrolidine-1-carbonyl}-2-methyl-propyl)-carbamic acid methyl ester

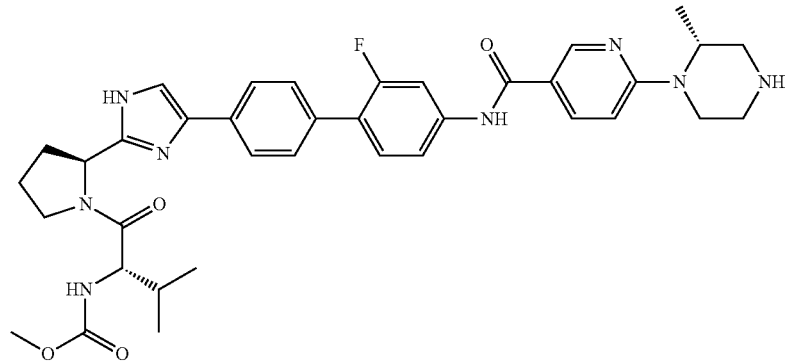 [SMILES: COC(=O)N[C@H](C(=O)N1CCC[C@H]1c1nc(-c2ccc(-c3ccc(NC(=O)c4ccc(N5CCNC[C@H]5C)nc4)cc3F)cc2)c[nH]1)C(C)C]

A mixture of [(S)-2-methyl-1-((S)-2-{4-[4-(4,4,5,5-tetramethyl-[1,3,2]dioxaborolan-2-yl)-phenyl]-1H-imidazol-2-yl}-pyrrolidine-1-carbonyl)-propyl]-carbamic acid methyl ester (99 mg, 0.20 mmol) and (R)-4-[5-(4-bromo-3-fluoro-phenylcarbamoyl)-pyridin-2-yl]-3-methyl-piperazine-1-carboxylic acid tert-butyl ester (100 mg, 0.2 mmol, Preparation 34) was dissolved in 1,2-dimethoxyethane (2.06 mL, 19.9 mmol) and Water (0.358 mL, 19.9 mmol) and the mixture was sparged under nitrogen. Sodium bicarbonate (62.6 mg, 0.75 mmol) was added, followed by tetrakis(triphenylphosphine)palladium(0) (34.4 mg, 0.030 mmol). The reaction mixture was further sparged with nitrogen, sealed under nitrogen, and heated at 90° C. overnight. The reaction mixture was extracted with ethyl acetate (5 mL) and water (3 mL); the organic layer was dried over sodium sulfate, filtered, and concentrated to produce a brown oil.

The oil from the previous step was treated with 4 M HCl in 1,4-dioxane (3 mL, 10 mmol), stirred at room temperature for 1 h, concentrated, and evaporated with ethyl acetate (2×) to produce the HCl salt of the title compound as a yellow solid, which was purified by reverse phase HPLC to yield the tri-TFA salt of the title compound (100 mg). (m/z): [M+H]$^+$ calcd for $C_{37}H_{43}FN_8O_4$ 683.34 found 683.8.

Preparation 36: 6-[(R)-4-((S)-2,2-Dimethyl-cyclopropanecarbonyl)-2-methyl-piperazin-1-yl]-nicotinic acid

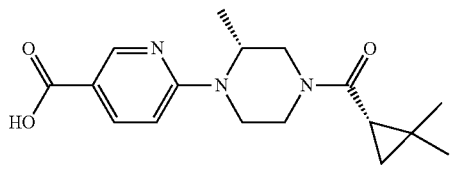 [SMILES: C[C@@H]1CN(C(=O)[C@H]2CC2(C)C)CCN1c1ccc(C(=O)O)cn1]

(a) 6-((R)-2-Methyl-piperazin-1-yl)-nicotinic acid methyl ester

To a mixture of (R)-4-(5-carboxy-pyridin-2-yl)-3-methyl-piperazine-1-carboxylic acid tert-butyl ester (50 g, 0.156 mol) and methanol (500 mL) was slowly added concentrated sulfuric acid (37 mL). The reaction mixture was warmed to 64° C., stirred at 64° C. overnight, cooled to RT and then ice water (800 mL) was added followed by 50% aqueous sodium hydroxide (60 mL). The reaction mixture was extracted with ethyl acetate (3×800 mL). Combined organic layers were dried over sodium sulfate and evaporated to give the title intermediate as an oil. HPLC Method A: Retention time 3.50 and 3.72 min.

(b) 6-[(R)-4-((S)-2,2-Dimethyl-cyclopropanecarbonyl)-2-methyl-piperazin-1-yl]-nicotinic acid methyl ester To a cooled solution of the oil from the previous step in dimethylformamide (600 mL) was added (S)-2,2-dimethyl-cyclopropanecarboxylic acid (16.89 g, 0.148 mol) and HCTU (61.23 g 0.148 mol), followed by N,N-diisopropylethylamine (51.6 mL, 0.296 mol). The reaction mixture was stirred at RT overnight, diluted with ethyl acetate (1 L) and washed with 1:1 sodium carbonate:water. The aqueous phase was extracted with ethyl acetate (500 mL). Combined organic phases were washed with saturated aqueous sodium bicarbonate (500 mL) and water (1 L). The organic layer was extracted with 3 N HCl (2×500 mL, 300 mL) and then 50% aqueous NaOH (169 g) was added to the combined aqueous extract. After 30 min, the reaction mixture was filtered to give a solid (51.1 g). To the crude solid was added acetone (300 mL), followed by water (450 mL). The reaction mixture was stirred at RT overnight and filtered to give the title intermediate (36.86 g, 71.5% y over two steps) as a slightly yellow solid. HPLC Method B: Retention time 15.05 min.

(c) 6-[(R)-4-((S)-2,2-Dimethyl-cyclopropanecarbonyl)-2-methyl-piperazin-1-yl]-nicotinic acid To a mixture of the product of the previous step (35.0 g, 0.106 mol) and methanol (280 mL) was added 2 M LiOH in water (106 mL, 0.211 mol) keeping the temperature under 30° C. The reaction mixture was stirred at RT overnight, concentrated under reduced pressure, and then ethanol (64 mL) was added, followed by 1 N HCl (230 mL). Seed crystals from a previous run at smaller scale were added after 160 mL HCl. After 1 h, the mixture was filtered to give the title compound (33.2 g, 99% yield) as a pale yellow solid. HPLC Method B: Retention time 8.27 min.

Preparation 37: ((S)-1-{(S)-2-[4-(4'-Amino-2'-chloro-biphenyl-4-yl)-1H-imidazol-2-yl]-pyrrolidine-1-carbonyl}-2-methyl-propyl)-carbamic acid methyl ester

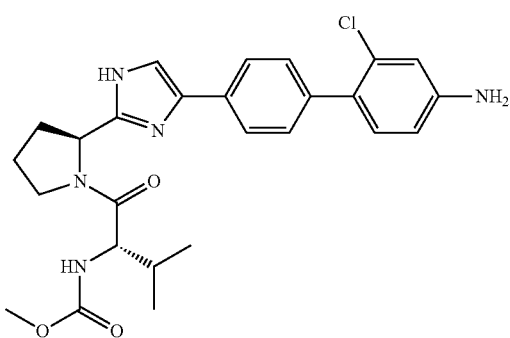 [SMILES: COC(=O)N[C@H](C(=O)N1CCC[C@H]1c1nc(-c2ccc(-c3ccc(N)cc3Cl)cc2)c[nH]1)C(C)C]

Saturated aqueous sodium carbonate (0.2 mL) was added to a mixture of [(S)-2-methyl-1-((S)-2-{4-[4-(4,4,5,5-tetramethyl-[1,3,2]dioxaborolan-2-yl)-phenyl]-1H-imidazol-2-yl}-pyrrolidine-1-carbonyl)-propyl]-carbamic acid methyl ester (100 mg, 0.20 mmol), 4-bromo-3-chloroaniline (46 mg, 0.22 mmol), tetrakis(triphenylphosphine)palladium(0) (23 mg, 0.02 mmol), and water (0.3 mL). The reaction mixture was purged with nitrogen and then 1,4-dioxane (0.7 mL) was added. The reaction mixture was degassed, stirred, and heated at 90° C. overnight. Water and ethyl acetate were added; the reaction mixture was concentrated; dissolved in 1:1 acetic acid:water (1 mL) and purified by preparative HPLC. Fractions were combined, adjusted to pH 8-9 with aqueous sodium bicarbonate, and extracted with DCM. Extracts were washed with water, dried with sodium sulfate, and concentrated. The concentrate was dissolved in methanol and concentrated under vacuum to provide the title compound (m/z): [M+H]$^+$ calcd for $C_{26}H_{30}ClN_5O_3$ 496.20 found 496.7.

Preparation 38-A: ((S)-1-{(S)-2-[4-(4-Bromo-3-fluoro-phenyl)-1H-imidazol-2-yl]-pyrrolidine-1-carbonyl}-2-methyl-propyl)-carbamic acid methyl ester

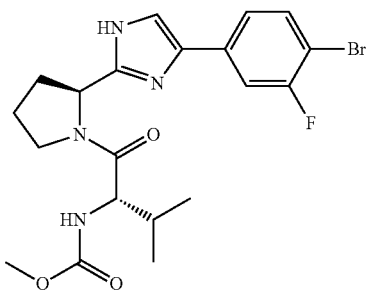

(a) 1-(4-Bromo-3-fluoro-phenyl)-2-chloro-ethanone

Oxalyl dichloride (6.1 g, 48 mmol) was added to a solution of 4-bromo-3-fluoro-benzoic acid (7 g, 32 mmol) in DCM (80 mL) at 0° C. followed by DMF (0.2 mL) and the reaction mixture was stirred at RT for 2 h and then conentrated under vacuum to provide crude 4-bromo-3-fluoro-benzoyl chloride.

To the crude product dissolved in DCM (50 mL) was added 2 N trimethylsilyldiazomethane (48 mL, 96 mmol) at 0° C. and the reaction mixture was stirred at RT for 3 h. Acetic acid was added and the reaction mixture was diluted with DCM, washed with brine, and concentrated to provide crude 1-(4-bromo-3-fluoro-phenyl)-2-diazenyl-2-trimethylsilanyl-ethanone (8.0 g).

To a solution of the product of the previous step (8.0 g) in THF (50 mL) was added 4 N HCl in dioxane (20 mL) at 0° C. and the reaction mixture was stirred at RT for 3 h, concentrated, and EtOAc (100 mL) was added. The solution was washed with sodium bicarbonate, dried, concentrated, and purified by silica gel chromatography (eluted with 5:1 petroleum ether:EtOAc) to give the title intermediate (6.5 g, 81% yield). (m/z): [M+H]$^+$ calcd for $C_8H_5BrClFO$ 252.93 found 252.7. $^1$H NMR (CDCl$_3$, 400 MHz) δ (ppm): 7.72-7.76 (2H, M), 7.63-7.65 (1H, m), 4.64 (2H, s).

(b) (S)-Pyrrolidine-1,2-dicarboxylic acid 2-[2-(4-bromo-3-fluoro-phenyl)-2-oxo-ethyl]ester 1-tert-butyl ester To a solution of the product of the previous step (6.1 g, 28.4 mmol) in DMF (100 mL) was added (S)-pyrrolidine-1,2-dicarboxylic acid 1-tert-butyl ester (6.5 g, 25.8 mmol) and cesium carbonate (16.8 g, 51.6 mmol) and the reaction mixture was stirred at RT for 2 h. Ethyl acetate (500 mL) was added and the solution was washed with brine (4×50 mL), dried, and concentrated to give the title intermediate as a dark oil (10 g). (m/z): [M+H-Boc]$^+$ calcd for $C_{18}H_{21}BrFNO_5$ 330.02 found 331.9.

(c) (S)-2-[4-(4-Bromo-3-fluoro-phenyl)-1H-imidazol-2-yl]-pyrrolidine-1-carboxylic acid tert-butyl ester Ammonium acetate (39.8 g, 516 mmol) was added to a solution of the product of the previous step (10 g, 25.8 mmol)

in toluene (150 mL) and the reaction mixture was stirred at reflux overnight. Ethyl acetate (200 mL) was added, and the solution was washed with water (3×50 mL), dried, concentrated, and purified by silica gel chromatography (eluted with 4:1 petroleum ether:EtOAc) to give the title product as a yellow solid (4.2 g). (m/z): [M+H]$^+$ calcd for $C_{18}H_{21}BrFN_3O_2$ 410.09 found 409.9. $^1$H NMR (CDCl$_3$, 400 MHz) δ (ppm): 7.41-7.56 (3H, m), 7.25 (1H, s), 4.97 (1H, d), 3.43 (2H, m), 3.01 (1H, s), 2.10 (2H, m), 1.98 (2H. m). 1.42-1.51 (10H, m).

(d) ((S)-1-{(S)-2-[4-(4-Bromo-3-fluoro-phenyl)-1H-imidazol-2-yl]-pyrrolidine-1-carbonyl}-2-methyl-propyl)-carbamic acid methyl ester To a solution of the product of the previous step (4.2 g, 10.24 mmol) in methanol was added 4 N HCl in dioxane (30 mL) and the reaction mixture was stirred at RT for 2 h and concentrated to give crude 4-(4-bromo-3-fluoro-phenyl)-2-(S)-pyrrolidin-2-yl-1H-imidazole (4.1 g)

To a solution of the crude product (4.1 g, 10.24 mmol) in DMF (70 mL) was added (S)-2-methoxycarbonylamino-3-methyl-butyric acid (1.97 g, 11.26 mmol), HATU (4.67 g, 12.29 mmol) and triethylamine (3.11 g, 30.72 mmol) and the reaction mixture was stirred at RT overnight. Ethyl acetate (200 mL) was added, and the solution was washed with brine (3×40 mL), dried, filtered, concentrated, and purified by silica gel chromatography (eluted with 2:1 petroleum ether:EtOAc) to give the title product as a yellow solid (2.6 g, 54% yield) (m/z): [M+H]$^+$ calcd for $C_{20}H_{24}BrN_4O_3$ 467.11 found 468.9. $^1$H NMR (CD$_3$OD, 400 MHz) δ (ppm): 7.51-7.62 (m, 2 H), 7.40-7.42 (m, 2 H), 5.12-5.16 (m, 1 H), 4.22-4.20 (m, 1 H), 4.05-3.95 (m, 1 H), 3.88-3.82 (m, 1 H), 3.65 (s, 3 H), 2.41-2.11 (m, 3 H), 2.05-1.99 (m, 1 H), 0.97-0.88 (m, 7 H).

Preparation 38-B: ((S)-1-{(S)-2-[4-(4'-Amino-2,2'-difluoro-biphenyl-4-yl)-1H-imidazol-2-yl]-pyrrolidine-1-carbonyl}-2-methyl-propyl)-carbamic acid methyl ester

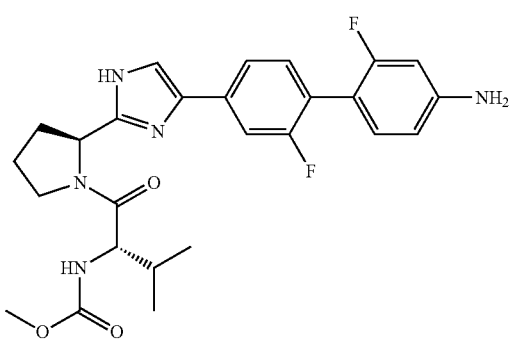

Potassium carbonate (300 mg, 2.1 mmol) was added to a solution of ((S)-1-{(S)-2-[4-(4-bromo-3-fluoro-phenyl)-1H-imidazol-2-yl]-pyrrolidine-1-carbonyl}-2-methyl-propyl)-carbamic acid methyl ester (200 mg, 0.4 mmol) and 3-fluoro-4-(4,4,5,5-tetramethyl-[1,3,2]dioxaborolan-2-yl)-phenylamine (130 mg, 0.55 mmol) dissolved in toluene (0.91 mL, 8.6 mmol) and water (0.38 mL, 21 mmol). The reaction mixture was sparged under nitrogen. Tetrakis(triphenylphosphine)palladium(0) (59 mg, 0.051 mmol) was added and the reaction mixture was sparged with nitrogen and heated at 100° C. overnight. The reaction mixture was diluted in ethyl acetate and washed with water and brine. The organic layer was dried over sodium sulfate, filtered and concentrated to produce a red solid. (m/z): [M+H]$^+$ calcd for $C_{26}H_{29}F_2N_5O_3$ 498.20 found 498.5

The red solid was purified by silica gel chromatography (0-100% ethyl acetate:hexanes) to produce the desired product as a yellow solid, containing triphenylphosphine oxide. A portion of the yellow solid (50 mg) was dissolved in 1:1 acetic acid:water (5 mL) and purified by reverse phase HPLC to produce the TFA salt of the title intermediate as a white powder (210 mg, 99.3% purity).

Preparation 39: ((S)-1-{(S)-2-[4-(4'-Amino-5'-fluoro-2'-trifluoromethyl-biphenyl-4-yl)-1H-imidazol-2-yl]-pyrrolidine-1-carbonyl}-2-methyl-propyl)-carbamic acid methyl ester

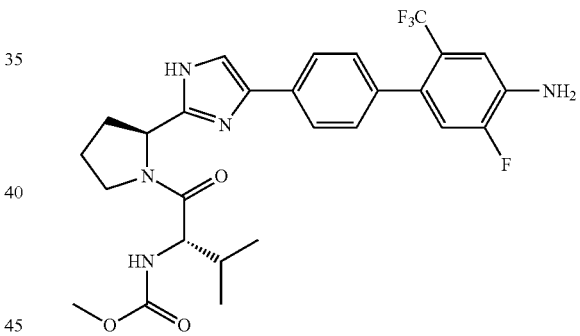

A mixture of 4-bromo-2-fluoro-5-(trifluoromethyl)aniline (78 mg, 0.302 mmol) and [(S)-2-methyl-1-((S)-2-{4-[4-(4,4,5,5-tetramethyl-[1,3,2]dioxaborolan-2-yl)-phenyl]-1H-imidazol-2-yl}-pyrrolidine-1-carbonyl)-propyl]-carbamic acid methyl ester (150 mg, 0.302 mmol) in toluene (0.6 mL, 6 mmol) and water (0.4 mL, 20 mmol) was purged with nitrogen. Potassium carbonate (208.8 g, 1.511 mmol) and tetrakis (triphenylphosphine)-palladium(0) (35 mg, 0.030 mmol) were added under an atmosphere of nitrogen. The reaction mixture was capped and heated at 100° C. overnight, cooled to RT, and partitioned between ethyl acetate (5.0 mL) and water (1.5 mL). The organic layer was dried over sodium sulfate, filtered, and concentrated to give a yellowish oil, which was purified by silica gel chromatography (12 g silica gel, 0-100% EtOAc/hexanes). Desired fractions were combined and concentrated to give the title intermediate as a yellowish solid (128 mg, 77% yield). (m/z): [M+H]+ calcd for C27H24F4N5O3 548.22 found 548.6.

Preparation 40: {(S)-1-[(S)-2-(4-{5'-Fluoro-4'-[(6-fluoro-pyridine-3-carbonyl)-amino]-2'-trifluoromethyl-biphenyl-4-yl}-1H-imidazol-2-yl)-pyrrolidine-1-carbonyl]-2-methyl-propyl}-carbamic acid methyl ester

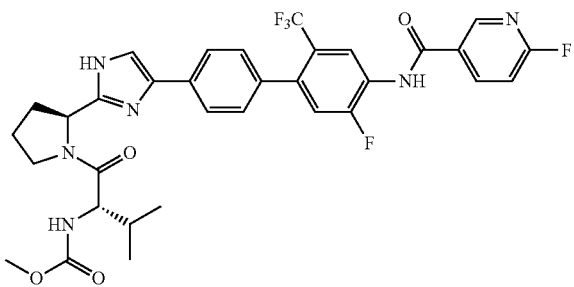 [SMILES: COC(=O)N[C@H](C(=O)N1CCC[C@H]1c1nc(-c2ccc(-c3cc(F)c(NC(=O)c4ccc(F)nc4)cc3C(F)(F)F)cc2)c[nH]1)C(C)C]

To a solution of ((S)-1-{(S)-2-[4-(4'-amino-5'-fluoro-2'-trifluoromethyl-biphenyl-4-yl)-1H-imidazol-2-yl]-pyrrolidine-1-carbonyl}-2-methyl-propyl)-carbamic acid methyl ester (128 mg, 0.234 mmol; Preparation 39) in DCM (3 mL, 47 mmol) and DMA (0.3 mL, 3 mmol) was added 2-fluoropyridine-5-carbonyl chloride (37 mg, 0.234 mmol), and the resulting solution was stirred at RT overnight. The reaction mixture was concentrated by rotary evaporation to give the monoHCl salt of the title intermediate as a brownish oil (163 mg), which was used without further purification. (m/z): [M+H]+ calcd for C33H31F5N6O4 671.23 found 671.7.

Preparation 41: ((S)-1-{(S)-2-[4-(5'-Fluoro-4'-{[6-((R)-2-methyl-piperazin-1-yl)-pyridine-3-carbonyl]-amino}-2'-trifluoromethyl-biphenyl-4-yl)-1H-imidazol-2-yl]-pyrrolidine-1-carbonyl}-2-methyl-propyl)-carbamic acid methyl ester A solution of {(S)-1-[(S)-2-(4-{5'-fluoro-4'-[(6-fluoro-pyridine-3-carbonyl)-amino]-2'-trifluoromethyl-biphenyl-4-yl}-1H-imidazol-2-yl)-pyrrolidine-1-carbonyl]-2-methyl-propyl}-carbamic acid methyl ester HCl (100 mg, 0.141 mmol, Preparation 40), (R)-3-methyl-piperazine-1-carboxylic acid tert-butyl ester (283 mg, 1.414 mmol), and N,N-diisopropylethylamine (246.3 uL, 1.414 mmol) was stirred in DMSO (1.5 mL, 21 mmol) at 120° C. overnight. The reaction mixture was concentrated by rotary evaporation to provide a crude intermediate which was treated with 4.0 M HCl in 1,4-dioxane (1.0 mL, 4.0 mmol) for 1 h, concentrated by rotary evaporation, dissolved in 1:1 acetic acid:water (8 mL), filtered and purified by reverse phase HPLC. Fractions were combined and lyophilized to give the tri-TFA salt of the title intermediate (54 mg, 35% yield). (m/z): [M+H]+ calcd for C38H42F4N8O4 751.33 found 751.7.

Preparation 42:
4-Bromo-2-fluoro-5-trifluoromethoxy-phenylamine

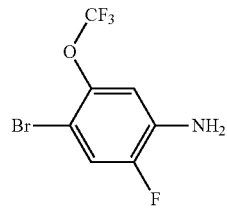

To a mixture of 2-fluoro-5-(trifluoromethoxy)aniline (1 g, 5 mmol) dissolved in DMF (2 mL) was slowly added a solution of N-bromosuccinimide (1.1 g, 6.2 mmol) dissolved in DMF (2 mL). The reaction mixture was stirred at room temperature for 1 h, concentrated and extracted with ethyl acetate/water. The organic layer was dried over sodium sulfate, filtered, concentrated and purified by silica gel chromatography (eluted 0-10% ethyl acetate:hexanes) to produce the

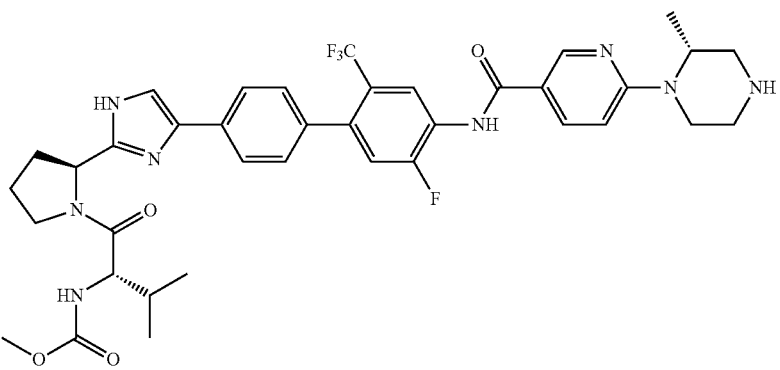 [SMILES: COC(=O)N[C@H](C(=O)N1CCC[C@H]1c1nc(-c2ccc(-c3cc(F)c(NC(=O)c4ccc(N5CCNC[C@H]5C)nc4)cc3C(F)(F)F)cc2)c[nH]1)C(C)C]

title intermediate as a red oil (818 mg, 58% yield). (m/z): [M+H]+ calcd for $C_7H_4BrF_4NO$ 273.94, 275.94 found 276.1.

Preparation 43: ((S)-1-{(S)-2-[4-(4'-Amino-5'-fluoro-2'-trifluoromethoxy-biphenyl-4-yl)-1H-imidazol-2-yl]-pyrrolidine-1-carbonyl}-2-methyl-propyl)-carbamic acid methyl ester

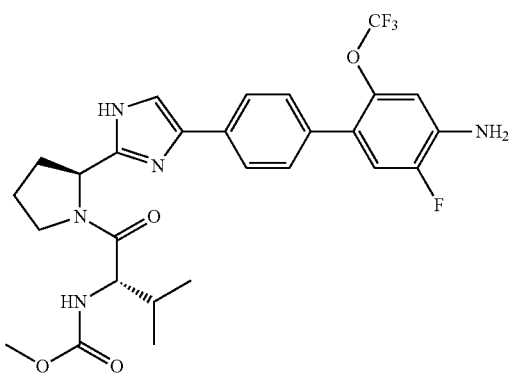 [SMILES: COC(=O)N[C@H](C(=O)N1CCC[C@H]1c1nc(-c2ccc(-c3cc(F)c(N)cc3OC(F)(F)F)cc2)c[nH]1)C(C)C]

Potassium carbonate (350 mg, 2.5 mmol) was added to a solution of [(S)-2-methyl-1-((S)-2-{4-[4-(4,4,5,5-tetramethyl-[1,3,2]dioxaborolan-2-yl)-phenyl]-1H-imidazol-2-yl}-pyrrolidine-1-carbonyl)-propyl]-carbamic acid methyl ester (250 mg, 0.50 mmol) and 4-bromo-2-fluoro-5-trifluoromethoxy-phenylamine (140 mg, 0.50 mmol; Preparation 42) dissolved in toluene (2 mL) and water (0.54 mL). The reaction mixture was sparged under nitrogen. Tetrakis(triphenylphosphine)palladium(0) (70 mg, 0.06 mmol) was added and the reaction mixture was sparged with nitrogen and heated at 100° C. overnight. The reaction mixture was diluted in ethyl acetate and washed with water and brine. The organic layer was dried over sodium sulfate, filtered, and concentrated to produce a red solid, which was purified by silica gel chromatography (0-100% ethyl acetate:hexanes) to produce the desired product as a white solid with some triphenylphosphine oxide impurity. (m/z): [M+H]+ calcd for $C_{27}H_{29}F_4N_5O_4$ 564.2 found 564.4.

The solid (50 mg) was dissolved in 1:1 acetic acid:water (5 mL) and purified by reverse phase HPLC to produce the TFA salt of the title intermediate as a white solid Preparation 44: ((S)-1-{(S)-2-[4-(5'-Fluoro-4'-{[6-((R)-2-methyl-piperazin-1-yl)-pyridine-3-carbonyl]-amino}-2'-trifluoromethoxy-biphenyl-4-yl)-1H-imidazol-2-yl]-pyrrolidine-1-carbonyl}-2-methyl-propyl)-carbamic acid methyl ester

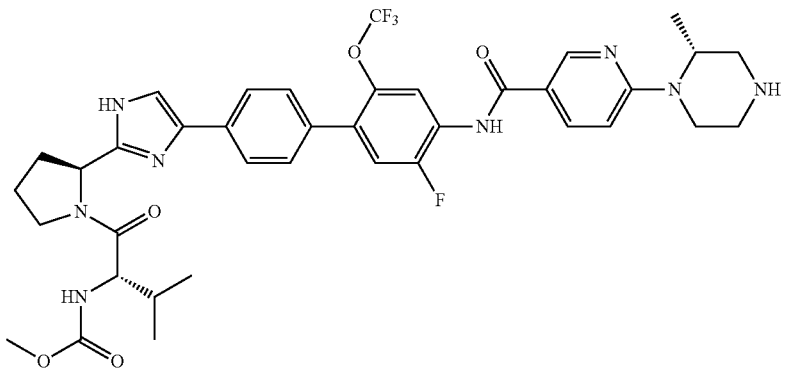 [SMILES: COC(=O)N[C@H](C(=O)N1CCC[C@H]1c1nc(-c2ccc(-c3cc(F)c(NC(=O)c4ccc(N5CCNC[C@H]5C)nc4)cc3OC(F)(F)F)cc2)c[nH]1)C(C)C]

(a) {(S)-1-[(S)-2-(4-{5'-Fluoro-4'-[(6-fluoro-pyridine-3-carbonyl)-amino]-2'-trifluoromethoxy-biphenyl-4-yl}-1H-imidazol-2-yl)-pyrrolidine-1-carbonyl]-2-methyl-propyl}-carbamic acid methyl ester To a solution of ((S)-1-{(S)-2-[4-(4'-amino-5'-fluoro-2'-trifluoromethoxy-biphenyl-4-yl)-1H-imidazol-2-yl]-pyrrolidine-1-carbonyl}-2-methyl-propyl)-carbamic acid methyl ester (50 mg, 0.09 mmol, Preparation 43) in DCM (0.6 mL, 9 mmol) was slowly added 2-fluoropyridine-5-carbonyl chloride (10 mg, 0.09 mmol;) and the reaction mixture was stirred at room temperature for 5 min and then concentrated to provide a colored solid.

(b) (R)-4-[5-(5-Fluoro-4'-{2-[(S)-1-((S)-2-methoxycarbonylamino-3-methyl-butyryl)-pyrrolidin-2-yl]-1H-imidazol-4-yl}-2-trifluoromethoxy-biphenyl-4-ylcarbamoyl)-pyridin-2-yl]-3-methyl-piperazine-1-carboxylic acid tert butyl ester The solid from the previous step was dissolved in a mixture of dimethyl sulfoxide (0.20 mL, 2.8 mmol) and N,N-diiso propylethylamine (0.32 mL, 1.8 mmol) and then (R)-3-methyl-piperazine-1-carboxylic acid tert-butyl ester (180 mg, 0.91 mmol) was added and the reaction mixture was heated at 120° C. overnight and concentrated by rotary evaporation to produce a dark colored oil.

(c) ((S)-1-{(S)-2-[4-(5'-Fluoro-4'-{[6-((R)-2-methyl-piperazin-1-yl)-pyridine-3-carbonyl]-amino}-2'-trifluoromethoxy-biphenyl-4-yl)-1H-imidazol-2-yl]-pyrrolidine-1-carbonyl}-2-methyl-propyl)-carbamic acid methyl ester The oil from the previous step was treated with 4 M HCl in 1,4-dioxane (2 mL, 8 mmol) and heated at 50° C. for 1 h. The reaction mixture was concentrated, and evaporated with ethyl acetate (2×) to produce the HCl salt of the desired product as a solid, which was purified by reverse phase HPLC to produce the tri-TFA salt of the desired product as a white solid (53 mg, 50% yield). (m/z): [M+H]$^+$ calcd for $C_{38}H_{42}F_4N_8O_5$ 767.32 found 767.7

Preparation 45: 4-Bromo-3-trifluoromethoxy-benzoic acid methyl ester

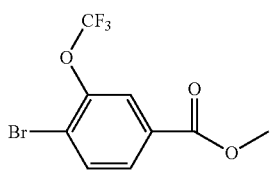

(a) 4-Amino-3-trifluoromethoxy-benzoic acid methyl ester

A mixture of 4-amino-3-(trifluoromethoxy)benzoic acid (5 g, 22.61 mmol), methanol (75 mL) and 4.0 M HCl in 1,4-dioxane (56.53 mL, 226.1 mmol) was stirred at RT for 2 days. The reaction mixture was concentrated and the resulting residue was evaporated with EtOAc (3×20 mL) and dried under vacuum to provide the HCl salt of the title intermediate (6.9 g).

(b) 4-Bromo-3-trifluoromethoxy-benzoic acid methyl ester

The product of the previous step (2.00 g, 7.36 mmol) was dissolved in a mixture of acetonitrile (89 mL) and water (9.2 mL) at RT. Copper(II) bromide (2.27 g, 10.2 mmol) was added followed by tert-butyl nitrite (1.51 mL, 12.7 mmol) dropwise. The resulting mixture was heated at 70° C. for 1 hour, cooled to RT, and treated wtih saturated sodium bicarbonate (30 mL). The mixture was extracted with EtOAc (100 mL). The aqueous layer was extracted with EtOAc (100 mL). Combined organic layers were washed with brine (30 mL), dried over sodium sulfate, filtered, and concentrated to give a brownish oil, which was purified by silica gel chromatography, (0-30% EtOAc/hexanes). Desired fractions were combined and concentrated to give the title intermediate as a light yellowish oil (1.57 g, 71% yield) which was confirmed by NMR.

Preparation 46: 4'-{2-[(S)-1-((S)-2-Methoxycarbonylamino-3-methyl-butyryl)-pyrrolidin-2-yl]-1H-imidazol-4-yl}-2-trifluoromethoxy-biphenyl-4-carboxylic acid

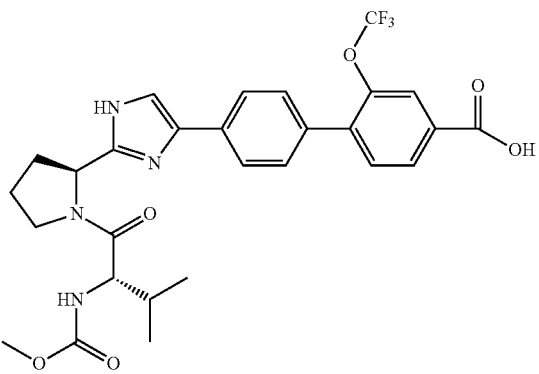 [SMILES: COC(=O)N[C@H](C(=O)N1CCC[C@H]1c1nc(-c2ccc(-c3ccc(C(=O)O)cc3OC(F)(F)F)cc2)c[nH]1)C(C)C]

To a mixture of 4-Bromo-3-trifluoromethoxy-benzoic acid methyl ester (331 mg, 1.11 mmol; Preparation 45) and [(S)-2-methyl-1-((S)-2-{4-[4-(4,4,5,5-tetramethyl-[1,3,2]dioxaborolan-2-yl)-phenyl]-1H-imidazol-2-yl}-pyrrolidine-1-carbonyl)-propyl]-carbamic acid methyl ester (500 mg, 1.01 mmol) in toluene (1 mL) and water (1 mL) at RT was added potassium carbonate (696 mg, 5.04 mmol). The mixture was degassed and flushed with nitrogen. Tetrakis(triphenylphosphine)palladium(0) (116 mg, 0.101 mmol) was added under niotrogen and then the reaction mixture was capped and was heated at 100° C. overnight, cooled to RT and partitioned between EtOAc (20 mL) and water (5 mL). The organic layer was dried over sodium sulfate, filtered and concentrated to give a brownish oil.

The oily residue from the previous step was treated with methanol (6 mL) and water (1 mL) and lithium hydroxide monohydrate (254 mg, 6.04 mmol) at 65° C. for 1 hour. The reaction mixture was concentrated and the resulting residue was treated with 1:1 acetic acid:water (20 mL), filtered, and purified by reverse phase HPLC. Desired fractions were combined and freeze dried to give the TFA salt of the title intermediate as a white solid (190 mg). (m/z): [M+H]$^+$ calcd for $C_{28}H_{29}F_3N_4O_6$ 575.20 found 575.5.

Preparation 47: (R)-2-Methyl-1-(5-nitro-pyridin-2-yl)-piperazine

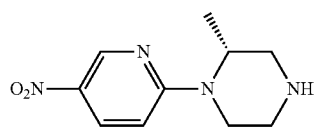

(a) (R)-3-Methyl-4-(5-nitro-pyridin-2-yl)-piperazine-1-carboxylic acid tert-butyl ester A mixture of 2-chloro-5-nitropyridine (1.0 g, 6.3 mmol), (R)-3-methyl-piperazine-1-carboxylic acid tert-butyl ester (1.4 g, 6.9 mmol) and potassium carbonate (1.308 g, 9.46 mmol) in DMSO (20 mL) was heated at 100° C. overnight. The reaction mixture was cooled to RT, and filtered through a pad of silica gel, eluted with EtOAc (150 mL). The filtrate was washed with water (2×20 mL) and brine (20 mL), dried over sodium sulfate, filtered and concentrated to give a brownish oil which was purified by silica gel chromatography (80 g silica gel, 0-60% EtOAc/hexanes). Desired fractions were combined and concentrated to give the title intermediate as a yellowish solid. (m/z): [M+H]$^+$ calcd for $C_{15}H_{22}N_4O_4$ 323.16 found 323.3.

(b) (R)-2-Methyl-1-(5-nitro-pyridin-2-yl)-piperazine

The solid from previous step was treated with 4 M HCl in 1,4-dioxane (47.3 mL) and HCl (11.6 mL) and the reaction mixture was stirred at RT for 2 h and concentrated to produce a yellow solid, which was evaporated twice with ethyl acetate to yield the diHCl salt of the title intermediate (940 mg, 50% yield) as a yellow solid. (m/z): [M+H]$^+$ calcd for $C_{10}H_{14}N_4O_2$ 223.11 found 223.2.

Preparation 48: ((S)-1-{(S)-2-[(R)-4-(5-Amino-pyridin-2-yl)-3-methyl-piperazine-1-carbonyl]-2-methyl-pyrrolidine-1-carbonyl}-2-methyl-propyl)-carbamic acid methylester (b) f(S)-1-{(S)-2-[(R)-4-(5-Amino-pyridin-2-yl)-3-methyl-piperazine-1-carbonyl]-2-methyl-pyrrolidine-1-carbonyl}-2-methyl-propyl)-carbamic acid methyl-ester The oil from the previous step was dissolved in methanol (15 mL) and treated with 50% wet palladium hydroxide on carbon (20% w/w) (13 mg, 0.45 mmol) and stirred for 2 h at RT. The reaction mixture was filtered through Celite, and concentrated under vacuum to produce a dark red oil, which was purified by silica gel chromatography (0-100% ethyl acetate:hexanes for 15 min then 0-5% methanol:EtOAc for another 15 min) to yield the title intermediate (375 mg; 40% yield) as a reddish solid. (m/z): [M+H]$^+$ calcd for $C_{23}H_{36}N_6O_4$ 461.28 found 461.6.

Preparation 49: (2S,5R)-4-[5-(4-Bromo-2-fluoro-5-trifluoromethoxy-phenylcarbamoyl)-pyridin-2-yl]-2,5-dimethyl-piperazine-1-carboxylic acid tert-butyl ester

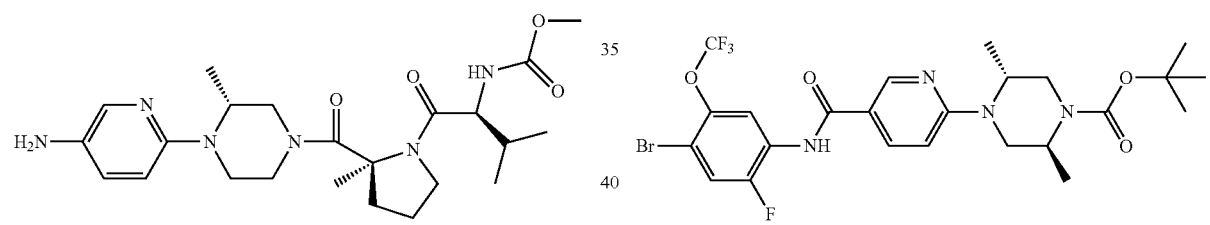

(a) ((S)-2-Methyl-1-{(S)-2-methyl-2-[(R)-3-methyl-4-(5-nitro-pyridin-2-yl)-piperazine-1-carbonyl]-pyrrolidine-1-carbonyl}-propyl)-carbamic acid methyl ester (S)-1-((S)-2-Methoxycarbonylamino-3-methyl-butyryl)-2-methyl-pyrrolidine-2-carboxylic acid (770 mg, 2.7 mmol) was dissolved in DMA (17 mL) and HATU (1.0 g, 2.7 mmol) was added. The reaction mixture was stirred for 20 min and then (R)-2-methyl-1-(5-nitro-pyridin-2-yl)-piperazine di-HCl (700 mg, 2 mmol; Preparation 47) was added followed by N,N-diisopropylethylamine (2.0 mL, 11 mmol) and the reaction mixture was stirred at 55° C. overnight, cooled to RT, concentrated by rotary evaporation and extracted with EtOAc/water. The organic layer was washed with water, and then brine, dried over sodium sulfate, concentrated under vacuum, and purified by silica gel chromatography (0-100% ethyl acetate:hexanes) to yield the title intermediate (970 mg) as a yellow oil. (m/z): [M+H]$^+$ calcd for $C_{23}H_{34}N_6O_6$ 491.25 found 491.7.

To a solution of 4-bromo-2-fluoro-5-trifluoromethoxy-phenylamine (500 mg, 2 mmol) dissolved in DCM (1 mL) was slowly added a solution of 2-fluoropyridine-5-carbonyl chloride (290 mg, 1.8 mmol) in DCM (1 mL). A few drops of DMA were added and the reaction mixture was concentrated to form N-(4-bromo-2-fluoro-5-trifluoromethoxy-phenyl)-6-fluoro-nicotinamide as a purple solid.

The solid from the previous step was dissolved in a mixture of N,N-diisopropylethylamine (0.7 mL, 4 mmol) and DMSO (0.7 mL, 10 mmol) and (2S,5R)-2,5-dimethyl-piperazine-1-carboxylic acid tert-butyl ester (590 mg, 2.7 mmol) was added and the reaction mixture heated at 120° C. overnight, concentrated by rotary evaporation, dissolved in a small amount of DCM and purified by silica gel chromatography (0-40% ethyl acetate:hexanes) to produce the title intermediate (613 mg, 57% yield) as a white solid. (m/z): [M+H]$^+$ calcd for $C_{24}H_{27}F_4N_4O_4$ 591.12 found 591.4.

Preparation 50: ((S)-1-{(S)-2-[4-(4'-{[6-((2R,5S)-2,5-Dimethyl-piperazin-1-yl)-pyridine-3-carbonyl]-amino}-5'-fluoro-2'-trifluoromethoxy-biphenyl-4-yl)-1H-imidazol-2-yl]-pyrrolidine-1-carbonyl}-2-methyl-propyl)-carbamic acid methyl ester

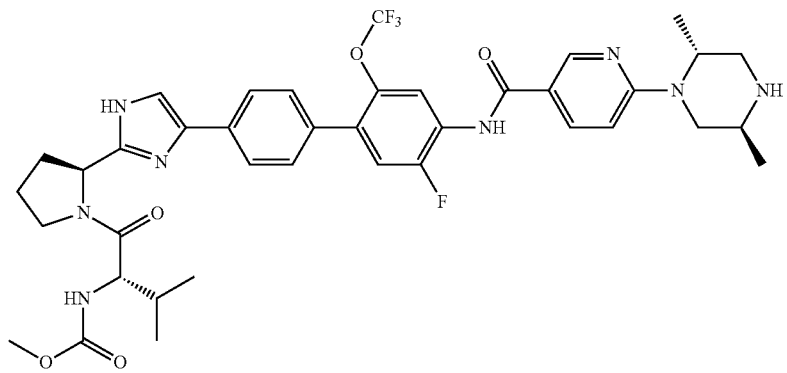

Potassium carbonate (470 mg, 3.4 mmol) was added to a solution of [(S)-2-methyl-1-((S)-2-{4-[4-(4,4,5,5-tetramethyl-[1,3,2]dioxaborolan-2-yl)-phenyl]-1H-imidazol-2-yl}-pyrrolidine-1-carbonyl)-propyl]-carbamic acid methyl ester (340 mg, 0.68 mmol) and (2S,5R)-4-[5-(4-bromo-2-fluoro-5-trifluoromethoxy-phenylcarbamoyl)-pyridin-2-yl]-2,5-dimethyl-piperazine-1-carboxylic acid tert-butyl ester (400 mg, 0.68 mmol; Preparation 49) dissolved in toluene (2.5 mL) and water (0.73 mL). The reaction mixture was sparged under nitrogen. Tetrakis(triphenylphosphine)palladium(0) (94 mg, 0.081 mmol) was added and the reaction mixture was sparged with nitrogen and heated at 100° C. for 4 h. The reaction mixture was diluted in ethyl acetate and washed with water and brine. The organic layer was dried over sodium sulfate, filtered, and concentrated to produce (2S,5R)-4-[5-(5-fluoro-4'-{2-[(S)-1-((S)-2-methoxycarbonylamino-3-methyl-butyryl)-pyrrolidin-2-yl]-1H-imidazol-4-yl}-2-trifluoromethoxy-biphenyl-4-ylcarbamoyl)-pyridin-2-yl]-2,5-dimethyl-piperazine-1-carboxylic acid tert-butyl ester as a red solid.

The solid from the previous step was treated with 4 M HCl in 1,4-dioxane (5 mL, 20 mmol) and stirred at 50° C. for 30 min. The reaction mixture was concentrated, dissolved in 1:1 acetic acid:water (8 mL) and purified by reverse phase HPLC. Fractions containing desired compound were combined and lyophilized to produce the tri-TFA salt of the title intermediate (490 mg, 64% yield) as a white powder. (m/z): [M+H]$^+$ calcd for $C_{39}H_{44}F_4N_8O_5$ 781.34 found 781.6.

Preparation 51:
5-Amino-2-bromo-4-chlorobenzotrifluoride

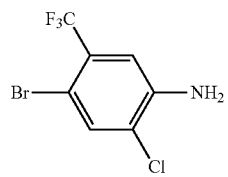 [SMILES: Nc1cc(C(F)(F)F)c(Br)cc1Cl]

A solution of N-bromosuccinimide (1.0 g, 5.6 mmol) dissolved in DMF (3 mL) was slowly added to a mixture of 3-amino-4-chlorobenzotrifluoride (1 g, 5 mmol) dissolved in DMF (2 mL) and the reaction mixture was stirred at RT for 20 min, concentrated, and extracted with ethyl acetate/water. The organic layer was dried over sodium sulfate, filtered, concentrated, and purified by flash chromatography (eluted with 100% hexanes) to produce the title intermediate as a reddish colored oil (970 mg, 70% yield). (m/z): [M+H]$^+$ calcd for $C_7H_4BrClF_3N$, 273.92, 275.92 found 276.2.

Preparation 52 ((S)-1-{(S)-2-[4-(4'-Amino-5'-chloro-2'-trifluoromethyl-biphenyl-4-yl)-1H-imidazol-2-yl]-pyrrolidine-1-carbonyl}-2-methyl-propyl)-carbamic acid methyl ester

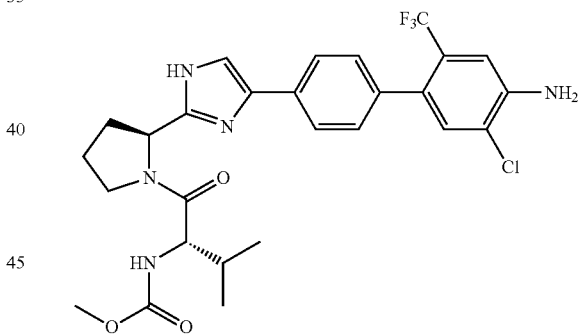

Potassium carbonate (280 mg, 2.0 mmol) was added to a solution of [(S)-2-methyl-1-((S)-2-{4-[4-(4,4,5,5-tetramethyl-[1,3,2]dioxaborolan-2-yl)-phenyl]-1H-imidazol-2-yl}-pyrrolidine-1-carbonyl)-propyl]-carbamic acid methyl ester (200 mg, 0.40 mmol) and 5-amino-2-bromo-4-chlorobenzotrifluoride (110 mg, 0.40 mmol; Preparation 51) dissolved in toluene (1.3 mL) and water (0.43 mL). The reaction mixture was sparged under nitrogen. Tetrakis(triphenylphosphine)palladium(0) (56 mg, 0.48 mmol) was added and the reaction mixture was sparged with nitrogen and heated at 100° C. for 4 h. The reaction mixture was diluted in ethyl acetate and washed with water and brine. The organic layer was dried over sodium sulfate, filtered, and concentrated to produce a red solid, which was purified by silica gel chromatography (0-100% ethyl acetate:hexanes) to produce the desired product as a yellow solid.

The solid (~30 mg) was dissolved in 1:1 acetic acid:water (5 mL) and purified by reverse phase HPLC to produce the di-TFA salt of the title intermediate (31.1 mg). (m/z): [M+H]$^+$ calcd for $C_{27}H_{29}ClF_3N_5O_3$ 564.19 found 564.2.

Preparation 53: ((S)-1-{(S)-2-[4-(5'-Chloro-4'-{[6-((R)-2-methyl-piperazin-1-yl)-pyridine-3-carbonyl]-amino}-2'-trifluoromethyl-biphenyl-4-yl)-1H-imidazol-2-yl]-pyrrolidine-1-carbonyl}-2-methyl-propyl)-carbamic acidmethyl ester

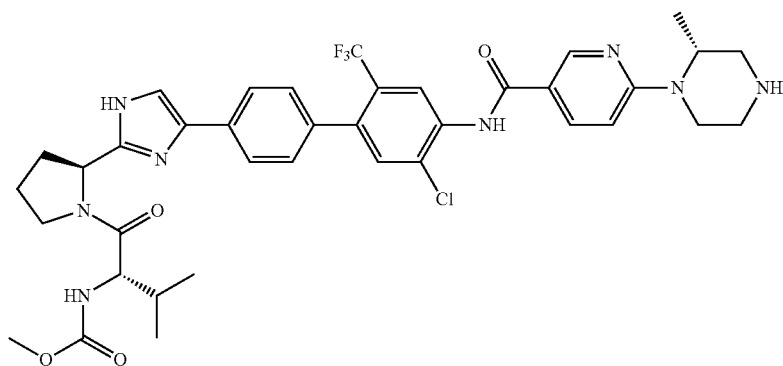

To a solution of ((S)-1-{(S)-2-[4-(4'-amino-5'-chloro-2'-trifluoromethyl-biphenyl-4-yl)-1H-imidazol-2-yl]-pyrrolidine-1-carbonyl}-2-methyl-propyl)-carbamic acid methyl ester (50 mg, 0.09 mmol; Preparation 52) dissolved in DCM (0.3 mL) was slowly added a solution of 2-fluoropyridine-5-carbonyl chloride (14 mg, 0.091 mmol) dissolved in DCM (0.3 mL). The reaction mixture was stirred at RT for 5 min and concentrated to produce {(S)-1-[(S)-2-(4-{5'-chloro-4'-[(6-fluoro-pyridine-3-carbonyl)-amino]-2'-trifluoromethyl-biphenyl-4-yl}-1H-imidazol-2-yl)-pyrrolidine-1-carbonyl]-2-methyl-propyl}-carbamic acid methyl ester as a yellow solid.

The yellow solid from the previous step was dissolved in a mixture of DMSO (0.3 mL, 4 mmol) and N,N-diisopropylethylamine (0.3 mL, 2 mmol) and (R)-3-methyl-piperazine-1-carboxylic acid tert-butyl ester (180 mg, 0.91 mmol) was added. The reaction mixture was heated at 100° C. for 72 h, and concentrated by rotary evaporation to produce (R)-4-[5-(5-chloro-4'-{2-[(S)-1-((S)-2-methoxycarbonylamino-3-methyl-butyryl)-pyrrolidin-2-yl]-1H-imidazol-4-yl}-2-trifluoromethyl-biphenyl-4-ylcarbamoyl)-pyridin-2-yl]-3-methyl-piperazine-1-carboxylic acid tert-butyl ester as a dark colored oil.

The oil from the previous step was treated with 4 M HCl in 1,4-dioxane (2 mL, 8 mmol) and the reaction mixture was stirred at 50° C. for 1 h, and concentrated under vacuum to produce the HCl salt of the desired product, which was dissolved in 1:1 acetic acid:water (5 mL) and purified by reverse phase HPLC. Fractions containing desired product were combined and lyophilized to produce the tri-TFA salt of the title intermediate (30 mg, 30% yield) as a white powder. (m/z): [M+H]$^+$ calcd for $C_{38}H_{42}ClF_3N_8O_4$ 767.30 found 767.5.

Preparation 54: (2S,5R)-4-[5-(4-Bromo-2-chloro-5-trifluoromethyl-phenylcarbamoyl)-pyridin-2-yl]-2,5-dimethyl-piperazine-1-carboxylic acid tert-butyl

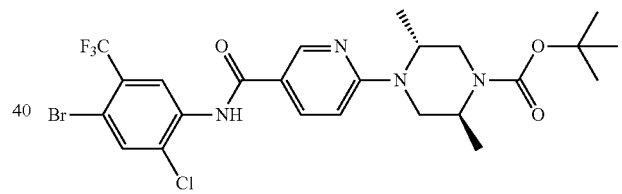

To a solution of 5-amino-2-bromo-4-chlorobenzotrifluoride (466 mg, 1.70 mmol) dissolved in DCM (1 mL) was slowly added a solution of 2-fluoropyridine-5-carbonyl chloride (270 mg, 1.70 mmol) in DCM (1 mL). A few drops of DMA were added and the reaction mixture was concentrated to form N-(4-bromo-2-chloro-5-trifluoromethyl-phenyl)-6-fluoro-nicotinamide as a purple solid.

Half of the solid from the previous step was treated with N,N-diisopropylethylamine (0.5 mL, 3 mmol), DMSO (0.5 mL, 7 mmol) and (2S,5R)-2,5-dimethyl-piperazine-1-carboxylic acid tert-butyl ester (273 mg, 1.27 mmol) and the reaction mixture was heated at 120° C. overnight, concentrated by rotary evaporation, dissolved in a small amount of DCM and purified by silica gel chromatography (0-50% ethyl acetate:hexanes) to produce the title intermediate (288 mg, 29% yield) as a yellow solid. (m/z): [M+H]$^+$ calcd for $C_{24}H_{27}F_4N_4O_4$ 591.09, 593.09 found 593.2.

Preparation 55: ((S)-1-{(S)-2-[4-5'-Chloro-(4'-{[6-((2R,5S)-2,5-dimethyl-piperazin-1-yl)-pyridine-3-carbonyl]-amino}-2'-trifluoromethyl-biphenyl-4-yl)-1H-imidazol-2-yl]-pyrrolidine-1-carbonyl}-2-methyl-propyl)-carbamic acid methyl ester

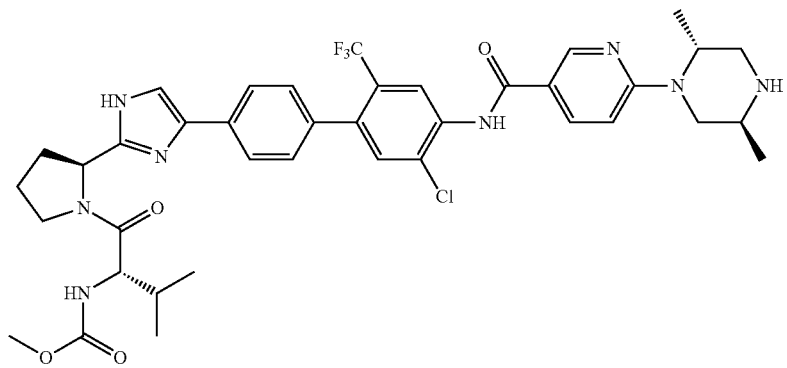

Following the procedure of Preparation 50 at the 0.24 mmol scale, substituting (2S,5R)-4-[5-(4-bromo-2-chloro-5-trifluoromethyl-phenylcarbamoyl)-pyridin-2-yl]-2,5-dimethyl-piperazine-1-carboxylic acid tert-butyl ester (140 mg, 0.24 mmol, Preparation 54) for (2S,5R)-4-[5-(4-bromo-2-fluoro-5-trifluoromethoxy-phenylcarbamoyl)-pyridin-2-yl]-2,5-dimethyl-piperazine-1-carboxylic acid tert-butyl ester (Preparation 49), the tri-TFA salt of the title intermediate (490 mg, 64% yield) was prepared as a white powder. (m/z): [M+H]+ calcd for $C_{39}H_{44}ClF_3N_8O_4$ 781.31 found 781.6.

Preparation 56: {(S)-2-Methyl-1-[(S)-2-(4-{4'46-((R)-2-methyl-piperazin-1-yl)-pyridin-3-ylcarbamoyl]-2'-trifluoromethoxy-biphenyl-4-yl}-1H-imidazol-2-yl)-pyrrolidine-1-carbonyl]-propyl}-carbamic acid methyl ester A mixture of 4'-{2-[(S)-1-((S)-2-methoxycarbonylamino-3-methyl-butyryl)-pyrrolidin-2-yl]-1H-imidazol-4-yl}-2-trifluoromethoxy-biphenyl-4-carboxylic acid TFA (600 mg, 0.9 mmol) and HATU (364 mg, 0.96 mmol) in DMA (8 mL) was stirred at RT for 15 min and then 0.5 M (R)-4-(5-amino-pyridin-2-yl)-3-methyl-piperazine-1-carboxylic acid tert-bu-tyl ester in DMA (1.7 mL) was added followed by N,N-diisopropylethylamine (0.76 mL, 4.36 mmol). The resulting mixture was heated at 55° C. overnight, washed with EtOAc (100 mL) and water (25 mL). The organic layer was washed again with water and then with brine, dried over sodium sulfate, filtered, and concentrated to yield a dark reddish oil which was purified by silica gel chromatography (40 g silica column, 0-80% hexane:EtOAc) to provide (R)-4-{5-[(4'-{2-[(S)-1-((S)-2-methoxycarbonylamino-3-methyl-butyryl)-pyrrolidin-2-yl]-1H-imidazol-4-yl}-2-trifluoromethoxy-biphenyl-4-carbonyl)-amino]-pyridin-2-yl}-3-methyl-piperazine-1-carboxylic acid tert-butyl ester (646 mg) as a light brownish solid.

The solid product was treated with 4.0 M HCl in 1,4-dioxane (6.5 mL, 26.14 mmol) and HCl (1.6 mL) and the reaction mixture was stirred at RT for 1 h, concentrated, and evaporated with EtOAc (2×1 mL) to to provide the tri-HCl

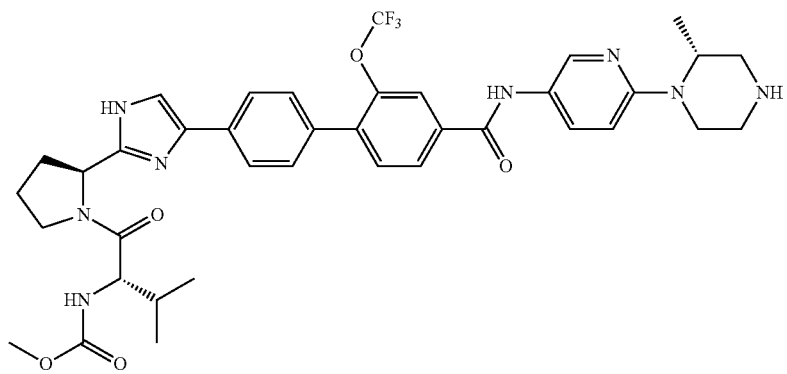 [SMILES: COC(=O)N[C@H](C(=O)N1CCC[C@H]1c1nc(-c2ccc(-c3ccc(C(=O)Nc4ccc(N5CCNC[C@H]5C)nc4)cc3OC(F)(F)F)cc2)c[nH]1)C(C)C]

salt of the title intermediate (693 mg) as a beige solid. (m/z): [M+H]+ calcd for $C_{38}H_{43}F_3N_8O_5$ 749.33 found 749.8.

Preparation 57: ((S)-2-Methyl-1-{(S)-2-[4-(4'-{6-[(R)-2-methyl-4-((S)-2-methyl-pyrrolidine-2-carbonyl)-piperazin-1-yl]-pyridin-3-ylcarbamoyl}-2'-trifluoromethoxy-biphenyl-4-yl)-1H-imidazol-2-yl]-pyrrolidine-1-carbonyl}-propyl)-carbamic acid methyl ester

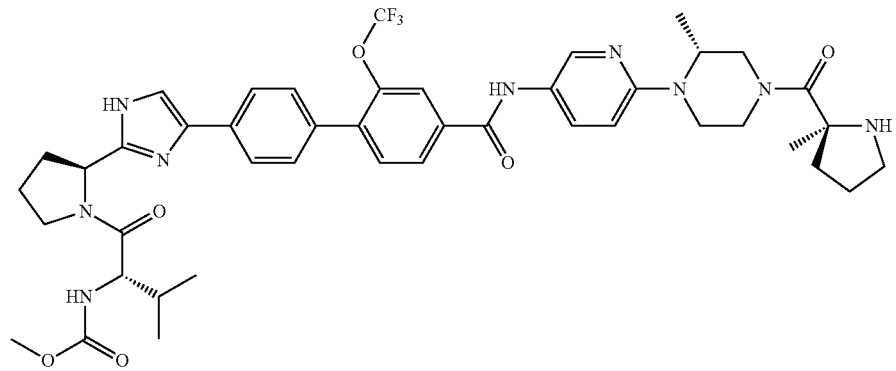 [SMILES: COC(=O)N[C@H](C(=O)N1CCC[C@H]1c1nc(-c2ccc(-c3ccc(C(=O)Nc4ccc(N5CCN(C(=O)[C@]6(C)CCCN6)C[C@H]5C)nc4)cc3OC(F)(F)F)cc2)c[nH]1)C(C)C]

To a mixture of (S)-2-methyl-pyrrolidine-1,2-dicarboxylic acid 1-tert-butyl ester (222 mg, 0.97 mmol) dissolved in DMA (6 mL) was added HATU (369 mg, 0.97 mmol) and the reaction mixture was stirred for 20 min and then {(S)-2-methyl-1-[(S)-2-(4-{4'-[6-((R)-2-methyl-piperazin-1-yl)-pyridin-3-ylcarbamoyl]-2'-trifluoromethoxy-biphenyl-4-yl}-1H-imidazol-2-yl)-pyrrolidine-1-carbonyl]-propyl}-carbamic acid methyl ester 3 HCl (693 mg, 0.81 mmol; Preparation 56) was added followed by N,N-diisopropylethylamine (0.71 mL, 4.04 mmol). The reaction mixture was stirred at 55° C. overnight, concentrated by rotary evaporation, and extracted with EtOAc (80 mL) and water (20 mL). The organic layer was washed again with water and then with brine, dried over sodium sulfate, filtered, and concentrated under vacuum, and purified by silica gel chromatography (40 g silica column, 0-100% ethyl acetate:hexanes) to yield 537 mg of a light brown solid.

The light brown solid from the previous step was treated with 4 M HCl in 1,4-dioxane (6.1 mL, 24.23 mmol) and HCl (1.5 mL) and stirred at RT for 1 h, concentrated, and evaporated with ethyl acetate (2×1 mL) to produce the tri-HCl salt of the title intermediate (569 mg) as a light yellow solid. (m/z): [M+H]+ calcd for $C_{44}H_{52}F_3N_9O_6$ 860.40 found 860.6.

Preparation 58: (2S,5R)-4-[5-(6-Bromo-2-methyl-pyridin-3-ylcarbamoyl)-pyridin-2-yl]-2,5-dimethyl-piperazine-1-carboxylic acid tert-butyl ester

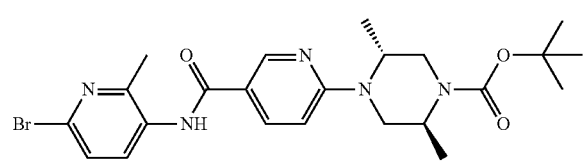 [SMILES: Cc1nc(Br)ccc1NC(=O)c1ccc(N2C[C@H](C)N(C(=O)OC(C)(C)C)C[C@H]2C)nc1]

(a) (2S,5R)-4-(5-Methoxycarbonyl-pyridin-2-yl)-2,5-dimethyl-piperazine-1-carboxylic acid tert-butyl ester A mixture of 6-fluoronicotinic acid methyl ester (1.0 g, 6.4 mmol), (2S,5R)-2,5-dimethyl-piperazine-1-carboxylic acid tert-butyl ester HCl (1.6 g, 6.4 mmol), and potassium carbonate (1.78 g, 12.9 mmol) were stirred in DMSO (10 mL) at 120° C. for 2 h, cooled, diluted with ethyl acetate (50 mL), washed with water (2×10 mL), dried over magnesium sulfate, filtered and concentrated.

(b) (2S,5R)-4-(5-Carboxy-pyridin-2-O-2,5-dimethyl-piperazine-1-carboxylic acid tert-butyl ester Lithium hydroxide (618 mg, 12.9 mmol) was added to a solution of the product of the previous step in methanol (15 mL) and water (3 mL), and the resulting mixture was stirred at 40° C. for 5 h, concentrated, and acidified with 1N HCl to pH 4. The resulting mixture was extracted with ethyl acetate (2×50 mL). The organic layer was dried over magnesium sulfate, filtered, concentrated, dissolved in 1:1 acetic acid: water (8 mL), filtered and purified by reverse phase HPLC to give the TFA salt of the title intermediate (1.55 g, 54% yield). (m/z): [M+H]+ calcd for $C_{17}H_{25}N_3O_4$ 336.18 found 336.4.

(c) (2S,5R)-4-[5-(6-Bromo-2-methyl-pyridin-3-ylcarbamoyl)-pyridin-2-yl]-2,5-dimethyl-piperazine-1-carboxylic acid tert-butyl ester The product of the previous step (180.2 mg, 0.40), EDC (115.3 mg, 0.60 mmol), and HOAt (81.9 mg, 0.60 mmol) were stirred in DMF (2 mL) atRT for 10 min and then 6-bromo-2-methyl-pyridin-3-ylamine (75 mg, 0.40 mmol) and N,N-diisopropylethylamine (0.35 mL, 2.01 mmol) were added, and the reaction mixture was stirred at 50° C. overnight, concentrated by rotary evaporation, dissolved in 1:1 acetic acid:water (5 mL), filtered, and purirfied by reverse phase HPLC. Fractions containing desired product were combined and lyophilized to give the TFA salt of the title intermediate (91 mg, 37% yield). (m/z): [M+H]+ calcd for $C_{23}H_{30}BrN_5O_3$ 504.15 found 504.3.

Preparation 59: [(S)-1-((S)-2-{4-[4-(5-{[6-((2R,5S)-2,5-Dimethyl-piperazin-1-yl)-pyridine-3-carbonyl]-amino}-6-methyl-pyridin-2-yl)-phenyl]-1H-imidazol-2-yl}-pyrrolidine-1-carbonyl)-2-methyl-propyl]-carbamic acid methyl ester

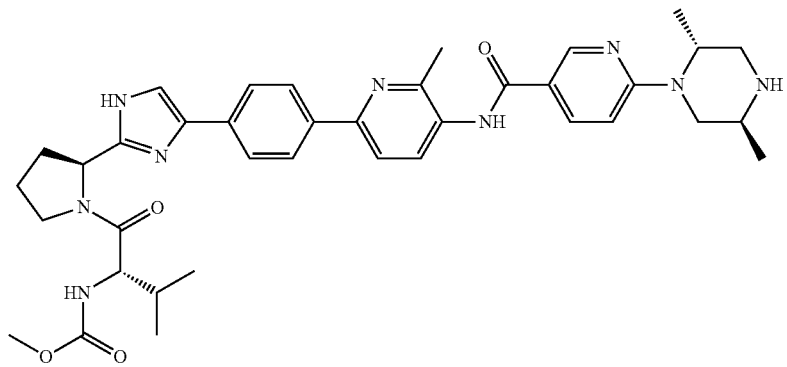

(a) (2S,5R)-4-{5-[6-(4-{2-[(S)-1-((S)-2-Methoxycarbonylamino-3-methyl-butyryl)-pyrrolidin-2-yl]-1H-imidazol-4-yl}-phenyl)-2-methyl-pyridin-3-ylcarbamoyl]-pyridin-2-yl}-2,5-dimethyl-piperazine-1-carboxylic acid tert-butyl ester A mixture of [(S)-2-methyl-1-((S)-2-{4-[4-(4,4,5,5-tetramethyl-[1,3,2]dioxaborolan-2-yl)-phenyl]-1H-imidazol-2-yl}-pyrrolidine-1-carbonyl)-propyl]-carbamic acid methyl ester (73.0 mg, 0.147 mmol;), (2S,5R)-4-[5-(6-bromo-2-methyl-pyridin-3-ylcarbamoyl)-pyridin-2-yl]-2,5-dimethyl-piperazine-1-carboxylic acid tert-butyl ester TFA (91.0 mg, 0.147 mmol; Preparation 58), and 2 M sodium carbonate in water (0.29 mL, 0.588 mmol) DMF (0.9 mL, 10 mmol) was sparged with nitrogen and then tetrakis(triphenylphosphine) palladium(0) (11.9 mg, 0.010 mmol) was added. The reaction mixture was purged with nitrogen, heated at 100° C. overnight, cooled, diluted with ethyl acetate (25 mL), washed with water (2×5 mL), dried over magnesium sulfate, filtered, concentrated, dissolved in 1:1 acetic acid:water (5 ml), filtered and purified by reverse phase HPLC. Fractions containing the desired product were combined and lyophilized to provide the tri-TFA salt of the title intermediate (100.3 mg) (m/z): [M+H]+ calcd for $C_{43}H_{55}N_9O_6$ 794.46 found 794.6.

(b) [(S)-1-((S)-2-{4-[4-(5-{[6-((2R,5S)-2,5-Dimethyl-piperazin-1-yl)-pyridine-3-carbonyl]-amino}-6-methyl-pyridin-2-yl)-phenyl]-1H-imidazol-2-yl}-pyrrolidine-1-carbonyl)-2-methyl-propyl]-carbamicacid methyl ester The product of the previous step was treated with 4 M HCl in 1,4-dioxane (1 mL, 4.0 mmol) for 1 h and the reaction mixture was concentrated by rotary evaporation to give the 4-HCl salt of the title intermediate (75 mg, 61% yield). (m/z): [M+H]+ calcd for $C_{38}H_{47}N_9O_4$ 694.38 found 694.6.

Preparation 60: [(S)-1-((S)-2-{4-[6-(4-Amino-2-trifluoromethoxy-phenyl)-pyridin-3-yl]-1H-imidazol-2-yl}-pyrrolidine-1-carbonyl)-2-methyl-propyl]-carbamic acid methyl ester

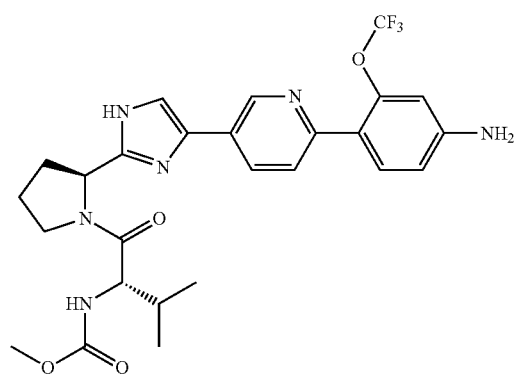 [SMILES: COC(=O)N[C@H](C(=O)N1CCC[C@H]1c1nc(-c2ccc(-c3ccc(N)cc3OC(F)(F)F)nc2)c[nH]1)C(C)C]

(a) 2-Bromo-1-(6-bromo-pyridin-3-yl)-ethanone

A solution of bromine (4 g, 25 mmol) in DCM (10 mL) was added drop wise over 5 min to a cooled (0° C.) solution of 1-(6-bromo-pyridin-3-yl)-ethanone (5 g, 25 mmol) and HBr (48%, 0.2 mL). The cooling bath was removed 40 min later and stirring was continued at RT for 66 h. The solid that formed was filtered, washed with DCM and dried at room temperature to give the impure title intermediate (8.1 g) as a yellow solid. $^1$H NMR (CD$_3$OD, 400 MHz) δ (ppm): 8.96 (m, 1H), 8.28-8.25 (m, 1H), 7.82-7.79 (m, 1H), 4.7 (s, 2H).

(b) ((S)-1-{(S)-2-[4-(6-Bromo-pyridin-3-yl)-1H-imidazol-2-yl]-pyrrolidine-1-carbonyl}-2-methyl-propyl)-carbamic acid methyl ester Following the general procedure of Preparation 29-A, substituting the product of step a (7.6 g) for 2-bromo-1-(4- bromo-3-methyl-phenyl)-ethanone, the title intermediate was prepared (3.5 g) as a yellow foam. ¹H NMR (CDCl₃, 400 MHz) δ (ppm): 8.73-8.68 (m, 1H), 7.93-7.9 (m, 1H), 7.45-7.43 (m, 1H), 7.25 (s, 1H), 5.52-5.49 (m, 1H), 5.24-5.21 (m, 1H), 4.34-4.29 (m, 1H), 3.87-3.81 (m, 1H), 3.69 (s, 1H), 2.36-2.31 (m, 1H), 2.29-2.20 (m, 1H), 2.19-2.07 (m, 1H), 1.98-1.92 (m, 1H), 1.08-1.01 (m, 1H), 0.92-0.81 (m, 6H).

(c) [4-(5-{2-[(S)-1-((S)-2-Methoxycarbonylamino-3-methyl-butyryl)-pyrrolidin-2-yl]-1H-imidazol-4-yl}-pyridin-2-yl)-3-trifluoromethoxy-phenyl]-carbamic acid tert-butyl ester A mixture of the product of the previous step (469 mg, 1.04 mmol), [4-(4,4,5,5-tetramethyl-[1,3,2]dioxaborolan-2-yl)-3-trifluoromethoxy-phenyl]-carbamic acid tert-butyl ester (420 mg, 1.04 mmol), Na₂CO₃ (331 mg, 3.12 mmol) and Pd(dppf)Cl₂ (50 mg) in dioxane (9 mL) and water (3 mL) was refluxed for 5 h. After filtration, the filtrate was concentrated under vacuum to give the crude product (700 m).

(d) [(S)-1-((S)-2-{4-[6-(4-Amino-2-trifluoromethoxy-phenyl)-pyridin-3-yl]-1H-imidazol-2-yl}-pyrrolidine-1-carbonyl)-2-methyl-propyl]-carbamic acid methyl ester The product of the previous step (700 mg, 1.08 mmol) was dissolved in HCl/dioxane (10 mL) and the mixture was stirred at RT for 3 h. The mixture was concentrated under vacuum to give the residue, which was purified by preparative HPLC to give the title intermediate (140 mg, yield 24%). ¹H NMR (CD₃OD, 400 MHz) δ (ppm): 9.18 (s, 1H), 8.69-8.67 (m, 1H), 8.2-8.15 (m, 2H), 7.68 (d, J=8.4 Hz, 1H), 7.02-6.98 (m, 2H), 5.26 (m, 1H), 4.23-4.21 (m, 1H), 4.09-4.05 (m, 1H), 3.9-3.88 (m, 1H), 3.65 (s, 3H), 2.64-2.5 (m, 1H), 2.38-2.0 (m, 4H), 0.92 (d, J=6.8 Hz, 3H), 0.88 (d, J=6.8 Hz, 3H).

Preparation 61: [(S)-2-Methyl-1-((S)-2-{4-[6-(4-{[6-((R)-2-methyl-piperazin-1-yl)-pyridine-3-carbonyl]-amino}-2-trifluoromethoxy-phenyl)-pyridin-3-yl]-1H-imidazol-2-yl}-pyrrolidine-1-carbonyl)-propyl]-carbamic acid methyl ester

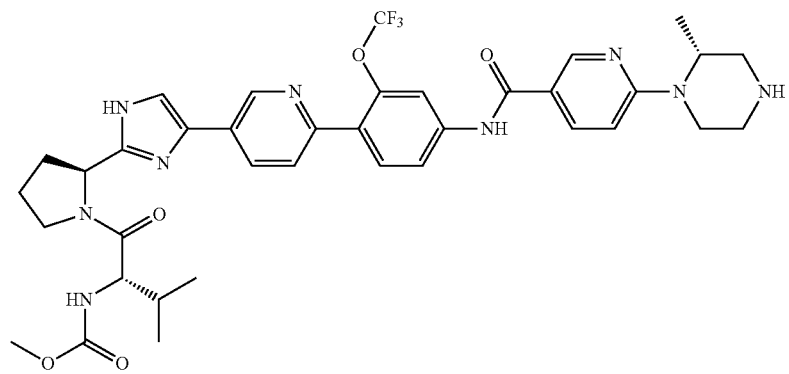 [SMILES: COC(=O)N[C@H](C(=O)N1CCC[C@H]1c1nc(-c2ccc(-c3ccc(NC(=O)c4ccc(N5CCNC[C@H]5C)nc4)cc3OC(F)(F)F)nc2)c[nH]1)C(C)C]

To a mixture of [(S)-1-((S)-2-{5-[6-(4-amino-2-trifluoromethoxy-phenyl)-pyridin-3-yl]-1H-imidazol-2-yl}-pyrrolidine-1-carbonyl)-2-methyl-propyl]-carbamic acid methyl ester (140 mg, 0.26 mmol, Preparation 60) in DCM (2.56 mL) and DMA (0.25 mL) was added N,N-diisopropylethylamine (0.14 mL, 0.77 mmol) followed by 2-fluoropyridine-5-carbonyl chloride (40.9 mg, 0.26 mmol). The reaction mixture was stirred at RT for 1 h and concentrated.

The resulting residue was dissolved in DMSO (0.5 mL) and (R)-3-methyl-piperazine-1-carboxylic acid tert-butyl ester (128 mg, 0.64 mmol), N,N-diisopropylethylamine (0.11 mL, 0.64 mmol) was added and the resulting mixture was heated at 120° C. overnight. cooled to RT, and partitioned between EtOAc (10 mL) and water (2 mL). The organic layer was washed with water (2 mL), dried over sodium sulfate, filtered and concentrated to give a brownish oil, which was treated with 4 M of HCl in 1,4-dioxane (1 mL) at RT for 1 h. The reaction mixture was concentrated, dissolved in 1:1 acetic acid:water (7 mL), filtered and purified by reverse phase prep HPLC to provide the tri-TFA salt of the title intermediate as a yellowish solid (57 mg, 20% yield). (m/z): [M+H]⁺ calcd for C₃₇H₄₂F₃N₉O₅ 750.33 found 750.8.

Preparation 62: (R)-4-[5-(4-Bromo-2-chloro-5-trifluoromethoxy-phenylcarbamoyl)-pyridin-2-yl]-3-methyl-piperazine-1-carboxylic acid tert-butyl

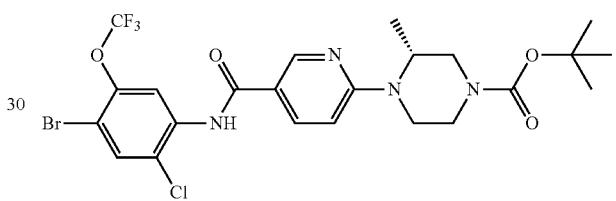

(a) 4-Bromo-2-chloro-5-trifluoromethoxy-phenylamine

To a mixture of 4-bromo-3-trifluoromethoxy-phenylamine (2.0 g, 7.8 mmol) in ACN (60 mL) was slowly added a solution of N-chlorosuccinimide (1.0 g, 7.8 mmol) in ACN (40 mL). The reaction mixture was heated at 60° C. overnight and extracted with ethyl actetate/water. The organic layer was dried over sodium sulfate and purified by flash chromatography (40 g column, 100% hexanes to 10% EtOAc:hexanes) to produce the desired product as an orange-ish colored oil (1.4 g, 64% yield).

(b) N-(4-Bromo-2-chloro-5-trifluoromethoxy-phenyl)-6-fluoro-nicotinamide

To a solution of the product of the previous step (1.2 g, 4.1 mmol) in DCM (5 mL) was slowly added a solution of 2-fluoropyridine-5-carbonyl chloride (0.66 g, 4.1 mmol) in DCM (3 mL) and 20 drops of DMA were added. The reaction mixture was concentrated to form a yellowish solid (2 g). (m/z): [M+H]$^+$ calcd for $C_{13}H_6BrClF_4N_2O_2$ 412.92, 414.92 found 413, 415.

(c) (R)-4-[5-(4-Bromo-2-chloro-5-trifluoromethoxy-phenylcarbamoyl)-pyridin-2-yl]-3-methyl-piperazine-1-carboxylic acid tert-butyl ester To a reaction mixture of the product of the previous step (999 mg, 2.42 mmol) in a mixture of N,N-diisopropylethylamine (0.84 mL, 4.83 mmol) and DMSO (0.86 mL, 12.08 mmol) was added (R)-3-methyl-piperazine-1-carboxylic acid tert-butyl ester (726 mg, 3.62 mmol) and the reaction mixture was heated at 120° C. overnight and extracted with ethyl acetate/water. The organic layer was dried over sodium sulfate and concentrated under vacuum. The dark oil was dissolved in a small amount of DCM and purified by silica gel chromatography (24 g column, 0-40% ethyl acetate:hexanes) to produce the title intermediate as a white solid (916 mg, 64% yield). (m/z): [M+H]$^+$ calcd for $C_{23}H_{25}BrClF_3N_4O_4$ 593.07, 595.07 found 595.4.

Preparation 63: ((S)-1-{(S)-2-[4-(5'-Chloro-4'-{[6-((R)-2-methyl-piperazin-1-yl)-pyridine-3-carbonyl]-amino}-2'-trifluoromethoxy-biphenyl-4-yl)-1H-imidazol-2-yl]-pyrrolidine-1-carbonyl}-2-methyl-propyl)-carbamic acid methyl ester

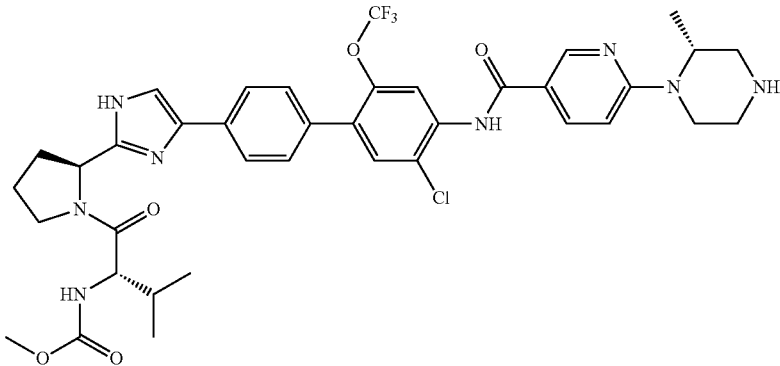

Following the procedure of Preparation 50, the product of Preparation 62 (534 mg, 0.9 mmol) was reacted to provide the tri-TFA salt of the title compound as a white powder (186 mg, ~18% yield). (m/z): [M+H]$^+$ calcd for $C_{38}H_{42}ClF_3N_8O_5$ 783.29 found 784.3

Example 1

{(S)-1-[(S)-2-(4-{4'-[4-(4-Cyclopropanecarbonyl-piperazin-1-yl)-benzoylamino]-biphenyl-4-yl}-1H-imidazol-2-yl)-pyrrolidine-1-carbonyl]-2-methyl-propyl}-carbamic acid methyl ester

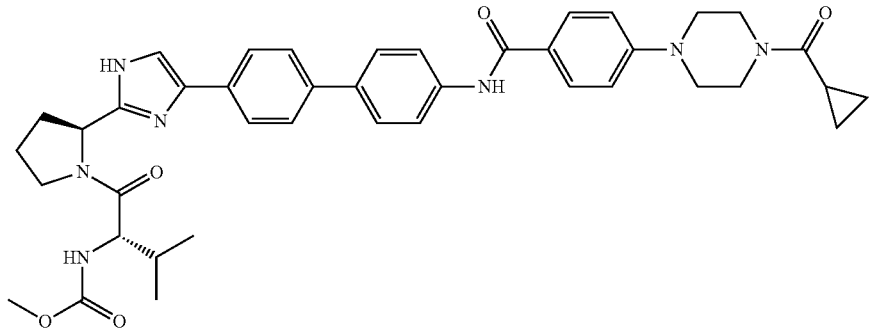 [SMILES: COC(=O)N[C@H](C(=O)N1CCC[C@H]1c1nc(-c2ccc(-c3ccc(NC(=O)c4ccc(N5CCN(C(=O)C6CC6)CC5)cc4)cc3)cc2)c[nH]1)C(C)C]

To a solution of 4-(4-cyclopropanecarbonyl-piperazin-1-yl)-benzoic acid (0.015 g, 0.055 mmol) in dichloromethane (2 mL, 30 mmol) were added N,N-dimethylformamide (0.004 mL, 0.055 mmol) and oxalyl chloride (0.014 mL, 0.164 mmol). The reaction mixture was stirred for 25 min and then N,N-diisopropylethylamine (0.048 mL, 0.273 mmol) was added, followed by ((S)-1-{(S)-2-[4-(4'-amino-biphenyl-4-yl)-1H-imidazol-2-yl]-pyrrolidine-1-carbonyl}-2-methyl-propyl)-carbamic acid methyl ester (0.025 g, 0.055 mmol). The reaction mixture was stirred for 90 min, dried by rotary evaporation, dissolved in 1:1 acetic acid:water (1.5 mL) and purified by preparative HPLC to provide the trifluoroacetic acid salt of the title compound (7.9 mg). (m/z): [M+H]$^+$ calcd for $C_{41}H_{47}N_7O_5$ 718.36. found 718.2. $^1$H NMR (d$_6$-DMSO, 400 MHz) δ (ppm) 10.07 (s, 1H), 8.09 (s, 1H), 7.90 (dd, J=8.9, 2.1 Hz, 4H), 7.83 (dd, J=18.2, 8.5 Hz, 4H), 7.74 (d, J=8.8 Hz, 2H), 7.32 (d, J=8.7 Hz, 1H), 7.04 (d, J=9.1 Hz, 2H), 5.11 (t, J=7.1 Hz, 1H), 4.10 (t, J=7.9 Hz, 1H), 3.96-3.55 (m, 9H), 3.53 (s, 3H), 3.42-3.22 (m, 4H), 2.45-2.28 (m, 1H), 2.20-1.92 (m, 5H), 0.82 (d, J=6.7 Hz, 3H), 0.80-0.69 (m, 6H).

Example 2

((S)-1-{(S)-2-[4-(4'-{4-[4-(2,2-Dimethyl-propionyl)-piperazin-1-yl]-benzoylamino}-biphenyl-4-yl)-1H-imidazol-2-yl]-pyrrolidine-1-carbonyl}-2-methyl-propyl)-carbamic acid methyl ester

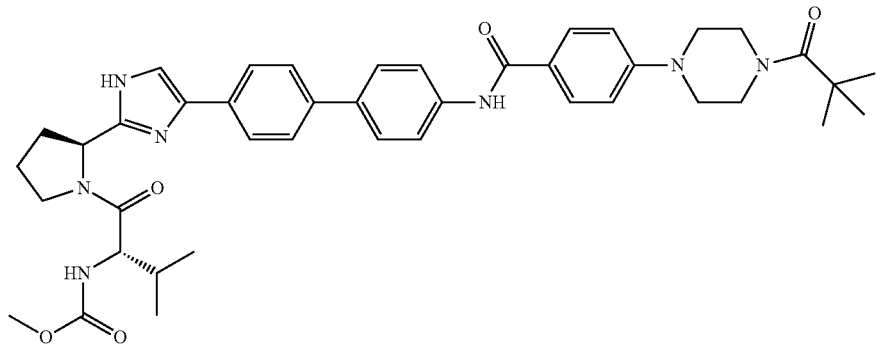 [SMILES: COC(=O)N[C@H](C(=O)N1CCC[C@H]1c1nc(-c2ccc(-c3ccc(NC(=O)c4ccc(N5CCN(C(=O)C(C)(C)C)CC5)cc4)cc3)cc2)c[nH]1)C(C)C]

A reaction mixture of 4-[4-(2,2-dimethyl-propionyl)-piperazin-1-yl]-benzoic acid (10.3 mg, 0.036 mmol), N-(3-dimethylaminopropyl)-N-ethylcarbodiimide hydrochloride (8.17 mg, 0.043 mmol), 1-hydroxy-7-azabenzotriazole (6.77 mg, 0.050 mmol) in dichloromethane (0.3 mL, 4 mmol) was stirred to dissolution and for an additional 20 min. Then ((S)-1-{(S)-2-[4-(4'-amino-biphenyl-4-yl)-1H-imidazol-2-yl]-pyrrolidine-1-carbonyl}-2-methyl-propyl)-carbamic acid methyl ester (8.2 mg, 0.018 mmol) and N,N-diisopropylethylamine (7.43 uL, 0.0426 mmol) were added at room temperature. The reaction mixture was stirred overnight, concentrated, dissolved in 1:1 acetic acid:water (1.5 mL) and purified by preparative HPLC to provide the title compound as the trifluoroacetic acid salt (5.6 mg). (m/z): [M+H]$^+$ calcd for $C_{42}H_{51}N_7O_5$ 734.40 found 734.4.

Example 3

4-[4-(4'-{2-[(S)-1-((S)-2-Methoxycarbonylamino-3-methyl-butyryl)-pyrrolidin-2-yl]-1H-imidazol-4-yl}-biphenyl-4-ylcarbamoyl)-phenyl]-piperazine-1-carboxylic acid tert-butyl ester

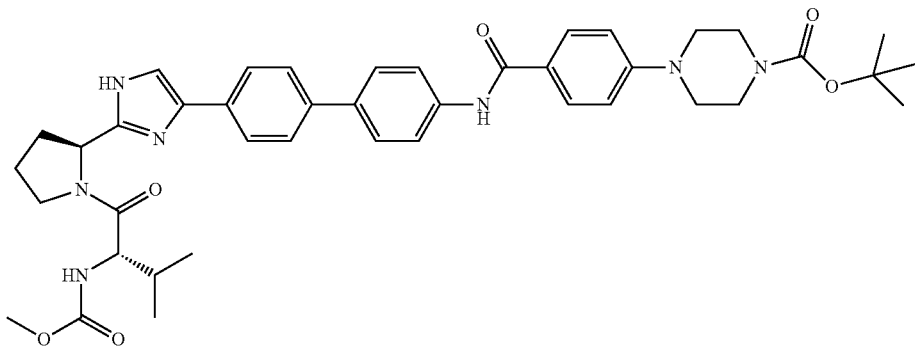 [SMILES: COC(=O)N[C@H](C(=O)N1CCC[C@H]1c1nc(-c2ccc(-c3ccc(NC(=O)c4ccc(N5CCN(C(=O)OC(C)(C)C)CC5)cc4)cc3)cc2)c[nH]1)C(C)C]

To a solution of 4-(4-(tert-butoxycarbonyl)piperazin-1-yl) benzoic acid (24.7 mg, 0.081 mmol) in dichloromethane (0.89 mL, 14 mmol) and N,N-dimethylformamide (0.4 mL, 6 mmol) was added N,N-diisopropylethylamine (0.071 mL, 0.407 mmol) and methyl chloroformate (0.006 mL, 0.081 mmol). The reaction mixture was stirred for 15 min at room temperature, then ((S)-1-{(S)-2-[4-(4'-amino-biphenyl-4-yl)-1H-imidazol-2-yl]-pyrrolidine-1-carbonyl}-2-methyl-propyl)-carbamic acid methyl ester (25.0 mg, 0.054 mmol) was added and the mixture was allowed to stir overnight. The reaction mixture was concentrated and then dissolved in DCM (5 mL) and washed with saturated aqueous sodium bicarbonate (2 mL). The organic layer was concentrated. Approximately 15 mg of the crude material was concentrated, dissolved in 1:1 acetic acid:water (1.5 mL), and purified by preparative HPLC to provide the trifluoroacetic acid salt of the title compound (7.3 mg). (m/z): $[M+H]^+$ calcd for $C_{42}H_{51}N_7O_6$ 750.39 found 750.4.

Example 4

{(S)-1-[(S)-2-(4-{4'-[4-(4-Methanesulfonyl-piperazin-1-yl)-benzoylamino]-biphenyl-4-yl}-1H-imidazol-2-yl)-pyrrolidine-1-carbonyl]-2-methyl-propyl}-carbamic acid methyl ester

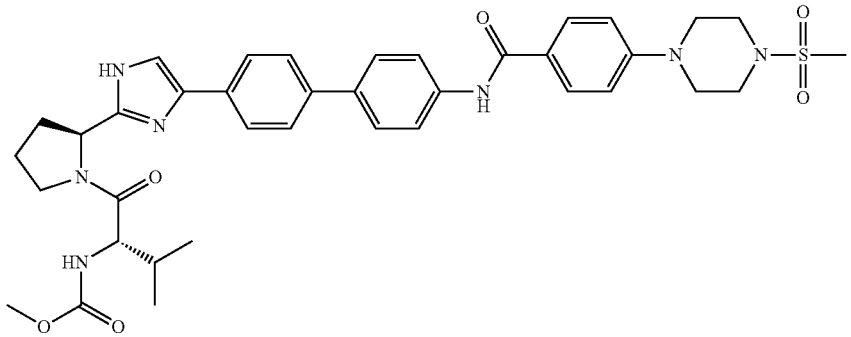

Methylenesulfonyl chloride (1.19 mg, 0.015 mmol) was added to a solution of [(S)-2-methyl-1-((S)-2-{4-[4'-(4-piperazin-1-yl-benzoylamino)-biphenyl-4-yl]-1H-imidazol-2-yl}-pyrrolidine-1-carbonyl)-propyl]-carbamic acid methyl ester (10.0 mg, 0.015 mmol) in dichloromethane (0.75 mL, 12 mmol), N,N-dimethylacetamide (0.75 mL, 8.1 mmol) and triethylamine (25 uL, 0.18 mmol). The reaction mixture was stirred for 15 min at room temperature, concentrated by rotary evaporation, dissolved in 1:1 acetic acid:water (1.5 mL) and then purified by preparative HPLC to provide the trifluoroacetic acid salt of the title compound (12.3 mg). (m/z): [M+H]$^+$ calcd for $C_{38}H_{45}N_7O_6S$ 728.32 found 728.2.

Example 5

((S)-1-{(S)-2-[4-(4'-{[6-(4-Cyclopropanecarbonyl-piperazin-1-yl)-pyridine-3-carbonyl]-amino}-biphenyl-4-yl)-1H-imidazol-2-yl]-pyrrolidine-1-carbonyl}-2-methyl-propyl)-carbamic acid methyl ester

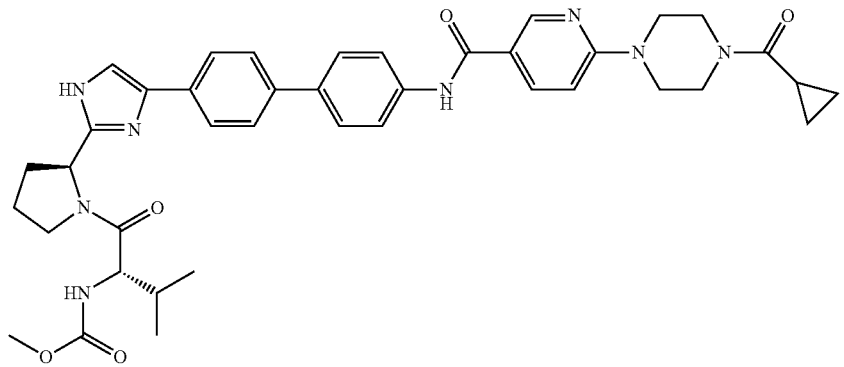 [SMILES: COC(=O)N[C@H](C(=O)N1CCC[C@H]1c1nc(-c2ccc(-c3ccc(NC(=O)c4ccc(N5CCN(C(=O)C6CC6)CC5)nc4)cc3)cc2)c[nH]1)C(C)C]

(a) {(S)-2-Methyl-1-[(S)-2-(4-{4'-[(6-piperazin-1-yl-pyridine-3-carbonyl)-amino]-biphenyl-4-yl}-1H-imidazol-2-yl)-pyrrolidine-1-carbonyl]-propyl}-carbamic acid methyl ester Oxalyl chloride (44.0 uL, 0.520 mmol) was added to a solution of 4-(5-carboxy-pyridin-2-yl)-piperazine-1-carboxylic acid tert-butyl ester (70.3 mg, 0.229 mmol) in dichloromethane (6.67 mL, 104 mmol) and N,N-dimethylformamide (2.01 uL, 0.026 mmol) The reaction mixture was stirred at room temperature for 20 min and then N,N-diisopropylethylamine (0.181 mL, 1.04 mmol) was added followed by ((S)-1-{(S)-2-[4-(4'-amino-biphenyl-4-yl)-1H-imidazol-2-yl]-pyrrolidine-1-carbonyl}-2-methyl-propyl)-carbamic acid methyl ester (100.0 mg, 0.217 mmol). The reaction mixture was stirred for 2 h at room temperature, then dried by rotary evaporation. The crude material was dissolved in dichloromethane (1 mL) and then washed with saturated aqueous sodium bicarbonate (1 mL). The organic layer was concentrated, dissolved in 4.0 M hydrogen chloride in 1,4-dioxane (6.7 mL, 27 mmol) and stirred for 1 h at room temperature until completely deprotected. The reaction mixture was concentrated and used directly in the next step.

(b) 1-{(S)-2-[4-4'-{[6-(4-Cyclopropanecarbonyl-piperazin-1-yl)-pyridine-3-carbonyl]-amino}-biphenyl-4-yl)-1H-imidazol-2-yl]-pyrrolidine-1-carbonyl}-2-methyl-propyl)-carbamic acid methyl ester Cyclopropanecarboxylic acid (26.86 mg, 0.312 mmol), N-(3-dimethylaminopropyl)-N-ethylcarbodiimide hydrochloride (59.81 mg, 0.312 mmol), and 1-hydroxy-7-azabenzotriazole (42.46 mg, 0.312 mmol) were dissolved in N,N-dimethylacetamide (3.868 mL, 41.60 mmol) and stirred for 5 min. Then half of the material from the previous step was added to the reaction mixture followed by N,N-diisopropylethylamine (0.269 g, 2.080 mmol. The reaction mixture was stirred overnight at room temperature, concentrated by rotary evaporation, dissolved in 1:1 acetic acid:water (1.5 mL) and purified by preparative HPLC to provide the trifluoroacetic acid salt of the title compound (39.9 mg). (m/z): [M+H]$^+$ calcd for $C_{40}H_{46}N_8O_5$ 719.36 found 719.2. $^1$H NMR (d$_6$-DMSO, 400 MHz) δ (ppm) 10.14 (s, 1H), 8.77 (d, J=2.5 Hz, 1H), 8.12 (dd, J=9.7, 3.1 Hz, 2H), 7.95-7.78 (m, 6H), 7.75 (d, J=8.8 Hz, 2H), 7.32 (d, J=8.4 Hz, 1H), 6.95 (d, J=9.3 Hz, 1H), 5.15-5.07 (m, 1H), 4.15-4.05 (m, 1H), 3.90-3.55 (m, 11H), 3.53 (s, 3H), 2.28-2.40 (m, 1H), 2.23-1.87 (m, 5H), 0.75-0.85 (m, 3H), 0.79-0.63 (m, 6H).

Example 6

4-{4-[(4'-{2-[(S)-1-((S)-2-Methoxycarbonylamino-3-methyl-butyryl)-pyrrolidin-2-yl]-1H-imidazol-4-yl}-biphenyl-4-carbonyl)-amino]-phenyl}-piperazine-1-carboxylic acid tert-butyl ester

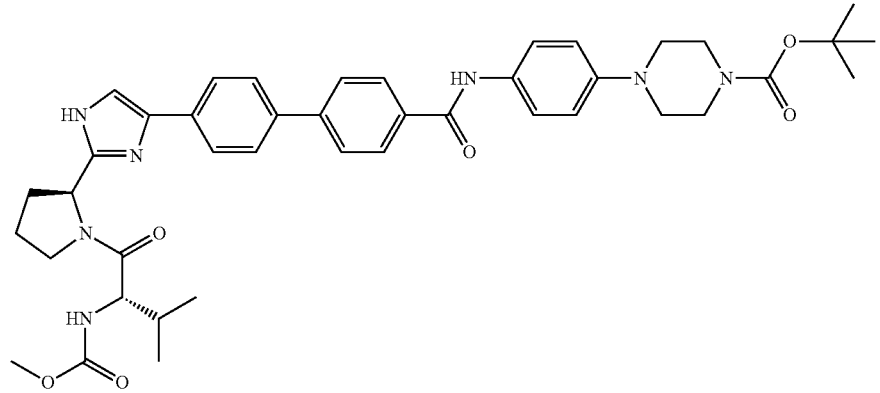 [SMILES: COC(=O)N[C@H](C(=O)N1CCC[C@H]1c1nc(-c2ccc(-c3ccc(C(=O)Nc4ccc(N5CCN(C(=O)OC(C)(C)C)CC5)cc4)cc3)cc2)c[nH]1)C(C)C]

A mixture of 4'-{2-[(S)-1-((S)-2-methoxycarbonylamino-3-methyl-butyryl)-pyrrolidin-2-yl]-3H-imidazol-4-yl}-biphenyl-4-carboxylic acid (15.0 mg, 0.031 mmol) and N,N,N',N'-tetramethyl-O-(7-azabenzotriazol-1-yl)uronium hexafluorophosphate (11.6 mg, 0.031 mmol) in N,N-dimethylformamide (0.5 mL, 6 mmol) was added to 4-(4-aminophenyl)piperazine-1-carboxylic acid tert-butyl ester (28.2 mg, 0.102 mmol) followed by N,N-diisopropylethylamine (10.6 uL, 0.061 mmol). The reaction mixture was stirred at RT overnight, concentrated, dissolved in 1:1 acetic acid:water (1.5 mL), filtered and purified by preparative HPLC to provide the trifluoroacetic acid salt of the title compound (26.2 mg). (m/z): [M+H]$^+$ calcd for $C_{42}H_{51}N_7O_6$ 750.39 found 750.4.

Example 7

{(S)-1-[(S)-2-(4-{4'-[4-(4-cyclopropanecarbonyl-piperazin-1-yl)-phenylcarbamoyl]-biphenyl-4-yl}-1H-imidazol-2-yl)-pyrrolidine-1-carbonyl]-2-methyl-propyl}-carbamic acid methyl ester

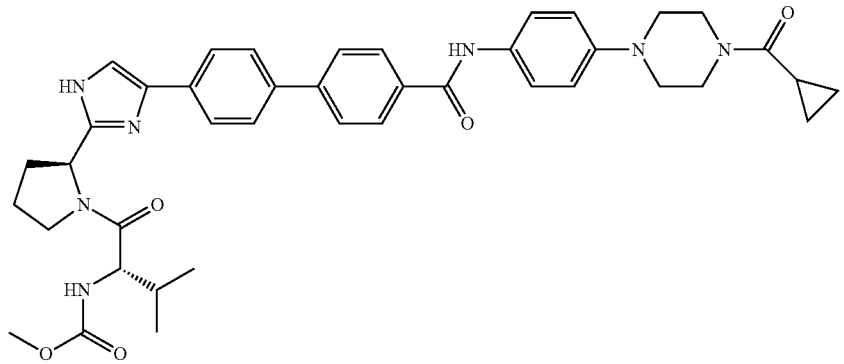 [SMILES: COC(=O)N[C@H](C(=O)N1CCC[C@H]1c1nc(-c2ccc(-c3ccc(C(=O)Nc4ccc(N5CCN(C(=O)C6CC6)CC5)cc4)cc3)cc2)c[nH]1)C(C)C]

(a) [(S)-2-Methyl-1-((S)-2-{4-[4'-(4-piperazin-1-yl-phenylcarbamoyl)-biphenyl-4-yl]-1H-imidazol-2-yl}-pyrrolidine-1-carbonyl)-propyl]-carbamic acid methyl ester To a solution of [4-{4-[(4'-{2-[(S)-1-((S)-2-methoxycarbonylamino-3-methyl-butyryl)-pyrrolidin-2-yl]-1H-imidazol-4-yl}-biphenyl-4-carbonyl)-amino]-phenyl}-piperazine-1-carboxylic acid tert-butyl ester (42.4 mg, 0.0565 mmol) in dichloromethane (0.67 mL, 10 mmol) was added trifluoroacetic acid (0.3 mL, 0.004 mmol). The reaction mixture was stirred for 1 h at room temperature, concentrated, dissolved in methanol (1 mL), passed through a Stratospheres™ PL-CO3 resin, and the filtrate was concentrated to provide the title compound. (m/z): [M+H]+ calcd for $C_{37}H_{43}N_7O_4$ 650.34 found 650.8.

(b) {(S)-1-[(S)-2-(4-{4'-[4-(4-cyclopropanecarbonyl-piperazin-1-yl)-phenylcarbamoyl]-biphenyl-4-yl}-1H-imidazol-2-yl)-pyrrolidine-1-carbonyl]-2-methyl-propyl}-carbamic acid methyl ester Cyclopropanecarboxylic acid (7.30 mg, 0.085 mmol), N-(3-dimethylaminopropyl)-N-ethylcarbodiimide hydrochloride (21.6 mg, 0.113 mmol), and 1-hydroxy-7-azabenzotriazole (15.4 mg, 0.113 mmol) were combined with dichloromethane (0.8 mL, 10 mmol), stirred to dissolution and then stirred for an additional 20 min. To the reaction mixture was added a solution of the product of the previous step in 1:1 dichloromethane:N,N-diisopropylethylamine (0.5 mL, 3 mmol) at room temperature. The resulting reaction mixture was stirred at RT overnight, concentrated under vacuum, dissolved in 1:1 acetic acid:water (1.5 mL), filtered and purified by preparative HPLC to provide the trifluoroacetic acid salt of the title compound (8.2 mg). (m/z): [M+H]+ calcd for $C_{41}H_{47}N_7O_5$ 718.36 found 718.4.

Example 8

{(S)-1-[(S)-2-(4-{4'-[4-(4-cyploroanecarbonyl-piperazin-1-yl)-benzoylamino]-2'-fluoro-biphenyl-4-yl}-1H-imidazol-2-yl)-pyrrolidine-1-carbonyl]-2-methyl-propyl}-carbamic acid methyl ester

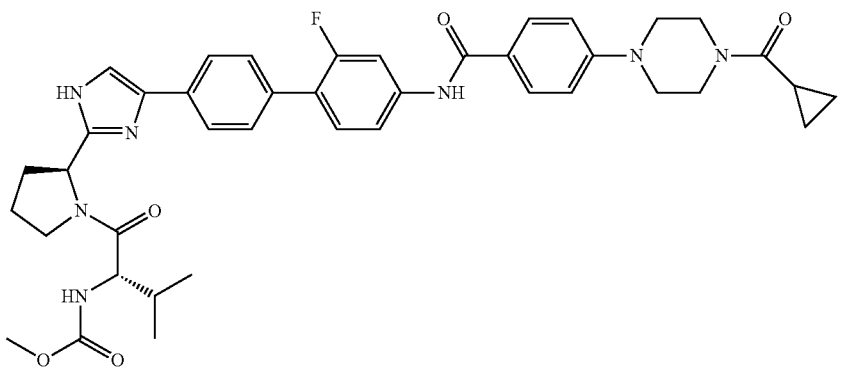 [SMILES: COC(=O)N[C@H](C(=O)N1CCC[C@H]1c1nc(-c2ccc(-c3ccc(NC(=O)c4ccc(N5CCN(C(=O)C6CC6)CC5)cc4)cc3F)cc2)c[nH]1)C(C)C]

To a solution of 4-(4-cyclopropanecarbonyl-piperazin-1-yl)-benzoic acid (13 mg, 0.047 mmol) in dichloromethane (1.0 mL, 16 mmol) and one drop of N,N-dimethylformamide was added oxalyl chloride (0.0119 mL, 0.141 mmol). The reaction mixture was stirred for 25 min and then N,N-diisopropylethylamine (0.027 mL, 0.16 mmol) was added, followed by ((S)-1-{(S)-2-[4-(4'-amino-biphenyl-4-yl)-1H-imidazol-2-yl]-pyrrolidine-1-carbonyl}-2-methyl-propyl)-carbamic acid methyl ester (15 mg, 0.031 mmol). The reaction mixture was stirred overnight, concentrated under vacuum, dissolved in 1:1 acetic acid:water and purified by preparative HPLC to provide the trifluoroacetic acid salt of the title compound (1.9 mg). (m/z): [M+H]+ calcd for $C_{41}H_{46}FN_7O_5$ 735.85. found 736.4.

Example 9

4-(4-Cyclopropanecarbonyl-piperazin-1-yl)-N-(4'-{2-[(S)-1-((R)-2-diethylamino-2-phenyl-acetyl)-pyrrolidin-2-yl]-1H-imidazol-4-yl}-biphenyl-4-yl)-benzamide

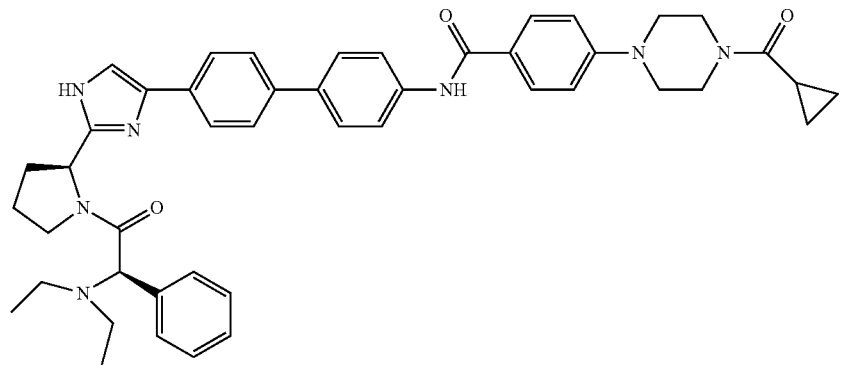 [SMILES: CCN(CC)[C@@H](C(=O)N1CCC[C@H]1c1nc(-c2ccc(-c3ccc(NC(=O)c4ccc(N5CCN(C(=O)C6CC6)CC5)cc4)cc3)cc2)c[nH]1)c1ccccc1]

A combination of (R)-diethylamino-phenyl-acetic acid (6.654 mg, 0.032 mmol) N-(3-dimethylaminopropyl)-N'-ethylcarbodiimide hydrochloride (6.154 mg, 0.032 mmol) and 1-hydroxy-7-azabenzotriazole (4.370 mg, 0.032 mmol) in N,N-dimethylacetamide (0.498 mL, 5.350 mmol) was stirred to dissolution and then for an additional 20 min. 4-(4-Cyclopropanecarbonyl-piperazin-1-yl)-N-[4'-((S)-2-pyrrolidin-2-yl-1H-imidazol-4-yl)-biphenyl-4-yl]-benzamide (15 mg, 0.027 mmol) and N,N-diisopropylethylamine (0.023 mL, 0.134 mmol) were added to the reaction mixture which was stirred at room temperature overnight. The reaction mixture was then concentrated and dissolved in 1:1 acetic acid:water (1.5 mL) and purified by preparative HPLC to provide the trifluoroacetic acid salt of the title compound to provide the title compound (6.4 mg). (m/z): [M+H]+ calcd for $C_{46}H_{51}N_7O_3$ 750.41. found 750.4.

Example 10

((S)-2-Methyl-1-{(S)-2-[4-(4'-{[6-(4-methylcarbamoyl-piperazin-1-yl)-pyridine-3-carbonyl]-amino}-biphenyl-4-yl)-1H-imidazol-2-yl]-pyrrolidine-1-carbonyl}-propyl)-carbamic acid methyl ester

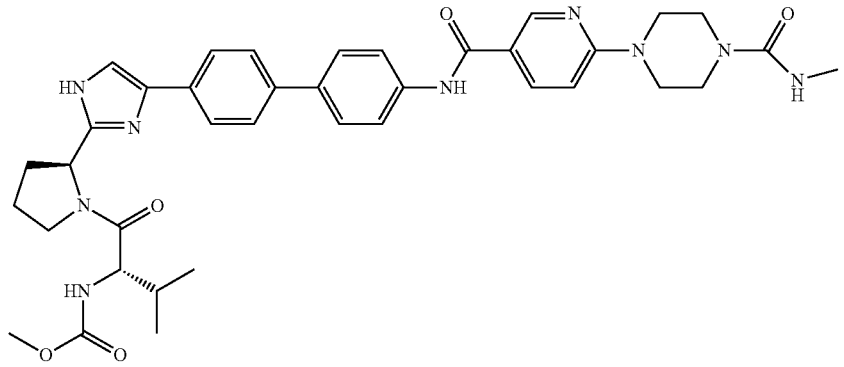

Half of the crude material from Example 5 step (a) was dissolved in N,N-dimethylformamide (3.22 mL, 41.6 mmol) and N,N-diisopropylethylamine (36.2 uL, 0.208 mmol) and then methyl isocyanate (12.36 uL, 0.208 mmol) was added. The reaction mixture was stirred overnight at room temperature, concentrated by rotary evaporation, dissolved in 1:1 acetic acid:water (1.5 mL) and purified by preparative HPLC to provide the trifluoroacetic acid salt of the title compound (35.7 mg). (m/z): [M+H]$^+$ calcd for $C_{38}H_{45}N_9O_5$ 708.35 found 708.2. $^1$H NMR (d$_6$-DMSO, 400 MHz) δ (ppm) 10.13 (s, 1H), 8.75 (d, J=2.6 Hz, 1H), 8.11 (dd, J=8.5, 3.0 Hz, 2H), 7.91-7.79 (m, 6H), 7.75 (d, J=8.8 Hz, 2H), 7.31 (d, J=8.6 Hz, 1H), 6.95 (d, J=9.1 Hz, 1H), 6.52 (br. s, 1H), 5.15-5.03 (m, 1H), 4.10 (t, J=7.9 Hz, 1H), 3.90-3.75 (m, 3H), 3.66-3.55 (m, 4H), 3.56-3.50 (m, 3H), 3.42-3.34 (m, 3H), 2.58 (s, 3H), 1.90-2.25 (m, 1H), 2.18-1.89 (m, 4H), 0.81 (d, J=6.8 Hz, 3H), 0.77 (d, J=6.7 Hz, 3H).

Example 11

{(S)-1-[(S)-2-(5-Chloro-4-{4'-[4-(4-methylcarbamoyl-piperazin-1-yl)-benzoylamino]-biphenyl-4-yl}-1H-imidazol-2-yl)-pyrrolidine-1-carbonyl]-2-methyl-propyl}-carbamic acid methyl ester

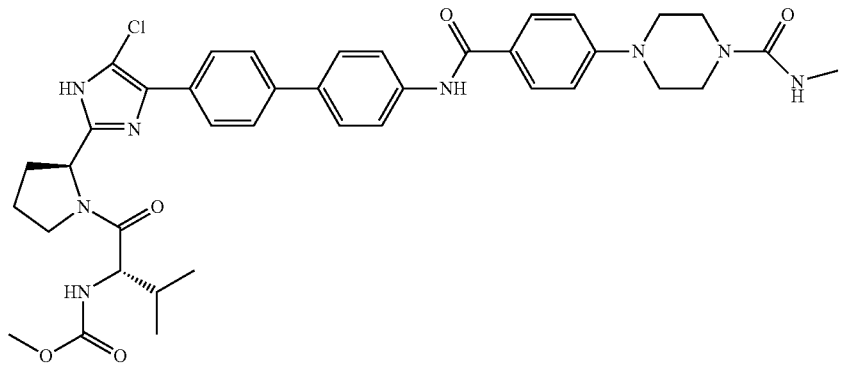

The TFA-salt of {(S)-2-methyl-1-[(S)-2-(4-{4'-[4-(4-methylcarbamoyl-piperazin-1-yl)-benzoylamino]-biphenyl-4-yl}-1H-imidazol-2-yl)-pyrrolidine-1-carbonyl]-propyl}-carbamic acid methyl ester (22.0 mg, 0.0311 mmol) was dissolved in methanol (5 mL) and treated with Stratospheres™ PL-CO3 resin and stirred for 15 min. The reaction mixture was filtered and the filtrate was concentrated. This crude material was dissolved in N,N-dimethylformamide (1.5 mL, 19 mmol) and then N-chlorosuccinimide (6.23 mg, 0.0467 mmol) was added. The reaction mixture was heated at 50° C. and stirred overnight at 50° C., concentrated by rotary evaporation, dissolved in 1:1 acetic acid:water (1.5 mL) and purified by preparative HPLC to provide the trifluoroacetic acid salt of the title compound (4.5 mg). (m/z): [M+H]+ calcd for $C_{39}H_{45}ClN_8O_5$ 741.32 found 741.5.

Example 12

((S)-1-{(S)-2-[4-(4'-{[6-((R)-4-Cyclopropanecarbonyl-2-methyl-piperazin-1-yl)-pyridine-3-carbonyl]-amino}-biphenyl-4-yl)-1H-imidazol-2-yl]-pyrrolidine-1-carbonyl}-2-methyl-propyl)-carbamic acid methyl ester

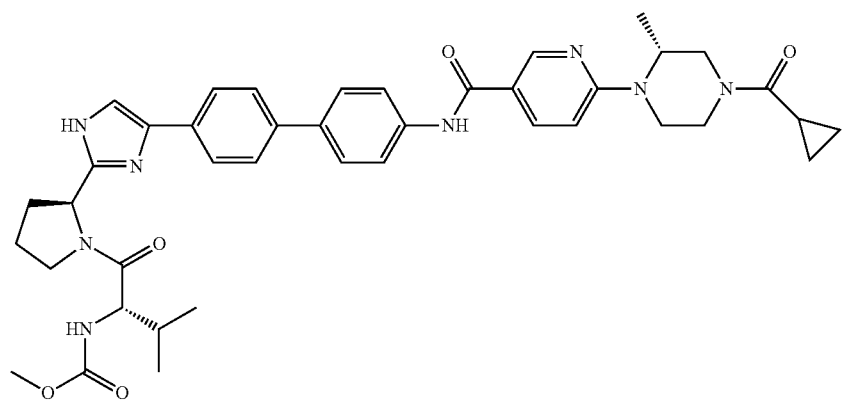 [SMILES: COC(=O)N[C@H](C(=O)N1CCC[C@H]1c1nc(-c2ccc(-c3ccc(NC(=O)c4ccc(N5CCN(C(=O)C6CC6)C[C@H]5C)nc4)cc3)cc2)c[nH]1)C(C)C]

(a) ((S)-2-Methyl-1-{(S)-2-[4-(4'-{[6-((R)-2-methyl-piperazin-1-yl)-pyridine-3-carbonyl]-amino}-biphenyl-4-yl)-1H-imidazol-2-yl]-pyrrolidine-1-carbonyl}-propyl)-carbamic acid methyl ester A mixture of the hydrochloride salt of {(S)-1-[(S)-2-(5-{4'-[(6-fluoro-pyridine-3-carbonyl)-amino]-biphenyl-4-yl}-1H-imidazol-2-yl)-pyrrolidine-1-carbonyl]-2-methyl-propyl}-carbamic acid methyl ester (728.1 mg, 1.17 mmol) [Reactant A] and (R)-3-methyl-piperazine-1-carboxylic acid tert-butyl ester (0.352 g, 1.76 mmol) [Reactant B] in dimethyl sulfoxide (3.7 mL) and N,N-diisopropylethylamine (1.23 mL, 7.03 mmol) was heated at 120° C. overnight. The reaction mixture was cooled to RT and water (5.0 mL) was added. The resulting mixture was centrifuged and filtered. The solid was combined with the product from a previous reaction in which Reactant A (237.8 mg, 0.383 mmol) was reacted with Reactant B (115.0 mg, 0.574 mmol) under the same conditions. The combined solids were dissolved in 1:1 acetic acid:water (20 mL), filtered, and split into three equal portions which were purified separately by reverse phase preparative HPLC. Desired fractions were combined and freeze dried to give a white solid. (805.5 mg total).

To the product of the previous step was added 4.0 M hydrogen chloride in 1,4-dioxane (6.0 mL, 24 mmol) and the reaction mixture was stirred at RT for 30 min, and then concentrated. The residue was coevaporated with ethyl acetate (3×5.0 mL) and dried under vacuum to give the tri-hydrochloride salt of the title intermediate as a light yellowish solid (655.9 mg).

(b) ((S)-1-{(S)-2-[4-(4'-{[6-((R)-4-Cyclopropanecarbonyl-2-methyl-piperazin-1-yl)-pyridine-3-carbonyl]-amino}-biphenyl-4-yl)-1H-imidazol-2-yl]-pyrrolidine-1-carbonyl}-2-methyl-propyl)-carbamic acid methyl ester Material from the previous step (350 mg) was dissolved in N,N-dimethylacetamide (2.7 mL, 29 mmol) at RT and N,N-diisopropylethylamine (0.52 mL, 3.0 mmol) was added followed by cyclopropanecarbonyl chloride (0.041 mL, 0.45 mmol). The reaction mixture was stirred for 10 min and additional acid chloride was added to consume all the starting material. The reaction mixture was concentrated and the residue was dissolved in 1:1 acetic acid:water (1.5 mL) and purified by preparative HPLC. Desired fractions were combined and freeze dried to give a white solid.

The white solid was dissolved in ethanol (15.0 mL) at RT and 4.0 M hydrogen chloride in 1,4-dioxane (6.0 mL) was added. The reaction mixture was stirred for 10 min, and concentrated. The residue was dissolved in 1:1 acetic acid:water (8 mL), filtered, and purified by reverse phase preparative HPLC. Desired fractions were combined and freeze dried to give the trifluoroacetic acid salt of the title compound as a white solid (194.6 mg) (m/z): [M+H]+ calcd for $C_{41}H_{48}N_8O_5$ 733.38 found 733.5. $^1$H NMR (CD$_3$OD, 400 MHz) δ (ppm): 8.65 (s, 1H), 8.08-8.10 (dd, 1H, J=10, 4), 7.67-7.77 (m, 7H), 7.60-7.62 (m, 2H), 6.86-6.88 (d, 1H, J=8), 5.13-5.17 (t, 1H, J=15.2), 4.52-4.56 & 4.64-4.68 (m, total 1H), 3.99-4.37 (m, 5H), 3.74-3.80 (m, 1H), 3.56 (s, 3H), 2.96-3.00 & 3.13-3.23 & 3.38-3.60 (m, total 3H), 2.45-2.52 (m, 1H), 1.91-2.20 (m, 4H), 1.09-1.18 (m, 4H), 0.76-0.90 (m, 10H).

Example 13

[(S)-1-((S)-2-{4-[4'-({6-[(S)-4-((S)-2,2-Dimethyl-cyclopropane-carbonyl)-2-methyl-piperazin-1-yl]-pyridine-3-carbonyl}-amino)-biphenyl-4-yl]-1H-imidazol-2-yl}-pyrrolidine-1-carbonyl)-2-methyl-propyl]-carbamic acid methyl ester

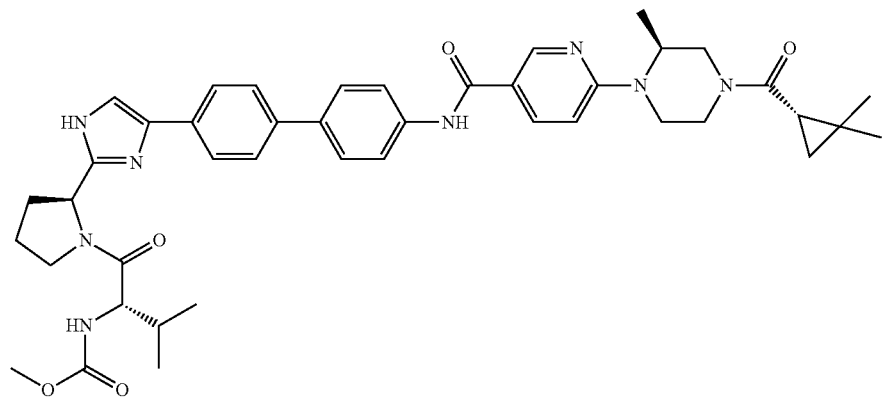

To a mixture of the TFA salt of ((S)-2-methyl-1-{(S)-2-[4-(4'-{[6-((S)-2-methyl-piperazin-1-yl)-pyridine-3-carbonyl]-amino}-biphenyl-4-yl)-1H-imidazol-2-yl]-pyrrolidine-1-carbonyl}-propyl)-carbamic acid methyl ester (320.0 mg, 0.318 mmol, Preparation 16) and (S)-(+)-2,2-dimethylcyclopropane carboxylic acid (39.9 mg, 0.350 mmol) in N,N-dimethylformamide (30.0 mL, 387.4 mmol) at RT was added N,N,N',N'-tetramethyl-O-(7-azabenzotriazol-1-yl)uronium hexafluorophosphate (0.133 g, 0.350 mmol) followed by N,N-diisopropylethylamine (0.277 mL, 1.589 mmol).

The reaction mixture was diluted with water (40.0 mL) and extracted with ethyl acetate (2×20.0 mL). Combined organic layers were washed with water (20.0 mL) and brine (20.0 mL), dried over sodium sulfate, filtered and concentrated to give a yellowish oil. The residue was dissolved in 1:1 acetic acid:water (8 mL), filtered and purified by reverse phase preparative HPLC. Desired fractions were combined and freeze dried. Material was repurified by reverse phase preparative HPLC. Desired fractions were combined and freeze dried to give the trifluoroacetic acid salt of the title compound as a white solid. (205.1 mg). (m/z): [M+H]$^+$ calcd for $C_{43}H_{52}N_8O_5$ 761.42 found 761.7. $^1$H NMR (CD$_3$OD, 400 MHz) δ (ppm): 8.65 (s, 1H), 8.12-8.15 (m, 1H), 7.67-7.77 (m, 7H), 7.6-7.62 (m, 2H), 6.94-6.96 (d, 1H, J=8), 5.13-5.17 (t, 1H, J=16), 4.56-4.65 (m, 1H), 4.33-4.36 (m, 1H), 3.99-4.25 (m, 4H), 3.75-3.81 (m, 1H), 3.56 (s, 3H), 3.4-3.53 (m, 1H), 3.24-3.3 (m, 1H), 2.95-3.11 (m, 1H), 2.45-2.52 (m, 1H), 1.93-2.21 (m, 4H), 1.65-1.71 (m, 1H), 1.16-1.24 (m, 4H), 1.00-1.09 (m, 4H), 0.79-0.93 (m, 8H), 0.68-0.71 (m, 1H).

Example 14

[(S)-1-((S)-2-{4-[4'-({6-[(R)-4-((S)-2,2-Dimethyl-cyclopropane-carbonyl)-2-methyl-piperazin-1-yl]-pyridine-3-carbonyl}-amino)-biphenyl-4-yl]-1H-imidazol-2-yl}-pyrrolidine-1-carbonyl)-2-methyl-propyl]-carbamic acid methyl ester

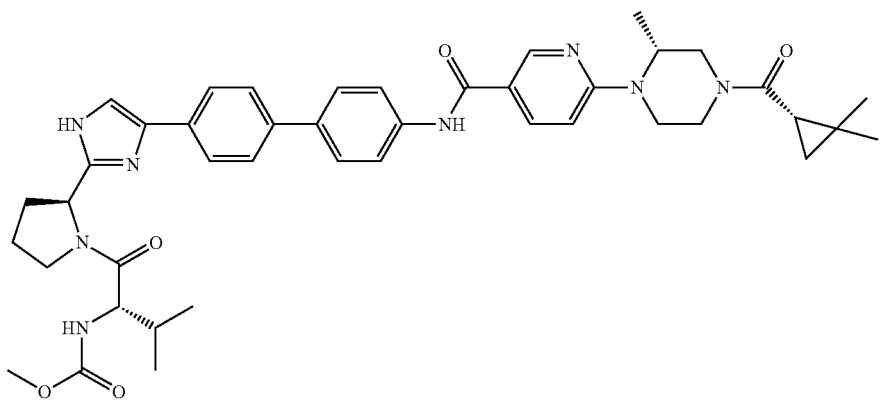

To a mixture of the hydrochloride salt of ((S)-2-methyl-1-{(S)-2-[4-(4'-{[6-((R)-2-methyl-piperazin-1-yl)-pyridine-3-carbonyl]-amino}-biphenyl-4-yl)-1H-imidazol-2-yl]-pyrrolidine-1-carbonyl}-propyl)-carbamic acid methyl ester (60.0 mg, 0.0775 mmol) and (S)-(+)-2,2-dimethylcyclopropane carboxylic acid (10.6 mg, 0.093 mmol) in N,N-dimethylformamide (1.5 mL, 19 mmol) at RT was added N,N,N',N'-tetramethyl-O-(7-azabenzotriazol-1-yl)uronium hexafluorophosphate (35.4 mg, 0.093 mmol) and N,N-diisopropylethylamine (54.0 uL, 0.310 mmol). The reaction mixture was stirred at RT overnight, and then concentrated. The residue was redissolved in 1:1 acetic acid:water (6 mL), filtered and purified by reverse phase preparative HPLC. Desired fractions were combined and freeze dried to give a white solid 34.1 mg). (m/z): [M+H]$^+$ calcd for $C_{43}H_{52}N_8O_5$ 761.42 found 761.7. $^1$H NMR (CD$_3$OD, 400 MHz) δ (ppm): 8.76 (s, 1H), 8.18-8.20 (m, 1H), 7.76-7.86 (m, 7H), 7.68-7.7 (m, 2H), 6.95-6.99 (m, 1H), 5.22-5.26 (t, 1H, J=16), 4.59-4.73 (m, 1H), 4.03-4.38 (m, 5H), 3.82-3.89 (m, 1H), 3.69-3.74 (m, 1H), 3.65 (s, 3H), 3.12-3.2 & 3.3-3.5 (m, total 2H), 2.53-2.6 (m, 1H), 2.0-2.3 (m, 4H), 1.75-1.78 & 1.82-1.85 (m, total 1H), 1.25 (s, 3H), 1.12 (s, 3H), 1.07-1.1 & 1.14-1.17 (m, total 1H), 0.96 (s, 3H), 0.88-0.96 & 1.21-1.27 (m, total 6H), 0.76-0.8 (m, 1H).

Example 15

[(S)-1-((S)-2-{5-[4'-({6-[(R)-4-((S)-1-Acetyl-2-methyl-pyrrolidine-2-carbonyl)2-methyl-piperazin-1-yl]-pyridine-3-carbonyl}-amino)-2'-methyl-biphenyl-4-yl]-1H-imidazol-2-yl}-pyrrolidine-1-carbonyl)-2-methyl-propyl]-carbamic acid methyl ester

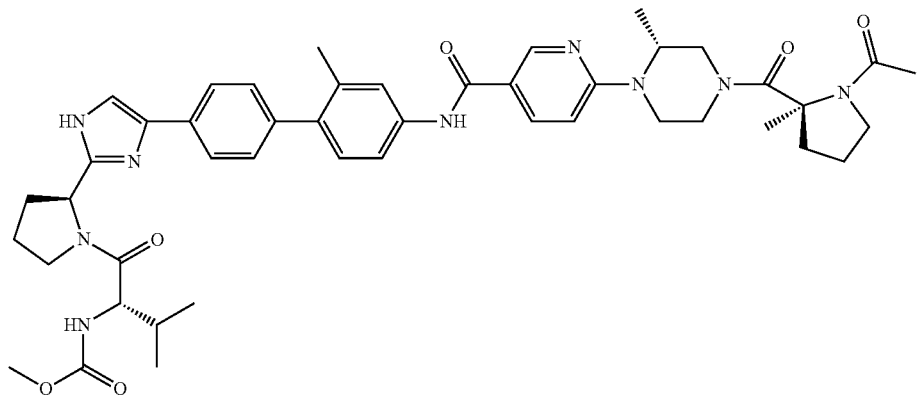 [SMILES: COC(=O)N[C@H](C(=O)N1CCC[C@H]1c1nc(-c2ccc(-c3ccc(NC(=O)c4ccc(N5CCN(C(=O)[C@]6(C)CCCN6C(C)=O)C[C@H]5C)nc4)cc3C)cc2)c[nH]1)C(C)C]

To a solution of K(S)-2-methyl-1-{(S)-2-[5-(2'-methyl-4'-{[6-((R)-2-methyl-piperazin-1-yl)-pyridine-3-carbonyl]-amino}-biphenyl-4-yl)-1H-imidazol-2-yl]-pyrrolidine-1-carbonyl}-propyl)-carbamic acid methyl ester tri-HCl (15 mg, 0.019 mmol; Preparation 18) and N,N-diisopropylethylamine (33.1 uL, 0.190 mmol) dissolved in DMA (0.6 mL, 7 mmol) was added (S)-1-acetyl-2-methyl-pyrrolidine-2-carboxylic acid (3.2 mg, 0.019 mmol, Preparation 19) and HATU (11 mg, 0.028 mmol). The reaction mixture was stirred at room temperature overnight, concentrated, dissolved in 1:1 acetic acid:water (4 mL) and purified by preparative HPLC to provide the di-TFA salt of the title compound (9.1 mg). (m/z): [M+H]$^+$ calcd for $C_{46}H_{57}N_9O_6$ 832.44 found 832.4.

Examples 16-20

Following the procedure of Example 15, the intermediate of Preparation 19 (20 mg, 0.02 mmol) was reacted with the appropriate reagents to provide the following compounds:

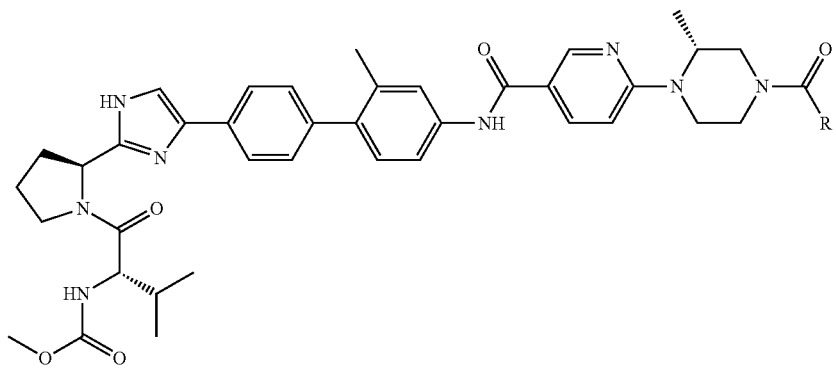

| Ex. No. | R | Reagent | Product |
|---|---|---|---|
| 16 | (S)-gem-dimethylcyclopropyl group | 0.5M (S)-(+)-2,2-dimethyl-cyclopropane carboxylic acid in DMA (38 uL, 0.019 mmol) HATU (11 mg, 0.028) | 2 TFA salt (11.4 mg) (m/z): [M + H]⁺ calcd for $C_{44}H_{54}N_8O_5$ 775.42 found 775.4 |
| 17 | gem-dimethylcyclopropyl group | cyclopropanecarbonyl chloride (1.7 uL, 0.019 mmol) | 2 TFA salt (16.3 mg) (m/z): [M + H]⁺ calcd for $C_{42}H_{50}N_8O_5$ 747.39 found 747.4 |
| 18 | NHCH₃ | 1M methyl isocyanate in toluene (19 uL, 0.019 mmol) | 2 TFA salt (14.8 mg) (m/z): [M + H]⁺ calcd for $C_{40}H_{49}N_9O_5$ 736.39 found 736.4 |
| 19 | imidazolyl group | imidazol-4-carboxylic acid (2.1 mg, 0.019 mmol), EDC (5.5 mg, 0.028 mmol), and HOAt (3.9 mg, 0.028 mmol) | 3 TFA salt (7.6 mg) (m/z): [M + H]⁺ calcd for $C_{42}H_{48}N_{10}O_5$ 773.38 found 773.4 |
| 20 | (R)-1-acetyl-2-methyl-pyrrolidine group | (R)-1-acetyl-2-methyl-pyrrolidine-2-carboxylic acid (3.2 mg, 0.019 mmol HATU (11 mg, 0.028 mmol). | 2 TFA salt (12.1 mg) (m/z): [M + H]⁺ calcd for $C_{46}H_{57}N_9O_6$ 832.44 found 832.4 |

Example 21

[(S)-1-((S)-2-{4-[2'-Ethoxy-4'-({6-[(R)-4-((S)-1-{(S)-2-methoxycarbonylamino-3-methyl-butyryl}-2-methyl-pyrrolidine-2-carbonyl)-2-methyl-piperazin-1-yl]-pyridine-3-carbonyl}-amino)-biphenyl-4-yl]-1H-imidazol-2-yl}-pyrrolidine-1-carbonyl)-2-methyl-propyl]-carbamic acid methyl ester (S)-1-((S)-2-methoxycarbonylamino-3-methyl-butyryl)-2-methyl-pyrrolidine-2-carboxylic acid in DMA (68.5 uL, 0.034 mmol) and HATU (13.0 mg, 0.034 mmol). The reaction mixture was stirred at room temperature overnight, concentrated, dissolved in 1:1 acetic acid:water (1.5 mL) and purified by preparative HPLC to provide the di-TFA salt of the title compound (13.5 mg). (m/z): [M+H]$^+$ calcd for $C_{52}H_{68}N_{10}O_9$ 977.52 found 977.6.

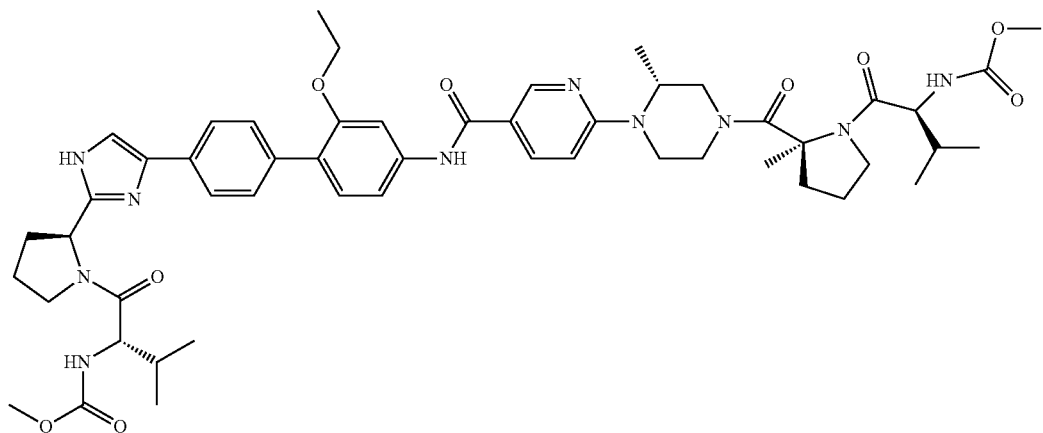

The tri-TFA salt of (S)-1-{(S)-2-[4-(2'-ethoxy-4'-{[6-((R)-2-methyl-piperazin-1-yl)-pyridine-3-carbonyl]-amino}-biphenyl-4-yl)-1H-imidazol-2-yl]-pyrrolidine-1-carbonyl}-2-methyl-propyl)-carbamic acid methyl ester (30 mg, 0.03 mmol; Preparation 22) was dissolved in DMA (1.0 mL, 11 mmol) and N,N-diisopropylethylamine (0.015 mL, 0.086 mmol) was added followed by a solution containing 0.5 M

Examples 22-24

Following the procedure of Example 21, the intermediate of Preparation 22 (30 mg, 0.03 mmol) was reacted with the appropriate reagents to provide the following compounds:

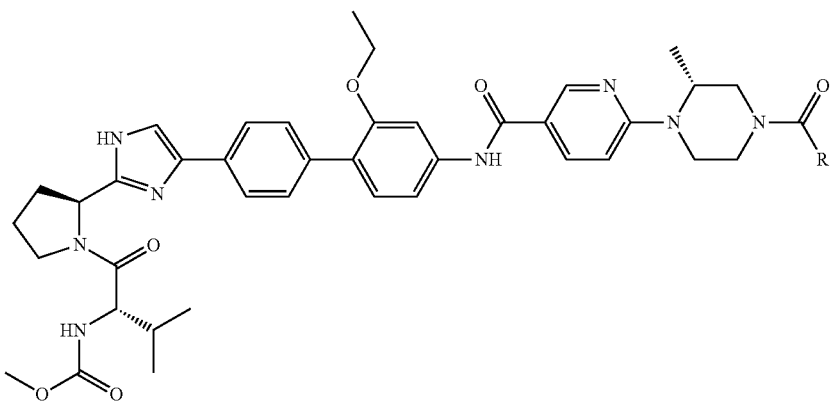

| Ex. No. | R | Reagent | Product |
|---|---|---|---|
| 22 | cyclopropyl (S)-dimethyl | 0.5M (S)-(+)-2,2-dimethyl-cyclopropane carboxylic acid in DMA (69.5 uL, 0.034 mmol), HATU (13 mg, 0.034) | 2 TFA salt (23.8 mg) (m/z): [M + H]$^+$ calcd for $C_{45}H_{56}N_8O_6$ 805.43 found 805.4 |
| 23 | NHCH$_3$ | 1M methyl isocyanate in toluene (34.2 μL, 0.034 mmol) | 2 TFA salt (26.2 mg) (m/z): [M + H]$^+$ calcd for $C_{41}H_{51}N_9O_6$ 766.40 found 766.4 |

| | | | |
|---|---|---|---|
| 24 | 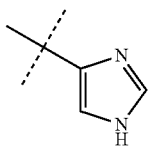 | imidazol-4-carboxylic acid (3.84 mg, 0.034 mmol), HATU (13 mg, 0.034) | 3 TFA salt (24 mg) (m/z): [M + H]+ calcd for $C_{43}H_{50}N_{10}O_6$ 803.39 found 803.4 |

Example 25

[(S)-1-((S)-2-{5-[4'-({6-[(R)-4-((S)-2,2-Dimethyl-cyclopropanecarbonyl)-2-methyl-piperazin-1-yl]-pyridine-3-carbonyl}-amino)-2'-trifluoromethoxy-biphenyl-4-yl]-1H-imidazol-2-yl}-pyrrolidine-1-carbonyl)-2-methyl-propyl]-carbamic acid methyl ester

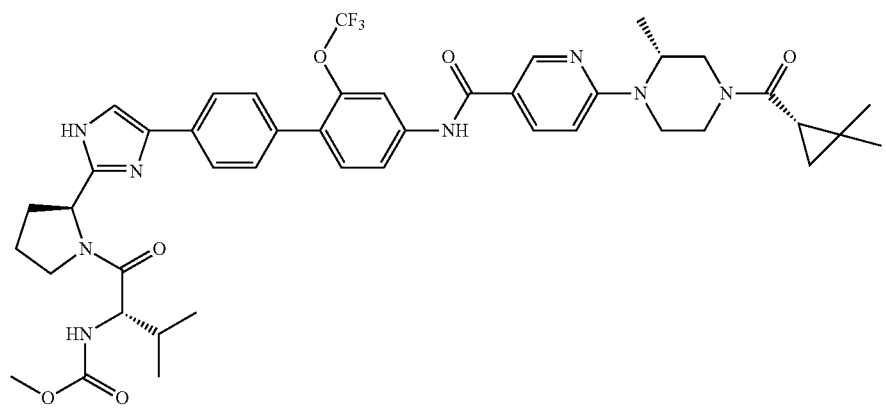

To a solution of ((S)-2-methyl-1-{(S)-2-[4-(4'-{[6-((R)-2-methyl-piperazin-1-yl)-pyridine-3-carbonyl]-amino}-2'-trifluoromethoxy-biphenyl-4-yl)-1H-imidazol-2-yl]-pyrrolidine-1-carbonyl}-propyl)-carbamic acid methyl ester 3[$C_2HF_3O_2$] (15 mg, 0.014 mmol; Preparation 24) and N,N-diisopropylethylamine (24 uL, 0.14 mmol) dissolved in DMA (0.5 mL, 5 mmol) was added 0.5 M (S)-(+)-2,2-dimethylcyclopropane carboxylic acid in DMA (28 uL, 0.014 mmol) and HATU (7.8 mg, 0.021 mmol). The reaction mixture was stirred at room temperature overnight, concentrated, dissolved in 1:1 acetic acid:water (1.5 mL) and purified by preparative HPLC to provide the di-TFA salt of the title compound (11.4 mg). (m/z): [M+H]+ calcd for $C_{44}H_{51}F_3N_8O_6$ 845.39 found 845.4.

Examples 26-28

Following the procedure of Example 25, the intermediate of Preparation 24 (15 mg, 0.014 mmol) was reacted with the appropriate reagents to provide the following compounds:

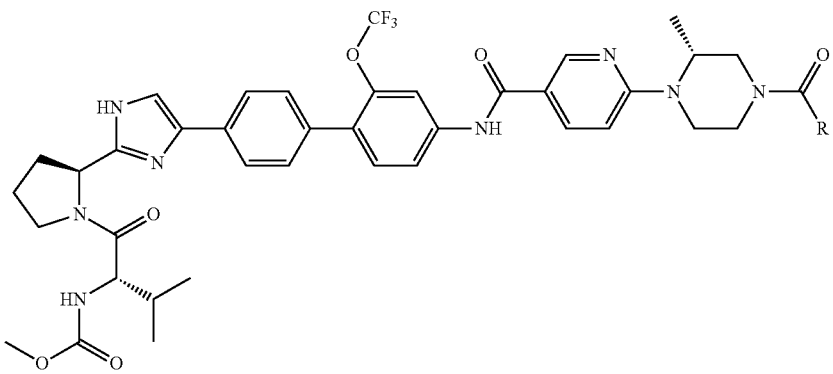

| Ex. No. | R | Reagent | Product |
|---|---|---|---|
| 26 | NHCH$_3$ | 1M methyl isocyanate in toluene (14 uL, 0.014 mmol) | 2 TFA salt (11.7 mg) (m/z): [M + H]+ calcd for $C_{40}H_{46}F_3N_9O_6$ 806.35 found 806.4 |

| | | -continued | |
|---|---|---|---|
| 27 | 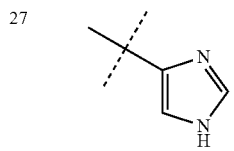 | imidazol-4-carboxylic acid (1.5 mg, 0.014 mmol), EDC (4.0 mg, 0.021 mmol), and HOAt (2.8 mg, 0.021 mmol) | 3 TFA salt (14.2 mg) (m/z): [M + H]⁺ calcd for $C_{42}H_{45}F_3N_{10}O_6$ 843.35 found 843.2 |
| 28 | 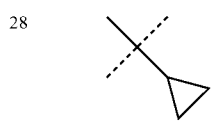 | cyclopropanecarbonyl chloride (1.2 uL, 0.014 mmol) | 2 TFA salt (8.8 mg) (m/z): [M + H]⁺ calcd for $C_{42}H_{47}F_3N_8O_6$ 817.36 found 817.2 |

Example 29

((S)-1-{(S)-2-[4-(4'-{[6-((2R,5S)-2,5-Dimethyl-4-methylcarbamoyl-piperazin-1-yl)-pyridine-3-carbonyl]-amino}-2'-trifluoromethoxy-biphenyl-4-yl)-1H-imidazol-2-yl]-pyrrolidine-1-carbonyl}-2-methyl-propyl)-carbamic acid methyl ester

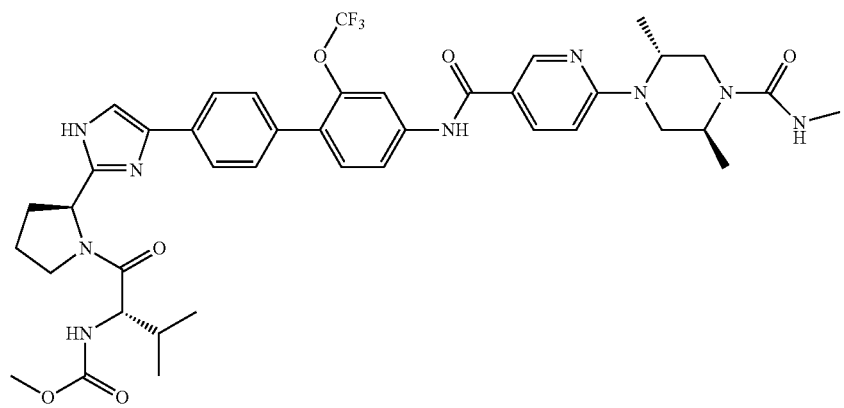

To a solution of ((S)-1-(S)-2-[4-(4'-[6-((2R,5S)-2,5-dimethyl-piperazin-1-yl)-pyridine-3-carbonyl]-amino}-2'-trifluoromethoxy-biphenyl-4-yl)-1H-imidazol-2-yl]-pyrrolidine-1-carbonyl}-2-methyl-propyl)-carbamic acid methyl ester tri-TFA (11.4 mg, 0.011 mmol; Preparation 28) and N,N-diisopropylethylamine (18 uL, 0.11 mmol) dissolved in DMA (0.4 mL, 4 mmol) was added 1.0 M methyl isocyanate in toluene (10 uL, 0.01 mmol). The reaction mixture was stirred at RT overnight, concentrated, dissolved in 1:1 acetic acid:water (1.5 mL) and purified by preparative HPLC to provide the di-TFA salt of the title compound (7.1 mg). (m/z): [M+H]⁺ calcd for $C_{41}H_{48}F_3N_9O_6$ 820.37 found 820.5.

Examples 30-33

Following the procedure of Example 29, the intermediate of Preparation 28 (11.4 mg, 0.011 mmol) was reacted with the appropriate reagents to provide the following compounds:

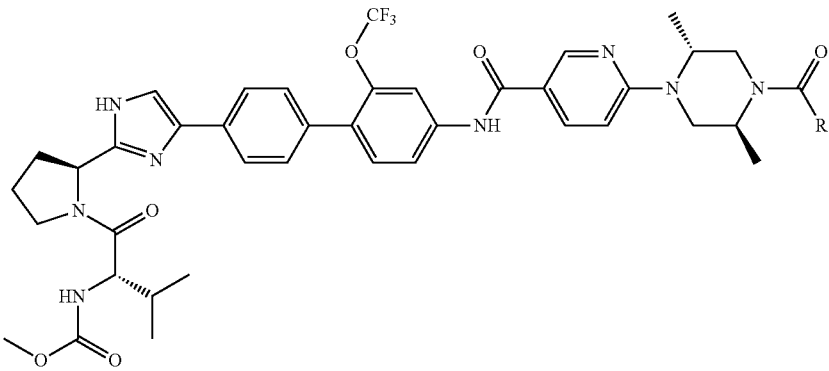

| Ex. No. | R | Reagent | Product |
|---|---|---|---|
| 30 | cyclopropylmethyl | cyclopropanecarbonyl chloride (0.94 uL, 0.01 mmol) | 2 TFA salt (9.7 mg) (m/z): [M + H]$^+$ calcd for $C_{43}H_{49}F_3N_8O_6$ 831.37 found 831.2 |
| 31 | (S)-1-(methoxycarbonyl)pyrrolidin-2-yl | 0.5M (S)-2-methyl-pyrrolidine-1,2-dicarboxylic acid 1-methyl ester in DMA (20.6 uL, 0.0103 mmol) HATU (5.9 mg, 0.0215 mmol). | 2 TFA salt (2.9 mg) (m/z): [M + H]$^+$ calcd for $C_{47}H_{56}F_3N_9O_8$ 932.42 found 932.4 |
| 32 | 1H-imidazol-4-yl | imidazol-4-carboxylic acid (2.1 mg, 0.019 mmol), EDC (3 mg, 0.015 mmol), and HOAt (2.1 mg, 0.015 mmol) | 3 TFA salt (12.2 mg) (m/z): [M + H]$^+$ calcd for $C_{43}H_{47}F_3N_{10}O_6$ 857.36 found 857.2 |
| 33 | (S)-2,2-dimethylcyclopropyl | 0.5M (S)-(+)-2,2-dimethyl-cyclopropane carboxylic acid in DMA (21 uL, 0.010 mmol) HATU (5.9 mg, 0.015) | 2 TFA salt (8.2 mg) (m/z): [M + H]$^+$ calcd for $C_{45}H_{53}F_3N_8O_5$ 859.40 found 859.4 |

Example 34

[(S)-1-((S)-2-{5-[4'-({6-[(R)-4-((S)-2,2-Dimethyl-cyclopropanecarbonyl)-2-methyl-piperazin-1-yl]-pyridine-3-carbonyl}-amino)-2'-trifluoromethyl-biphenyl-4-yl]-1H-imidazol-2-yl}-pyrrolidine-1-carbonyl)-2-methyl-propyl]-carbamic acid methyl ester

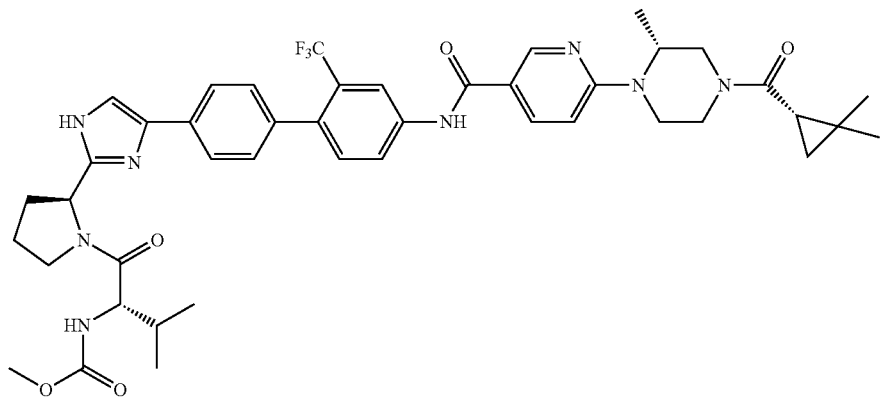

To a solution of ((S)-2-methyl-1-{(S)-2-[4-(4'-{[6-((R)-2-methyl-piperazin-1-yl)-pyridine-3-carbonyl]-amino}-2'-trifluoromethyl-biphenyl-4-yl)-1H-imidazol-2-yl]-pyrrolidine-1-carbonyl}-propyl)-carbamic acid methyl ester tri-TFA (17 mg, 0.016 mmol; Preparation 25) and N,N-diisopropylethylamine (27.5 uL, 0.158 mmol) dissolved in DMA (0.5 mL, 6 mmol) was added 0.5 M (S)-(+)-2,2-dimethylcyclopropane carboxylic acid in DMA (32 uL, 0.016 mmol) and HATU (9 mg, 0.024 mmol). The reaction mixture was stirred at room temperature overnight, concentrated, dissolved in 1:1 acetic acid:water (1.5 mL) and purified by preparative HPLC to provide the di-TFA salt of the title compound (8.3 mg). (m/z): [M+H]$^+$ calcd for $C_{44}H_{51}F_3N_8O_5$ 829.39 found 829.4.

Examples 35-38

Following the procedure of Example 34, the intermediate of Preparation 25 (17 mg, 0.016 mmol) was reacted with the appropriate reagents to provide the following compounds:

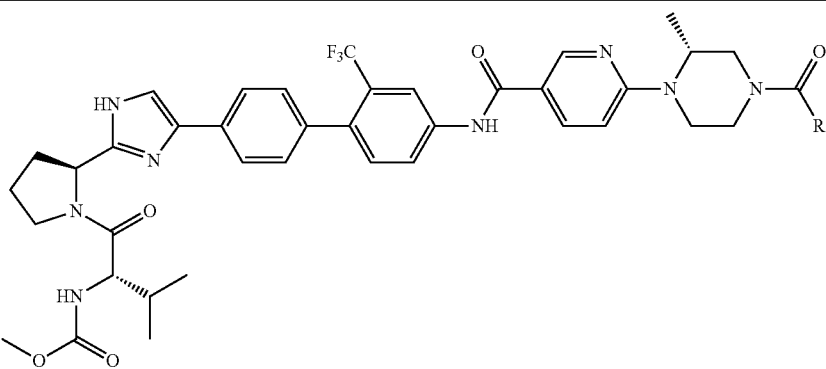

| Ex. No. | R | Reagent | Product |
|---|---|---|---|
| 35 | cyclopropyl (dashed bond) | cyclopropanecarbonyl chloride (1.4 uL, 0.016 mmol) | 2 TFA salt (14.1 mg) (m/z): [M + H]$^+$ calcd for $C_{42}H_{47}F_3N_8O_5$ 801.36 found 801.2 |
| 36 | NHCH$_3$ | 1.0M methyl isocyanate in toluene (16 uL, 0.016 mmol) | 2 TFA salt (12.3 mg) (m/z): [M + H]$^+$ calcd for $C_{40}H_{46}F_3N_9O_5$ 790.36 found 790.2 |
| 37 | imidazol-4-yl (dashed bond) | imidazol-4-carboxylic acid (2 mg, 0.02 mmol), EDC (4.5 mg, 0.024 mmol), and HOAt (3.2 mg, 0.024 mmol) | 3 TFA salt (14.4 mg) (m/z): [M + H]$^+$ calcd for $C_{42}H_{45}F_3N_{10}O_5$ 827.36 found 827.2 |

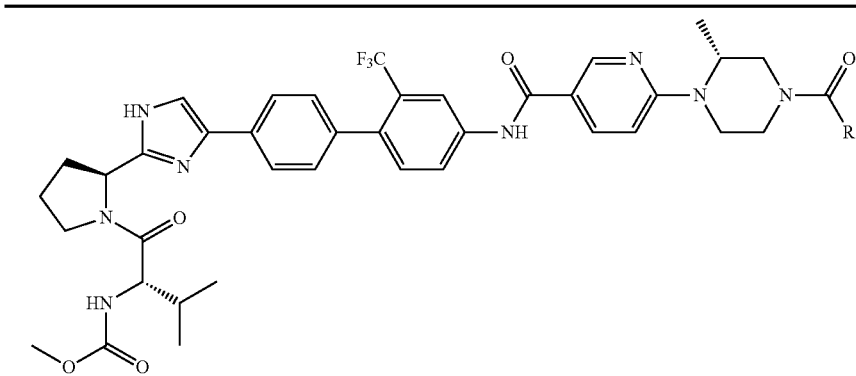

| Ex. No. | R | Reagent | Product |
|---|---|---|---|
| 38 | (S) pyrrolidine with tert-butyl group and methyl carbamate | 0.5M (S)-2-methyl-pyrrolidine-1,2-dicarboxylic acid 1-methyl ester in DMA (31.6 uL, 0.016 mmol) HATU (9 mg, 0.024 mmol). | 2 TFA salt (6.8 mg) (m/z): [M + H]+ calcd for $C_{46}H_{54}F_3N_9O_7$ 902.41 found 902.4 |

Example 39

[(S)-1-((S)-2-{4-[4'-({6-[(2R,5S)-4-((S)-2,2-Dimethyl-cyclopropanecarbonyl)-2,5-dimethyl-piperazin-1-yl]-pyridine-3-carbonyl}-amino)-2,2'-dimethyl-biphenyl-4-yl]-1H-imidazol-2-yl}-pyrrolidine-1-carbonyl)-2-methyl-propyl]-carbamic acid methyl ester To a mixture of (S)-(+)-2,2-dimethylcyclopropane carboxylic acid (2.39 mg, 0.021 mmol) and ((S)-1-{(S)-2-[4-(4'-{[6-((2R,5S)-2,5-dimethyl-piperazin-1-yl)-pyridine-3-carbonyl]-amino}-2,2'-dimethyl-biphenyl-4-yl)-1H-imidazol-2-yl]-pyrrolidine-1-carbonyl}-2-methyl-propyl)-carbamic acid methyl ester tri-TFA (20 mg, 0.019 mmol, Preparation 30) in DMF (0.5 mL, 6 mmol) at RT was added HATU (7.98 mg, 0.021 mmol) followed by N,N-diisopropylethylamine (16.60 uL, 0.095 mmol). The reaction mixture was stirred at RT overnight, concentrated, dissolved in 1:1 acetic acid:water (1.5 mL), filtered, and purified by preparative HPLC to provide the di-TFA salt of the title compound (15 mg).

(m/z): [M+H]+ calcd for $C_{46}H_{58}N_8O_5$ 803.45 found 803.4.

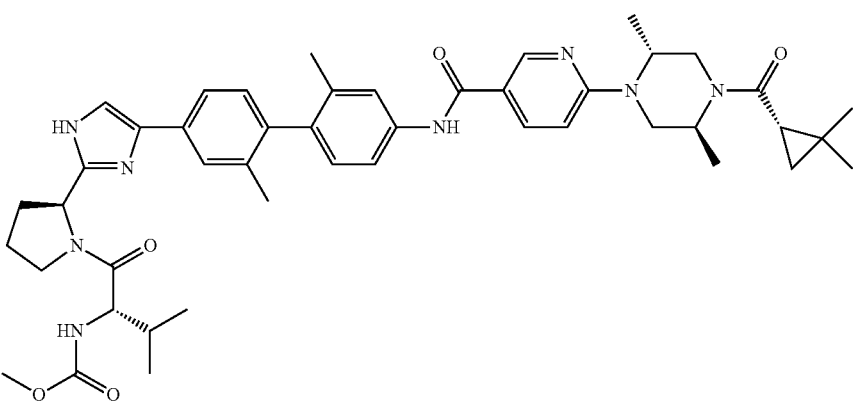

Example 40

Following the procedure of Example 39, the intermediate of Preparation 30 (20 mg, 0.019 mmol) was reacted with (S)-1-((S)-2-methoxycarbonylamino-3-methyl-butyryl)-2-methyl-pyrrolidine-2-carboxylic acid (6 mg, 0.021 mmol) to provide the di-TFA salt of the following compound (6 mg) (m/z): [M+H]+ calcd for $C_{53}H_{70}N_{10}O_8$ 975.45 found 975.6.

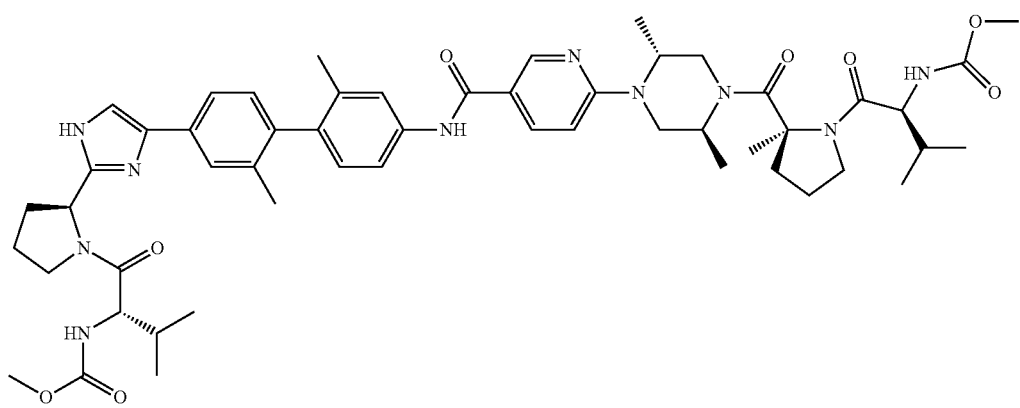

Example 41

[(S)-1-((S)-2-{5-[4'-({6-[(R)-4-((S)-2,2-Dimethyl-cyclopropanecarbonyl)-2-methyl-piperazin-1-yl]-pyridine-3-carbonyl}-amino)-2',6'-difluoro-biphenyl-4-yl]-1H-imidazol-2-yl}-pyrrolidine-1-carbonyl)-2-methyl-propyl]-carbamic acid methyl ester

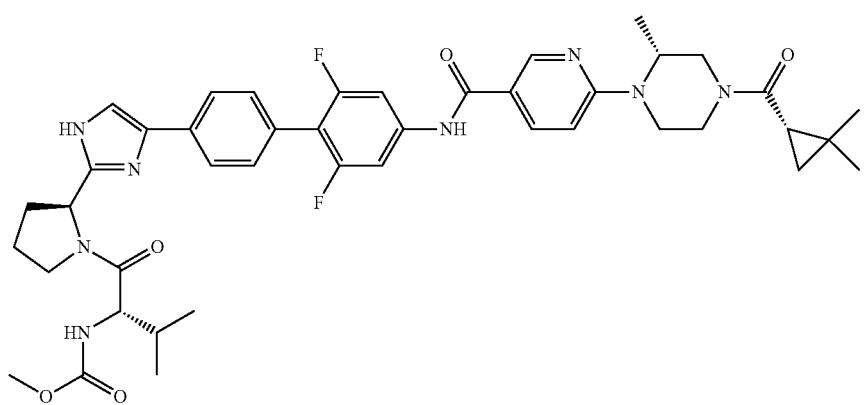

To a solution of ((S)-1-{(S)-2-[4-(2',6'-difluoro-4'-{[6-((R)-2-methyl-piperazin-1-yl)-pyridine-3-carbonyl]-amino}-biphenyl-4-yl)-1H-imidazol-2-yl]-pyrrolidine-1-carbonyl}-2-methyl-propyl)-carbamic acid methyl ester tri-TFA (20 mg, 0.02 mmol; Preparation 32) and N,N-diisopropylethylamine (33.4 uL, 0.192 mmol) dissolved in DMA (0.6 mL, 7 mmol) was added 0.5 M (S)-(+)-2,2-dimethylcyclopropane carboxylic acid in DMA (38 uL, 0.019 mmol) and HATU (11 mg, 0.029 mmol). The reaction mixture was stirred at room temperature overnight, concentrated, dissolved in 1:1 acetic acid:water (1.5 mL) and purified by preparative HPLC to provide the di-TFA salt of the title compound (10.1 mg). (m/z): [M+H]$^+$ calcd for $C_{43}H_{50}F_2N_8O_5$ 797.39 found 797.4.

Examples 42-44

Following the procedure of Example 41, the intermediate of Preparation 32 (20 mg, 0.02 mmol) was reacted with the appropriate reagents to provide the following compounds:

To a solution of ((S)-1-{(S)-2-[4-(2'-fluoro-4'-[6-((R)-2-methyl-piperazin-1-yl)-pyridine-3-carbonyl]-amino}-biphenyl-4-yl)-1H-imidazol-2-yl]-pyrrolidine-1-carbonyl}-2-methyl-propyl)-carbamic acid methyl ester 3[C₂HF₃O₂] (15 mg, 0.015 mmol; Preparation 35) and N,N-diisopropylethy-

| Ex. No. | R | Reagent | Product |
|---|---|---|---|
| 42 | cyclopropyl (dashed bond to quaternary C with methyl) | cyclopropanecarbonyl chloride (1.7 uL, 0.019 mmol) | 2 TFA salt (7.2 mg) (m/z): [M + H]⁺ calcd for $C_{41}H_{44}F_2N_8O_5$ 769.36 found 769.2 |
| 43 | NHCH₃ | 1M methyl isocyanate in toluene (19 uL, 0.19 mmol) | 2 TFA salt (4.1 mg) (m/z): [M + H]⁺ calcd for $C_{39}H_{45}F_2N_9O_5$ 758.35 found 758.4 |
| 44 | imidazol-4-yl | imidazol-4-carboxylic acid (2.1 mg, 0.019 mmol), EDC (5.5 mg, 0.029 mmol), and HOAt (3.9 mg, 0.029 mmol) | 3 TFA salt (5.1 mg) (m/z): [M + H]⁺ calcd for $C_{41}H_{44}F_2N_{10}O_5$ 795.35 found 795.2 |

Example 45

[(S)-1-((S)-2-{5-[4'-({6-[(R)-4-((S)-2,2-Dimethyl-cyclopropanecarbonyl)-2-methyl-piperazin-1-yl]-pyridine-3-carbonyl}-amino)-2'-fluoro-biphenyl-4-yl]-1H-imidazol-2-yl}-pyrrolidine-1-carbonyl)-2-methyl-propyl]-carbamic acid methyl ester lamine (25.5 uL, 0.146 mmol) dissolved in DMA (0.5 mL, 5 mmol) was added 0.5 M (S)-(+)-2,2-dimethylcyclopropane carboxylic acid in DMA (29 uL, 0.015 mmol) and HATU (8.3 mg, 0.022 mmol). The reaction mixture was stirred at room temperature overnight, concentrated, dissolved in 1:1 acetic acid:water (1.5 mL) and purified by preparative HPLC to provide the di-TFA salt of the title compound (9.5 mg). (m/z): [M+H]⁺ calcd for $C_{43}H_{51}FN_8O_5$ 779.40 found 779.4.

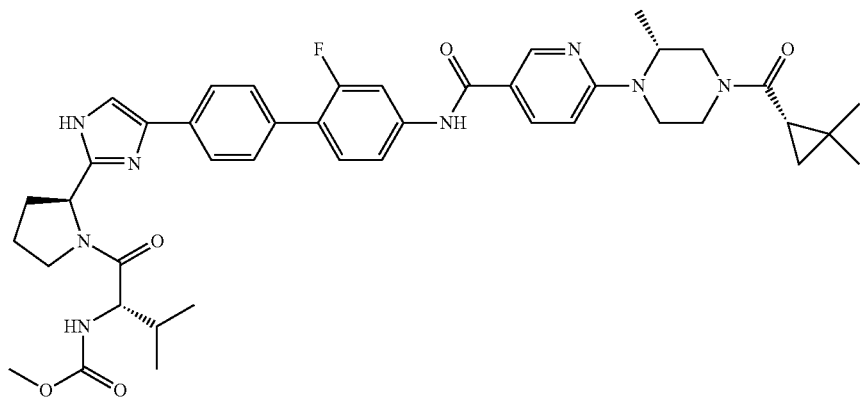

Examples 46-48

Following the procedure of Example 45, the intermediate of Preparation 35 (15 mg, 0.015 mmol) was reacted with the appropriate reagents to provide the following compounds:

A mixture of 6-[(R)-4-((S)-2,2-dimethyl-cyclopropanecarbonyl)-2-methyl-piperazin-1-yl]-nicotinic acid (4.54 mg, 0.014 mmol; Preparation 36), HCTU (8.0 mg, 0.019 mmol), N,N-diisopropylethylamine (0.013 mL, 0.072 mmol), and DMA (0.2 mL, 2 mmol) was stirred for 30 min at

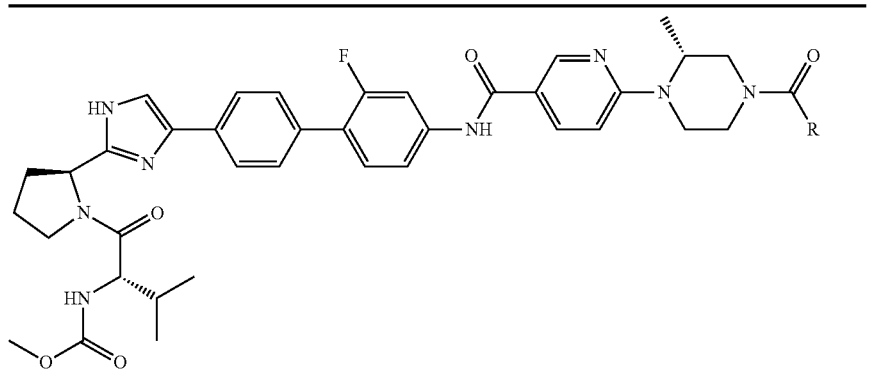

| Ex. No. | R | Reagent | Product |
|---|---|---|---|
| 46 | cyclopropyl (dashed bond) | cyclopropanecarbonyl chloride (1.3 uL, 0.015 mmol) | 2 TFA salt (12 mg) (m/z): [M + H]⁺ calcd for $C_{41}H_{47}FN_8O_5$ 751.37 found 751.2 |
| 47 | NHCH₃ | 1M methyl isocyanate in toluene (15 uL, 0.15 mmol) | 2 TFA salt (10.9 mg) (m/z): [M + H]⁺ calcd for $C_{39}H_{46}FN_9O_5$ 740.36 found 740.4 |
| 48 | imidazol-4-yl (dashed bond) | imidazol-4-carboxylic acid (1.6 mg, 0.015 mmol), EDC (4.2 mg, 0.022 mmol), and HOAt (3.0 mg, 0.022 mmol) | 3 TFA salt (10.7 mg) (m/z): [M + H]⁺ calcd for $C_{41}H_{45}FN_{10}O_5$ 777.36 found 777.2 |

Example 49

[(S)-1-((S)-2-{4-[2'-Chloro-4'-({6-[(R)-4-((S)-2,2-dimethyl-cyclopropanecarbonyl)-2-methyl-piperazin-1-yl]-pyridine-3-carbonyl}-amino)-biphenyl-4-yl]-1H-imidazol-2-yl}-pyrrolidine-1-carbonyl)-2-methyl-propyl]-carbamic acid methyl ester 50° C. and then ((S)-1-{(S)-2-[4-(4'-amino-2'-chloro-biphenyl-4-yl)-1H-imidazol-2-yl]-pyrrolidine-1-carbonyl}-2-methyl-propyl)-carbamic acid methyl ester (7.1 mg, 0.014 mmol; Preparation 37) was added. The reaction mixture was stirred overnight and then HCTU (8 mg) was added and the reaction mixture was heated to 55° C. After 5 h, the reaction mixture was cooled to RT, ethyl acetate and water were added. The organic layer was concentrated under vacuum and puri-

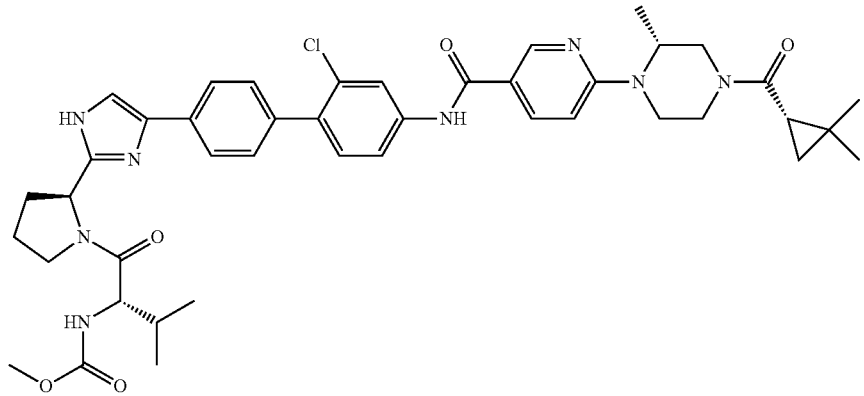

fied by preparative HPLC to provide the di-TFA salt of the title compound (1.3 mg). (m/z): [M+H]+ calcd for $C_{43}H_{51}ClN_8O_5$ 795.37 found 795.4.

Example 50

[(S)-1-((S)-2-{4-[4'-({6-[(R)-4-((S)-2,2-dimethyl-cyclopropanecarbonyl)-2-methyl-piperazin-1-yl]-pyridine-3-carbonyl}-amino)-2,2'-difluoro-biphenyl-4-yl]-1H-imidazol-2-yl}-pyrrolidine-1-carbonyl)-2-methyl-propyl]-carbamicacid methyl ester

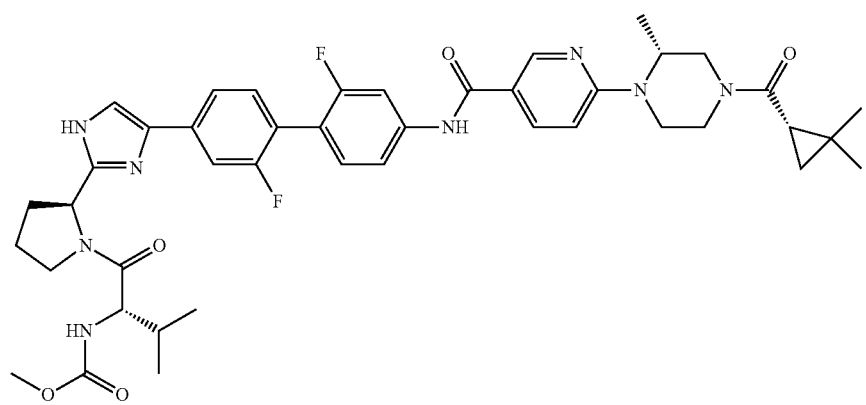

To a solution of 6-[(R)-4-((S)-2,2-dimethyl-cyclopropanecarbonyl)-2-methyl-piperazin-1-yl]-nicotinic acid (6.4 mg, 0.020 mmol; Preparation 36) was added EDC (5.8 mg, 0.030 mmol) and HOAt (4.2 mg, 0.030 mmol) in DMA (0.5 mL, 5 mmol). The reaction mixture was stirred at RT for 30 min and then ((S)-1-{(S)-2-[4-(4'-amino-2,2'-difluoro-biphenyl-4-yl)-1H-imidazol-2-yl]-pyrrolidine-1-carbonyl}-2-methyl-propyl)-carbamic acid methyl ester (10 mg, 0.02 mmol; Preparation 38-B) and N,N-diisopropylethylamine (18 uL, 0.10 mmol) were added and the reaction mixture was stirred at RT overnight. The reaction mixture was concentrated by rotary evaporation, dissolved in 1:1 acetic acid:water (1.5 mL) and purified by reverse phase HPLC to provide the di-TFA salt of the title compound (6.8 mg). (m/z): [M+H]+ calcd for $C_{43}H_{50}F_2N_8O_5$ 797.39 found 797.4.

Example 51

[(S)-1-((S)-2-{4-[4'-({6-[(R)-4-((S)-2,2-Dimethyl-cyclopropanecarbonyl)-2-methyl-piperazin-1-yl]-pyridine-3-carbonyl}-amino)-5'-fluoro-2'-trifluoromethyl-biphenyl-4-yl]-1H-imidazol-2-yl}-pyrrolidine-1-carbonyl)-2-methyl-propyl]carbamic acid methyl ester mg, 0.018 mmol, Preparation 41) and N,N-diisopropylethylamine (15.94 uL, 0.091 mmol) were added. The reaction mixture was stirred at RT overnight, concentrated by rotary evaporation, dissolved in 1:1 acetic acid:water (1.5 mL), filtered, and purified by preparative HPLC to provide the di-TFA salt of the title compound (4.8 mg). (m/z): [M+H]+ calcd for $C_{44}H_{50}F_4N_8O_5$ 847.38 found 847.4.

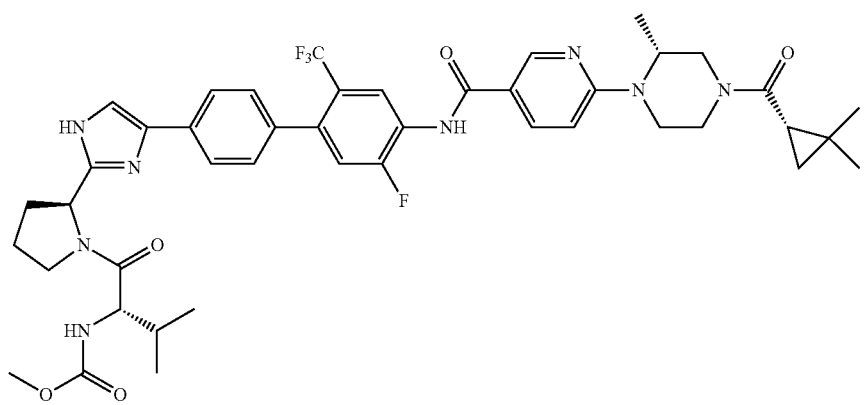

A mixture of (S)-(+)-2,2-dimethylcyclopropane carboxylic acid (2.09 mg, 0.018 mmol) and HATU (8.35 mg, 0.022 mmol) was stirred in DMA (1.0 mL, 11 mmol) for 10 min. and then ((S)-1-{(S)-2-[4-(5'-fluoro-4'-{[6-((R)-2-methyl-piperazin-1-yl)-pyridine-3-carbonyl]-amino}-2'-trifluoromethyl-biphenyl-4-yl)-1H-imidazol-2-yl]-pyrrolidine-1-carbonyl}-2-methyl-propyl)-carbamic acid methyl ester tri-TFA (20.0

Example 52

Following the procedure of Example 51, the intermediate of Preparation 41 (20 mg, 0.019 mmol) was reacted with (S)-1-((S)-2-methoxycarbonylamino-3-methyl-butyryl)-2-methyl-pyrrolidine-2-carboxylic acid (5.24 mg, 0.018 mmol) to provide the di-TFA salt of the following compound (2.8 mg) (m/z): [M+H]+ calcd for $C_{51}H_{62}F_4N_{10}O_8$ 1019.47 found 1019.4.

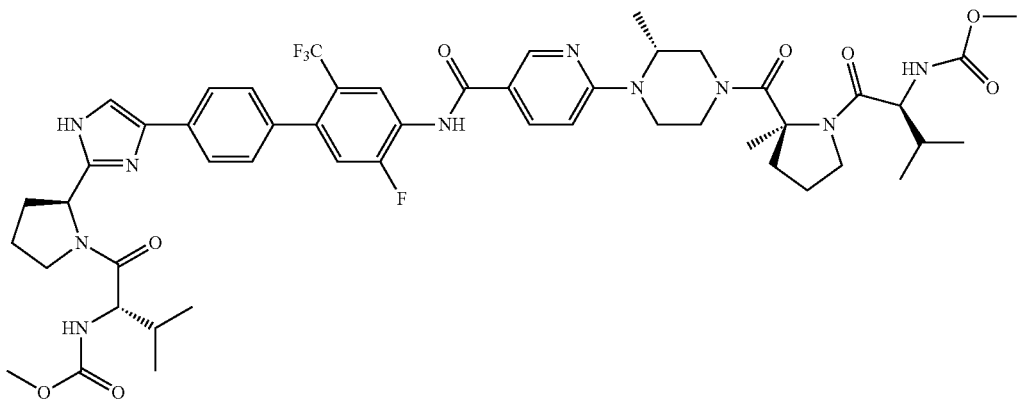

Example 53

((S)-1-{(S)-2-[4-(5'-Fluoro-4'-{[6-OR)-2-methyl-4-methylcarbamoyl-piperazin-1-yl)-pyridine-3-carbonyl]-amino}-2'-trifluoromethoxy-biphenyl-4-yl)-1H-imidazol-2-yl]-pyrrolidine-1-carbonyl}-2-methyl-propyl)-carbamic acid methyl ester

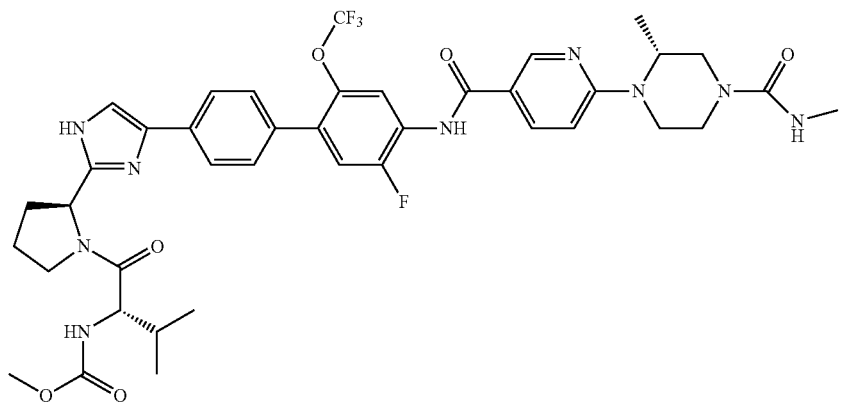

To a solution of 1.0 M methyl isocyanate in toluene (11.4 uL, 0.011 mmol) dissolved in DMA (0.5 mL), was added ((S)-1-{(S)-2-[4-(5'-fluoro-4'-{[6-((R)-2-methyl-piperazin-1-yl)-pyridine-3-carbonyl]-amino}-2'-trifluoromethoxy-biphenyl-4-yl)-1H-imidazol-2-yl]-pyrrolidine-1-carbonyl}-2-methyl-propyl)-carbamic acid methyl ester tri-TFA (12.7 mg, 0.011 mmol; Preparation 44) and N,N-diisopropylethylamine (19.9 uL, 0.114 mmol) and the reaction mixture was stirred at room temperature overnight, concentrated, dissolved in 1:1 acetic acid:water (1.5 mL) and purified by preparative HPLC to provide the di-TFA salt of the title compound (7.7 mg). (m/z): [M+H]$^+$ calcd for $C_{40}H_{48}F_4N_9O_6$ 824.34 found 824.4.

Examples 54-55

Following the procedure of Example 53, the intermediate of Preparation 44 (12.7 mg, 0.011 mmol) was reacted with the appropriate reagents to provide the following compounds:

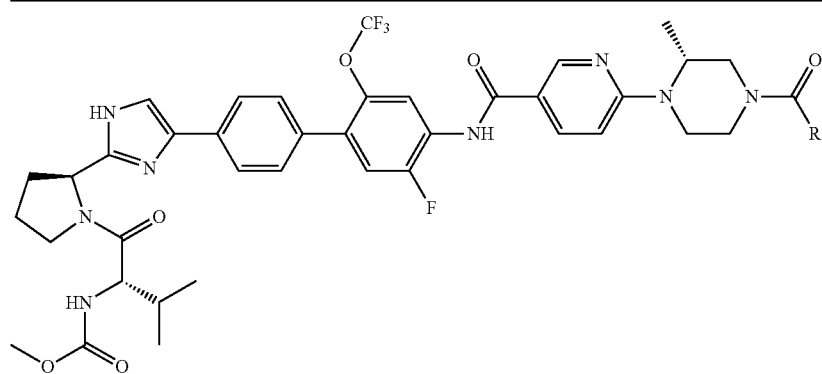

| Ex. No. | R | Reagent | Product |
|---|---|---|---|
| 54 | ![cyclopropyl (S)] | 0.5M (S)-(+)-2,2-dimethyl-cyclopropane carboxylic acid in DMA (22.9 uL, 0.011 mmol) HATU (6.5 mg, 0.017) | 2 TFA salt (11.8 mg) (m/z): [M + H]$^+$ calcd for $C_{44}H_{50}F_4N_8O_6$ 863.38 found 863.4 |

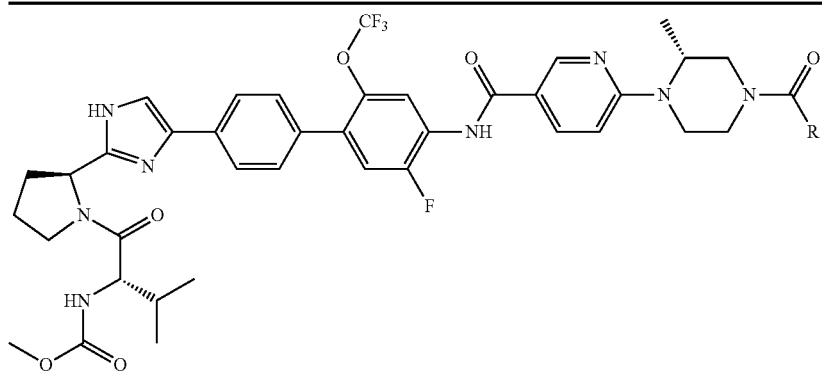

| Ex. No. | R | Reagent | Product |
|---|---|---|---|
| 55 | (structure shown) | (S)-1-((S)-2-methoxycarbonyl-amino- 3-methyl-butyryl)-2-methyl- pyrrolidine-2-carboxylic acid (3.27 mg, 0.011 mmol) HATU (6.5 mg, 0.017) | 2 TFA salt (6.7 mg) (m/z): [M + H]$^+$ calcd for $C_{51}H_{62}F_4N_{10}O_9$ 1,035.46 found 1035.4 |

Example 56

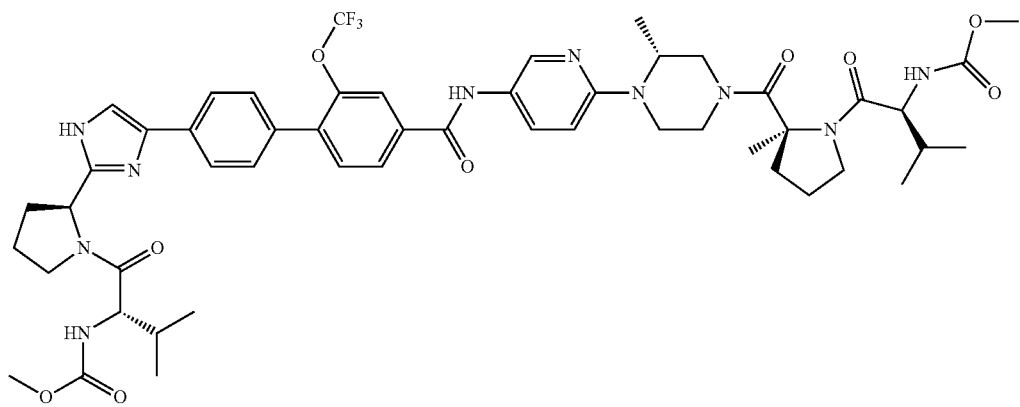

To a mixture of 4'-{2-[(S)-1-((S)-2-methoxycarbonylamino-3-methyl-butyryl)-pyrrolidin-2-yl]-1H-imidazol-4-yl}-2-trifluoromethoxy-biphenyl-4-carboxylic acid TFA (23.0 mg, 0.033 mmol; Preparation 46) and ((S)-1-{(S)-2-[(R)-4-(5-amino-pyridin-2-yl)-3-methyl-piperazine-1-carbonyl]-2-methyl-pyrrolidine-1-carbonyl}-2-methyl-propyl)-carbamic acid methyl ester (15.4 mg, 0.033 mmol; Preparation 48) in DMF (0.5 mL) at RT was added HATU (14.0 mg, 0.037 mmol) and N,N-diisopropylethylamine (29.1 μL, 0.167 mmol). The resulting mixture was stirred at RT for 2 h, and then partitioned between EtOAc (10 mL) and water (2 mL). The organic layer was washed with water (2 mL), dried over sodium sulfate, filtered and concentrated to give a brownish oil. The residue was dissolved in 1:1 acetic acid: water (1.5 mL), filtered and purified by reverse phase HPLC. Desired fractions were combined and freeze dried to give the di-TFA salt of the title compound (9.1 mg, 22% yield) as a light pinkish solid. (m/z): [M+H]$^+$ calcd for $C_{51}H_{63}F_3N_{10}O_9$ 1,017.47 found 1017.9.

Example 57

[(S)-1-((S)-2-{4-[4'-({6-[(2R),5S)-4-((S)-2,2-Dimethyl-cyclopropanecarbonyl)-2,5-dimethyl-piperazin-1-yl]-pyridine-3-carbonyl}-amino)-5'-fluoro-2'-trifluoromethyl-biphenyl-4-yl]-1H-imidazol-2-yl}-pyrrolidine-1-carbonyl)-2-methyl-propyl]-carbamic acid methyl ester

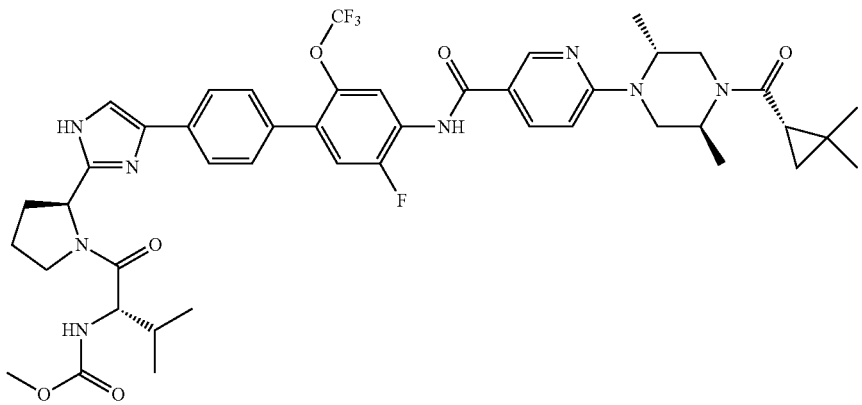

To a solution of ((S)-1-{(S)-2-[4-(4'-{[6-((2R,5S)-2,5-dimethyl-piperazin-1-yl)-pyridine-3-carbonyl]-amino}-5'-fluoro-2'-trifluoromethoxy-biphenyl-4-yl)-1H-imidazol-2-yl]-pyrrolidine-1-carbonyl}-2-methyl-propyl)-carbamic acid methyl ester 3-TFA (15 mg, 0.013 mmol; Preparation 50) and N,N-diisopropylethylamine (23 uL, 0.13 mmol) dissolved in DMA (0.5 mL, 5 mmol;) was added 0.5 M (S)-(+)-2,2-dimethylcyclopropane carboxylic acid in DMA (27 μL, 0.013 mmol) and HATU (7.6 mg, 0.020 mmol). The reaction mixture was stirred at 50° C. for 2 h, concentrated, dissolved in 1:1 acetic acid:water (1.5 mL) and purified by reverse phase HPLC to provide the title compound (9.1 mg) as the di-TFA salt. (m/z): [M+H]$^+$ calcd for $C_{45}H_{52}F_4N_8O_6$ 877.39 found 878.0.

Examples 58-60

Following the procedure of Example 57, the intermediate of Preparation 50 (15 mg, 0.013 mmol) was reacted with the appropriate reagents to provide the following compounds:

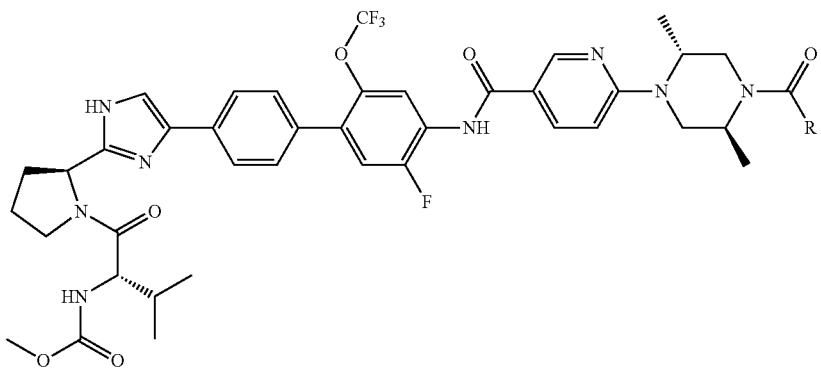

| Ex. No. | R | Reagent | Product |
|---|---|---|---|
| 58 | NHCH$_3$ | 1M methyl isocyanate in toluene (13 uL, 0.013 mmol) | 2 TFA salt (4.5 mg) (m/z): [M + H]$^+$ calcd for $C_{41}H_{47}F_4N_9O_6$ 838.36 found 839.0 |
| 59 | ![imidazole] | imidazol-4-carboxylic acid (1.5 mg, 0.013 mmol), HATU (7.6 mg, 0.020 mmol) | 3 TFA salt (6.6 mg) (m/z): [M + H]$^+$ calcd for $C_{43}H_{46}F_4N_{10}O_6$ 875.35 found 876.0 |

-continued

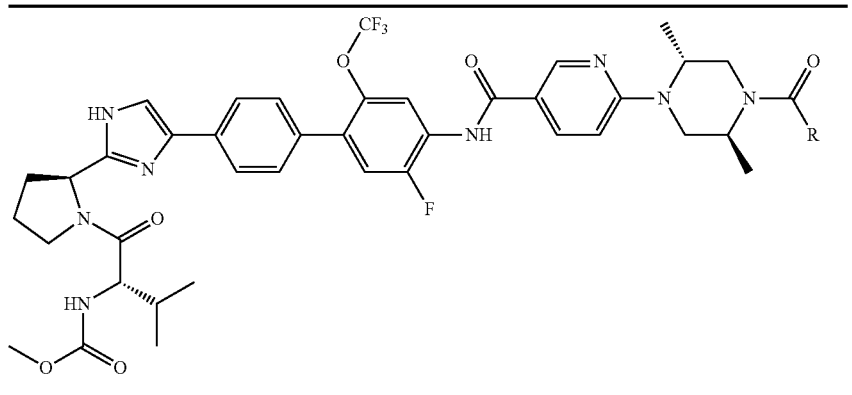

| Ex. No. | R | Reagent | Product |
|---|---|---|---|
| 60 | (3-pyrazolyl) | 4-pyrazolecarboxylic acid (1.5 mg, 0.013 mmol) HATU (7.6 mg, 0.020 mmol) | 3 TFA salt (6.7 mg) (m/z): [M + H]$^+$ calcd for $C_{43}H_{46}F_4N_{10}O_6$ 875.35 found 876.0 |

Example 61

[(S)-1-((S)-2-{4-[5'-Chloro-4'-({6-[(R)-4-((S)-2,2-dimethyl-cyclopropanecarbonyl)-2-methyl-piperazin-1-yl]-pyridine-3-carbonyl}-amino)-2'-trifluoromethyl-biphenyl-4-yl]-1H-imidazol-2-yl}-pyrrolidine-1-carbonyl)-2-methyl-propyl]-carbamic acid methyl ester To a solution of 0.5 M (S)-(+)-2,2-dimethylcyclopropane carboxylic acid in DMA (28.9 µL, 0.015 mmol;), and HATU (8.25 mg, 0.022 mmol) dissolved in DMA (0.5 mL), was added ((S)-1-{(S)-2-[4-(5'-Chloro-4'-{[6-((R)-2-methyl-piperazin-1-yl)-pyridine-3-carbonyl]-amino}-2'-trifluoromethyl-biphenyl-4-yl)-1H-imidazol-2-yl]-pyrrolidine-1-carbonyl}-2-methyl-propyl)-carbamic acid methyl ester 3 TFA (16 mg, 0.014 mmol; Preparation 53) and N,N-diisopropylethylamine (25.2 uL, 0.15 mmol) and the reaction mixture was stirred at RT overnight, concentrated, dissolved in 1:1 acetic acid:water (1.5 mL) and purified by reverse phase HPLC to provide the title compound (8.6 mg) as the di-TFA salt. (m/z): [M+H]$^+$ calcd for $C_{11}H_{50}ClF_3N_8O_5$ 863.35 found 863.4.

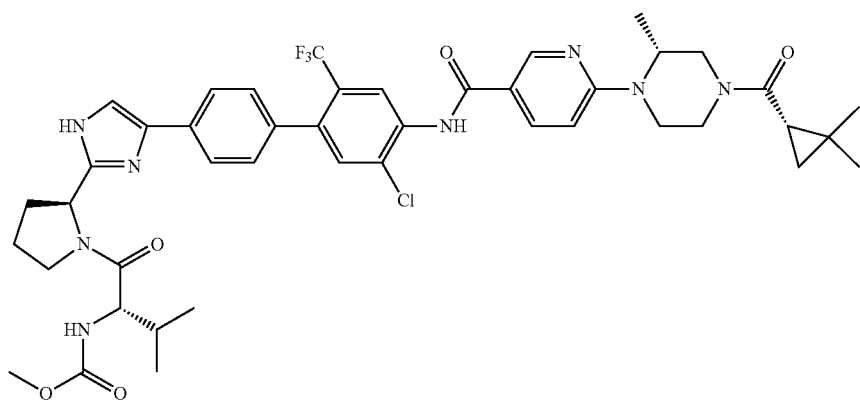

Example 62

Following the procedure of Example 61 the intermediate of Preparation 53 (16 mg, 0.014 mmol) was reacted with (S)-1-((S)-2-methoxycarbonylamino-3-methyl-butyryl)-2-methyl-pyrrolidine-2-carboxylic acid (4.14 mg, 0.015 mmol) to provide the di-TFA salt of the following compound (6.5 mg) (m/z): [M+H]$^+$ calcd for $C_{51}H_{62}ClF_3N_{10}O_8$ 1,035.44 found 1035.4.

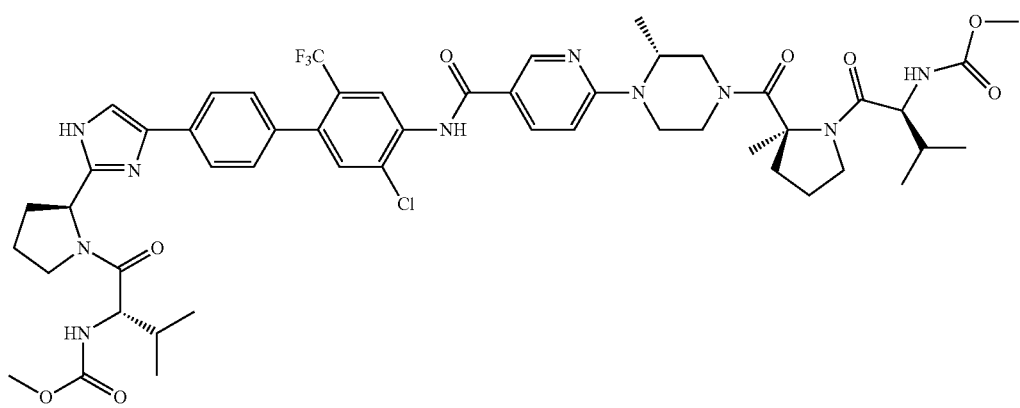

Example 63-65

Following the procedure of Example 57, substituting the intermediate of Preparation 55 (15 mg, 0.013 mmol) for the intermediate of Preparation 50 (15 mg, 0.013 mmol), the following compounds were prepared

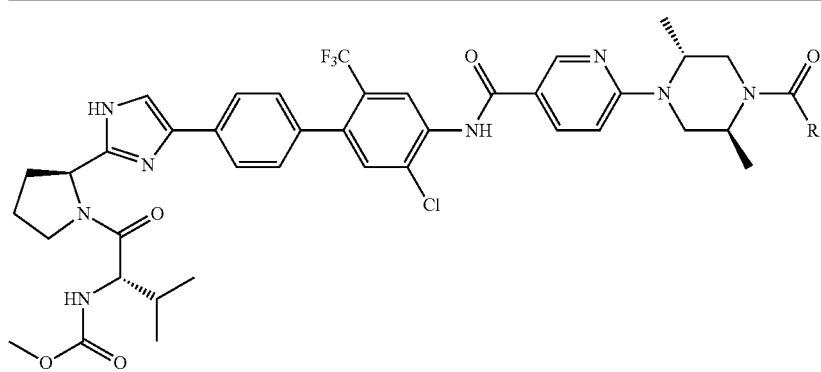

| Ex. No. | R | Reagent | Product |
|---|---|---|---|
| 63 | (S) dimethylcyclopropyl | 0.5M (S)-(+)-2,2-dimethyl-cyclopropane carboxylic acid in DMA (27 μL, 0.013 mmol) HATU (7.6 mg, 0.02) | 2 TFA salt (14.6 mg) (m/z): [M + H]+ calcd for $C_{45}H_{52}ClF_3N_8O_5$ 877.37 found 878.0 |
| 64 | NHCH₃ | 1M methyl isocyanate in toluene (13 uL, 0.013 mmol) | 2 TFA salt (15.3 mg) (m/z): [M + H]+ calcd for $C_{43}H_{46}ClF_3N_{10}O_5$ 875.33 found 876.0 |
| 65 | imidazolyl | imidazol-4-carboxylic acid (1.5 mg, 0.013 mmol), HATU (7.6 mg, 0.020 mmol) | 3 TFA salt (15.3 mg) (m/z): [M + H]+ calcd for $C_{43}H_{46}ClF_3N_{10}O_5$ 875.33 found 876.0 |

Example 66

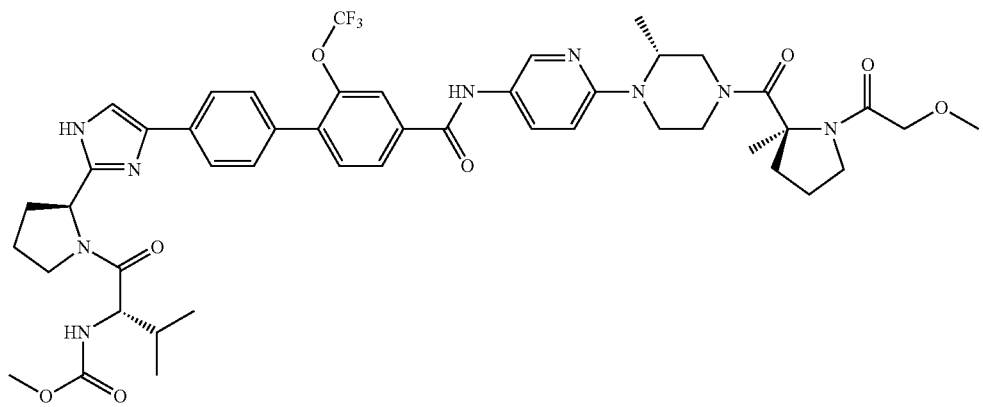

Methoxyacetic acid (1.14 µL, 0.014 mmol) was dissolved in DMA (1 mL) and HATU (5.65 mg, 0.015 mmol) was added. The reaction mixture was stirred at RT for 15 min and then ((S)-2-methyl-1-{(S)-2-[4-(4'-{6-[(R)-2-methyl-4-((S)-2-methyl-pyrrolidine-2-carbonyl)-piperazin-1-yl]-pyridin-3-ylcarbamoyl}-2'-trifluoromethoxy-biphenyl-4-yl)-1H-imidazol-2-yl]-pyrrolidine-1-carbonyl}-propyl)-carbamic acid methyl ester 3 HCl (12.0 mg, 0.012 mmol; Preparation 57) was added followed by N,N-diisopropylethylamine (10.8 µL, 0.062 mmol) and the reaction mixture was stirred at 55° C. overnight, concentrated, dissolved in 1:1 acetic acid:water (1.5 mL) and purified by reverse phase HPLC to provide the di-TFA salt of the title compound (8.3 mg) (m/z): $[M+H]^+$ calcd for $C_{47}H_{56}F_3N_9O_8$ 932.42 found 932.4.

Examples 67-70

Following the procedure of Example 66, the intermediate of Preparation 57 (12.0 mg, 0.012 mmol) was reacted with the appropriate reagents to provide the following compounds:

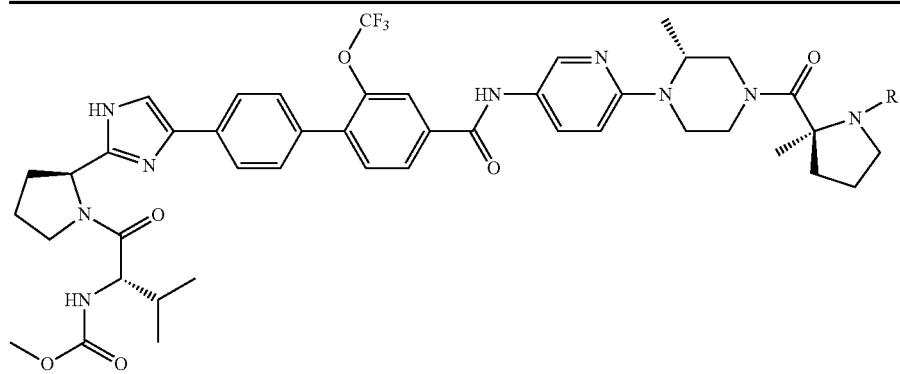

| Ex. No. | R | Reagent | Product |
|---|---|---|---|
| 67 | (2S,3S)-3-hydroxy-2-methoxycarbonylamino-butyric acid (2.63 mg, 0.015 mmol) HATU (5.65 mg, 0.015 mmol)* | 2 TFA salt (1.7 mg) (m/z): $[M + H]^+$ calcd for $C_{50}H_{61}F_3N_{10}O_{10}$ 1,019.45 found 1019.4 |
| 68 | | glycolic acid (1.13 mg, 0.015 mmol) HATU (5.65 mg, 0.015 mmol) | 2 TFA salt (1.5 mg) (m/z): $[M + H]^+$ calcd for $C_{46}H_{54}F_3N_9O_8$ 918.41 found 918.4 |
| 69 | | 2-hydroxy-2-methyl-propionic acid (1.55 mg, 0.015 mmol) HATU (5.65 mg, 0.015 mmol) | 2 TFA salt (0.6 mg) (m/z): $[M + H]^+$ calcd for $C_{48}H_{58}F_3N_9O_8$ 946.44 found 946.4 |

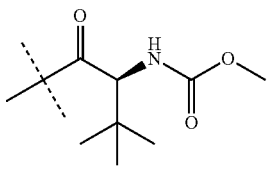

| Ex. No. | R | Reagent | Product |
|---|---|---|---|
| 70 | ![R group structure] | (S)-2-Methoxycarbonylamino-3,3-dimethyl-butyric acid (2.81 mg, 0.015 mmol) HATU (5.65 mg, 0.015 mmol)* | 2 TFA salt (1 mg) (m/z): [M + H]$^+$ calcd for $C_{52}H_{65}F_3N_{10}O_9$ 1,031.49 found 1031.4 |

*Prior to isolation and purification, another equivalent of the corresponding acid, along with HOAt (2.53 mg, 0.019 mmol) and EDC (3.56 mg, 0.019 mmol), previously stirred at RT for 15 min, were added to the reaction mixture which was stirred at 60° C. overnight

Example 71

{(S)-1-[(S)-2-(4-{4-[5-({6-[(2R,5S)-4-((S)-2,2-Dimethyl-cyclopropanecarbonyl)-2,5-dimethyl-piperazin-1-yl]-pyridine-3-carbonyl}-amino)-6-methyl-pyridin-2-yl]-phenyl}-1H-imidazol-2-yl)-pyrrolidine-1-carbonyl]-2-methyl-propyl}-carbamic acid methyl ester A mixture of (s)-(+)-2,2-dimethylcyclopropane carboxylic acid (2.13 mg, 0.019 mmol), and HATU (8.52 mg, 0.022 mmol) was stirred in DMA (1 mL) for 10 min and then [(S)-1-((S)-2-{4-[4-(5-{[6-((2R,5S)-2,5-dimethyl-piperazin-1-yl)-pyridine-3-carbonyl]-amino}-6-methyl-pyridin-2-yl)-phenyl]-1H-imidazol-2-yl}-pyrrolidine-1-carbonyl)-2-methyl-propyl]-carbamic acid methyl ester 4 HCl (15 mg, 0.018 mmol; Preparation 59) and N,N-diisopropylethylamine (16.3 µL, 0.093 mmol) were added. The reaction mixture was stirred at RT overnight, concentrated by rotary evaporation, dissolved in 1:1 acetic acid:water (1.5 mL) and purified by reverse phase HPLC to provide the tri-TFA salt of the title compound (11 mg). m/z): [M+H]$^+$ calcd for $C_{44}H_{55}N_9O_5$ 790.43 found 790.4.

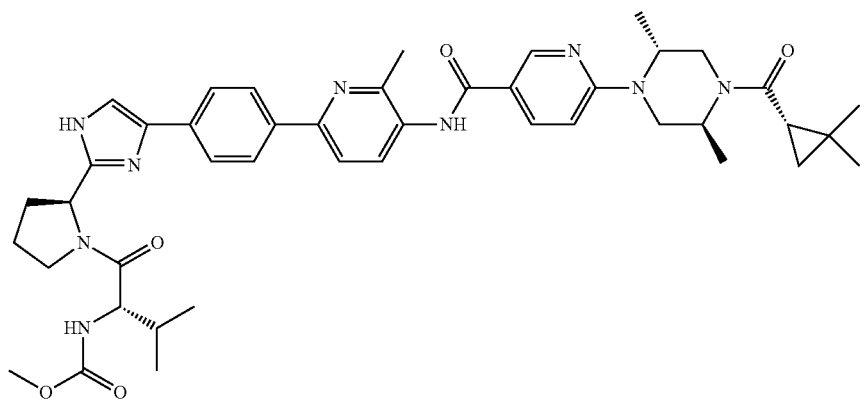

Examples 72-75

Following the procedure of Example S, the intermediate of Preparation 59 (15.0 mg, 0.018 mmol) was reacted with the appropriate reagents to provide the following compounds:

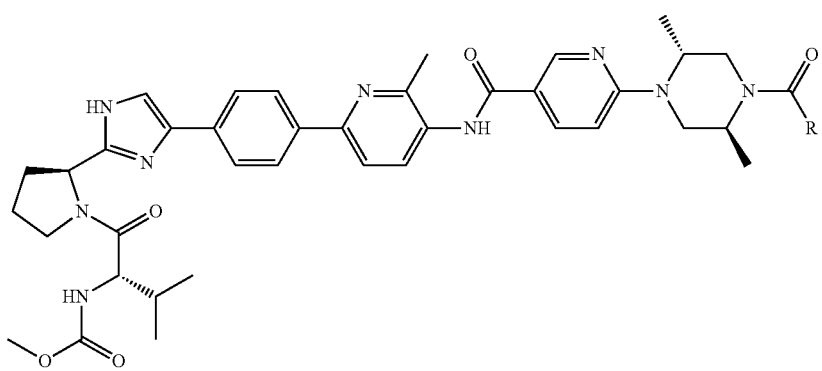

| Ex. No. | R | Reagent | Product |
|---|---|---|---|
| 72 | 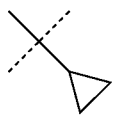 | (S)-1-((S)-2-methoxycarbonyl-amino-3-methyl-butyryl)-2-methyl-pyrrolidine-2-carboxylic acid (5.35 mg, 0.019 mmol) HATU (8.52 mg, 0.022 mmol) | 3 TFA salt (1.7 mg) (m/z): [M + H]$^+$ calcd for $C_{51}H_{67}N_{11}O_8$ 962.52 found 962.4 |
| 73 | 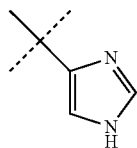 | cyclopropanecarbonyl chloride (1.95 mg, 0.019 mmol) | 3 TFA salt (6.5 mg) (m/z): [M + H]$^+$ calcd for $C_{42}H_{51}N_9O_5$ 762.40 found 762.4 |
| 74 | NHCH$_3$ | methylaminoformyl chloride (1.75 mg, 0.019 mmol) | 3 TFA salt (4 mg) (m/z): [M + H]$^+$ calcd for $C_{40}H_{50}N_{10}O_5$ 751.40 found 751.4 |
| 75 | | imidazol-4-carboxylic acid (2.09 mg, 0.019 mmol), EDC (5.37 mg, 0.028 mmol) | 3 TFA salt (5.4 mg) (m/z): [M + H]$^+$ calcd for $C_{42}H_{49}N_{11}O_5$ 788.39 found 788.4 |

Example 76

{(S)-1-[(S)-2-(4-{6-[4-({6-[(R)-4-((S)-2,2-Dimethyl-cyclopropanecarbonyl)-2-methyl-piperazin-1-yl]-pyridine-3-carbonyl}-amino)-trifluoromethoxyphenyl]-pyridin-3-yl}-1H-imidazol-2-yl)-pyrrolidine-1-carbonyl]-2-methyl-propyl}-carbamic acid methyl ester

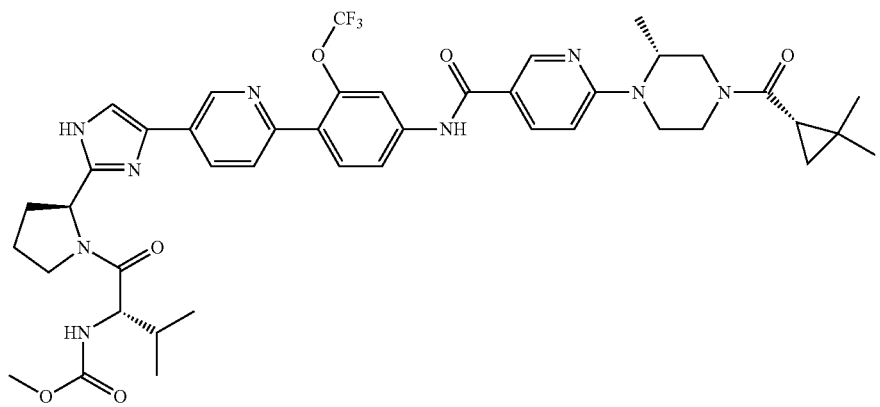

To a mixture of [(S)-2-methyl-1-((S)-2-{4-[6-(4-{[6-((R)-2-methyl-piperazin-1-yl)-pyridine-3-carbonyl]-amino}-2-trifluoromethoxy-phenyl)-pyridin-3-yl]-1H-imidazol-2-yl}-pyrrolidine-1-carbonyl)-propyl]-carbamic acid methyl ester 3-TFA (14.25 mg, 0.013 mmol; Preparation 61) and (S)-(+)-2,2-dimethylcyclopropane carboxylic acid (2.2 mg, 0.020 mmol) and HATU (7.4 mg, 0.020 mmol) in DMF (0.5 mL) at RT was added N,N-diisopropylethylamine (11.37 µL, 0.065 mmol). The reaction mixture was stirred at RT overnight, concentrated, dissolved in 1:1 acetic acid:water (1.5 mL), and purified by reverse phase HPLC to provide the tri-TFA salt of the title compound (10.8 mg). m/z): [M+H]$^+$ calcd for $C_{43}H_{50}F_3N_9O_6$ 846.38 found 847.0.

Example 77

(a) [(S)-1-((S)-2-{4-[5'-Chloro-2'-trifluoromethoxy-4'-({6-[(R)-2-methyl-4-((S)-2-methyl-pyrrolidine-2-carbonyl)-piperazin-1-yl]-pyridine-3-carbonyl}-amino)-biphenyl-4-yl]-1H-imidazol-2-yl}-pyrrolidine-1-carbonyl)-2-methyl-propyl]-carbamic acid methyl ester

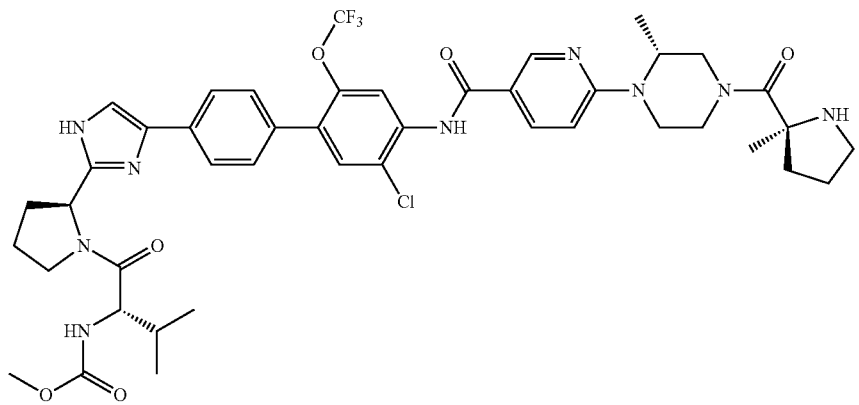 [SMILES: COC(=O)N[C@H](C(=O)N1CCC[C@H]1c1nc(-c2ccc(-c3cc(Cl)c(NC(=O)c4ccc(N5CCN(C(=O)[C@]6(C)CCCN6)C[C@H]5C)nc4)cc3OC(F)(F)F)cc2)c[nH]1)C(C)C]

A mixture of (S)-2-methyl-pyrrolidine-1,2-dicarboxylic acid 1-tert-butyl ester (23.2 mg, 0.10 mmol) and HATU (38.5 mg, 0.10 mmol) in DMA (1 mL) was stirred at RT for 20 min and then ((S)-1-{(S)-2-[4-(5'-chloro-4'-{[6-((R)-2-methyl-piperazin-1-yl)-pyridine-3-carbonyl]-amino}-2'-trifluoromethoxy-biphenyl-4-yl)-1H-imidazol-2-yl]-pyrrolidine-1-carbonyl}-2-methyl-propyl)-carbamic acid methyl ester 3TFA (95.0 mg, 0.084 mmol; Preparation 62) was added followed by N,N-diisopropylethylamine (0.074 mL, 0.42 mmol) and the reaction mixture was stirred at 55° C. overnight. The reaction mixture was diluted in ethyl acetate and washed with water followed by brine. The organic layer was dried over sodium sulfate, filtered and concentrated to produce a yellow oil.

The oil from the previous step was treated with 4 M HCl in 1,4-dioxane (0.63 mL, 2.53 mmol) and HCl (0.16 mL) and the reaction mixture was stirred at RT for 1 h, concentrated, and evaporated with EtOAc (2x) to produce the tri-HCl salt of the title intermediate as a light yellow solid (87.3 mg).

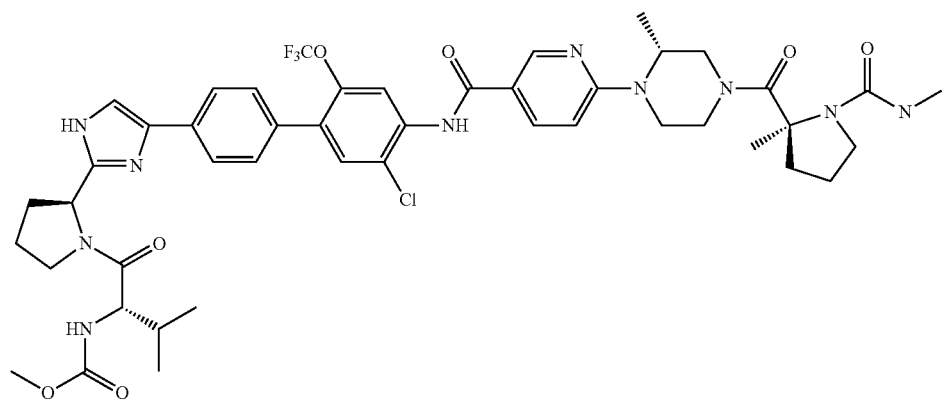

To the product of the previous step (22 mg, 0.022 mmol) dissolved in DMA was added 0.5 M methylaminoformyl chloride in DMA (52.6 µL, 0.026 mmol), followed by N,N-diisopropylethylamine (0.016 mL, 0.089 mmol) and the reaction mixture was stirred at RT overnight, concentrated, dissolved in 1:1 acetic acid:water (1.5 mL) and purified by reverse phase HPLC to provide the di-TFA salt of the title compound (14.4 mg). m/z: [M+H]$^+$ calcd for $C_{46}H_{54}ClF_3N_{10}O_7$ 951.38 found 951.6.

Example 78

Alternative synthesis of ((S)-1-{(S)-2-[4-(4'-{[6-((2R,5S)-2,5-Dimethyl-4-methylcarbamoyl-piperazin-1-yl)-pyridine-3-carbonyl]-amino}-2'-trifluoromethoxy-biphenyl-4-yl)-1H-imidazol-2-yl]-pyrrolidine-1-carbonyl}-2-methyl-propyl)-carbamic acid methyl ester (a) N-(4-Bromo-3-trifluoromethoxy-phenyl)-6-fluoro-nicotinamide

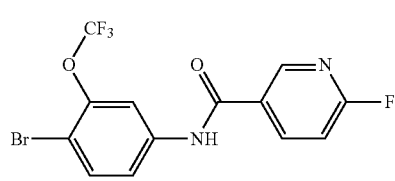 [SMILES: O=C(Nc1ccc(Br)c(OC(F)(F)F)c1)c1ccc(F)nc1]

To a solution of 4-bromo-3-trifluoromethoxy-phenylamine (3.15 g, 12.3 mmol) and triethylamine (3.43 mL, 24.6 mmol) in DCM (25 mL) was slowly added a solution of 2-fluoropyridine-5-carbonyl chloride (2.36 g, 14.8 mmol) in DCM (10 mL). After 2 h at RT, MTBE (90 mL) was added and the reaction mixture was washed with water, brine, and saturated sodium carbonate, dried, and evaporated to give a solid (5.4 g). Ethanol (43 mL) was added to the solid and then water (43 mL) was slowly added. The reaction mixture was stirred for 1.5 h, filtered, and washed with 1:4 ethanol:water (2×25 mL) to give the title intermediate as a white solid (3.87 g). HPLC method C: Retention time=21.3 min.

(b) (2S,5R)-4-[5-(4-Bromo-3-trifluoromethoxy-phenylcarbamoyl)-pyridin-2-yl]-2,5-dimethyl-piperazine-1-carboxylic acid tert-butyl ester

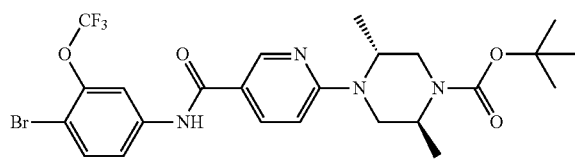 [SMILES: C[C@@H]1CN(C(=O)OC(C)(C)C)[C@@H](C)CN1c1ccc(C(=O)Nc2ccc(Br)c(OC(F)(F)F)c2)cn1]

The product of the previous step (3.86 g, 10.2 mmol) (2S, 5R)-2,5-dimethyl-piperazine-1-carboxylic acid tert-butyl ester (2.62 g, 12.2 mmol) and N,N-diisopropylethylamine (5.32 mL, 30.5) was dissolved in DMSO (12 mL). The reaction mixture heated at 120° C. for 3 h, diluted with EtOAc (100 mL), washed with water, and saturated NH₄Cl, water, and brine. The reaction mixture was evaporated to about 40% volume and 3 M HCl in cyclopentyl methyl ether (4.24 mL, 12.7 mmol) was added slowly. Seeds from a previous run at smaller scale were added and the reaction mixture was stirred for 2 days and filtered to provide the HCl salt of the title intermediate (5.15 g, 83% yield). HPLC method C: Retention time=21.1 min (c) (2S,5R)-4-[5-(4'-{2-[(S)-1-((S)-2-Methoxycarbonylamino-3-methyl-butyryl)-pyrrolidin-2-yl]-1H-imidazol-4-yl}-2-trifluoromethoxy-biphenyl-4-ylcarbamoyl)-pyridin-2-yl]-2,5-dimethyl-piperazine-1-carboxylic acid tert-butyl ester

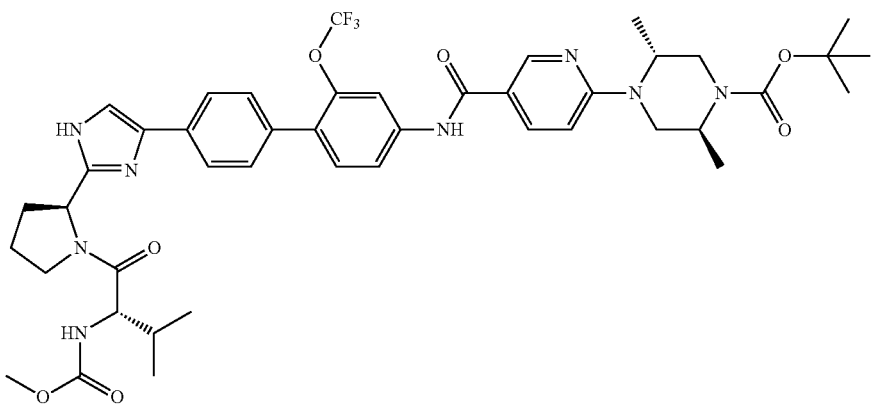 [SMILES: COC(=O)N[C@H](C(=O)N1CCC[C@H]1c1nc(-c2ccc(-c3ccc(NC(=O)c4ccc(N5C[C@H](C)N(C(=O)OC(C)(C)C)C[C@H]5C)nc4)cc3OC(F)(F)F)cc2)c[nH]1)C(C)C]

To a solution of ((S)-1-{(S)-2-[4-(4-bromo-phenyl)-1H-imidazol-2-yl]-pyrrolidine-1-carbonyl}-2-methyl-propyl)-carbamic acid methyl ester (3.05 g, 6.8 mmol;), bis(pinacolato)diboron (1.81 g, 7.1 mmol) and potassium acetate (1.00 g, 10.2 mmol) was added nitrogen sparged toluene (15 mL). The resulting mixture was sparged with nitrogen and 1,1'-bis(diphenylphosphino)ferrocene-palladium(II)dichloride dichloromethane (Pd catalyst) (0.17 g, 0.204 mmol) was added. The reaction mixture was stirred at 90° C. overnight.

The reaction mixture was cooled to RT and to this mixture was added nitrogen sparged water (7.6 mL), potassium carbonate (5.16 g, 37.3 mmol). The reaction mixture was stirred at 95° C. overnight.

Another portion of the Pd catalyst used above (0.08 g, 0.10 mmol) was added to the reaction mixture. After 5 h, the reaction mixture was cooled to RT, diluted with EtOAc (150 mL), washed with water (150 mL) and brine (100 mL), dried over sodium sulfate, and evaporated to give a black residue (6.7 g), which was purified by silica gel chromatography (eluted with 50-100% EtOAc/hexane) to provide the title intermediate (5.3 g, 90% yield). HPLC method C: Retention time=14.7 min.

(d) ((S)-1-{(S)-2-[4-(4'-{[6-((2R,5S)-2,5-Dimethyl-piperazin-1-yl)-pyridine-3-carbonyl]-amino}-2'-trifluoromethoxy-biphenyl-4-yl)-1H-imidazol-2-yl]-pyrrolidine-1-carbonyl}-2-methyl-propyl)-carbamic acid methyl ester

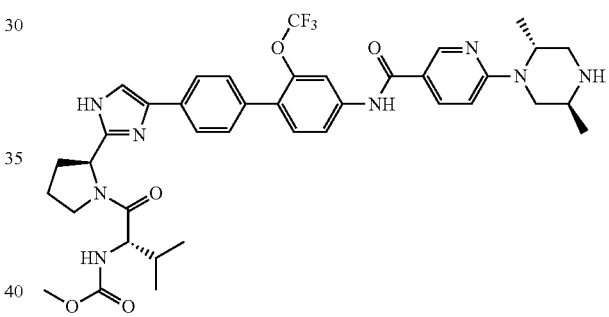

Acetyl chloride (2.57 mL, 36.2 mmol) was added to ethanol (18 mL) and stirred at RT for 1 h. To the resulting HCl solution was added a solution of the product of the previous step (3.90 g, 4.5 mmol) in ethanol (18 mL). The reaction mixture was warmed to 35° C. and stirred overnight. Acetyl chloride (1.28 mL, 18.1 mmol) was added to ethanol (7.8 mL)

and stirred for 30 min. The resulting HCl solution was added to the reaction mixture at 35° C. The temperature was raised to 40° C. The mixture was concentrated to dryness chased by dichloromethane to provide the crude tri-HCl salt of the title intermediate (5.4 g) which was used directly in the next step. HPLC method C: Retention time=10.1 min.

(e) ((S)-1-{(S)-2-[4-(4'-{[6-((2R,5S)-2,5-Dimethyl-4-methylcarbamoyl-piperazin-1-yl)-pyridine-3-carbonyl]-amino}-2'-trifluoromethoxy-biphenyl-4-yl)-1H-imidazol-2-yl]-pyrrolidine-1-carbonyl}-2-methyl-propyl)-carbamic acid methyl ester

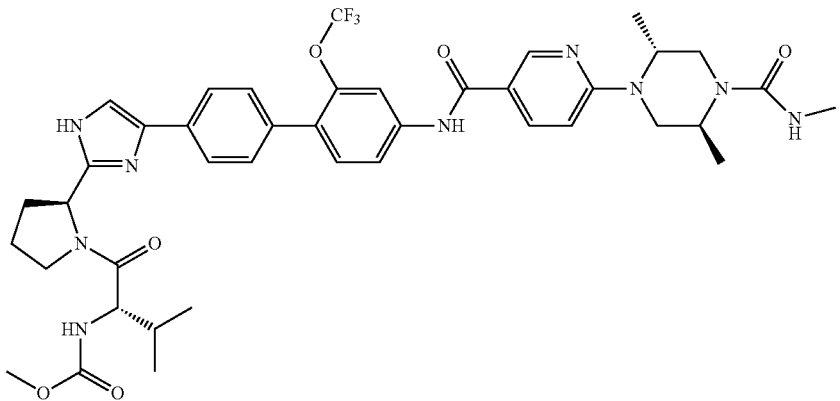

To a solution of the product of the previous step (5.4 g crude, ca. 3.96 mmol) and N,N-diisopropylethylamine (6.89 mL, 39.6 mmol) in DCM (52 mL) was slowly added 1 M methylaminoformyl chloride in DMA (4.3 mL). The reaction mixture stirred at room temperature for 1 h, and then water (50 mL) was added. The organic layer was washed with saturated $NH_4Cl$ and then brine, dried over $Na_2SO_4$ and evaporated to give 5.2 g crude product, which was purified by silica gel chromatography (133 g silica, 2 to 8% methanol/DCM for 15 min then 8% methanol/DCM for 40 min) to provide the title compound (2.4 g, 74% yield). HPLC method C: Retention time 11.2 min.

Using similar synthetic methods, the compounds of Tables 1-34 were prepared where a blank in any column denotes hydrogen and further when more than one variable is listed in a single column, (e.g. Table 5) any variable not specified is hydrogen:

TABLE 1

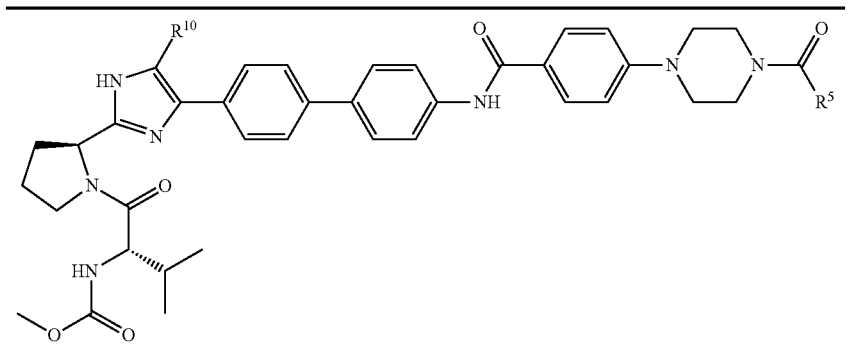

| Ex. No. | $R^5$ | $R^{10}$ | Formula | Calc [M + H]$^+$ | Found [M + H]$^+$ |
|---|---|---|---|---|---|
| 1-1 | $OCH_3$ | | $C_{39}H_{45}N_7O_6$ | 708.34 | 708.2 |
| 1-2 | $OCH_2$phenyl | | $C_{45}H_{49}N_7O_6$ | 784.37 | 784.2 |
| 1-3 | $CH_3$ | | $C_{38}H_{45}N_7O_4$ | 664.35 | 664.2 |
| 1-4 | $CH_2OCH_3$ | | $C_{40}H_{47}N_7O_6$ | 722.36 | 722.4 |
| 1-5 | CH((S)-iPr)NHC(O)$OCH_3$ | | $C_{44}H_{54}N_8O_7$ | 807.41 | 807.4 |
| 1-6 | CH((S)-iPr)N(Et)$_2$ | | $C_{46}H_{60}N_8O_5$ | 805.47 | 805.4 |
| 1-7 | CH((R)-phenyl)NH—C(O)$OCH_3$ | | $C_{47}H_{52}N_8O_7$ | 841.4 | 841.4 |
| 1-8 | CH((R)-phenyl)N(Et)$_2$ | | $C_{49}H_{58}N_8O_5$ | 839.45 | 839.4 |

TABLE 1-continued

| Ex. No. | R⁵ | R¹⁰ | Formula | Calc [M + H]⁺ | Found [M + H]⁺ |
|---|---|---|---|---|---|
| 1-9 | CH₂N(CH₃)C(O)OtBu | | $C_{45}H_{56}N_8O_7$ | 821.43 | 821.4 |
| 1-10 | CH₂NHC(O)OtBu | | $C_{44}H_{54}N_8O_7$ | 807.41 | 807.0 |
| 1-11 | CH₂N(CH₃)₂ | | $C_{41}H_{50}N_8O_5$ | 735.39 | 735.4 |
| 1-12 | CH₂NH₂ | | $C_{39}H_{46}N_8O_5$ | 707.36 | 707.2 |
| 1-13 | CH₂NHCH₃ | | $C_{40}H_{48}N_8O_5$ | 721.38 | 721.4 |
| 1-14 | CH₂OH | | $C_{39}H_{45}N_7O_6$ | 708.34 | 708.2 |
| 1-15 | NHCH₃ | | $C_{39}H_{46}N_8O_5$ | 707.36 | 707.4 |
| 1-16 | N(CH₃)₂ | | $C_{40}H_{48}N_8O_5$ | 721.38 | 721.2 |
| 1-17 | 1H-1,2,4-triazol-3-yl | | $C_{40}H_{44}N_{10}O_5$ | 745.35 | 745.4 |
| 1-18 | furan-2-yl | | $C_{42}H_{45}N_7O_6$ | 744.34 | 744.2 |
| 1-19 | pyridin-2-yl | | $C_{43}H_{46}N_8O_5$ | 755.36 | 755.4 |
| 1-20 | furan-3-yl | | $C_{42}H_{45}N_7O_6$ | 744.34 | 744.2 |
| 1-21 | pyrimidin-2-yl | | $C_{42}H_{45}N_9O_5$ | 756.35 | 756.4 |
| 1-22 | 1H-pyrazol-4-yl | | $C_{41}H_{45}N_9O_5$ | 744.35 | 744.2 |

TABLE 1-continued

| Ex. No. | R⁵ | R¹⁰ | Formula | Calc [M + H]⁺ | Found [M + H]⁺ |
|---|---|---|---|---|---|
| 1-23 | (4-oxazolyl, gem-dimethyl) | | $C_{41}H_{44}N_8O_6$ | 745.34 | 745.2 |
| 1-24 | $NH_2$ | | $C_{38}H_{44}N_8O_5$ | 693.34 | 693.4 |
| 1-25 | cPr | Cl | $C_{41}H_{46}ClN_7O_5$ | 752.33 | 752.2 |
| 1-26 | (CH₂NHC(O)CH₃, gem-dimethyl) | | $C_{41}H_{48}N_8O_6$ | 749.37 | 749.2 |
| 1-27 | CH((S)iPr)NHC(O)OtBu | | $C_{47}H_{60}N_8O_7$ | 849.46 | 849.4 |
| 1-28 | CH((S)iPr)NH₂ | | $C_{42}H_{52}N_8O_5$ | 749.41 | 749.4 |
| 1-29 | CH₃ | | $C_{39}H_{45}N_7O_5$ | 692.35 | 692.2 |
| 1-30 | (1-(methylamino)cyclopropyl, gem-dimethyl) | | $C_{42}H_{50}N_8O_5$ | 747.39 | 747.4 |
| 1-31 | CH((S)OH)iPr | | $C_{42}H_{51}N_7O_6$ | 750.39 | 750.2 |
| 1-32 | (1-methylpyrrolidin-2-yl, gem-dimethyl) | | $C_{43}H_{52}N_8O_5$ | 761.41 | 761.4 |
| 1-33 | C(CH₃)₂NHCH₃ | | $C_{42}H_{52}N_8O_5$ | 749.41 | 749.4 |
| 1-34 | (1-hydroxycyclopropyl, gem-dimethyl) | | $C_{41}H_{47}N_7O_6$ | 734.36 | 734.2 |
| 1-35 | CH₂iPr | | $C_{42}H_{49}N_7O_5$ | 732.38 | 732.4 |
| 1-36 | (6-azaspiro[2.5]octane, gem-dimethyl) | | $C_{45}H_{54}N_8O_5$ | 787.42 | 787.4 |
| 1-37 | CH((R)OH)iPr | | $C_{42}H_{51}N_7O_6$ | 750.39 | 750.4 |
| 1-38 | NHiPr | | $C_{41}H_{50}N_8O_5$ | 735.39 | 735.4 |
| 1-39 | O-iPr | | $C_{41}H_{49}N_7O_6$ | 736.37 | 736.2 |

TABLE 1-continued
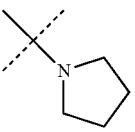
| Ex. No. | R⁵ | R¹⁰ | Formula | Calc [M + H]⁺ | Found [M + H]⁺ |
|---|---|---|---|---|---|
| 1-40 | 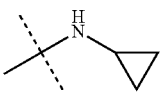 | | $C_{42}H_{50}N_8O_5$ | 747.39 | 747.4 |
| 1-41 | OCH$_2$CH$_3$ | | $C_{40}H_{47}N_7O_6$ | 722.36 | 722.2 |
| 1-42 | NHCH$_2$CH$_3$ | | $C_{40}H_{48}N_8O_5$ | 721.38 | 721.4 |
| 1-43 | NHCH$_2$-iPr | | $C_{42}H_{52}N_8O_5$ | 749.41 | 749.4 |
| 1-44 | cPr | CH$_3$ | $C_{42}H_{49}N_7O_5$ | 732.38 | 732.7 |
| 1-45 | NHCH$_3$ | CH$_3$ | $C_{40}H_{48}N_8O_5$ | 721.38 | 721.6 |
| 1-46 | 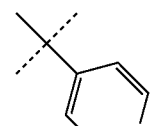 | | $C_{41}H_{48}N_8O_5$ | 733.38 | 733.4 |
| 1-47 | NH-tBu | | $C_{42}H_{52}N_8O_5$ | 749.41 | 749.4 |
| 1-48 | 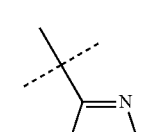 | | $C_{43}H_{46}N_8O_5$ | 755.36 | 755.2 |
| 1-49 | iPr | | $C_{41}H_{49}N_7O_5$ | 720.38 | 720.2 |
| 1-50 | 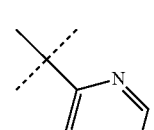 | | $C_{42}H_{47}N_9O_5$ | 758.37 | 758.2 |
| 1-51 | 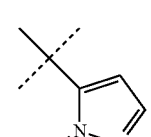 | | $C_{42}H_{45}N_9O_5$ | 756.35 | 756.2 |
| 1-52 | 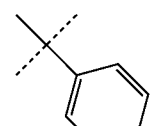 | | $C_{42}H_{47}N_9O_5$ | 758.37 | 758.2 |
| 1-53 |  | | $C_{43}H_{46}N_8O_5$ | 755.36 | 755.2 |

TABLE 1-continued

| Ex. No. | R[5] | R[10] | Formula | Calc [M + H]+ | Found [M + H]+ |
|---|---|---|---|---|---|
| 1-54 | | | C40H45N11O5 | 760.36 | 760.2 |
| 1-55 | CH((S)CH2OH)NH2 | | C40H48N8O6 | 737.37 | 737.4 |
| 1-56 | | | C41H45N9O5 | 744.35 | 744.2 |
| 1-57 | | | C41H45N9O5 | 744.35 | 744.2 |
| 1-58 | | | C41H48N8O5 | 733.38 | 733.2 |
| 1-59 | CH((S)CH2OH)NHC(O)OtBu | | C45H56N8O8 | 837.42 | 837.4 |
| 1-60 | | Cl | C42H44ClN7O6 | 778.30 | 778.2 |
| 1-61 | | Cl | C42H44ClN9O5 | 790.32 | 790.4 |
| 1-62 | CH((R))cPrNH2 | | C42H50N8O5 | 747.39 | 747.4 |
| 1-63 | | | C43H50N8O6 | 775.39 | 775.4 |
| 1-64 | CH((R)cPr)NHC(O)CH3 | | C44H52N8O6 | 789.40 | 789.4 |

TABLE 1-continued

| Ex. No. | R⁵ | R¹⁰ | Formula | Calc [M + H]⁺ | Found [M + H]⁺ |
|---|---|---|---|---|---|
| 1-65 | (1-methyl-N-acetyl-aminocyclopropyl-dimethyl group) | | $C_{44}H_{52}N_8O_6$ | 789.40 | 789.4 |
| 1-66 | CH₂N(CH₃)C(O)CH₃ | | $C_{42}H_{50}N_8O_6$ | 763.39 | 763.4 |
| 1-67 | (1-Boc-amino-cyclopropyl-dimethyl group) | | $C_{46}H_{56}N_8O_7$ | 833.43 | 833.4 |
| 1-68 | (1-amino-cyclopropyl-dimethyl group) | | $C_{41}H_{48}N_8O_5$ | 733.38 | 733.4 |
| 1-69 | CH₂NHC(O)CH₃ | Cl | $C_{41}H_{47}ClN_8O_6$ | 783.33 | 783.2 |
| 1-70 | tBu | Cl | $C_{42}H_{50}ClN_7O_5$ | 768.36 | 768.2 |
| 1-71 | CH((R)CH₃)NH₂ | | $C_{40}H_{48}N_8O_5$ | 721.38 | 721.2 |
| 1-72 | CH((R)CH₂OH)NHCH₃ | | $C_{41}H_{50}N_8O_6$ | 751.39 | 751.2 |
| 1-73 | CH((R)Pr)NHC(O)CH₃ | | $C_{44}H_{54}N_8O_6$ | 791.42 | 791.4 |
| 1-74 | CH((S)CH₃)NHC(O)OtBu | | $C_{45}H_{56}N_8O_7$ | 821.43 | 821.4 |
| 1-75 | CH((S)CH₃)N(CH₃)C(O)OtBu | | $C_{46}H_{58}N_8O_7$ | 835.44 | 835.4 |
| 1-76 | CH((S)iPr) NHC(O)CH₃ | | $C_{45}H_{56}N_8O_6$ | 805.43 | 805.4 |
| 1-77 | CH((S)CH₃)NHCH₃ | | $C_{41}H_{50}N_8O_5$ | 735.39 | 735.4 |
| 1-78 | CH((S)CH₃)NH₂ | | $C_{40}H_{48}N_8O_5$ | 721.38 | 721.2 |
| 1-79 | CH((R)CH₃)N(CH₃)C(O)OtBu | | $C_{45}H_{56}N_8O_7$ | 821.43 | 821.4 |

TABLE 2
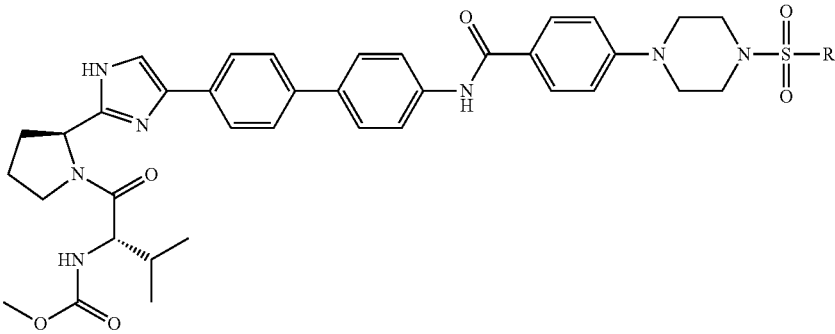
| Ex. No. | R6 | Formula | Calc [M + H]+ | Found [M + H]+ |
|---|---|---|---|---|
| 2-1 | 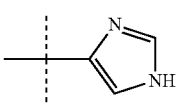 | C40H45N9O6S | 780.32 | 780.4 |
| 2-2 | NH2 | C37H44N8O6S | 729.31 | 729.2 |
| 2-3 | cyclopropyl | C40H47N7O6S | 754.33 | 754.2 |
| 2-4 | phenyl | C43H47N7O6S | 790.33 | 790.2 |
TABLE 3
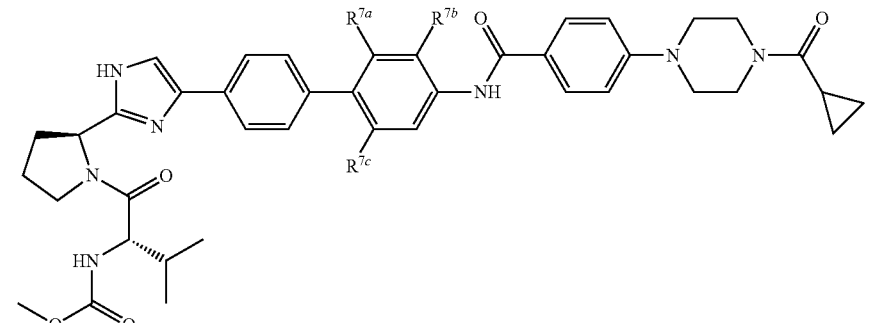
| Ex. No. | R7a | R7b | R7c | Formula | Calc [M + H]+ | Found [M + H]+ |
|---|---|---|---|---|---|---|
| 3-1 | F | | | C41H46FN7O5 | 736.35 | 736.4 |
| 3-2 | OCH3 | | | C42H49N7O6 | 748.37 | 748.4 |
| 3-3 | F | | F | C41H45F2N7O5 | 754.35 | 754.2 |
| 3-4 | Cl | | | C41H46ClN7O5 | 752.33 | 752.4 |
| 3-5 | Cl | | Cl | C41H45Cl2N7O5 | 786.29 | 786.2 |
| 3-6 | | F | | C41H46FN7O5 | 736.35 | 736.4 |
| 3-7 | | Cl | | C41H46ClN7O5 | 752.33 | 752.2 |

TABLE 4

| Ex. No. | R | R¹⁰ | Formula | Calc [M + H]⁺ | Found [M + H]⁺ |
|---------|---|-----|---------|---------------|----------------|
| 4-1 | CH((S)-iPr)NHSO₂CH₃ | | $C_{40}H_{47}N_7O_5S$ | 738.34 | 738.2 |
| 4-2 | CH((S)-iPr)NHC(O)NHCH₃ | | $C_{41}H_{48}N_8O_4$ | 717.38 | 717.2 |
| 4-3 | CH((S)-iPr)N(C₂H₅)₂ | | $C_{43}H_{53}N_7O_3$ | 716.42 | 716.4 |
| 4-4 | CH((S)-iPr)NHC(O)OtBu | | $C_{44}H_{53}N_7O_5$ | 760.41 | 760.4 |
| 4-5 | CH((R)phenyl)NHC(O)OCH₃ | | $C_{44}H_{45}N_7O_5$ | 752.35 | 752.2 |
| 4-6 | CH((S)-iPr)NHC(O)cPr | | $C_{43}H_{49}N_7O_4$ | 728.38 | 728.4 |
| 4-7 | CH((S)-iPr)NH₂ | | $C_{39}H_{45}N_7O_3$ | 660.36 | 660.2 |
| 4-8 | CH((R)phenyl)N(C₂H₅)₂ | Cl | $C_{46}H_{50}ClN_7O_3$ | 784.37 | 785.2 |

TABLE 5

| Ex. No. | R⁵ | R¹⁰ | T | R⁸ᵃ, R⁸ᵇ, R⁹ᵃ, R⁹ᵈ* | Formula | Calc [M + H]⁺ | Found [M + H]⁺ |
|---------|----|-----|---|---------------------|---------|---------------|----------------|
| 5-1 | OtBu | | CH | | $C_{42}H_{51}N_7O_6$ | 750.39 | 750.4 |
| 5-2 | cPr | Br | CH | | $C_{41}H_{46}BrN_7O_5$ | 796.27 | 796.2 |
| 5-3 | OtBu | Br | CH | | $C_{42}H_{50}BrN_7O_6$ | 828.30 | 828.5 |
| 5-4 | CH₂iPr | Br | CH | | $C_{42}H_{50}BrN_7O_5$ | 812.31 | 812.2 |
| 5-5 | CH₃ | | CH | | $C_{39}H_{45}N_7O_5$ | 692.35 | 692.4 |
| 5-6 | OtBu | | N | | $C_{41}H_{50}N_8O_6$ | 751.39 | 751.4 |
| 5-7 | OtBu | | CH | R⁹ᵃ=(S)CH₃ | $C_{43}H_{53}N_7O_6$ | 764.41 | 764.4 |
| 5-8 | OtBu | | CH | R⁹ᵃ=(R)CH₃ | $C_{43}H_{53}N_7O_6$ | 764.41 | 764.4 |
| 5-9 | cPr | | C | R⁸ᵇ=F | $C_{41}H_{46}FN_7O_5$ | 736.35 | 736.4 |
| 5-10 | OtBu | | CH | R⁹ᵇ=(S)iPr | $C_{45}H_{57}N_7O_6$ | 792.44 | 792.4 |
| 5-11 | cPr | | C | R⁸ᵇ=OMe | $C_{42}H_{49}N_7O_6$ | 748.37 | 748.4 |
| 5-12 | cPr | | CH | R⁹ᵃ=(R)CH₃ | $C_{42}H_{49}N_7O_5$ | 732.38 | 732.4 |
| 5-13 | cPr | | CH | R⁹ᵃ=(S)CH₃ | $C_{42}H_{49}N_7O_5$ | 732.38 | 732.4 |
| 5-14 | cPr | | C | R⁸ᵇ=Me | $C_{42}H_{49}N_7O_5$ | 732.38 | 732.4 |
| 5-15 | cPr | | C | R⁸ᵇ=Cl | $C_{41}H_{46}ClN_7O_5$ | 752.33 | 752.2 |
| 5-16 | cPr | | CH | R⁹ᵇ=(S)iPr | $C_{44}H_{53}N_7O_5$ | 760.41 | 760.4 |
| 5-17 | cPr | | CH | R⁸ᵃ=Me | $C_{42}H_{49}N_7O_5$ | 732.38 | 732.4 |
| 5-18 | OtBu | | C | R⁸ᵇ=COOH | $C_{43}H_{51}N_7O_8$ | 794.38 | 794.2 |
| 5-19 | cPr | | CH | R⁸ᵃ=Cl | $C_{41}H_{46}ClN_7O_5$ | 752.33 | 752.2 |
| 5-20 | OtBu | | C | R⁸ᵇ=COOMe | $C_{44}H_{53}N_7O_8$ | 808.40 | 808.2 |
| 5-21 | cPr | H | C | R⁸ᵇ=CH₂NH₂ | $C_{42}H_{50}N_8O_5$ | 747.39 | 747.4 |

*R⁸ᵃ, R⁹ᵃ, R⁹ᵇ, R¹⁰ are each H where not specified

TABLE 6

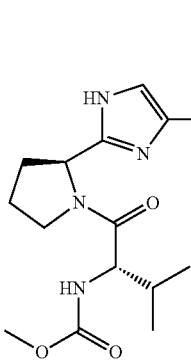

| Ex. No. | R⁵ | R⁹ᵃ | R⁹ᵇ | R⁹ᶜ | Formula | Calc [M + H]⁺ | Found [M + H]⁺ |
|---|---|---|---|---|---|---|---|
| 6-1 | OMe | | | | $C_{37}H_{43}N_9O_6$ | 710.33 | 710.2 |
| 6-2 | cPr | | | | $C_{39}H_{45}N_9O_5$ | 720.35 | 720.2 |
| 6-3 | NHCH₃ | | | | $C_{37}H_{44}N_{10}O_5$ | 709.35 | 710.4 |
| 6-4 | OtBu | (S)CH₃ | | (R)CH₃ | $C_{42}H_{53}N_9O_6$ | 780.41 | 780.4 |
| 6-5 | OtBu | (R)CH₃ | | | $C_{41}H_{51}N_9O_6$ | 766.40 | 766.4 |
| 6-6 | OtBu | | | | $C_{40}H_{49}N_9O_6$ | 752.38 | 752.4 |
| 6-7 | OtBu | | (S)CH₃ | | $C_{41}H_{51}N_9O_6$ | 766.40 | 766.4 |
| 6-8 | OtBu | | (R)CH₃ | | $C_{41}H_{51}N_9O_6$ | 766.40 | 766.4 |
| 6-9 | OtBu | (S)CH₃ | | | $C_{41}H_{51}N_9O_6$ | 766.40 | 766.4 |

TABLE 7

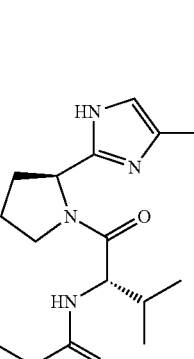

| Ex No. | R⁵ | R⁹ᵃ | R⁹ᵇ | Formula | Calc [M + H]⁺ | Found [M + H]⁺ |
|---|---|---|---|---|---|---|
| 7-1 | OtBu | (R)CH₃ | | $C_{41}H_{51}N_9O_6$ | 766.4 | 766.2 |
| 7-2 | OtBu | | | $C_{40}H_{49}N_9O_6$ | 752.38 | 752.2 |
| 7-3 | OtBu | | (R)CH₃ | $C_{41}H_{51}N_9O_6$ | 766.40 | 766.4 |
| 7-4 | cPr | | | $C_{39}H_{45}N_9O_5$ | 720.35 | 720.2 |
| 7-5 | Me | | | $C_{37}H_{43}N_9O_5$ | 694.34 | 694.2 |
| 7-6 | NHCH₃ | | | $C_{37}H_{44}N_{10}O_5$ | 709.35 | 709.2 |
| 7-7 | Me | | (R)CH₃ | $C_{38}H_{45}N_9O_5$ | 708.35 | 708.2 |
| 7-8 | cPr | | (R)CH₃ | $C_{40}H_{47}N_9O_5$ | 734.37 | 734.2 |
| 7-9 | NHCH₃ | | (R)CH₃ | $C_{38}H_{46}N_{10}O_5$ | 723.37 | 723.4 |
| 7-10 | cPr | (R)CH₃ | | $C_{40}H_{47}N_9O_5$ | 734.37 | 734.2 |
| 7-11 | NHCH₃ | (R)CH₃ | | $C_{38}H_{46}N_{10}O_5$ | 723.37 | 723.4 |

TABLE 8

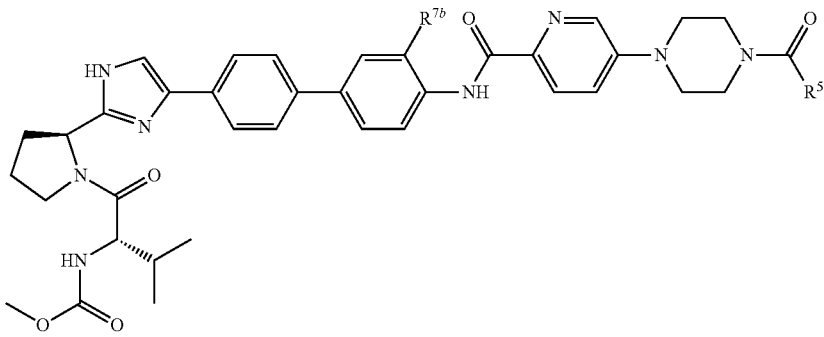

| Ex No. | $R^5$ | $R^{7b}$ | Formula | Calc [M + H]⁺ | Found [M + H]⁺ |
|---|---|---|---|---|---|
| 8-1 | cPr | | $C_{40}H_{46}N_8O_5$ | 719.36 | 719.2 |
| 8-2 | Me | | $C_{38}H_{44}N_8O_5$ | 693.34 | 693.2 |
| 8-3 | NHSO$_2$CH$_3$ | | $C_{39}H_{48}N_8O_6S$ | 757.34 | 757.2 |
| 8-4 | OtBu | OCH$_3$ | $C_{42}H_{52}N_8O_7$ | 781.40 | 781.4 |
| 8-5 | cPr | OCH$_3$ | $C_{41}H_{48}N_8O_6$ | 749.37 | 749.2 |

TABLE 9

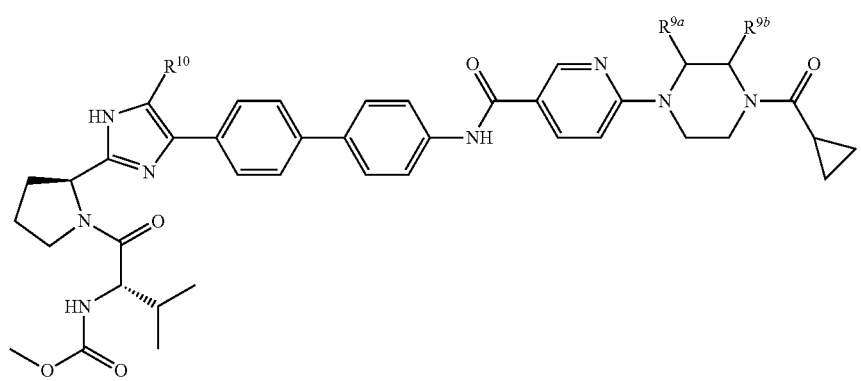

| Ex No. | $R^{9a}$ | $R^{9b}$ | $R^{10}$ | Formula | Calc [M + H]⁺ | Found [M + H]⁺ |
|---|---|---|---|---|---|---|
| 9-1 | | | | $C_{40}H_{46}N_8O_5$ | 719.36 | 719.2 |
| 9-2 | (S)CH$_3$ | | | $C_{41}H_{48}N_8O_5$ | 733.38 | 733.2 |
| 9-3 | (R)CH$_3$ | | | $C_{41}H_{48}N_8O_5$ | 733.38 | 733.4 |
| 9-4 | | (R)CH$_3$ | | $C_{41}H_{48}N_8O_5$ | 733.38 | 733.4 |
| 9-5 | | (S)CH$_3$ | | $C_{41}H_{48}N_8O_5$ | 733.38 | 733.4 |
| 9-6 | (R)CH$_2$OH | | | $C_{41}H_{48}N_8O_6$ | 749.37 | 749.4 |
| 9-7 | (S)CH$_2$OH | | | $C_{41}H_{48}N_8O_6$ | 749.37 | 749.4 |
| 9-8 | | (S)CH$_2$OH | | $C_{41}H_{48}N_8O_6$ | 749.37 | 749.4 |
| 9-9 | | (R)CH$_2$OH | | $C_{41}H_{48}N_8O_6$ | 749.37 | 749.4 |
| 9-10 | | (R)CH$_2$OCH$_3$ | | $C_{42}H_{50}N_8O_6$ | 763.39 | 763.4 |
| 9-11 | | | Cl | $C_{40}H_{45}ClN_8O_5$ | 753.32 | 753.2 |
| 9-12 | | (S)C(O)NH$_2$ | | $C_{41}H_{47}N_9O_6$ | 762.37 | 762.4 |
| 9-13 | | (R)C(O)NH$_2$ | | $C_{41}H_{47}N_9O_6$ | 762.37 | 762.4 |
| 9-14 | | (S)C(O)N(CH$_3$)$_2$ | | $C_{43}H_{51}N_9O_6$ | 790.40 | 790.4 |
| 9-15 | | (R)C(O)N(CH$_3$)$_2$ | | $C_{43}H_{51}N_9O_6$ | 790.40 | 790.4 |

TABLE 10

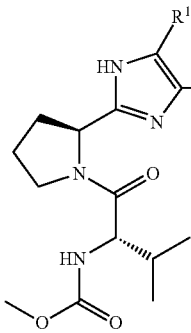

| Ex No. | $R^{9a}$ | $R^{9b}$ | $R^{9c}$ | $R^{9d}$ | $R^{10}$ | Formula | Calc [M + H]$^+$ | Found [M + H]$^+$ |
|---|---|---|---|---|---|---|---|---|
| 10-1 | | | | | | $C_{42}H_{50}N_8O_5$ | 747.39 | 747.4 |
| 10-2 | | (R)CH$_3$ | | | | $C_{43}H_{52}N_8O_5$ | 761.41 | 762.0 |
| 10-3 | | (S)CH$_3$ | | | | $C_{43}H_{52}N_8O_5$ | 761.41 | 761.4 |
| 10-4 | | (S)CH$_2$OH | | | | $C_{43}H_{52}N_8O_6$ | 777.4 | 789.2 |
| 10-5 | | (R)CH$_2$OH | | | | $C_{43}H_{52}N_8O_6$ | 777.4 | 799.4 |
| 10-6 | | (R)CH$_2$OCH$_3$ | | | | $C_{44}H_{54}N_8O_6$ | 791.42 | 792.4 |
| 10-7 | | (R)CH$_3$ | | | Cl | $C_{43}H_{51}ClN_8O_5$ | 795.37 | 795.4 |
| 10-8 | | (S)C(O)N(CH$_3$)$_2$ | | | | $C_{45}H_{55}N_9O_6$ | 818.43 | 818.4 |
| 10-9 | | (R)C(O)N(CH$_3$)$_2$ | | | | $C_{45}H_{55}N_9O_6$ | 818.43 | 818.4 |
| 10-10 | | (S)CH$_3$ | (R)CH$_3$ | | | $C_{44}H_{54}N_8O_5$ | 775.42 | 775.4 |
| 10-11 | | (S)CH$_3$ | | (R)CH$_3$ | | $C_{44}H_{54}N_8O_5$ | 775.42 | 775.4 |
| 10-12 | | (S)CH$_3$ | | | Cl | $C_{43}H_{51}ClN_8O_5$ | 795.37 | 795.4 |
| 10-13 | (R)CH$_2$OH | | | | | $C_{43}H_{52}N_8O_6$ | 777.40 | 777.3 |
| 10-14 | (S)CH$_2$OH | | | | | $C_{43}H_{52}N_8O_6$ | 777.40 | 777.4 |
| 10-15 | | (S)CH$_2$OCH$_3$ | | | | $C_{44}H_{54}N_8O_6$ | 791.42 | 791.4 |
| 10-16 | | (R)CH$_2$OH | | | Cl | $C_{43}H_{51}ClN_8O_6$ | 811.36 | 811.2 |
| 10-17 | | (S)CH$_2$OH | | | Cl | $C_{43}H_{51}ClN_8O_6$ | 811.36 | 811.2 |
| 10-18 | | (R)CH$_3$ | | | Et | $C_{45}H_{56}N_8O_5$ | 789.44 | 789.4 |
| 10-19 | | (S)C$_2$H$_5$ | | | | $C_{44}H_{54}N_8O_5$ | 775.42 | 775.4 |
| 10-20 | | (R)CH$_3$ | (S)CH$_3$ | | | $C_{44}H_{54}N_8O_5$ | 775.42 | 775.4 |
| 10-21 | (S)CH$_3$ | | (R)CH$_3$ | | | $C_{44}H_{54}N_8O_5$ | 775.42 | 775.4 |
| 10-22 | | (a) | | | | $C_{49}H_{61}N_9O_6$ | 872.47 | 872.4 |
| 10-23 | (R)C$_2$H$_5$ | | | | | $C_{44}H_{54}N_8O_5$ | 775.42 | 775.4 |
| 10-24 | | (b) | | | | $C_{51}H_{59}N_9O_7$ | 910.45 | 910.4 |
| 10-25 | | (R)CH$_2$SCH$_3$ | | | | $C_{44}H_{54}N_8O_5S$ | 807.39 | 807.2 |
| 10-26 | (S)C$_2$H$_5$ | | | | | $C_{44}H_{54}N_8O_5$ | 775.42 | 776.2 |
| 10-27 | | (R)CH$_2$S(O)$_2$CH$_3$ | | | | $C_{44}H_{54}N_8O_7S$ | 839.38 | 839.4 |
| 10-28 | | (S)C(O)NH$_2$ | | | | $C_{43}H_{51}N_9O_6$ | 790.40 | 790.4 |

(a) (R)CH$_2$NH(S)C(O)(1,1-di-methylcyclopropyl)
(b) (R)CH$_2$NHC(O)OCH$_2$phenyl

TABLE 11

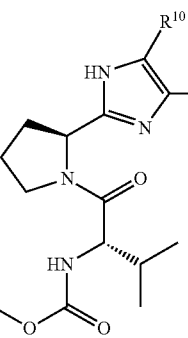

| Ex No. | $R^{9a}$ | $R^{9b}$ | $R^{9c}$ | $R^{9d}$ | Formula | Calc [M + H]$^+$ | Found [M + H]$^+$ |
|---|---|---|---|---|---|---|---|
| 11-1 | | | | | $C_{41}H_{50}N_8O_6$ | 751.39 | 751.4 |
| 11-2 | CH$_3$ | | | | $C_{42}H_{52}N_8O_7$ | 781.40 | 781.2 |

TABLE 11-continued

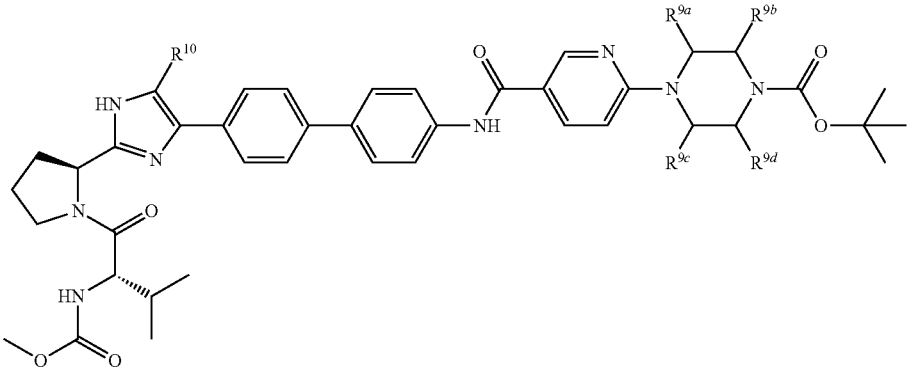

| Ex No. | $R^{9a}$ | $R^{9b}$ | $R^{9c}$ | $R^{9d}$ | Formula | Calc [M + H]$^+$ | Found [M + H]$^+$ |
|---|---|---|---|---|---|---|---|
| 11-3 | (S)CH$_3$ | | | | C$_{42}$H$_{52}$N$_8$O$_6$ | 765.40 | 765.4 |
| 11-4 | (R)CH$_3$ | | | | C$_{42}$H$_{52}$N$_8$O$_6$ | 765.40 | 765.4 |
| 11-5 | | (R)CH$_3$ | | | C$_{42}$H$_{52}$N$_8$O$_6$ | 765.40 | 765.2 |
| 11-6 | | (S)CH$_3$ | | | C$_{42}$H$_{52}$N$_8$O$_6$ | 765.40 | 765.4 |
| 11-7 | (S)CH$_2$OH | | | | C$_{42}$H$_{52}$N$_8$O$_7$ | 781.40 | 781.7 |
| 11-8 | | (S)CH$_2$OH | | | C$_{42}$H$_{52}$N$_8$O$_7$ | 781.40 | 781.4 |
| 11-9 | | (R)CH$_2$OH | | | C$_{42}$H$_{52}$N$_8$O$_7$ | 781.40 | 781.4 |
| 11-10 | | (R)CH$_2$OCH$_3$ | | | C$_{43}$H$_{54}$N$_8$O$_7$ | 795.41 | 795.4 |
| 11-11* | | (S)CH$_2$OH | | | C$_{42}$H$_{51}$ClN$_8$O$_7$ | 815.36 | 815.6 |
| 11-12* | | (R)CH$_2$OH | | | C$_{42}$H$_{51}$ClN$_8$O$_7$ | 815.36 | 815.7 |
| 11-13 | (S)CONH$_2$ | | | | C$_{42}$H$_{51}$N$_9$O$_7$ | 794.39 | 795.4 |
| 11-14 | | (S)CONH$_2$ | | | C$_{42}$H$_{51}$N$_9$O$_7$ | 794.39 | 794.4 |
| 11-15 | | (R)CONH$_2$ | | | C$_{42}$H$_{51}$N$_9$O$_7$ | 794.39 | 794.2 |
| 11-16 | (R)COOH | | | | C$_{42}$H$_{50}$N$_8$O$_8$ | 795.38 | 795.4 |
| 11-17 | (S)COOH | | | | C$_{42}$H$_{50}$N$_8$O$_8$ | 795.38 | 795.4 |
| 11-18 | | (R)COOH | | | C$_{42}$H$_{50}$N$_8$O$_8$ | 795.38 | 795.4 |
| 11-19 | | (R)CH$_2$CH$_3$ | | | C$_{43}$H$_{54}$N$_8$O$_6$ | 779.42 | 779.4 |
| 11-20 | | (S)CH$_2$CH$_3$ | | | C$_{43}$H$_{54}$N$_8$O$_6$ | 779.42 | 779.4 |
| 11-21 | | COOCH$_3$ | | | C$_{43}$H$_{52}$N$_8$O$_8$ | 809.39 | 809.2 |
| 11-22 | | (R)COOCH$_3$ | | | C$_{43}$H$_{52}$N$_8$O$_8$ | 809.39 | 809.4 |
| 11-23 | | (S)COOCH$_3$ | | | C$_{43}$H$_{52}$N$_8$O$_8$ | 809.39 | 809.4 |
| 11-24 | | (S)CH(CH$_3$)$_2$ | | | C$_{44}$H$_{56}$N$_8$O$_6$ | 793.43 | 793.4 |
| 11-25 | | (R)CH(CH$_3$)$_2$ | | | C$_{44}$H$_{56}$N$_8$O$_6$ | 793.43 | 793.4 |
| 11-26 | | (S)CON(CH$_3$)$_2$ | | | C$_{44}$H$_{55}$N$_9$O$_7$ | 822.42 | 822.4 |
| 11-27 | | (R)CON(CH$_3$)$_2$ | | | C$_{44}$H$_{55}$N$_9$O$_7$ | 822.42 | 822.4 |
| 11-28 | (S)CH$_3$ | | | (R)CH$_3$ | C$_{43}$H$_{54}$N$_8$O$_6$ | 779.42 | 780.0 |
| 11-29 | (R)CH$_3$ | | | (S)CH$_3$ | C$_{43}$H$_{54}$N$_8$O$_6$ | 779.42 | 780.4 |
| 11-30 | (R)CH$_3$ | | | (R)CH$_3$ | C$_{43}$H$_{54}$N$_8$O$_6$ | 779.42 | 779.4 |
| 11-31 | | (S)CH$_3$ | | (R)CH$_3$ | C$_{43}$H$_{54}$N$_8$O$_6$ | 779.42 | 779.4 |
| 11-32 | (S)CH$_3$ | | (R)CH$_3$ | | C$_{43}$H$_{54}$N$_8$O$_6$ | 779.42 | 779.4 |
| 11-33 | (S)C(O)NH$_2$ | | | | C$_{42}$H$_{51}$N$_9$O$_7$ | 794.39 | 795.4 |
| 11-34 | | (R)C(O)NH$_2$ | | | C$_{42}$H$_{51}$N$_9$O$_7$ | 794.39 | 794.2 |
| 11-35 | | (S)C(O)NH$_2$ | | | C$_{42}$H$_{51}$N$_9$O$_7$ | 794.39 | 794.4 |

*$R^{10}$ is Cl; all other $R^{10}$ are hydrogen

TABLE 12

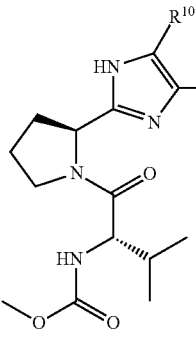

| Ex No. | $R^{9a}$ | $R^{9b}$ | $R^{9c}$ | $R^{9d}$ | $R^{10}$ | Formula | Calc [M + H]$^+$ | Found [M + H]$^+$ |
|---|---|---|---|---|---|---|---|---|
| 12-1 | | | (R)CH$_3$ | | | C$_{42}$H$_{52}$N$_8$O$_5$ | 749.41 | 750.4 |
| 12-2 | | | (S)CH$_3$ | | | C$_{42}$H$_{52}$N$_8$O$_5$ | 749.41 | 749.4 |
| 12-3 | | | (R)CH$_2$OH | | | C$_{42}$H$_{52}$N$_8$O$_6$ | 765.40 | 766.4 |
| 12-4 | | (S)CH$_3$ | | (R)CH$_3$ | | C$_{43}$H$_{54}$N$_8$O$_5$ | 763.42 | 763.4 |

TABLE 13

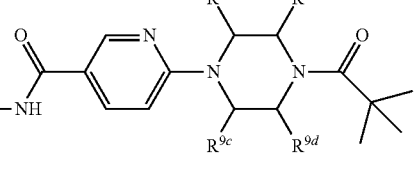

| Ex No. | $R^{9a}$ | $R^{9b}$ | $R^{9d}$ | $R^{10}$ | Formula | Calc [M + H]$^+$ | Found [M + H]$^+$ |
|---|---|---|---|---|---|---|---|
| 13-1 | | | | | C$_{38}$H$_{45}$N$_9$O$_5$ | 708.35 | 708.2 |
| 13-2 | | | | CH$_3$ | C$_{39}$H$_{47}$N$_9$O$_5$ | 722.37 | 722.2 |
| 13-3 | | | | Cl | C$_{38}$H$_{44}$ClN$_9$O$_5$ | 742.32 | 742.2 |
| 13-4 | (S)CH$_3$ | | | | C$_{39}$H$_{47}$N$_9$O$_5$ | 722.37 | 722.2 |
| 13-5 | (R)CH$_3$ | | | | C$_{39}$H$_{47}$N$_9$O$_5$ | 722.37 | 722.4 |
| 13-6 | (R)CH$_3$ | | | Cl | C$_{39}$H$_{46}$ClN$_9$O$_6$ | 772.33 | 772.2 |
| 13-7 | | (R)CH$_3$ | | | C$_{39}$H$_{47}$N$_9$O$_5$ | 722.37 | 722.4 |
| 13-8 | | (R)CH$_3$ | | Cl | C$_{39}$H$_{46}$ClN$_9$O$_5$ | 756.33 | 756.2 |
| 13-9 | | (S)CH$_3$ | | | C$_{39}$H$_{47}$N$_9$O$_5$ | 722.37 | 722.2 |
| 13-10 | | (S)CH$_3$ | | Cl | C$_{39}$H$_{46}$ClN$_9$O$_5$ | 756.33 | 756.2 |
| 13-11 | (R)CH$_2$OH | | | | C$_{39}$H$_{47}$N$_9$O$_6$ | 738.37 | 738.4 |
| 13-12 | (S)CH$_2$OH | | | | C$_{39}$H$_{47}$N$_9$O$_6$ | 738.37 | 738.2 |
| 13-13 | | (S)CH$_2$OH | | | C$_{39}$H$_{47}$N$_9$O$_6$ | 738.37 | 738.4 |
| 13-14 | | (R)CH$_2$OH | | | C$_{39}$H$_{47}$N$_9$O$_6$ | 738.37 | 738.2 |
| 13-15 | | (S)CH$_2$OCH$_3$ | | | C$_{40}$H$_{49}$N$_9$O$_6$ | 752.38 | 752.4 |
| 13-16 | | (S)CH$_3$ | (R)CH$_3$ | | C$_{40}$H$_{49}$N$_9$O$_5$ | 736.39 | 736.4 |

TABLE 14

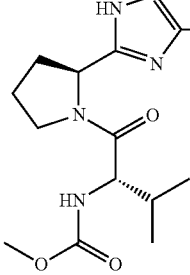

| Ex No. | $R^{9a}$ | $R^{9b}$ | $R^{9d}$ | Formula | Calc [M + H]$^+$ | Found [M + H]$^+$ |
|---|---|---|---|---|---|---|
| 14-1 | | | | $C_{41}H_{44}N_{10}O_5$ | 757.35 | 757.4 |
| 14-2 | (S)CH$_3$ | | | $C_{42}H_{46}N_{10}O_5$ | 771.37 | 771.4 |
| 14-3 | (R)CH$_3$ | | | $C_{42}H_{46}N_{10}O_5$ | 771.37 | 771.4 |
| 14-4 | | (R)CH$_3$ | | $C_{42}H_{46}N_{10}O_5$ | 771.37 | 771.4 |
| 14-5 | | (S)CH$_3$ | | $C_{42}H_{46}N_{10}O_5$ | 771.37 | 771.4 |
| 14-6 | (R)CH$_2$OH | | | $C_{42}H_{46}N_{10}O_6$ | 787.36 | 787.4 |
| 14-7 | (S)CH$_2$OH | | | $C_{42}H_{46}N_{10}O_6$ | 787.36 | 787.4 |
| 14-8 | | (S)CH$_2$OH | | $C_{42}H_{46}N_{10}O_6$ | 787.36 | 788.2 |
| 14-9 | | (R)CH$_2$OH | | $C_{42}H_{46}N_{10}O_6$ | 787.36 | 787.4 |
| 14-10 | | (S)CH$_2$OCH$_3$ | | $C_{43}H_{48}N_{10}O_6$ | 801.38 | 801.4 |
| 14-11 | | (S)CH$_3$ | (R)CH$_3$ | $C_{43}H_{48}N_{10}O_5$ | 785.38 | 785.4 |

TABLE 15

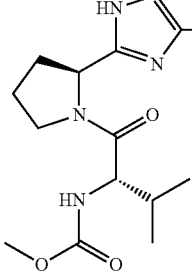

| Ex No. | $R^{9a}$ | $R^{9b}$ | $R^{9d}$ | Formula | Calc [M + H]$^+$ | Found [M + H]$^+$ |
|---|---|---|---|---|---|---|
| 15-1 | | | | $C_{40}H_{44}N_{10}O_5$ | 745.35 | 745.4 |
| 15-2 | (S)CH$_3$ | | | $C_{41}H_{46}N_{10}O_5$ | 759.37 | 759.2 |
| 15-3 | (R)CH$_3$ | | | $C_{41}H_{46}N_{10}O_5$ | 759.37 | 759.4 |
| 15-4 | | (R)CH$_3$ | | $C_{41}H_{46}N_{10}O_5$ | 759.37 | 759.4 |
| 15-5 | | (S)CH$_3$ | | $C_{41}H_{46}N_{10}O_5$ | 759.37 | 759.2 |
| 15-6 | (R)CH$_2$OH | | | $C_{41}H_{46}N_{10}O_6$ | 775.36 | 775.4 |
| 15-7 | (S)CH$_2$OH | | | $C_{41}H_{46}N_{10}O_6$ | 775.36 | 775.2 |
| 15-8 | | (S)CH$_2$OH | | $C_{41}H_{46}N_{10}O_6$ | 775.36 | 775.2 |
| 15-9 | | (R)CH$_2$OH | | $C_{41}H_{46}N_{10}O_6$ | 775.36 | 775.2 |
| 15-10 | | (S)CH$_2$OCH$_3$ | | $C_{42}H_{48}N_{10}O_6$ | 789.38 | 789.4 |
| 15-11 | | (S)CH$_3$ | (R)CH$_3$ | $C_{42}H_{48}N_{10}O_5$ | 773.38 | 773.4 |

TABLE 16

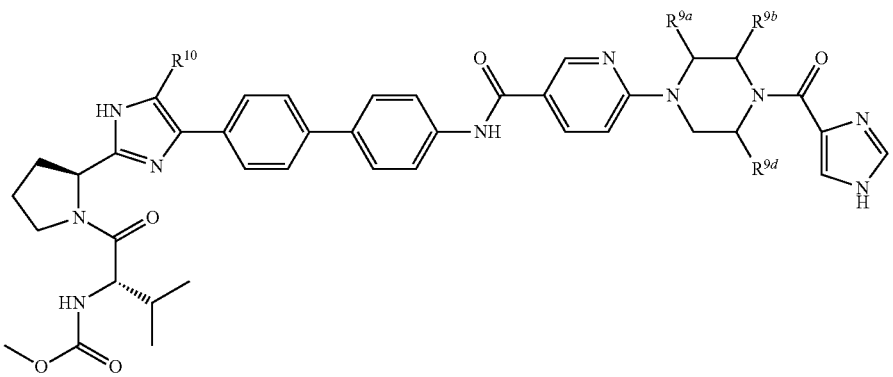

| Ex No. | R⁹ᵃ | R⁹ᵇ | R⁹ᵈ | R¹⁰ | Formula | Calc [M + H]⁺ | Found [M + H]⁺ |
|---|---|---|---|---|---|---|---|
| 16-1 | | | | | $C_{40}H_{44}N_{10}O_5$ | 745.35 | 745.4 |
| 16-2 | (S)CH₃ | | | | $C_{41}H_{46}N_{10}O_5$ | 759.37 | 759.4 |
| 16-3 | (R)CH₃ | | | | $C_{41}H_{46}N_{10}O_5$ | 759.37 | 759.2 |
| 16-4 | | (R)CH₃ | | | $C_{41}H_{46}N_{10}O_5$ | 759.37 | 759.4 |
| 16-5 | | (R)CH₃ | | Cl | $C_{41}H_{45}ClN_{10}O_5$ | 793.33 | 793.4 |
| 16-6 | | (S)CH₃ | | | $C_{41}H_{46}N_{10}O_5$ | 759.37 | 759.4 |
| 16-7 | | (S)CH₃ | | Cl | $C_{41}H_{45}ClN_{10}O_5$ | 793.33 | 793.2 |
| 16-8 | (R)CH₂OH | | | | $C_{41}H_{46}N_{10}O_6$ | 775.36 | 775.4 |
| 16-9 | (S)CH₂OH | | | | $C_{41}H_{46}N_{10}O_6$ | 775.36 | 775.4 |
| 16-10 | | (S)CH₂OH | | | $C_{41}H_{46}N_{10}O_6$ | 775.36 | 775.4 |
| 16-11 | | (R)CH₂OH | | | $C_{41}H_{46}N_{10}O_6$ | 775.36 | 775.4 |
| 16-12 | | (S)CH₂OCH₃ | | | $C_{42}H_{48}N_{10}O_6$ | 789.38 | 789.4 |
| 16-13 | | (S)CH₃ | (R)CH₃ | | $C_{42}H_{48}N_{10}O_5$ | 773.38 | 773.4 |

TABLE 17

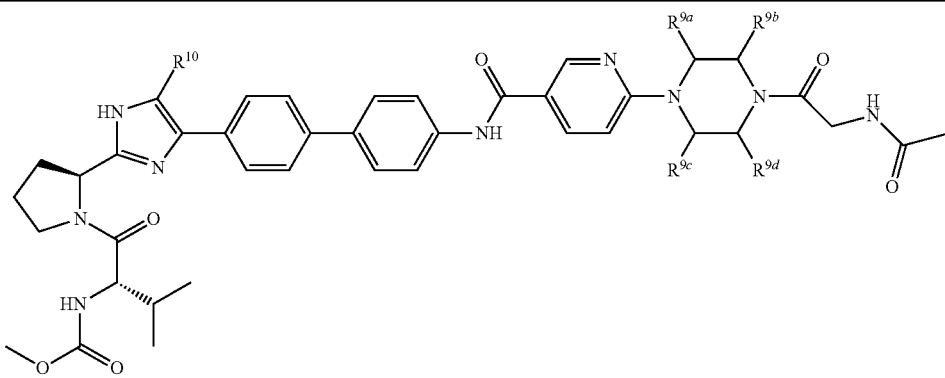

| Ex No. | R⁹ᵃ | R⁹ᵇ | R⁹ᶜ | R⁹ᵈ | Formula | Calc [M + H]⁺ | Found [M + H]⁺ |
|---|---|---|---|---|---|---|---|
| 17-1 | | | | | $C_{40}H_{47}N_9O_6$ | 750.37 | 750.3 |
| 17-2⁽ᵇ⁾ | | | | | $C_{41}H_{49}N_9O_6$ | 764.38 | 764.4 |
| 17-3 | (S)CH₃ | | | | $C_{41}H_{49}N_9O_6$ | 764.38 | 764.2 |
| 17-4⁽ᵃ⁾ | (S)CH₃ | | | | $C_{41}H_{48}ClN_9O_6$ | 798.34 | 798.2 |
| 17-5 | (R)CH₃ | | | | $C_{41}H_{49}N_9O_6$ | 764.38 | 764.2 |
| 17-6 | | (R)CH₃ | | | $C_{41}H_{49}N_9O_6$ | 764.38 | 764.8 |
| 17-7⁽ᵃ⁾ | | (R)CH₃ | | | $C_{41}H_{48}ClN_9O_6$ | 798.34 | 798.2 |
| 17-8 | | (S)CH₃ | | | $C_{41}H_{49}N_9O_6$ | 764.38 | 764.4 |
| 17-9⁽ᵃ⁾ | | (S)CH₃ | | | $C_{41}H_{48}ClN_9O_6$ | 798.34 | 798.2 |
| 17-10 | (R)CH₂OH | | | | $C_{41}H_{49}N_9O_7$ | 780.38 | 780.4 |
| 17-11 | (S)CH₂OH | | | | $C_{41}H_{49}N_9O_7$ | 780.38 | 780.4 |
| 17-12 | | (S)CH₂OH | | | $C_{41}H_{49}N_9O_7$ | 780.38 | 780.4 |
| 17-13 | | (R)CH₂OH | | | $C_{41}H_{49}N_9O_7$ | 780.38 | 780.4 |
| 17-14 | | (S)CH₃ | (R)CH₃ | | $C_{42}H_{48}N_{10}O_6$ | 789.38 | 789.2 |
| 17-15 | | (S)CH₂OCH₃ | | | $C_{42}H_{51}N_9O_7$ | 794.39 | 795.4 |
| 17-16 | | (S)CH₃ | | (R)CH₃ | $C_{42}H_{51}N_9O_6$ | 778.4 | 778.4 |
| 17-17 | | (S)C(O)NH₂ | | | $C_{41}H_{48}N_{10}O_7$ | 793.37 | 793.2 |

TABLE 17-continued

| Ex No. | R⁹ᵃ | R⁹ᵇ | R⁹ᶜ | R⁹ᵈ | Formula | Calc [M + H]⁺ | Found [M + H]⁺ |
|---|---|---|---|---|---|---|---|
| 17-18 | | (R)C(O)NH₂ | | | $C_{41}H_{48}N_{10}O_7$ | 793.37 | 793.4 |
| 17-19 | | (S)CON(CH₃)₂ | | | $C_{43}H_{52}N_{10}O_7$ | 821.4 | 821.4 |
| 17-20 | | (R)CON(CH₃)₂ | | | $C_{43}H_{52}N_{10}O_7$ | 821.4 | 821.4 |

(a) R¹⁰ is Cl
(b) R¹⁰ is CH₃

TABLE 18

| Ex No. | R⁹ᵃ | R⁹ᵇ | R⁹ᵈ | R¹⁰ | Formula | Calc [M + H]⁺ | Found [M + H]⁺ |
|---|---|---|---|---|---|---|---|
| 18-1 | | | | | $C_{41}H_{46}N_{10}O_5$ | 759.37 | 759.4 |
| 18-2 | (S)CH₃ | | | | $C_{42}H_{48}N_{10}O_5$ | 773.38 | 774 |
| 18-3 | (R)CH₃ | | | | $C_{42}H_{48}N_{10}O_5$ | 773.38 | 773.4 |
| 18-4 | | (R)CH₃ | | | $C_{42}H_{48}N_{10}O_5$ | 773.38 | 774.4 |
| 18-5 | | (R)CH₃ | | Cl | $C_{42}H_{47}ClN_{10}O_5$ | 807.34 | 807.2 |
| 18-6 | | (S)CH₃ | | | $C_{42}H_{48}N_{10}O_5$ | 773.38 | 773.4 |
| 18-7 | | (S)CH₃ | | Cl | $C_{42}H_{47}ClN_{10}O_5$ | 807.34 | 807.4 |
| 18-8 | (R)CH₂OH | | | | $C_{42}H_{48}N_{10}O_6$ | 789.38 | 789.4 |
| 18-9 | (S)CH₂OH | | | | $C_{42}H_{48}N_{10}O_6$ | 789.38 | 789.4 |
| 18-10 | | (S)CH₂OH | | | $C_{42}H_{48}N_{10}O_6$ | 789.38 | 789.4 |
| 18-11 | | (S)CH₂OH | | Cl | $C_{42}H_{47}ClN_{10}O_6$ | 823.34 | 823.2 |
| 18-12 | | (R)CH₂OH | | | $C_{42}H_{48}N_{10}O_6$ | 789.38 | 789.4 |
| 18-13 | | (R)CH₂OH | | Cl | $C_{42}H_{47}ClN_{10}O_6$ | 823.34 | 823.2 |
| 18-14 | | (R)CH₂OCH₃ | | | $C_{43}H_{50}N_{10}O_6$ | 803.39 | 803.4 |
| 18-15 | | (S)CH₂OCH₃ | | | $C_{43}H_{50}N_{10}O_6$ | 803.39 | 803.4 |
| 18-16 | | (S)CH₃ | (R)CH₃ | | $C_{43}H_{50}N_{10}O_5$ | 787.40 | 787.4 |
| 18-17 | | (S)CON(CH₃)₂ | | | $C_{44}H_{51}N_{11}O_6$ | 830.40 | 830.4 |
| 18-18 | | (R)CON(CH₃)₂ | | | $C_{44}H_{51}N_{11}O_6$ | 830.40 | 830.4 |

TABLE 19
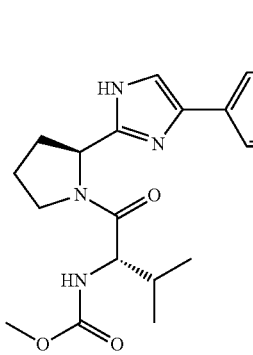
| Ex No. | $R^{9a}$ | $R^{9b}$ | $R^{9c}$ | $R^{9d}$ | * | Formula | Calc $[M + H]^+$ | Found $[M + H]^+$ |
|---|---|---|---|---|---|---|---|---|
| 19-1 | | | | | (R) | $C_{43}H_{51}N_9O_6$ | 790.4 | 790.4 |
| 19-2 | | | | | (S) | $C_{43}H_{51}N_9O_6$ | 790.4 | 790.4 |
| 19-3 | (R)CH$_3$ | | | | (R) | $C_{44}H_{53}N_9O_6$ | 804.41 | 804.4 |
| 19-4 | | (R)CH$_3$ | | | (R) | $C_{44}H_{53}N_9O_6$ | 804.41 | 804.4 |
| 19-5 | | (S)CH$_3$ | | | (R) | $C_{44}H_{53}N_9O_6$ | 804.41 | 804.4 |
| 19-6 | | (S)CH$_2$OH | | | (R) | $C_{44}H_{53}N_9O_7$ | 820.41 | 820.4 |
| 19-7 | | (R)CH$_2$OH | | | (R) | $C_{44}H_{53}N_9O_7$ | 820.41 | 820.4 |
| 19-8 | | (R)CH$_3$ | (R)CH$_3$ | | (R) | $C_{45}H_{55}N_9O_6$ | 818.43 | 818.4 |
| 19-9 | | (S)CH$_3$ | | (R)CH$_3$ | (R) | $C_{45}H_{55}N_9O_6$ | 818.43 | 818.4 |
TABLE 20
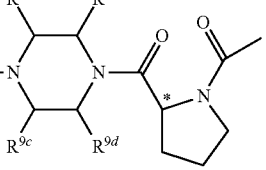
| Ex No. | R | $R^{10}$ | Formula | Calc $[M + H]^+$ | Found $[M + H]^+$ |
|---|---|---|---|---|---|
| 20-1 | 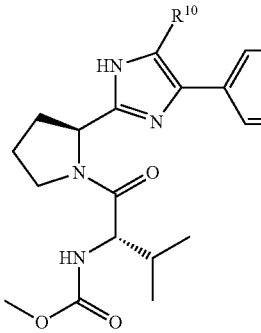 | | $C_{41}H_{49}N_9O_6$ | 764.38 | 764.2 |
| 20-2 | 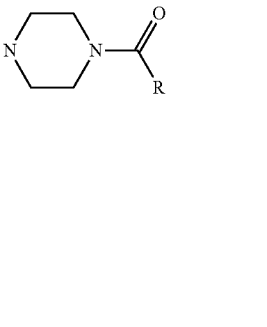 | | $C_{41}H_{48}N_8O_6$ | 749.37 | 749.6 |
| 20-3 | CH$_2$SO$_2$CH$_3$ | CH$_3$ | $C_{40}H_{48}N_8O_7S$ | 785.34 | 785.2 |
| 20-4 | 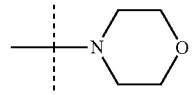 | | $C_{44}H_{46}N_{10}O_5$ | 759.37 | 759.4 |

TABLE 20-continued

| Ex No. | R | R[10] | Formula | Calc [M + H]+ | Found [M + H]+ |
|---|---|---|---|---|---|
| 20-5 | C(CH$_3$)$_2$OH | | C$_{40}$H$_{48}$N$_8$O$_6$ | 737.37 | 737.2 |
| 20-6 | CH(CH$_2$OH)NHC(O)CH$_3$ | | C$_{41}$H$_{49}$N$_9$O$_7$ | 780.38 | 780.2 |
| 20-7 | CH((R)iPr)NHC(O)CH$_3$ | | C$_{43}$H$_{53}$N$_9$O$_6$ | 792.41 | 792.4 |
| 20-8 | CH((S)CH$_3$)NHC(O)CH$_3$ | | C$_{41}$H$_{49}$N$_9$O$_6$ | 764.38 | 764.2 |
| 20-9 | NHiPr | | C$_{40}$H$_{49}$N$_9$O$_5$ | 736.39 | 736.4 |
| 20-10 | (4,6-dimethylpyrimidin-2-yl) | | C$_{43}$H$_{48}$N$_{10}$O$_5$ | 785.38 | 785.4 |
| 20-11 | (quinazolin-2-yl) | | C$_{45}$H$_{46}$N$_{10}$O$_5$ | 807.37 | 807.4 |
| 20-12 | (CH$_2$-imidazol-1-yl, dimethyl) | | C$_{44}$H$_{46}$N$_{10}$O$_5$ | 759.37 | 759.4 |
| 20-13 | (2-chloropyridin-3-yl) | | C$_{42}$H$_{44}$ClN$_9$O$_5$ | 790.32 | 790.2 |
| 20-14 | (5-fluoropyridin-2-yl) | | C$_{42}$H$_{44}$FN$_9$O$_5$ | 774.35 | 774.3 |
| 20-15 | (6-chloropyridin-3-yl) | | C$_{42}$H$_{44}$ClN$_9$O$_5$ | 790.32 | 790.2 |
| 20-16 | (thiazol-5-yl) | | C$_{40}$H$_{43}$N$_9$O$_5$S | 762.31 | 762.2 |
| 20-17 | (1H-benzimidazol-5-yl) | | C$_{44}$H$_{46}$N$_{10}$O$_5$ | 795.37 | 795.4 |

TABLE 20-continued
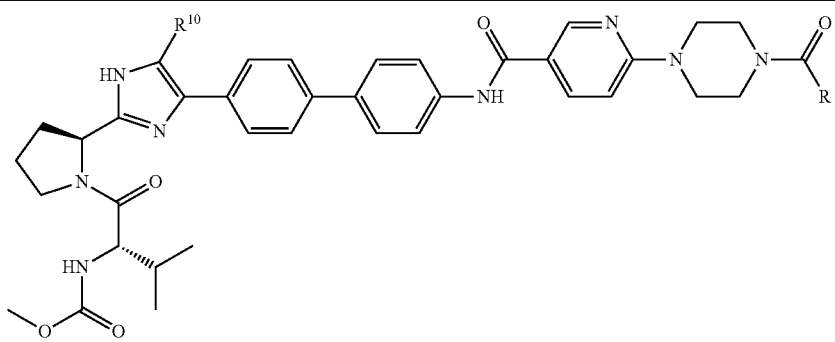
| Ex No. | R | R10 | Formula | Calc [M + H]+ | Found [M + H]+ |
|---|---|---|---|---|---|
| 20-18 | 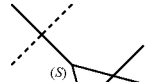 | | C40H43N9O5S | 762.31 | 762.2 |
| 20-19 | phenyl | | C43H46N8O5 | 755.36 | 755.4 |
| 20-20 | CH2SO2CH3 | | C39H46N8O7S | 771.32 | 771.2 |
TABLE 21
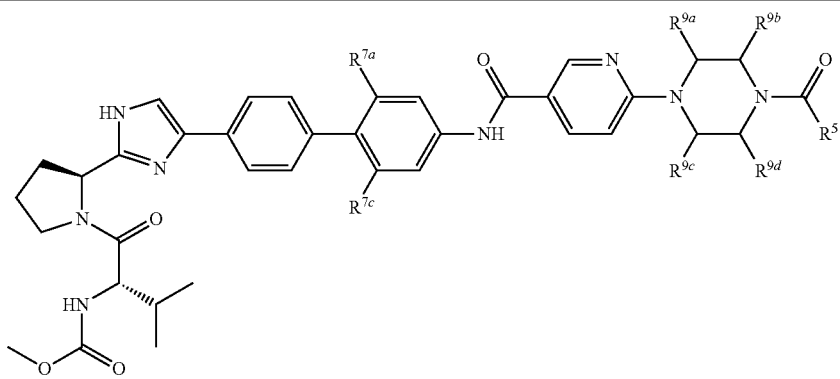
| Ex No. | R7a, R7c | R9a, R9b, R9c, R9d | R5 | Formula | Calc [M + H]+ | Found [M + H]+ |
|---|---|---|---|---|---|---|
| 21-1 | R7a = CH3 | R9a = (R)CH3 | OtBu | C43H54N8O6 | 779.42 | 779.4 |
| 21-2 | R7a = CH3 | R9a = (R)CH3 |  (S) | C44H54N8O5 | 775.42 | 775.4 |
| 21-3 | R7a = CH3 | R9a = (R)CH3 | 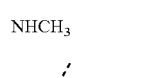 | C42H50N8O5 | 747.39 | 747.4 |
| 21-4 | R7a = CH3 | R9a = (R)CH3 | NHCH3 | C40H49N9O5 | 736.39 | 736.4 |
| 21-5 | R7a = CH3 | R9a = (R)CH3 | | C42H48N10O5 | 773.38 | 773.4 |

TABLE 21-continued

| Ex No. | R⁷ᵃ, R⁷ᶜ | R⁹ᵃ, R⁹ᵇ, R⁹ᶜ, R⁹ᵈ | R⁵ | Formula | Calc [M + H]⁺ | Found [M + H]⁺ |
|---|---|---|---|---|---|---|
| 21-6 | R⁷ᵃ = CH₃ | R⁹ᵃ = (R)CH₃ | (S)-acetylpyrrolidinyl with gem-dimethyl | $C_{46}H_{57}N_9O_6$ | 832.44 | 832.4 |
| 21-7 | R⁷ᵃ = CH₃ | R⁹ᵃ = (R)CH₃ | (R)-acetylpyrrolidinyl with gem-dimethyl | $C_{46}H_{57}N_9O_6$ | 832.44 | 832.4 |
| 21-8 | | R⁹ᵇ = (S)CH₃, R⁹ᶜ = (R)CH₃ | (R)-acetylpyrrolidinyl with gem-dimethyl | $C_{46}H_{57}N_9O_6$ | 832.44 | 832.4 |
| 21-9 | | R⁹ᵇ = (S)CH₃, R⁹ᶜ = (R)CH₃ | (S)-acetylpyrrolidinyl with gem-dimethyl | $C_{46}H_{57}N_9O_6$ | 832.44 | 832.4 |
| 21-10 | R⁷ᵃ = CH₃, R⁷ᶜ = CH₃ | R⁹ᵃ = (R)CH₃ | NHCH₃ | $C_{41}H_{51}N_9O_5$ | 750.40 | 750.4 |
| 21-11 | R⁷ᵃ = CH₃, R⁷ᶜ = CH₃ | R⁹ᵃ = (R)CH₃ | (S)-dimethylcyclopropyl | $C_{45}H_{56}N_8O_5$ | 789.44 | 789.4 |
| 21-12 | R⁷ᵃ = CH₃, R⁷ᶜ = CH₃ | R⁹ᵃ = (R)CH₃ | dimethyl-(1H-imidazol-4-yl) | $C_{43}H_{50}N_{10}O_5$ | 787.40 | 787.4 |
| 21-13 | R⁷ᵃ = CH₃, R⁷ᶜ = CH₃ | R⁹ᵃ = (R)CH₃ | dimethyl-cyclopropyl | $C_{43}H_{52}N_8O_5$ | 761.41 | 761.4 |

TABLE 21-continued

| Ex No. | R$^{7a}$, R$^{7c}$ | R$^{9a}$, R$^{9b}$, R$^{9c}$, R$^{9d}$ | R$^5$ | Formula | Calc [M + H]$^+$ | Found [M + H]$^+$ |
|---|---|---|---|---|---|---|
| 21-14 | R$^{7a}$ = CH$_3$ | R$^{9a}$ = (R)CH$_3$ | methyl (S)-2-methylpyrrolidine-1-carboxylate group | C$_{46}$H$_{57}$N$_9$O$_7$ | 848.44 | 848.4 |
| 21-15 | R$^{7a}$ = CH$_3$ | R$^{9b}$ = (S)CH$_3$, R$^{9d}$ = (R)CH$_3$ | 2-(1H-imidazol-4-yl)propan-2-yl group | C$_{43}$H$_{50}$N$_{10}$O$_5$ | 787.40 | 787.2 |
| 21-16 | R$^{7a}$ = CH$_3$ | R$^{9b}$ = (S)CH$_3$, R$^{9d}$ = (R)CH$_3$ | NHCH$_3$ | C$_{41}$H$_{51}$N$_9$O$_5$ | 750.40 | 750.4 |
| 21-17 | R$^{7a}$ = CH$_3$ | R$^{9b}$ = (S)CH$_3$, R$^{9d}$ = (R)CH$_3$ | (S)-2,2-dimethylcyclopropyl group | C$_{45}$H$_{56}$N$_8$O$_5$ | 789.44 | 789.4 |
| 21-18 | R$^{7a}$ = CH$_3$ | R$^{9b}$ = (S)CH$_3$, R$^{9d}$ = (R)CH$_3$ | 1-cyclopropyl-1-methyl group | C$_{43}$H$_{52}$N$_8$O$_5$ | 761.41 | 761.4 |
| 21-19 | R$^{7a}$ = CH$_3$ | R$^{9a}$ = (R)CH$_3$, R$^{9d}$ = (S)CH$_3$ | methyl (S)-2-methylpyrrolidine-1-carboxylate group | C$_{47}$H$_{59}$N$_9$O$_7$ | 862.45 | 862.4 |
| 21-20 | R$^{7a}$ = CH$_3$ | R$^{9a}$ = (R)CH$_3$, R$^{9d}$ = (S)CH$_3$ | (S)-2,2-dimethylcyclopropyl group | C$_{45}$H$_{56}$N$_8$O$_5$ | 789.44 | 789.4 |
| 21-21 | R$^{7a}$ = CH$_3$ | R$^{9a}$ = (R)CH$_3$, R$^{9d}$ = (S)CH$_3$ | 1-cyclopropyl-1-methyl group | C$_{43}$H$_{52}$N$_8$O$_5$ | 761.41 | 761.4 |
| 21-22 | R$^{7a}$ = CH$_3$ | R$^{9a}$ = (R)CH$_3$, R$^{9d}$ = (S)CH$_3$ | NHCH$_3$ | C$_{41}$H$_{51}$N$_9$O$_5$ | 750.40 | 750.4 |

TABLE 21-continued

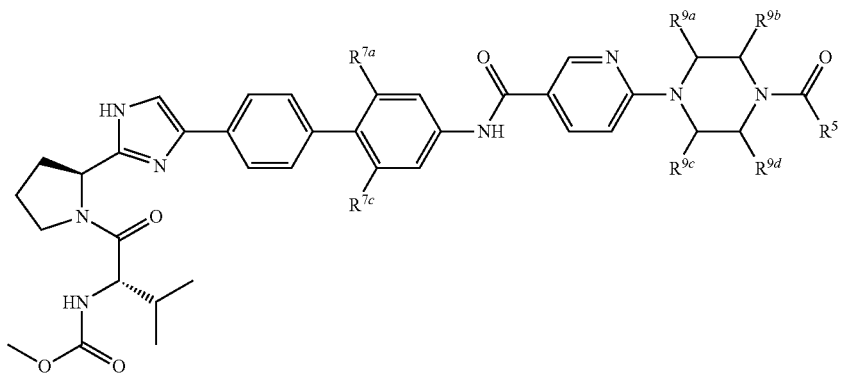

| Ex No. | R$^{7a}$, R$^{7c}$ | R$^{9a}$, R$^{9b}$, R$^{9c}$, R$^{9d}$ | R$^5$ | Formula | Calc [M + H]$^+$ | Found [M + H]$^+$ |
|---|---|---|---|---|---|---|
| 21-23 | R$^{7a}$ = CH$_3$ | R$^{9a}$ = (R)CH$_3$, R$^{9d}$ = (S)CH$_3$ | (1H-imidazol-4-yl dimethyl) | C$_{43}$H$_{50}$N$_{10}$O$_5$ | 787.40 | 787.4 |
| 21-24 | R$^{7a}$ = CF$_3$ | R$^{9a}$ = (R)CH$_3$ | (dimethyl cyclopropyl) | C$_{42}$H$_{47}$F$_3$N$_8$O$_5$ | 801.36 | 801.2 |
| 21-25 | R$^{7a}$ = CF$_3$ | R$^{9a}$ = (R)CH$_3$ | (S)-trimethylcyclopropyl | C$_{44}$H$_{51}$F$_3$N$_8$O$_5$ | 829.39 | 829.4 |
| 21-26 | R$^{7a}$ = CF$_3$ | R$^{9a}$ = (R)CH$_3$ | NHCH$_3$ | C$_{40}$H$_{46}$F$_3$N$_9$O$_5$ | 790.36 | 790.2 |
| 21-27 | R$^{7a}$ = CF$_3$ | R$^{9a}$ = (R)CH$_3$ | (1H-imidazol-4-yl dimethyl) | C$_{42}$H$_{45}$F$_3$N$_{10}$O | 827.35 | 827.4 |
| 21-28 | R$^{7a}$ = CF$_3$ | R$^{9a}$ = (R)CH$_3$ | (S)-methyl pyrrolidine carboxylate dimethyl | C$_{46}$H$_{54}$F$_3$N$_9$O$_7$ | 902.41 | 902.4 |
| 21-29 | R$^{7a}$ = CN | R$^{9a}$ = (R)CH$_3$ | NHCH$_3$ | C$_{40}$H$_{46}$N$_{10}$O$_5$ | 747.37 | 747.4 |
| 21-30 | R$^{7a}$ = CN | R$^{9a}$ = (R)CH$_3$ | (S)-trimethylcyclopropyl | C$_{44}$H$_{51}$N$_9$O$_5$ | 786.40 | 786.4 |
| 21-31 | R$^{7a}$ = CN | R$^{9a}$ = (R)CH$_3$ | (1H-imidazol-4-yl dimethyl) | C$_{42}$H$_{45}$N$_{11}$O$_5$ | 784.36 | 784.4 |

TABLE 21-continued

| Ex No. | $R^{7a}, R^{7c}$ | $R^{9a}, R^{9b}, R^{9c}, R^{9d}$ | $R^5$ | Formula | Calc [M + H]$^+$ | Found [M + H]$^+$ |
|---|---|---|---|---|---|---|
| 21-32 | $R^{7a}$ = CN | $R^{9a}$ = (R)CH$_3$ | (methyl pyrrolidine-1-carboxylate, (S)) | C$_{46}$H$_{54}$N$_{10}$O$_7$ | 859.42 | 859.4 |
| 21-33 | $R^{7a}$ = CH$_3$ | $R^{9a}$ = (R)CH$_2$SO$_2$CH$_3$ | (2,2-dimethylcyclopropyl, (S)) | C$_{45}$H$_{56}$N$_8$O$_7$S | 853.40 | 853.4 |
| 21-34 | $R^{7a}$ = OCF$_3$ | $R^{9a}$ = (R)CH$_3$ | (2,2-dimethylcyclopropyl, (S)) | C$_{44}$H$_{51}$F$_3$N$_8$O$_6$ | 845.39 | 845.4 |
| 21-35 | $R^{7a}$ = OCF$_3$ | $R^{9a}$ = (R)CH$_3$ | NHCH$_3$ | C$_{40}$H$_{46}$F$_3$N$_9$O$_6$ | 806.35 | 806.4 |
| 21-36 | $R^{7a}$ = OCF$_3$ | $R^{9a}$ = (R)CH$_3$ | (1H-imidazol-4-yl with gem-dimethyl) | C$_{42}$H$_{45}$F$_3$N$_{10}$O$_6$ | 843.35 | 843.2 |
| 21-37 | $R^{7a}$ = OCF$_3$ | $R^{9a}$ = (R)CH$_3$ | (cyclopropyl with gem-dimethyl) | C$_{42}$H$_{47}$F$_3$N$_8$O$_6$ | 817.36 | 817.2 |
| 21-38 | $R^{7a}$ = OCH$_3$ | $R^{9a}$ = (R)CH$_3$ | (methyl pyrrolidine-1-carboxylate, (S)) | C$_{46}$H$_{57}$N$_9$O$_8$ | 864.43 | 864.4 |
| 21-39 | $R^{7a}$ = OCH$_3$ | $R^{9a}$ = (R)CH$_3$ | NHCH$_3$ | C$_{40}$H$_{49}$N$_9$O$_6$ | 752.38 | 752.4 |
| 21-40 | $R^{7a}$ = OCH$_3$ | $R^{9a}$ = (R)CH$_3$ | (2,2-dimethylcyclopropyl, (S)) | C$_{44}$H$_{54}$N$_8$O$_6$ | 791.42 | 791.4 |

TABLE 21-continued

| Ex No. | $R^{7a}, R^{7c}$ | $R^{9a}, R^{9b}, R^{9c}, R^{9d}$ | $R^5$ | Formula | Calc [M + H]$^+$ | Found [M + H]$^+$ |
|---|---|---|---|---|---|---|
| 21-41 | $R^{7a}$ = OCF$_3$ | $R^{9a}$ = (R)CH$_3$ | (S)-methyl pyrrolidine-1-carboxylate | C$_{46}$H$_{54}$F$_3$N$_9$O$_8$ | 918.41 | 918.4 |
| 21-42 | $R^{7a}$ = OCF$_3$ | $R^{9a}$ = (R)CH$_3$ | 2-oxopyrrolidin-3-yl | C$_{43}$H$_{48}$F$_3$N$_9$O$_7$ | 860.36 | 860.4 |
| 21-43 | $R^{7a}$ = OCF$_3$ | $R^{9a}$ = (R)CH$_3$, $R^{9d}$ = (S)CH$_3$ | cyclopropyl | C$_{43}$H$_{49}$F$_3$N$_8$O$_6$ | 831.37 | 831.2 |
| 21-44 | $R^{7a}$ = OCF$_3$ | $R^{9a}$ = (R)CH$_3$, $R^{9d}$ = (S)CH$_3$ | (S)-methyl pyrrolidine-1-carboxylate | C$_{47}$H$_{56}$F$_3$N$_9$O$_8$ | 932.42 | 932.4 |
| 21-45 | $R^{7a}$ = OCF$_3$ | $R^{9a}$ = (R)CH$_3$, $R^{9d}$ = (S)CH$_3$ | 1H-imidazol-4-yl | C$_{43}$H$_{47}$F$_3$N$_{10}$O$_6$ | 857.36 | 857.2 |
| 21-46 | $R^{7a}$ = OCF$_3$ | $R^{9a}$ = (R)CH$_3$, $R^{9d}$ = (S)CH$_3$ | (S)-2,2-dimethylcyclopropyl | C$_{45}$H$_{53}$F$_3$N$_8$O$_6$ | 859.40 | 859.4 |
| 21-47 | $R^{7a}$ = OCF$_3$ | $R^{9a}$ = (R)CH$_3$, $R^{9d}$ = (S)CH$_3$ | NHCH$_3$ | C$_{41}$H$_{48}$F$_3$N$_9$O$_6$ | 820.37 | 820.5 |
| 21-48 | $R^{7a}$ = OCF$_3$ | $R^{9b}$ = (R)CH$_3$, $R^{9d}$ = (S)CH$_3$ | cyclopropyl | C$_{43}$H$_{49}$F$_3$N$_8$O$_6$ | 831.37 | 831.4 |
| 21-49 | $R^{7a}$ = OCF$_3$ | $R^{9b}$ = (R)CH$_3$, $R^{9d}$ = (S)CH$_3$ | NHCH$_3$ | C$_{41}$H$_{48}$F$_3$N$_9$O$_6$ | 820.37 | 820.4 |

TABLE 21-continued

| Ex No. | R$^{7a}$, R$^{7c}$ | R$^{9a}$, R$^{9b}$, R$^{9c}$, R$^{9d}$ | R$^5$ | Formula | Calc [M + H]$^+$ | Found [M + H]$^+$ |
|---|---|---|---|---|---|---|
| 21-50 | R$^{7a}$ = OCF$_3$ | R$^{9b}$ = (R)CH$_3$, R$^{9d}$ = (S)CH$_3$ | imidazole | C$_{43}$H$_{47}$F$_3$N$_{10}$O$_6$ | 857.36 | 857.4 |
| 21-51 | R$^{7a}$ = OCF$_3$ | R$^{9b}$ = (R)CH$_3$, R$^{9d}$ = (S)CH$_3$ | (S)-dimethylcyclopropyl | C$_{45}$H$_{53}$F$_3$N$_8$O$_6$ | 859.40 | 860.2 |
| 21-52 | R$^{7a}$ = F | R$^{9a}$ = (R)CH$_3$ | cyclopropyl | C$_{41}$H$_{47}$FN$_8$O$_5$ | 751.37 | 751.2 |
| 21-53 | R$^{7a}$ = F | R$^{9a}$ = (R)CH$_3$ | NHCH$_3$ | C$_{39}$H$_{46}$FN$_9$O$_5$ | 740.36 | 740.4 |
| 21-54 | R$^{7a}$ = F | R$^{9a}$ = (R)CH$_3$ | imidazole | C$_{41}$H$_{45}$FN$_{10}$O$_5$ | 777.36 | 777.2 |
| 21-55 | R$^{7a}$ = F | R$^{9a}$ = (R)CH$_3$ | (S)-dimethylcyclopropyl | C$_{43}$H$_{51}$FN$_8$O$_5$ | 779.40 | 779.4 |
| 21-56 | R$^{7a}$ = F, R$^{7c}$ = F | R$^{9a}$ = (R)CH$_3$ | cyclopropyl | C$_{41}$H$_{46}$F$_2$N$_8$O$_5$ | 769.36 | 769.2 |
| 21-57 | R$^{7a}$ = F, R$^{7c}$ = F | R$^{9a}$ = (R)CH$_3$ | (S)-dimethylcyclopropyl | C$_{43}$H$_{50}$F$_2$N$_8$O$_5$ | 797.39 | 797.4 |
| 21-58 | R$^{7a}$ = F, R$^{7c}$ = F | R$^{9a}$ = (R)CH$_3$ | NHCH$_3$ | C$_{39}$H$_{45}$F$_2$N$_9$O$_5$ | 758.35 | 758.4 |
| 21-59 | R$^{7a}$ = F, R$^{7c}$ = F | R$^{9a}$ = (R)CH$_3$ | imidazole | C$_{41}$H$_{44}$F$_2$N$_{10}$O$_5$ | 795.35 | 795.2 |

TABLE 21-continued
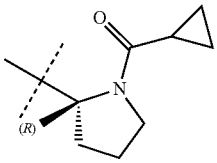
| Ex No. | $R^{7a}, R^{7c}$ | $R^{9a}, R^{9b}, R^{9c}, R^{9d}$ | $R^5$ | Formula | Calc [M + H]+ | Found [M + H]+ |
|---|---|---|---|---|---|---|
| 21-60 | | | 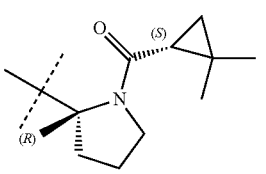 | $C_{45}H_{53}N_9O_6$ | 816.41 | 816.4 |
| 21-61 | | | 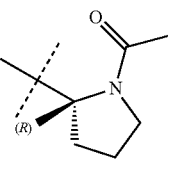 | $C_{47}H_{57}N_9O_6$ | 844.44 | 844.4 |
| 21-62 | | | 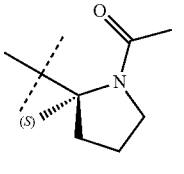 | $C_{44}H_{53}N_9O_6$ | 804.41 | 804.4 |
| 21-63 | | | 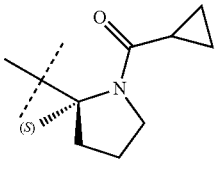 | $C_{44}H_{53}N_9O_6$ | 804.41 | 804.2 |
| 21-64 | | | 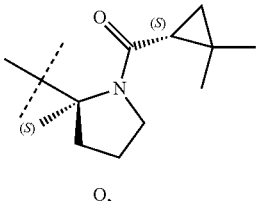 | $C_{46}H_{55}N_9O_6$ | 830.43 | 830.4 |
| 21-65 | | | 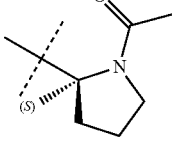 | $C_{48}H_{59}N_9O_6$ | 858.46 | 858.4 |
| 21-66 | | $R^{9a} = (S)CH_3$ | | $C_{45}H_{55}N_9O_6$ | 818.43 | 818.4 |

TABLE 21-continued

| Ex No. | R⁷ᵃ, R⁷ᶜ | R⁹ᵃ, R⁹ᵇ, R⁹ᶜ, R⁹ᵈ | R⁵ | Formula | Calc [M + H]⁺ | Found [M + H]⁺ |
|---|---|---|---|---|---|---|
| 21-67 | | R⁹ᵇ = (S)CH₂OCH₃ | | C₄₆H₅₇N₉O₇ | 848.44 | 848.4 |
| 21-68 | | R⁹ᵇ = (R)CH₂OH | | C₄₅H₅₅N₉O₇ | 834.42 | 834.4 |
| 21-69 | | R⁹ᵇ = (S)CH₂OH | | C₄₅H₅₅N₉O₇ | 834.42 | 834.4 |
| 21-70 | | R⁹ᵃ = (R)CH₃ | | C₄₅H₅₅N₉O₆ | 818.43 | 818.4 |
| 21-71 | | | | C₄₃H₅₀FN₉O₆ | 808.39 | 808.4 |
| 21-72 | | R⁹ᵃ = (R)CH₃ | | C₄₅H₅₅N₉O₇ | 834.42 | 834.4 |

TABLE 21-continued
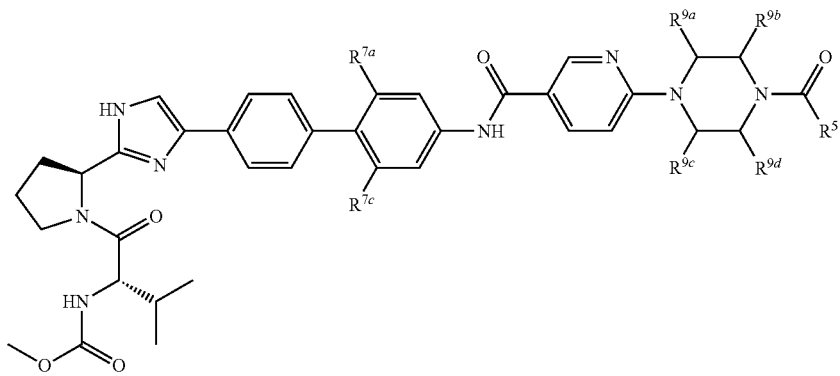
| Ex No. | $R^{7a}$, $R^{7c}$ | $R^{9a}$, $R^{9b}$, $R^{9c}$, $R^{9d}$ | $R^5$ | Formula | Calc $[M + H]^+$ | Found $[M + H]^+$ |
|---|---|---|---|---|---|---|
| 21-73 | | $R^{9a}$ = (R)CH$_2$CH$_3$ | | $C_{46}H_{57}N_9O_6$ | 832.44 | 832.4 |
| 21-74 | | $R^{9a}$ = (S)CH$_2$CH$_3$ | | $C_{46}H_{57}N_9O_6$ | 832.44 | 832.4 |
| 21-75 | | $R^{9a}$ = (R)CH$_3$ | (b) | $C_{50}H_{64}N_{10}O_8$ | 933.49 | 933.4 |
| 21-76 | | $R^{9a}$ = (R)CH$_3$ | (a) | $C_{50}H_{64}N_{10}O_8$ | 933.49 | 933.4 |
| 21-77 | $R^{7a}$ = OCH$_3$ | $R^{9a}$ = (R)CH$_3$ | (a) | $C_{51}H_{66}N_{10}O_9$ | 963.50 | 963.4 |
(a)
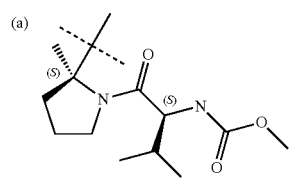
(b)
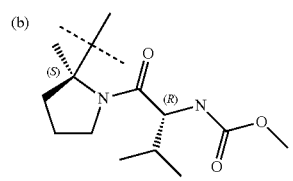

TABLE 22

| Ex No. | R¹ | R⁹ᵃ | R⁵ | Formula | Calc [M + H]⁺ | Found [M + H]⁺ |
|---|---|---|---|---|---|---|
| 22-1 | (S)CH$_3$ | | cyclopropyl-gem-dimethyl | C$_{38}$H$_{42}$N$_8$O$_5$ | 691.33 | 691.2 |
| 22-2 | (S)CH$_2$OH | | cyclopropyl-gem-dimethyl | C$_{38}$H$_{42}$N$_8$O$_6$ | 707.32 | 707.7 |
| 22-3 | (S)C(CH$_3$)$_2$OH | | cyclopropyl-gem-dimethyl | C$_{40}$H$_{46}$N$_8$O$_6$ | 735.35 | 735.2 |
| 22-4 | (R)phenyl | | cyclopropyl-gem-dimethyl | C$_{43}$H$_{44}$N$_8$O$_5$ | 753.34 | 753.2 |
| 22-5 | (S)CH$_2$((S)CH$_3$)OCH$_3$ | | cyclopropyl-gem-dimethyl | C$_{40}$H$_{46}$N$_8$O$_6$ | 735.35 | 735.2 |
| 22-6 | (S)CH$_3$ | (R)CH$_3$ | (S)-dimethylcyclopropyl | C$_{41}$H$_{48}$N$_8$O$_5$ | 733.38 | 733.4 |
| 22-7 | (S)CH$_2$OH | (R)CH$_3$ | (S)-dimethylcyclopropyl | C$_{41}$H$_{48}$N$_8$O$_6$ | 749.37 | 749.4 |
| 22-8 | (R)phenyl | (R)CH$_3$ | (S)-dimethylcyclopropyl | C$_{46}$H$_{50}$N$_8$O$_5$ | 795.39 | 795.4 |
| 22-9 | (S)CH$_2$((S)CH$_3$)OCH$_3$ | (R)CH$_3$ | (S)-dimethylcyclopropyl | C$_{43}$H$_{52}$N$_8$O$_6$ | 777.40 | 777.4 |

TABLE 22-continued

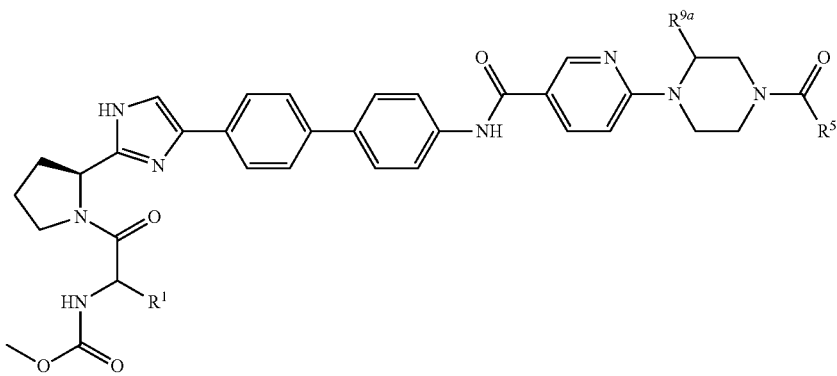

| Ex No. | $R^1$ | $R^{9a}$ | $R^5$ | Formula | Calc [M + H]$^+$ | Found [M + H]$^+$ |
|---|---|---|---|---|---|---|
| 22-10 | (S)C(CH$_3$)$_3$ | (R)CH$_3$ | (S) dimethylcyclopropyl | C$_{44}$H$_{54}$N$_8$O$_5$ | 775.42 | 775.4 |
| 22-11 | (S)cPr | (R)CH$_3$ | (S) dimethylcyclopropyl | C$_{43}$H$_{50}$N$_8$O$_5$ | 759.39 | 759.4 |
| 22-12 | (R)CH(CH$_3$)$_2$ | (R)CH$_3$ | (S) dimethylcyclopropyl | C$_{43}$H$_{52}$N$_8$O$_5$ | 761.41 | 761.4 |

TABLE 23

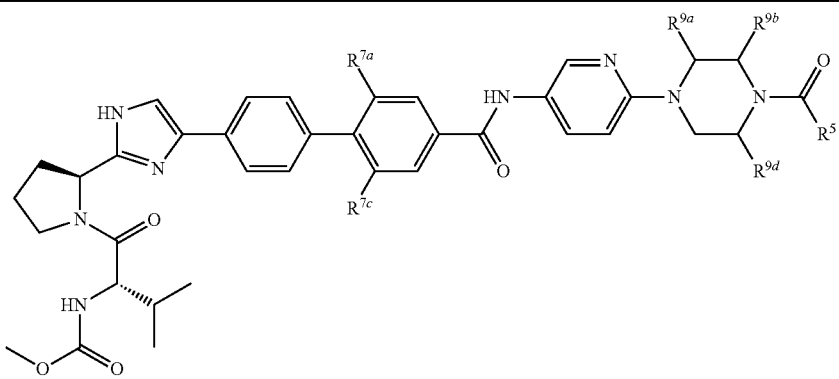

| Ex No. | $R^{7a}, R^{7c}$ | $R^{9a}, R^{9b}, R^{9d}$ | $R^5$ | Formula | Calc [M + H]$^+$ | Found [M + H]$^+$ |
|---|---|---|---|---|---|---|
| 23-1 | | $R^{9a}$ = (R)CH$_3$ | (S) dimethylcyclopropyl | C$_{43}$H$_{52}$N$_8$O$_5$ | 761.41 | 761.7 |
| 23-2 | | $R^{9a}$ = (R)CH$_3$ | cyclopropyl-OMe | C$_{44}$H$_{56}$N$_8$O$_6$ | 793.43 | 793.4 |

TABLE 23-continued

| Ex No. | $R^{7a}, R^{7c}$ | $R^{9a}, R^{9b}, R^{9d}$ | $R^5$ | Formula | Calc [M + H]⁺ | Found [M + H]⁺ |
|---|---|---|---|---|---|---|
| 23-3 | | $R^{9a}$ = (R)CH$_3$ | (imidazolyl-dimethyl) | $C_{41}H_{46}N_{10}O_5$ | 759.37 | 759.4 |
| 23-4 | | $R^{9a}$ = (R)CH$_3$ | (S-acetylpyrrolidinyl-methyl) | $C_{45}H_{55}N_9O_7$ | 834.42 | 834.4 |
| 23-5 | | $R^{9a}$ = (R)CH$_3$ | NHCH$_3$ | $C_{39}H_{47}N_9O_5$ | 722.37 | 722.4 |
| 23-6 | | $R^{9a}$ = (R)CH$_3$ | (S-dimethylcyclopropyl) | $C_{44}H_{54}N_8O_5$ | 775.42 | 775.4 |
| 23-7 | | $R^{9a}$ = (R)CH$_3$ $R^{9d}$ = (S)CH$_3$ | (imidazolyl-dimethyl) | $C_{42}H_{48}N_{10}O_5$ | 773.38 | 773.4 |
| 23-8 | | $R^{9a}$ = (R)CH$_3$ $R^{9d}$ = (S)CH$_3$ | (a) | $C_{51}H_{66}N_{10}O_8$ | 947.51 | 947.6 |
| 23-9 | | $R^{9a}$ = (R)CH$_3$ $R^{9d}$ = (S)CH$_3$ | NHCH$_3$ | $C_{40}H_{49}N_9O_5$ | 736.39 | 736.4 |
| 23-10 | | $R^{9a}$ = (R)CH$_3$ | (a) | $C_{50}H_{64}N_{10}O_8$ | 933.49 | 933.4 |
| 23-11 | $R^{7a}$ = OCH$_3$ | $R^{9a}$ = (R)CH$_3$ | (S-dimethylcyclopropyl) | $C_{44}H_{54}N_8O_6$ | 791.42 | 791.4 |
| 23-12 | $R^{7a}$ = CH$_3$ | $R^{9a}$ = (R)CH$_3$ | NHCH$_3$ | $C_{40}H_{49}N_9O_3$ | 736.39 | 736.4 |

TABLE 23-continued
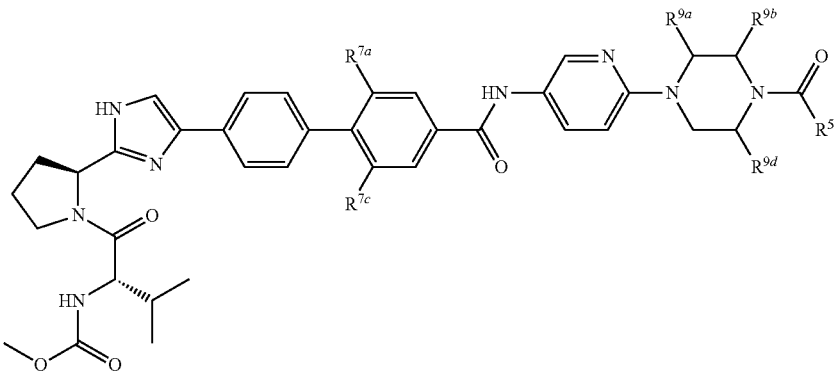
| Ex No. | $R^{7a}, R^{7c}$ | $R^{9a}, R^{9b}, R^{9d}$ | $R^5$ | Formula | Calc [M + H]$^+$ | Found [M + H]$^+$ |
|---|---|---|---|---|---|---|
| 23-13 | $R^{7a}$ = OCF$_3$ | $R^{9a}$ = (R)CH$_3$ | | $C_{44}H_{51}F_3N_8O_6$ | 845.39 | 845.8 |
| 23-14 | $R^{7a}$ = OCF$_3$ | $R^{9a}$ = (R)CH$_3$ | (a) | $C_{51}H_{63}F_3N_{10}O_9$ | 1017.47 | 1017.9 |
(a)
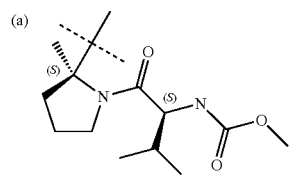
TABLE 24
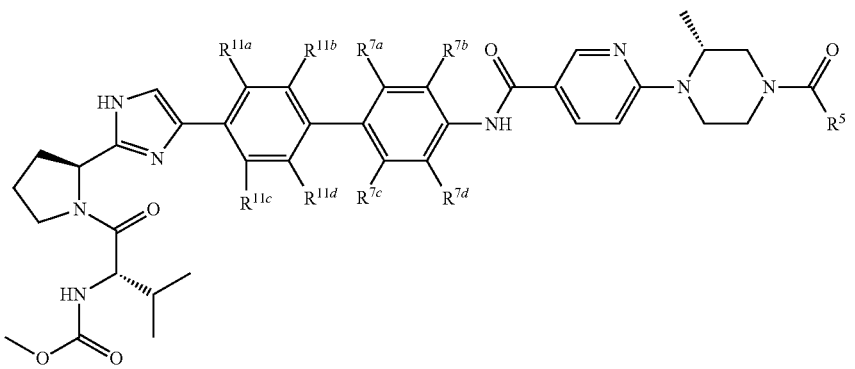
| Ex No. | $R^{11a} R^{11b}$ $R^{11c} R^{11d}$ | $R^{7a} R^{7b} R^{7c}$ $R^{7d}$ | $R^5$ | Formula | Calc [M + H]$^+$ | Found [M + H]$^+$ |
|---|---|---|---|---|---|---|
| 24-1 | | | 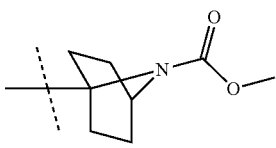 | $C_{46}H_{55}N_9O_7$ | 846.42 | 846.4 |
| 24-2 | | | 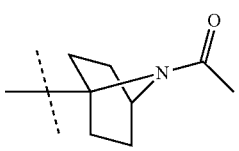 | $C_{46}H_{55}N_9O_6$ | 830.43 | 830.4 |

TABLE 24-continued

| Ex No. | R11a R11b R11c R11d | R7a R7b R7c R7d | R5 | Formula | Calc [M + H]+ | Found [M + H]+ |
|---|---|---|---|---|---|---|
| 24-3 | | | | C51H64N10O8 | 945.49 | 945.4 |
| 24-4 | | | | C47H60N10O6 | 861.47 | 861.4 |
| 24-5 | | | | C49H62N10O7 | 903.48 | 903.4 |
| 24-6 | | | | C51H66N10O8 | 947.51 | 945.4 |
| 24-7 | | | | C43H52N8O5 | 761.41 | 761.4 |
| 24-8 | | | | C49H62N10O8 | 919.48 | 919.6 |
| 24-9 | | | | C43H53N9O5 | 776.42 | 776.4 |

TABLE 24-continued

| Ex No. | $R^{11a} R^{11b}$ $R^{11c} R^{11d}$ | $R^{7a} R^{7b} R^{7c}$ $R^{7d}$ | $R^5$ | Formula | Calc $[M + H]^+$ | Found $[M + H]^+$ |
|---|---|---|---|---|---|---|
| 24-10 | | | CH$_2$t-Bu | C$_{43}$H$_{54}$N$_8$O$_5$ | 763.42 | 763.4 |
| 24-11 | | | | C$_{41}$H$_{49}$N$_9$O$_5$ | 748.39 | 748.4 |
| 24-12 | | | NHC(CH$_3$)$_2$CH$_2$OH | C$_{42}$H$_{53}$N$_9$O$_6$ | 780.41 | 780.4 |
| 24-13 | | | | C$_{47}$H$_{57}$N$_9$O$_8$ | 876.43 | 876.4 |
| 24-14 | | | | C$_{43}$H$_{52}$N$_8$O$_6$ | 777.4 | 777.4 |
| 24-15 | | $R^{7a}$ = OiPr | NHCH$_3$ | C$_{42}$H$_{53}$N$_9$O$_6$ | 780.41 | 780.4 |
| 24-16 | | | | C$_{47}$H$_{60}$N$_{10}$O$_6$ | 861.47 | 861.6 |
| 24-17 | | | | C$_{47}$H$_{60}$N$_{10}$O$_7$ | 877.47 | 877.4 |
| 24-18 | | | | C$_{48}$H$_{62}$N$_{10}$O$_6$ | 875.49 | 875.6 |

TABLE 24-continued

| Ex No. | $R^{11a} R^{11b}$ $R^{11c} R^{11d}$ | $R^{7a} R^{7b} R^{7c}$ $R^{7d}$ | $R^5$ | Formula | Calc [M + H]$^+$ | Found [M + H]$^+$ |
|---|---|---|---|---|---|---|
| 24-19 | | | | $C_{49}H_{62}N_{10}O_8$ | 919.48 | 919.4 |
| 24-20 | $R^{11b} = CH_3$ | | | $C_{46}H_{55}N_9O_6$ | 830.43 | 830.7 |
| 24-21 | | | | $C_{43}H_{53}N_9O_5$ | 776.42 | 776.4 |
| 24-22 | | $R^{7a} = OCHF_2$ | NHCH$_3$ | $C_{40}H_{47}F_2N_9O_6$ | 788.36 | 788.4 |
| 24-23 | $R^{11b} = OCF_3$ | | NHCH$_3$ | $C_{40}H_{46}F_3N_9O_6$ | 806.35 | 806.4 |
| 24-24 | | $R^{7a} = CH_3$ $R^{7d} = F$ | NHCH$_3$ | $C_{40}H_{48}FN_9O_5$ | 754.38 | 754.8 |
| 24-25 | | $R^{7a} = OCH_3$ $R^{7d} = Cl$ | | $C_{42}H_{49}ClN_8O_6$ | 797.35 | 798.0 |
| 24-26 | | $R^{7b} = OH$ | NHCH$_3$ | $C_{39}H_{47}N_9O_6$ | 738.37 | 738.8 |
| 24-27 | | $R^{7b} = CH_2CH_3$ | | $C_{43}H_{50}N_{10}O_5$ | 787.4 | 787.8 |
| 24-28 | | $R^{7b} = CH_2CH_3$ | NHCH$_3$ | $C_{41}H_{51}N_9O_5$ | 750.4 | 750.8 |

TABLE 24-continued
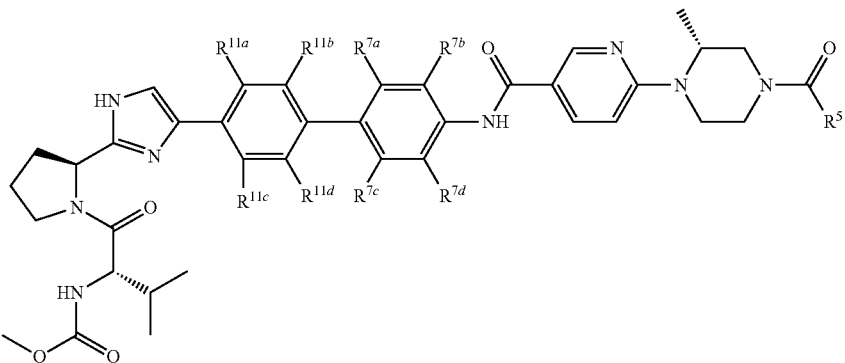
| Ex No. | $R^{11a} R^{11b}$ $R^{11c} R^{11d}$ | $R^{7a} R^{7b} R^{7c}$ $R^{7d}$ | $R^5$ | Formula | Calc [M + H]⁺ | Found [M + H]⁺ |
|---|---|---|---|---|---|---|
| 24-29 | | $R^{7a}$ = Cl $R^{7b}$ = F | 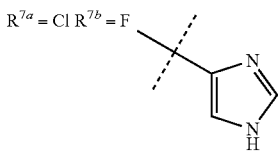 | $C_{41}H_{44}ClFN_{10}O_5$ | 811.32 | 811.6 |
| 24-30 | | $R^{7a}$ = Cl $R^{7b}$ = F | NHCH₃ | $C_{39}H_{45}ClFN_9O_5$ | 774.32 | 774.8 |
| 24-31 | | $R^{7a}$ = Cl $R^{7b}$ = F | 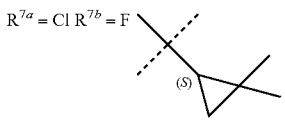 | $C_{43}H_{50}ClFN_8O_5$ | 813.36 | 813.6 |
| 24-32 | | $R^{7a}$ = Cl $R^{7b}$ = F | 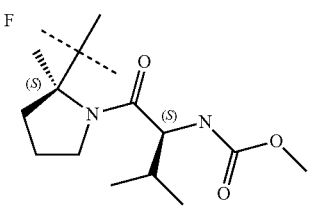 | $C_{50}H_{62}ClFN_{10}O_8$ | 985.44 | 985.6 |
| 24-33 | | $R^{7a}$ = OCH₃ $R^{7c}$ = OCH₃ | 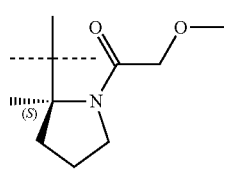 | $C_{48}H_{61}N_9O_9$ | 908.46 | 907.8 |

TABLE 25

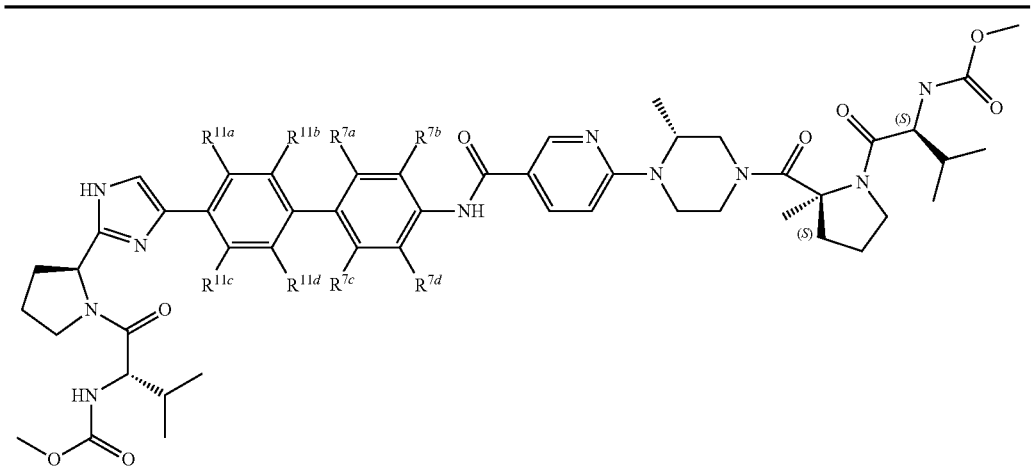

| Ex No. | $R^{11a}\ R^{11b}\ R^{11c}\ R^{11d}$ | $R^{7a}\ R^{7b}\ R^{7c}\ R^{7d}$ | Formula | Calc [M + H]$^+$ | Found [M + H]$^+$ |
|---|---|---|---|---|---|
| 25-1  |                        | $R^{7a} = CF_3$                  | $C_{51}H_{63}F_3N_{10}O_8$      | 1,001.48 | 1001.4 |
| 25-2  |                        | $R^{7a} = CN$                    | $C_{51}H_{63}N_{11}O_8$         | 958.49   | 958.4  |
| 25-3  | $R^{11b} = CH_3$       |                                  | $C_{51}H_{66}N_{10}O_8$         | 947.51   | 947.8  |
| 25-4  |                        | $R^{7a} = CH_3$                  | $C_{51}H_{66}N_{10}O_8$         | 947.51   | 947.4  |
| 25-5  |                        | $R^{7a} = O(CH_2)_2OCH_3$        | $C_{53}H_{70}N_{10}O_{10}$      | 1,007.53 | 1007.4 |
| 25-6  |                        | $R^{7a} = OiPr$                  | $C_{53}H_{70}N_{10}O_9$         | 991.53   | 991.6  |
| 25-7  | $R^{11b} = F$          |                                  | $C_{50}H_{63}FN_{10}O_8$        | 951.48   | 951.4  |
| 25-8  | $R^{11b} = CF_3$       |                                  | $C_{51}H_{63}F_3N_{10}O_8$      | 1,001.48 | 1001.4 |
| 25-9  |                        | $R^{7b} = F\ R^{7d} = F$         | $C_{50}H_{62}F_2N_{10}O_8$      | 969.47   | 969.4  |
| 25-10 | $R^{11b} = OCH_3$      |                                  | $C_{51}H_{66}N_{10}O_9$         | 963.5    | 963.4  |
| 25-11 | $R^{11b} = F$          | $R^{7a} = F$                     | $C_{50}H_{62}F_2N_{10}O_8$      | 969.47   | 969.6  |
| 25-12 |                        | $R^{7a} = CH_3\ R^{7c} = CH_3$   | $C_{52}H_{68}N_{10}O_8$         | 961.52   | 961.6  |
| 25-13 |                        | $R^{7a} = Cl$                    | $C_{50}H_{63}ClN_{10}O_8$       | 967.45   | 967.4  |
| 25-14 |                        | $R^{7a} = F\ R^{7c} = F$         | $C_{50}H_{62}F_2N_{10}O_8$      | 969.47   | 969.4  |
| 25-15 | $R^{11b} = OCF_3$      |                                  | $C_{51}H_{63}F_3N_{10}O_9$      | 1,017.47 | 1017.4 |
| 25-16 | $R^{11a} = CH_3$       | $R^{7c} = F$                     | $C_{51}H_{65}FN_{10}O_8$        | 965.5    | 965.4  |
| 25-17 | $R^{11b} = CF_3$       | $R^{7a} = F$                     | $C_{51}H_{62}F_4N_{10}O_8$      | 1,019.47 | 1019.4 |
| 25-18 |                        | $R^{7b} = OCH_3$                 | $C_{51}H_{66}N_{10}O_9$         | 963.5    | 963.4  |
| 25-19 |                        | $R^{7b} = CF_3$                  | $C_{51}H_{63}F_3N_{10}O_8$      | 1,001.48 | 1001.4 |
| 25-20 | $R^{11a} = CH_3$       |                                  | $C_{51}H_{66}N_{10}O_8$         | 947.51   | 947.6  |
| 25-21 |                        | $R^{7b} = F$                     | $C_{50}H_{63}FN_{10}O_8$        | 951.48   | 951.4  |
| 25-22 |                        | $R^{7b} = Cl$                    | $C_{50}H_{63}ClN_{10}O_8$       | 967.45   | 967.6  |
| 25-23 | $R^{11b} = OCHF_2$     |                                  | $C_{51}H_{64}F_2N_{10}O_9$      | 999.48   | 999.6  |
| 25-24 |                        | $R^{7a} = CF_3\ R^{7b} = F$      | $C_{51}H_{62}F_4N_{10}O_8$      | 1,019.47 | 1019.4 |
| 25-25 |                        | $R^{7a} = OCF_3\ R^{7b} = F$     | $C_{51}H_{62}F_4N_{10}O_9$      | 1,035.46 | 1035.4 |
| 25-26 | $R^{11b} = CH_3$       | $R^{7a} = F$                     | $C_{51}H_{65}FN_{10}O_8$        | 965.5    | 965.4  |
| 25-27 | $R^{11a} = CF_3$       |                                  | $C_{51}H_{63}F_3N_{10}O_8$      | 1,001.48 | 1001.4 |
| 25-28 | $R^{11a} = F$          |                                  | $C_{50}H_{63}FN_{10}O_8$        | 951.48   | 951.4  |
| 25-29 | $R^{11a} = OCF_3$      |                                  | $C_{51}H_{63}F_3N_{10}O_9$      | 1,017.47 | 1017.4 |
| 25-30 |                        | $R^{7b} = CN$                    | $C_{51}H_{63}N_{11}O_8$         | 958.49   | 958.4  |
| 25-31 |                        | $R^{7a} = Cl\ R^{7d} = OCH_3$    | $C_{51}H_{65}ClN_{10}O_9$       | 997.46   | 997.6  |
| 25-32 | $R^{11b} = CH_3$       | $R^{7a} = F\ R^{7c} = F$         | $C_{51}H_{64}F_2N_{10}O_8$      | 983.49   | 983.4  |
| 25-33 |                        | $R^{7a} = F\ R^{7d} = F$         | $C_{50}H_{62}F_2N_{10}O_8$      | 969.47   | 969.6  |
| 25-34 |                        | $R^{7a} = Cl\ R^{7d} = F$        | $C_{50}H_{62}ClFN_{10}O_8$      | 985.44   | 985.4  |
| 25-35 |                        | $R^{7a} = CH_3\ R^{7d} = F$      | $C_{51}H_{65}FN_{10}O_8$        | 965.5    | 965.6  |
| 25-36 |                        | $R^{7a} = OCH_3\ R^{7d} = Cl$    | $C_{51}H_{65}ClN_{10}O_9$       | 997.46   | 998.2  |
| 25-37 |                        | $R^{7b} = OH$                    | $C_{50}H_{64}N_{10}O_9$         | 949.49   | 950.2  |
| 25-38 |                        | $R^{7a} = OCH_3\ R^{7c} = OCH_3$ | $C_{52}H_{68}N_{10}O_{10}$      | 993.51   | 994.2  |
| 25-39 |                        | $R^{7a} = F\ R^{7b} = F$         | $C_{50}H_{62}F_2N_{10}O_8$      | 969.47   | 969.4  |
| 25-40 |                        | $R^{7a} = F\ R^{7d} = Cl$        | $C_{50}H_{62}ClFN_{10}O_8$      | 985.44   | 985.4  |
| 25-41 |                        | $R^{7b} = CH_2CH_3$              | $C_{52}H_{68}N_{10}O_8$         | 961.52   | 961.6  |

TABLE 26

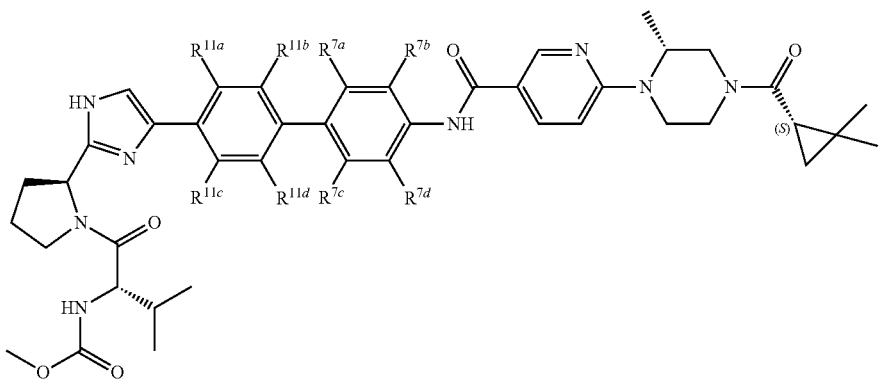

| Ex. No. | $R^{11a} R^{11b} R^{11c} R^{11d}$ | $R^{7a} R^{7b} R^{7c} R^{7d}$ | Formula | Calc [M + H]+ | Found [M + H]+ |
|---|---|---|---|---|---|
| 26-1 | $R^{11b}$ = CH$_3$ | | C$_{44}$H$_{54}$N$_8$O$_5$ | 775.42 | 775.4 |
| 26-2 | | $R^{7a}$ = O(CH$_2$)$_2$OCH$_3$ | C$_{46}$H$_{58}$N$_8$O$_7$ | 835.44 | 835.4 |
| 26-3 | | $R^{7a}$ = OiPr | C$_{46}$H$_{58}$N$_8$O$_6$ | 819.45 | 819.4 |
| 26-4 | $R^{11b}$ = F | | C$_{43}$H$_{51}$FN$_8$O$_5$ | 779.4 | 779.4 |
| 26-5 | | $R^{7b}$ = F $R^{7d}$ = F | C$_{43}$H$_{50}$F$_2$N$_8$O$_5$ | 797.39 | 797.4 |
| 26-6 | $R^{11b}$ = OCH$_3$ | | C$_{44}$H$_{54}$N$_8$O$_6$ | 791.42 | 791.4 |
| 26-7 | $R^{11b}$ = CF$_3$ | $R^{7a}$ = F | C$_{44}$H$_{50}$F$_4$N$_8$O$_5$ | 847.38 | 847.4 |
| 26-8 | $R^{11b}$ = CF$_3$ | | C$_{44}$H$_{51}$F$_3$N$_8$O$_5$ | 829.39 | 829.6 |
| 26-9 | $R^{11a}$ = CH$_3$ | $R^{7c}$ = F | C$_{44}$H$_{53}$FN$_8$O$_5$ | 793.41 | 793.4 |
| 26-10 | $R^{11b}$ = OCF$_3$ | | C$_{44}$H$_{51}$F$_3$N$_8$O$_6$ | 845.39 | 845.0 |
| 26-11 | | $R^{7b}$ = OCH$_3$ | C$_{44}$H$_{54}$N$_8$O$_6$ | 791.42 | 791.4 |
| 26-12 | | $R^{7b}$ = CF$_3$ | C$_{44}$H$_{51}$F$_3$N$_8$O$_5$ | 829.39 | 829.4 |
| 26-13 | $R^{11a}$ = CH$_3$ | | C$_{44}$H$_{54}$N$_8$O$_5$ | 775.42 | 775.4 |
| 26-14 | | $R^{7b}$ = F | C$_{43}$H$_{51}$FN$_8$O$_5$ | 779.4 | 779.4 |
| 26-15 | | $R^{7b}$ = Cl | C$_{43}$H$_{51}$ClN$_8$O$_5$ | 795.37 | 795.4 |
| 26-16 | | $R^{7b}$ = OCHF$_2$ | C$_{44}$H$_{52}$F$_2$N$_8$O$_6$ | 827.4 | 827.4 |
| 26-17 | $R^{11a}$ = CF$_3$ | | C$_{44}$H$_{51}$F$_3$N$_8$O$_5$ | 829.39 | 829.4 |
| 26-18 | $R^{11a}$ = OCF$_3$ | | C$_{44}$H$_{51}$F$_3$N$_8$O$_6$ | 845.39 | 845.4 |
| 26-19 | $R^{11a}$ = F | | C$_{43}$H$_{51}$FN$_8$O$_5$ | 779.4 | 779.4 |
| 26-20 | | $R^{7a}$ = CF$_3$ $R^{7b}$ = F | C$_{44}$H$_{50}$F$_4$N$_8$O$_5$ | 847.38 | 847.4 |
| 26-21 | | $R^{7a}$ = OCF$_3$ $R^{7b}$ = F | C$_{44}$H$_{50}$F$_4$N$_8$O$_6$ | 863.38 | 863.4 |
| 26-22 | | $R^{7b}$ = CN | C$_{44}$H$_{51}$N$_9$O$_5$ | 786.4 | 786.4 |
| 26-23 | | $R^{7a}$ = Cl $R^{7d}$ = OCH$_3$ | C$_{44}$H$_{53}$ClN$_8$O$_6$ | 825.38 | 825.4 |
| 26-24 | $R^{11b}$ = CH$_3$ | $R^{7a}$ = F | C$_{44}$H$_{53}$FN$_8$O$_5$ | 793.41 | 793.0 |
| 26-25 | $R^{11b}$ = CH$_3$ | $R^{7a}$ = F $R^{7c}$ = F | C$_{44}$H$_{52}$F$_2$N$_8$O$_5$ | 811.4 | 811.4 |
| 26-26 | | $R^{7a}$ = F $R^{7d}$ = F | C$_{43}$H$_{50}$F$_2$N$_8$O$_5$ | 797.39 | 797.4 |
| 26-27 | | $R^{7a}$ = Cl $R^{7d}$ = F | C$_{43}$H$_{50}$ClFN$_8$O$_5$ | 813.36 | 813.4 |
| 26-28 | | $R^{7a}$ = F $R^{7b}$ = F | C$_{43}$H$_{50}$F$_2$N$_8$O$_5$ | 797.39 | 797.4 |
| 26-29 | | $R^{7a}$ = F $R^{7d}$ = Cl | C$_{43}$H$_{50}$ClFN$_8$O$_5$ | 813.36 | 813.4 |
| 26-30 | | $R^{7a}$ = CH$_3$ $R^{7d}$ = F | C$_{44}$H$_{53}$FN$_8$O$_5$ | 793.41 | 793.8 |
| 26-31 | | $R^{7a}$ = OCH$_3$ $R^{7d}$ = Cl | C$_{44}$H$_{53}$ClN$_8$O$_6$ | 825.38 | 826.0 |
| 26-32 | | $R^{7b}$ = OH | C$_{43}$H$_{52}$N$_8$O$_6$ | 777.4 | 778.0 |
| 26-33 | | $R^{7a}$ = OCH$_3$ $R^{7c}$ = OCH$_3$ | C$_{45}$H$_{56}$N$_8$O$_7$ | 821.43 | 822.0 |
| 26-34 | | $R^{7b}$ = CH$_2$CH$_3$ | C$_{45}$H$_{56}$N$_8$O$_5$ | 789.44 | 789.8 |

TABLE 27

| Ex No. | R^7d | R^5 | Formula | Calc [M + H]^+ | Found [M + H]^+ |
|---|---|---|---|---|---|
| 27-1 | | (S)-pyrrolidine-(S)-Val-NHC(O)OMe | $C_{51}H_{63}F_3N_{10}O_9$ | 1,017.47 | 1017.4 |
| 27-2 | | NH(CH$_2$)$_2$OCH$_3$ | $C_{42}H_{50}F_3N_9O_7$ | 850.38 | 850.4 |
| 27-3 | | NH-t-Bu (gem-dimethyl) | $C_{43}H_{52}F_3N_9O_6$ | 848.40 | 848.4 |
| 27-4 | | NH-iPr | $C_{42}H_{50}F_3N_9O_6$ | 834.38 | 834.4 |
| 27-5 | | t-Bu | $C_{43}H_{51}F_3N_8O_6$ | 833.39 | 833.4 |
| 27-6 | | NH-cyclopropyl | $C_{42}H_{48}F_3N_9O_6$ | 832.37 | 832.4 |
| 27-7 | | CH$_2$-pyrazole | $C_{43}H_{47}F_3N_{10}O_6$ | 857.36 | 857.4 |
| 27-8 | F | (S)-pyrrolidine-Boc | $C_{49}H_{59}F_4N_9O_8$ | 978.44 | 977.6 |
| 27-9 | F | (S)-pyrrolidine-NH | $C_{44}H_{51}F_4N_9O_6$ | 878.39 | 877.8 |
| 27-10 | | (R),(S)-bicyclic pyrrolidine NH | $C_{44}H_{50}F_3N_9O_6$ | 858.38 | 857.6 |

TABLE 27-continued

| Ex No. | R⁷ᵈ | R⁵ | Formula | Calc [M + H]⁺ | Found [M + H]⁺ |
|---|---|---|---|---|---|
| 27-11 | | | $C_{43}H_{47}F_3N_{10}O_6$ | 857.36 | 856.6 |
| 27-12 | | | $C_{45}H_{52}F_3N_9O_8$ | 904.39 | 903.6 |
| 27-13 | | O(CH₂)₂OCH₃ | $C_{42}H_{49}F_3N_8O_8$ | 851.36 | 850.6 |
| 27-14 | | | $C_{43}H_{49}F_3N_8O_6$ | 831.37 | 830.6 |
| 27-15 | | | $C_{48}H_{59}F_3N_{10}O_8$ | 961.45 | 961.6 |
| 27-16 | | | $C_{47}H_{56}F_3N_9O_8$ | 932.42 | 932.6 |
| 27-17 | | | $C_{48}H_{59}F_3N_{10}O_7$ | 945.45 | 945.6 |
| 27-18 | | | $C_{48}H_{59}F_3N_{10}O_7$ | 945.45 | 945.6 |

TABLE 27-continued

| Ex No. | R$^{7d}$ | R$^5$ | Formula | Calc [M + H]$^+$ | Found [M + H]$^+$ |
|---|---|---|---|---|---|
| 27-19 | | | C$_{46}$H$_{55}$F$_3$N$_{10}$O$_7$ | 917.42 | 917.6 |
| 27-20 | | | C$_{48}$H$_{58}$F$_3$N$_9$O$_9$ | 962.43 | 962.6 |
| 27-21 | | | C$_{48}$H$_{58}$F$_3$N$_9$O$_8$ | 946.44 | 946.6 |
| 27-22 | | | C$_{49}$H$_{61}$F$_3$N$_{10}$O$_7$ | 959.47 | 959.6 |
| 27-23 | | | C$_{48}$H$_{57}$F$_3$N$_{10}$O$_7$ | 943.44 | 943.6 |
| 27-24 | | | C$_{44}$H$_{50}$F$_3$N$_9$O$_6$ | 858.38 | 858.6 |
| 27-25 | | | C$_{46}$H$_{56}$F$_3$N$_9$O$_8$ | 920.42 | 920.6 |

TABLE 27-continued

| Ex No. | R7d | R5 | Formula | Calc [M + H]+ | Found [M + H]+ |
|---|---|---|---|---|---|
| 27-26 | | | C45H54F3N9O6 | 874.42 | 874.6 |
| 27-27 | | | C46H56F3N9O8 | 920.42 | 920.6 |
| 27-28 | OCH3 | | C52H65F3N10O10 | 1,047.48 | 1046.6 |
| 27-29 | OCH3 | | C43H47F3N10O7 | 873.36 | 872.6 |
| 27-30 | OCH3 | | C45H53F3N8O7 | 875.4 | 874.6 |
| 27-31 | OCH3 | | C48H58F3N9O9 | 962.43 | 961.6 |
| 27-32 | OCH3 | NHCH3 | C41H48F3N9O7 | 836.36 | 835.8 |
| 27-33 | F | | C42H44F4N10O6 | 861.34 | 862.0 |

TABLE 27-continued

| Ex No. | R$^{7d}$ | R$^5$ | Formula | Calc [M + H]$^+$ | Found [M + H]$^+$ |
|---|---|---|---|---|---|
| 27-34 | F | (1H-pyrazol-3-yl, gem-dimethyl) | C$_{42}$H$_{44}$F$_4$N$_{10}$O$_6$ | 861.34 | 862.0 |
| 27-35 | F | (pyrimidin-2-yl, gem-dimethyl) | C$_{43}$H$_{44}$F$_4$N$_{10}$O$_6$ | 873.34 | 874.0 |
| 27-36 | F | (1H-pyrazol-1-ylmethyl, gem-dimethyl) | C$_{43}$H$_{46}$F$_4$N$_{10}$O$_6$ | 875.35 | 876.0 |
| 27-37 | F | (acetamidomethyl, gem-dimethyl) | C$_{42}$H$_{47}$F$_4$N$_9$O$_7$ | 866.35 | 867.0 |
| 27-38 | F | (2-methoxyethylamino, gem-dimethyl) | C$_{42}$H$_{49}$F$_4$N$_9$O$_7$ | 868.37 | 869.0 |
| 27-39 | F | (isopropylamino, gem-dimethyl) | C$_{42}$H$_{49}$F$_4$N$_9$O$_6$ | 852.37 | 853.0 |
| 27-40 | F | (cyclopropylamino, gem-dimethyl) | C$_{42}$H$_{47}$F$_4$N$_9$O$_6$ | 850.36 | 851.0 |
| 27-41 | F | O(CH$_2$)$_2$OCH$_3$ | C$_{42}$H$_{48}$F$_4$N$_8$O$_8$ | 869.35 | 870.0 |
| 27-42 | F | ((S)-methyl pyrrolidine carboxylate, gem-dimethyl) | C$_{46}$H$_{53}$F$_4$N$_9$O$_8$ | 936.40 | 937.0 |

TABLE 27-continued
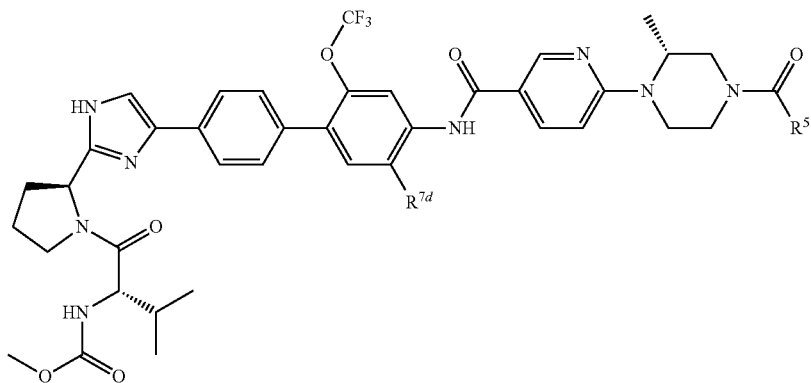
| Ex No. | R[7d] | R[5] | Formula | Calc [M + H]+ | Found [M + H]+ |
|---|---|---|---|---|---|
| 27-43 | F | 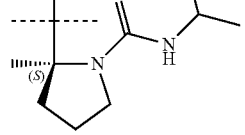 | $C_{48}H_{58}F_4N_{10}O_7$ | 963.44 | 964.2 |
| 27-44 | F | 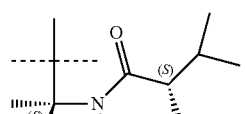 | $C_{49}H_{60}F_4N_{10}O_7$ | 977.46 | 978.2 |
| 27-45 | F | 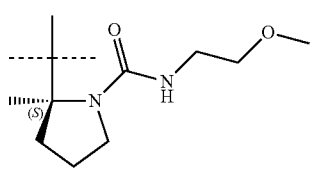 | $C_{48}H_{58}F_4N_{10}O_8$ | 979.44 | 980.0 |
| 27-46 | F | 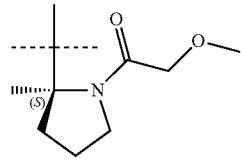 | $C_{47}H_{55}F_4N_9O_8$ | 950.41 | 951.0 |
| 27-47 | F | 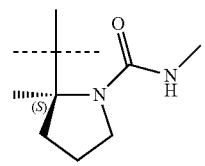 | $C_{46}H_{54}F_4N_{10}O_7$ | 935.41 | 937.0 |
| 27-48 | F | 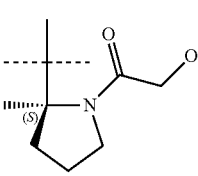 | $C_{46}H_{53}F_4N_9O_8$ | 936.4 | 936.0 |

TABLE 27-continued

| Ex No. | R^7d | R^5 | Formula | Calc [M + H]+ | Found [M + H]+ |
|---|---|---|---|---|---|
| 27-49 | F | | $C_{47}H_{55}F_4N_9O_8$ | 950.41 | 951.0 |
| 27-50 | F | | $C_{48}H_{58}F_4N_{10}O_7$ | 963.44 | 964.0 |
| 27-51 | | | $C_{47}H_{57}F_3N_{10}O_7$ | 931.44 | 932.0 |
| 27-52 | | | $C_{48}H_{57}F_3N_{10}O_9$ | 975.43 | 976.0 |
| 27-53 | | | $C_{42}H_{48}F_3N_9O_8$ | 864.36 | 865.0 |
| 27-54 | | | $C_{44}H_{51}F_3N_8O_7$ | 861.38 | 862.0 |
| 27-55 | | | $C_{43}H_{50}F_3N_9O_8$ | 878.37 | 879.0 |

TABLE 27-continued
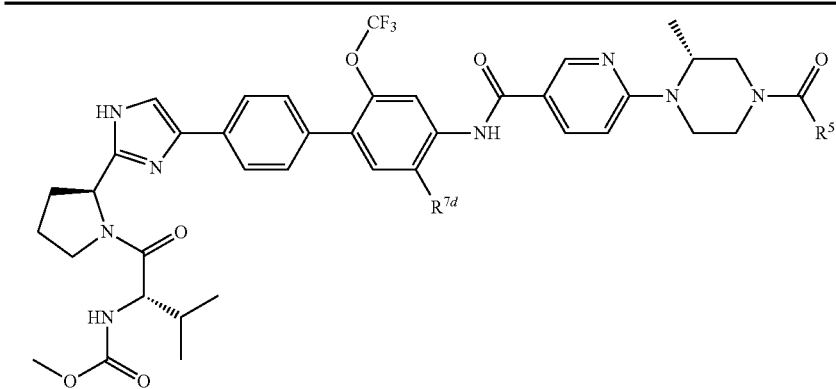
| Ex No. | R[7d] | R[5] | Formula | Calc [M + H]+ | Found [M + H]+ |
|---|---|---|---|---|---|
| 27-56 | | | $C_{45}H_{54}F_3N_9O_9$ | 922.4 | 923.0 |
| 27-57 | | | $C_{43}H_{50}F_3N_9O_8$ | 878.37 | 879.0 |
| 27-58 | | | $C_{51}H_{63}F_3N_{10}O_9$ | 1,017.47 | 1018.2 |
| 27-59 | | | $C_{47}H_{56}F_3N_9O_8$ | 932.42 | 933.0 |
| 27-60 | | | $C_{47}H_{56}F_3N_9O_8$ | 932.42 | 933.0 |
| 27-61 | | $CH_2N(CH_3)_2$ | $C_{42}H_{50}F_3N_9O_6$ | 834.38 | 834.8 |
| 27-62 | | | $C_{44}H_{50}F_3N_9O_6$ | 858.38 | 858.8 |
| 27-63 | | $CH_2Oi\text{-}Pr$ | $C_{43}H_{51}F_3N_8O_7$ | 849.38 | 849.8 |
| 27-64 | | $CH(CH_3)OCH_3$ | $C_{42}H_{49}F_3N_8O_7$ | 835.37 | 835.8 |

TABLE 27-continued

| Ex No. | R$^{7d}$ | R$^5$ | Formula | Calc [M + H]$^+$ | Found [M + H]$^+$ |
|---|---|---|---|---|---|
| 27-65 | | NH(CH$_2$)$_3$OCH$_3$ | C$_{43}$H$_{52}$F$_3$N$_9$O$_7$ | 864.39 | 864.8 |
| 27-66 | Cl | (4-imidazolyl with gem-dimethyl) | C$_{42}$H$_{44}$ClF$_3$N$_{10}$O$_6$ | 877.31 | 877.6 |
| 27-67 | Cl | NH(CH$_2$)$_3$OCH$_3$ | C$_{42}$H$_{49}$ClF$_3$N$_9$O$_7$ | 884.34 | 884.6 |
| 27-68 | Cl | NHCH$_3$ | C$_{40}$H$_{45}$ClF$_3$N$_9$O$_6$ | 840.31 | 840.6 |
| 27-69 | Cl | (S)-dimethylcyclopropyl | C$_{44}$H$_{50}$ClF$_3$N$_8$O$_6$ | 879.35 | 879.6 |
| 27-70 | Cl | (R,S)-bicyclic pyrrolidine | C$_{44}$H$_{49}$ClF$_3$N$_9$O$_6$ | 892.35 | 892.6 |
| 27-71 | Cl | (S)-pyrrolidine-imidazole carbonyl | C$_{48}$H$_{53}$ClF$_3$N$_{11}$O$_7$ | 988.38 | 989.6 |
| 27-72 | Cl | (S)-pyrrolidine-N,N-dimethylglycyl | C$_{48}$H$_{58}$ClF$_3$N$_{10}$O$_7$ | 979.41 | 979.6 |
| 27-73 | Cl | (S)-pyrrolidine-N-methylurea | C$_{46}$H$_{54}$ClF$_3$N$_{10}$O$_7$ | 951.38 | 951.6 |

TABLE 27-continued

| Ex No. | R<sup>7d</sup> | R<sup>5</sup> | Formula | Calc [M + H]<sup>+</sup> | Found [M + H]<sup>+</sup> |
|---|---|---|---|---|---|
| 27-74 | Cl | | $C_{48}H_{58}ClF_3N_{10}O_8$ | 995.41 | 995.6 |
| 27-75 | Cl | | $C_{49}H_{60}ClF_3N_{10}O_7$ | 993.43 | 993.5 |
| 27-76 | Cl | | $C_{46}H_{53}ClF_3N_9O_8$ | 952.37 | 952.9 |

TABLE 28

| Ex No. | R<sup>7d</sup> | R<sup>5</sup> | Formula | Calc [M + H]<sup>+</sup> | Found [M + H]<sup>+</sup> |
|---|---|---|---|---|---|
| 28-1 | | | $C_{43}H_{47}F_5N_8O_6$ | 867.35 | 867.4 |

TABLE 28-continued
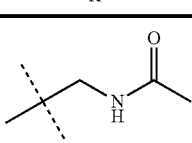
| Ex No. | R[7d] | R[5] | Formula | Calc [M + H]+ | Found [M + H]+ |
|---|---|---|---|---|---|
| 28-2 | | 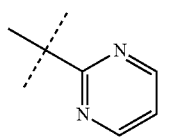 | C43H50F3N9O7 | 862.38 | 862.4 |
| 28-3 | | 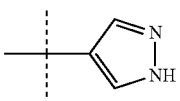 | C44H47F3N10O6 | 869.36 | 869.4 |
| 28-4 | | 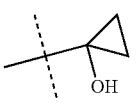 | C43H47F3N10O6 | 857.36 | 857.4 |
| 28-5 | | C(CH3)2OH | C43H51F3N8O7 | 849.38 | 849.4 |
| 28-6 | | 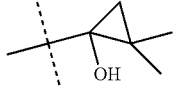 | C43H49F3N8O7 | 847.37 | 847.4 |
| 28-7 | | 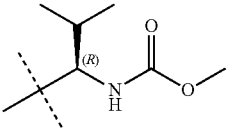 | C45H53F3N8O7 | 875.4 | 875.4 |
| 28-8 | | 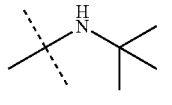 | C46H56F3N9O8 | 920.42 | 920.4 |
| 28-9 | | 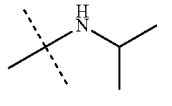 | C44H54F3N9O6 | 862.42 | 862.4 |
| 28-10 | | 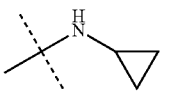 | C43H52F3N9O6 | 848.4 | 848.4 |
| 28-11 | | NH(CH2)2OCH3 | C43H52F3N9O7 | 864.39 | 864.4 |
| 28-12 | |  | C43H50F3N9O6 | 846.38 | 846.4 |

TABLE 28-continued

| Ex No. | R^{7d} | R^5 | Formula | Calc [M + H]^+ | Found [M + H]^+ |
|---|---|---|---|---|---|
| 28-13 | | | $C_{44}H_{49}F_3N_{10}O_6$ | 871.38 | 871.4 |
| 28-14 | | | $C_{44}H_{51}F_3N_8O_6$ | 845.39 | 845.4 |
| 28-15 | | | $C_{44}H_{49}F_3N_{10}O_6$ | 871.38 | 871.4 |
| 28-16 | | | $C_{48}H_{58}F_3N_9O_8$ | 946.44 | 946.4 |
| 28-17 | | | $C_{49}H_{61}F_3N_{10}O_7$ | 959.47 | 959.4 |
| 28-18 | | | $C_{49}H_{61}F_3N_{10}O_7$ | 959.47 | 959.4 |
| 28-19 | | | $C_{49}H_{61}F_3N_{10}O_8$ | 975.46 | 975.4 |

TABLE 28-continued

| Ex No. | R^7d | R^5 | Formula | Calc [M + H]+ | Found [M + H]+ |
|---|---|---|---|---|---|
| 28-20 | | | $C_{49}H_{59}F_3N_{10}O_7$ | 957.45 | 957.4 |
| 28-21 | | O(CH$_2$)$_2$OCH$_3$ | $C_{43}H_{51}F_3N_8O_8$ | 865.38 | 865.4 |
| 28-22 | | | $C_{45}H_{52}F_3N_9O_6$ | 872.40 | 872.4 |
| 28-23 | | tBu | $C_{44}H_{53}F_3N_8O_6$ | 847.40 | 848.4 |
| 28-24 | | | $C_{46}H_{54}F_3N_9O_8$ | 918.41 | 918.6 |
| 28-25 | | | $C_{50}H_{63}F_3N_{10}O_7$ | 973.48 | 973.6 |
| 28-26 | | | $C_{47}H_{57}F_3N_{10}O_7$ | 931.44 | 931.6 |
| 28-27 | | | $C_{46}H_{56}F_3N_9O_6$ | 888.43 | 888.6 |

TABLE 28-continued
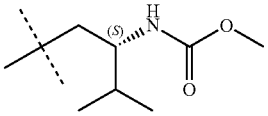
| Ex No. | R7d | R5 | Formula | Calc [M + H]+ | Found [M + H]+ |
|---|---|---|---|---|---|
| 28-28 | | 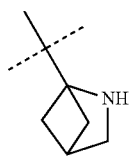 | C47H58F3N9O8 | 934.44 | 934.6 |
| 28-29 | | 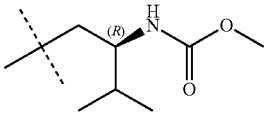 | C45H52F3N9O6 | 872.40 | 872.6 |
| 28-30 | | 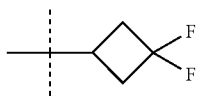 | C47H58F3N9O8 | 934.44 | 934.6 |
| 28-31 | | 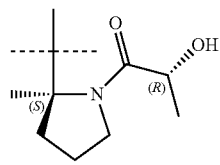 | C44H49F5N8O6 | 881.37 | 882.0 |
| 28-32 | | 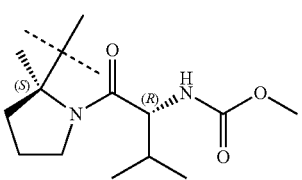 | C48H58F3N9O8 | 946.44 | 947.0 |
| 28-33 | | 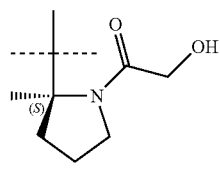 | C52H65F3N10O9 | 1,031.49 | 1032.2 |
| 28-34 | |  | C47H56F3N9O8 | 932.42 | 933.0 |
| 28-35 | | CH2N(CH3)2 | C43H52F3N9O6 | 848.4 | 848.8 |
| 28-36 | Cl | NHCH3 | C41H47ClF3N9O6 | 854.33 | 854.6 |
| 28-37 | Cl | NH(CH2)2OCH3 | C43H51ClF3N9O7 | 898.36 | 898.6 |

TABLE 28-continued
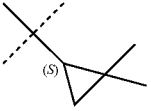
| Ex No. | R^{7d} | R^5 | Formula | Calc [M + H]^+ | Found [M + H]^+ |
|---|---|---|---|---|---|
| 28-38 | Cl | 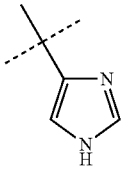 | $C_{45}H_{52}ClF_3N_8O_6$ | 893.37 | 893.6 |
| 28-39 | Cl | 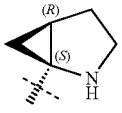 | $C_{43}H_{46}ClF_3N_{10}O_6$ | 891.32 | 891.6 |
| 28-40 | Cl | 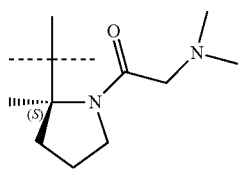 | $C_{45}H_{51}ClF_3N_9O_6$ | 906.36 | 906.6 |
| 28-41 | Cl | 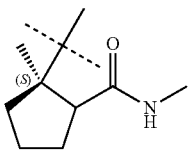 | $C_{49}H_{60}ClF_3N_{10}O_7$ | 993.43 | 993.4 |
| 28-42 | Cl | 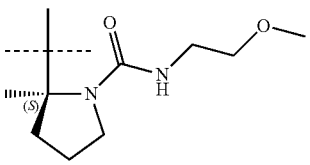 | $C_{47}H_{56}ClF_3N_{10}O_7$ | 965.4 | 965.4 |
| 28-43 | Cl |  | $C_{49}H_{60}ClF_3N_{10}O_8$ | 1,009.42 | 1009.5 |

TABLE 29
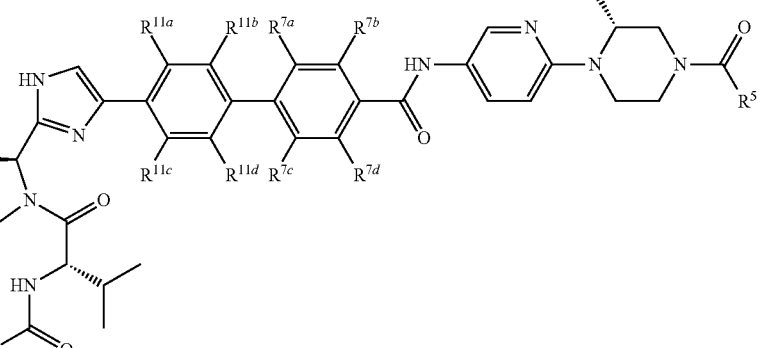
| Ex No. | R11a R11b R11c R11d | R7a R7b R7c R7d | R5 | Formula | Calc [M + H]+ | Found [M + H]+ |
|---|---|---|---|---|---|---|
| 29-1 | | R7a = CF3 | 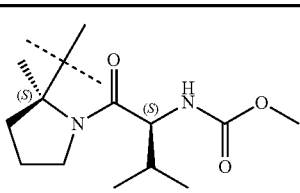 | C51H63F3N10O8 | 1,001.48 | 1001.4 |
| 29-2 | | R7a = CF3 | 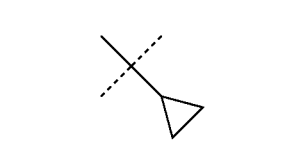 | C42H47F3N8O5 | 801.36 | 801.4 |
| 29-3 | | R7a = CF3 | NHCH3 | C40H46F3N9O5 | 790.36 | 790.2 |
| 29-4 | | R7a = CF3 | 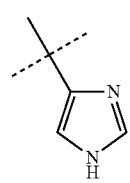 | C42H45F3N10O5 | 827.35 | 827.2 |
| 29-5 | | R7a = CF3 | 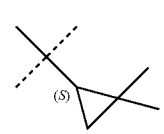 | C44H51F3N8O5 | 829.39 | 829.4 |
| 29-6 | | R7a = CH3 | 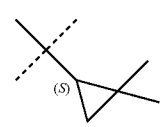 | C44H54N8O5 | 775.42 | 775.4 |
| 29-7 | | R7a = OCH2CHF2 | 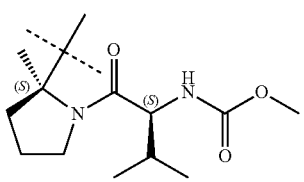 | C52H66F2N10O9 | 1,013.50 | 1013.6 |
| 29-8 | R11b = CH3 | | 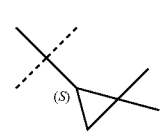 | C44H54N8O5 | 775.42 | 775.4 |

TABLE 29-continued
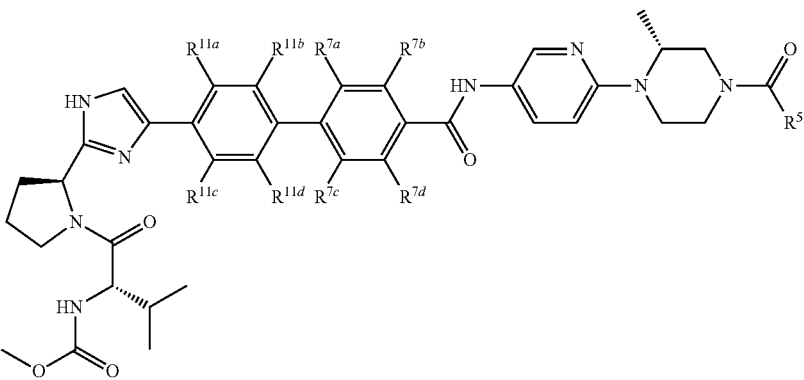
| Ex No. | $R^{11a}\,R^{11b}$ $R^{11c}\,R^{11d}$ | $R^{7a}\,R^{7b}$ $R^{7c}\,R^{7d}$ | $R^5$ | Formula | Calc $[M+H]^+$ | Found $[M+H]^+$ |
|---|---|---|---|---|---|---|
| 29-9 | | $R^{7a}$ = OCH$_2$cPr | 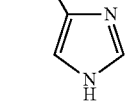 | $C_{45}H_{52}N_{10}O_6$ | 829.41 | 829.4 |
| 29-10 | | $R^{7a}$ = OCH$_2$cPr | 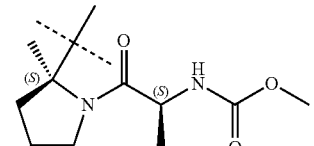 | $C_{54}H_{70}N_{10}O_9$ | 1,003.53 | 1004.0 |
| 29-11 | | $R^{7a}$ = OCH$_3$ | 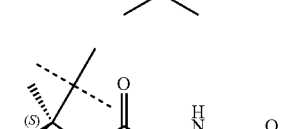 | $C_{51}H_{66}N_{10}O_9$ | 963.5 | 963.6 |
| 29-12 | | $R^{7a}$ = O(CH$_2$)$_2$OCH$_3$ | 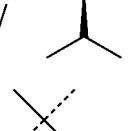 | $C_{46}H_{58}N_8O_7$ | 835.44 | 835.4 |
| 29-13 | | $R^{7a}$ = Oi-Pr | NHCH$_3$ | $C_{42}H_{53}N_9O_6$ | 780.41 | 780.4 |
| 29-14 | $R^{11d}$ = CH$_3$ | $R^{7a}$ = OCF$_3$ | 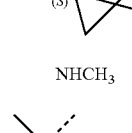 | $C_{45}H_{53}F_3N_8O_6$ | 859.4 | 859.4 |
| 29-15 | | $R^{7a}$ = OCH$_2$t-Bu | 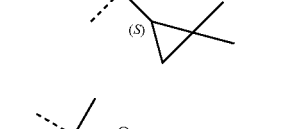 | $C_{55}H_{74}N_{10}O_9$ | 1,019.56 | 1019.6 |
| 29-16 | | $R^{7a}$ = OcPr | 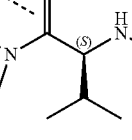 | $C_{46}H_{56}N_8O_6$ | 817.43 | 817.4 |

TABLE 29-continued

| Ex No. | R11a R11b R11c R11d | R7a R7b R7c R7d | R5 | Formula | Calc [M + H]+ | Found [M + H]+ |
|---|---|---|---|---|---|---|
| 29-17 | | R7a = OCF3 | tert-butyl (S)-pyrrolidine-1-carboxylate with methyl | C49H60F3N9O8 | 960.45 | 960.4 |
| 29-18 | | R7a = OCF3 | (S)-2-(dimethylamino)-1-(pyrrolidin-1-yl)ethanone with methyl | C48H59F3N10O7 | 945.45 | 945.4 |
| 29-19 | | R7a = OCF3 | 1-((S)-pyrrolidin-1-yl)ethanone with methyl | C46H54F3N9O7 | 902.41 | 902.4 |
| 29-2- | | R7a = OCF3 | methyl (S)-pyrrolidine-1-carboxylate with methyl | C46H54F3N9O8 | 918.41 | 918.4 |
| 29-21 | | R7a = OCF3 | cyclopropyl((S)-pyrrolidin-1-yl)methanone with methyl | C48H56F3N9O7 | 928.43 | 928.4 |
| 29-22 | R11b = CF3 | | (S)-pyrrolidine with (S)-methyl carbamate valine | C51H63F3N10O8 | 1,001.48 | 1001.4 |
| 29-23 | R11b = OCH3 | | (S)-dimethylcyclopropyl | C44H54N8O6 | 791.42 | 791.4 |

TABLE 29-continued

| Ex No. | $R^{11a} R^{11b}$ $R^{11c} R^{11d}$ | $R^{7a} R^{7b}$ $R^{7c} R^{7d}$ | $R^5$ | Formula | Calc $[M+H]^+$ | Found $[M+H]^+$ |
|---|---|---|---|---|---|---|
| 29-24 | $R^{11b} = F$ | | | $C_{43}H_{51}FN_8O_5$ | 779.4 | 779.4 |
| 29-25 | | $R^{7a} = OCH_3$ $R^{7c} = OCH_3$ | | $C_{52}H_{68}N_{10}O_{10}$ | 993.51 | 993.4 |
| 29-26 | $R^{11b} = OCF_3$ | | | $C_{44}H_{51}F_3N_8O_6$ | 845.39 | 845.4 |
| 29-27 | $R^{11a} = CH_3$ | | | $C_{51}H_{66}N_{10}O_8$ | 947.51 | 947.6 |
| 29-28 | | $R^{7a} = OCHF_2$ | | $C_{51}H_{64}F_2N_{10}O_9$ | 999.48 | 999.4 |
| 29-29 | | $R^{7a} = OCF_3$ | | $C_{48}H_{57}F_3N_{10}O_7$ | 943.44 | 943.4 |
| 29-30 | | $R^{7a} = OCF_3$ | | $C_{47}H_{56}F_3N_9O_8$ | 932.42 | 932.4 |

TABLE 29-continued

| Ex No. | $R^{11a}$ $R^{11b}$ $R^{11c}$ $R^{11d}$ | $R^{7a}$ $R^{7b}$ $R^{7c}$ $R^{7d}$ | $R^5$ | Formula | Calc [M + H]$^+$ | Found [M + H]$^+$ |
|---|---|---|---|---|---|---|
| 29-31 | | $R^{7a}$ = OCF$_3$ | | $C_{51}H_{63}F_3N_{10}O_9$ | 1,017.47 | 1017.4 |
| 29-32 | $R^{11a}$ = OCF$_3$ | | | $C_{51}H_{63}F_3N_{10}O_9$ | 1,017.47 | 1017.4 |
| 29-33 | $R^{11a}$ = CF$_3$ | | | $C_{51}H_{63}F_3N_{10}O_8$ | 1,001.48 | 1001.4 |
| 29-34 | $R^{11d}$ = CH$_3$ | $R^{7a}$ = CH$_3$ | | $C_{45}H_{56}N_8O_5$ | 789.44 | 789.4 |
| 29-35 | $R^{11a}$ = OCH$_3$ | | | $C_{44}H_{54}N_8O_6$ | 791.42 | 792.0 |
| 29-36 | | $R^{7b}$ = F | | $C_{50}H_{63}FN_{10}O_8$ | 951.48 | 952.2 |
| 29-37 | $R^{11a}$ = Cl | | | $C_{45}H_{55}ClN_{10}O_6$ | 867.4 | 867.0 |

TABLE 30

| Ex No. | $R^{11a}$ $R^{11b}$ $R^{11c}$ $R^{11d}$ | $R^{7a}$ $R^{7b}$ $R^{7c}$ $R^{7d}$ | $R^5$ | Formula | Calc [M + H]+ | Found [M + H]+ |
|---|---|---|---|---|---|---|
| 30-1 | | | CH((R)OH)CH$_2$OH | C$_{41}$H$_{50}$N$_8$O$_7$ | 767.38 | 767.6 |
| 30-2 | $R^{11b}$ = CH$_3$ | | (S)-1,1-dimethylcyclopropyl | C$_{45}$H$_{56}$N$_8$O$_5$ | 789.44 | 789.4 |
| 30-3 | | $R^{7a}$ = OCH$_2$CHF$_2$ | 1H-imidazol-4-yl substituent | C$_{44}$H$_{50}$F$_2$N$_{10}$O$_6$ | 853.39 | 853.4 |
| 30-4 | | $R^{7a}$ = OCH$_2$CHF$_2$ | (S)-1,1-dimethylcyclopropyl | C$_{46}$H$_{56}$F$_2$N$_8$O$_6$ | 855.43 | 855.4 |
| 30-5 | $R^{11b}$ = CH$_3$ | | (S)-prolinyl-(S)-Val-OMe carbamate | C$_{52}$H$_{68}$N$_{10}$O$_8$ | 961.52 | 961.6 |
| 30-6 | | $R^{7a}$ = OCH$_3$ | (S)-1,1-dimethylcyclopropyl | C$_{45}$H$_{56}$N$_8$O$_6$ | 805.43 | 805.4 |
| 30-7 | | $R^{7a}$ = CF$_3$ | (S)-1,1-dimethylcyclopropyl | C$_{45}$H$_{53}$F$_3$N$_8$O$_5$ | 843.41 | 843.4 |

TABLE 30-continued

| Ex No. | $R^{11a} R^{11b}$ $R^{11c} R^{11d}$ | $R^{7a} R^{7b}$ $R^{7c} R^{7d}$ | $R^5$ | Formula | Calc [M + H]$^+$ | Found [M + H]$^+$ |
|---|---|---|---|---|---|---|
| 30-8 | | $R^{7a} = OCH_2CH_3$ | | $C_{53}H_{70}N_{10}O_9$ | 991.53 | 991.4 |
| 30-9 | | $R^{7a} = OCF_3$ | | $C_{45}H_{53}F_3N_8O_6$ | 859.4 | 859.4 |

TABLE 31

| Ex No. | $R^{9a}$ | $R^{9b}$ | Formula | Calc [M + H]$^+$ | Found [M + H]$^+$ |
|---|---|---|---|---|---|
| 31-1 | | (R)CH$_3$ | $C_{44}H_{51}F_3N_8O_6$ | 845.39 | 845.4 |
| 31-2 | | (S)CH$_3$ | $C_{44}H_{51}F_3N_8O_6$ | 845.39 | 845.4 |
| 31-3 | (S)CH$_3$ | | $C_{44}H_{51}F_3N_8O_6$ | 845.39 | 845.4 |

TABLE 32

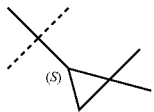

| Ex No. | $R^{9a}$ $R^{9b}$ $R^{9c}$ $R^{9d}$ | $R^5$ | Formula | Calc $[M + H]^+$ | Found $[M + H]^+$ |
|---|---|---|---|---|---|
| 32-1 | $R^{9b}$ = (S)CH$_2$OCH$_3$ | 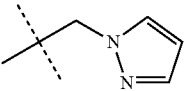 | $C_{45}H_{55}N_7O_6$ | 790.42 | 790.4 |
| 32-2 | $R^{9b}$ = (R)CH$_3$ | CH$_2$NHC(O)CH$_3$ | $C_{42}H_{50}N_8O_6$ | 763.39 | 763.4 |
| 32-3 | $R^{9b}$ = (R)CH$_3$ | 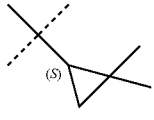 | $C_{43}H_{49}N_9O_5$ | 772.39 | 772.4 |
| 32-4 | $R^{9b}$ = (R)CH$_3$ | 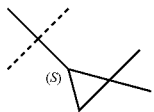 | $C_{44}H_{53}N_7O_5$ | 760.41 | 760.4 |
| 32-5 | $R^{9b}$ = (S)CH$_3$ | CH$_2$NHC(O)CH$_3$ | $C_{42}H_{47}N_9O_5$ | 758.37 | 758.4 |
| 32-6 | $R^{9b}$ = (S)CH$_3$ |  | $C_{44}H_{53}N_7O_5$ | 760.41 | 760.4 |
| 32-7 | $R^{9a}$ = (R)CH$_3$ | tBu | $C_{43}H_{53}N_7O_5$ | 748.41 | 748.4 |
| 32-8 | $R^{9a}$ = (R)CH$_3$ | NHCH$_3$ | $C_{40}H_{48}N_8O_5$ | 721.38 | 721.2 |
| 32-9 | $R^{9a}$ = (R)CH$_3$ | 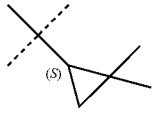 | $C_{44}H_{53}N_7O_5$ | 760.41 | 760.4 |
| 32-10 | $R^{9a}$ = (R)CH$_3$ | 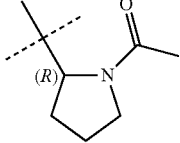 | $C_{45}H_{54}N_8O_6$ | 803.42 | 803.4 |
| 32-11 | $R^{9a}$ = (S)CH$_3$ | 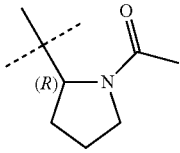 | $C_{45}H_{54}N_8O_6$ | 803.42 | 803.4 |
| 32-12 | $R^{9a}$ = (S)CH$_3$ | 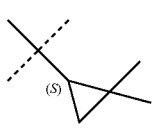 | $C_{44}H_{53}N_7O_5$ | 760.41 | 760.4 |

TABLE 32-continued

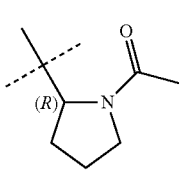

| Ex No. | $R^{9a}\ R^{9b}\ R^{9c}\ R^{9d}$ | $R^5$ | Formula | Calc [M + H]$^+$ | Found [M + H]$^+$ |
|---|---|---|---|---|---|
| 32-13 | $R^{9b}$ = (S)CH$_2$OCH$_3$ | 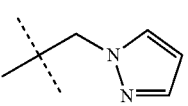 | C$_{46}$H$_{56}$N$_8$O$_7$ | 833.43 | 833.4 |
| 32-14 | $R^{9b}$ = (R)CH$_2$OCH$_3$ | 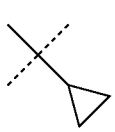 | C$_{44}$H$_{51}$N$_9$O$_6$ | 802.4 | 802.4 |
| 32-15 | $R^{9b}$ = (R)CH$_2$OCH$_3$ | CH$_2$NHC(O)CH$_3$ | C$_{43}$H$_{52}$N$_8$O$_7$ | 793.4 | 793.4 |
| 32-16 | $R^{9a}$ = (S)CH$_3$<br>$R^{9c}$ = (R)CH$_3$ | 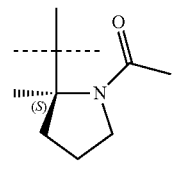 | C$_{43}$H$_{51}$N$_7$O$_5$ | 746.4 | 746.4 |
| 32-17 | $R^{9a}$ = (R)CH$_3$ | 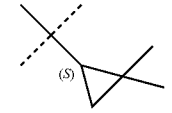 | C$_{46}$H$_{56}$N$_8$O$_6$ | 817.43 | 817.4 |
| 32-18 | $R^{9b}$ = (S)CH$_2$OH | 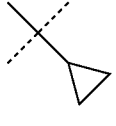 | C$_{44}$H$_{53}$N$_7$O$_6$ | 776.41 | 776.2 |
| 32-19 | $R^{9b}$ = (S)CH$_3$<br>$R^{9d}$ = (R)CH$_3$ | 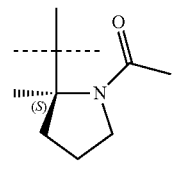 | C$_{43}$H$_{51}$N$_7$O$_5$ | 746.4 | 746.4 |
| 32-20 | $R^{9b}$ = (S)CH$_3$<br>$R^{9c}$ = (R)CH$_3$ | 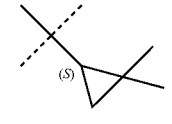 | C$_{45}$H$_{55}$N$_7$O$_5$ | 774.43 | 774.4 |
| 32-21 | $R^{9a}$ = (R)CH$_3$ | 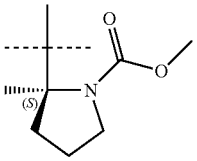 | C$_{46}$H$_{56}$N$_8$O$_7$ | 833.43 | 833.4 |

TABLE 32-continued
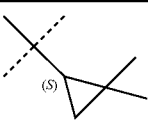
| Ex No. | $R^{9a}\ R^{9b}\ R^{9c}\ R^{9d}$ | $R^5$ | Formula | Calc [M + H]+ | Found [M + H]+ |
|---|---|---|---|---|---|
| 32-22 | $R^{9b}$ = (R)CH$_3$<br>$R^{9c}$ = (S)CH$_3$ | 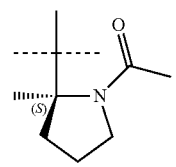 | $C_{45}H_{55}N_7O_5$ | 774.43 | 774.4 |
| 32-23 | $R^{9b}$ = (R)CH$_3$<br>$R^{9c}$ = (S)CH$_3$ | 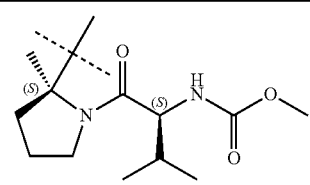 | $C_{47}H_{58}N_8O_6$ | 831.45 | 831.4 |
TABLE 33
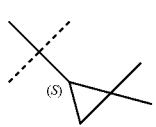
| Ex No. | $R^{7b}\ R^{7c}\ R^{7d}$ | $R^5$ | Formula | Calc [M + H]+ | Found [M + H]+ |
|---|---|---|---|---|---|
| 33-1 | $R^{7c}$ = CH$_3$ |  | $C_{50}H_{65}N_{11}O_8$ | 948.5 | 948.4 |
| 33-2 | $R^{7c}$ = CH$_3$ |  | $C_{43}H_{53}N_9O_5$ | 776.42 | 776.4 |

TABLE 33-continued

| Ex No. | R$^{7b}$ R$^{7c}$ R$^{7d}$ | R$^5$ | Formula | Calc [M + H]$^+$ | Found [M + H]$^+$ |
|---|---|---|---|---|---|
| 33-3 | R$^{7c}$ = CF$_3$ | | C$_{43}$H$_{50}$F$_3$N$_9$O$_5$ | 830.39 | 830.4 |
| 33-4 | R$^{7c}$ = CF$_3$ | | C$_{50}$H$_{62}$F$_3$N$_{11}$O$_8$ | 1,002.47 | 1002.4 |
| 33-5 | R$^{7c}$ = CF$_3$ | | C$_{41}$H$_{44}$F$_3$N$_{11}$O$_5$ | 828.35 | 828.4 |
| 33-6 | R$^{7b}$ = OCH$_3$ | | C$_{50}$H$_{65}$N$_{11}$O$_9$ | 964.5 | 964.6 |
| 33-7 | | | C$_{42}$H$_{51}$N$_9$O$_5$ | 762.40 | 762.9 |
| 33-8 | | | C$_{49}$H$_{63}$N$_{11}$O$_8$ | 934.49 | 934.1 |

TABLE 34

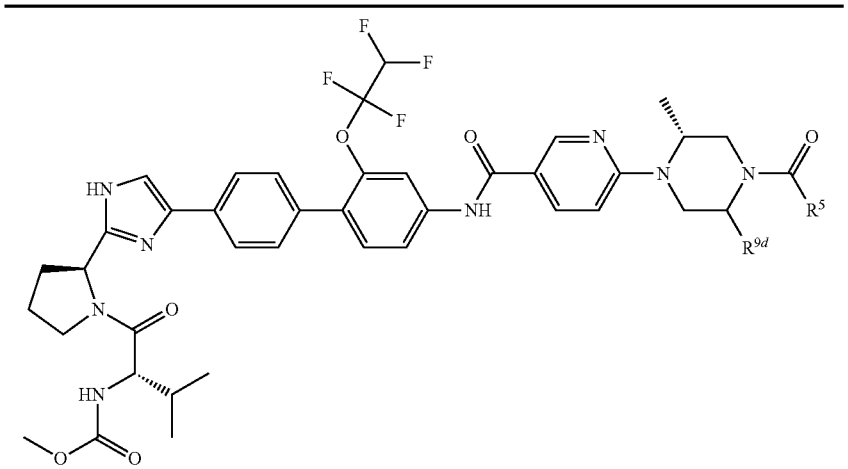

| Ex No. | $R^{9d}$ | $R^5$ | Formula | Calc [M + H]⁺ | Found [M + H]⁺ |
|---|---|---|---|---|---|
| 34-1 | (S)CH₃ | (4-imidazolyl-t-butyl) | C₄₄H₄₈F₄N₁₀O₆ | 889.37 | 889.6 |
| 34-2 | (S)CH₃ | (S)-cyclopropyl-t-butyl | C₄₆H₅₄F₄N₈O₆ | 891.41 | 891.6 |
| 34-3 | (S)CH₃ | NHCH₃ | C₄₂H₄₉F₄N₉O₆ | 852.37 | 852.6 |
| 34-4 | | (S)-cyclopropyl-t-butyl | C₄₅H₅₂F₄N₈O₆ | 877.39 | 877.6 |
| 34-5 | | (4-imidazolyl-t-butyl) | C₄₃H₄₆F₄N₁₀O₆ | 875.35 | 875.4 |
| 34-6 | | NHCH₃ | C₄₁H₄₇F₄N₉O₆ | 838.36 | 838.4 |

Biological Assays

The hepatitis C virus has been classified into six major different genotypes on the basis of nucleotide sequence, and further divided into subtypes within genotypes. Compounds of the invention demonstrated inhibition of HCV replication in one or more of the following HCV replicon assays.

Assay 1: HCV Genotype 1b Replicon Assay

The HCV genotype 1b replicon cell line was obtained from Apath LLC (Brooklyn, N.Y.) (APC144; Huh7 cell background). This subgenomic replicon contains the N-terminus of the HCV core protein fused to the neomycin-resistance selectable marker. The EMCV IRES lies downstream and drives expression of humanized Renilla luciferase fused to the non-structural proteins NS3-NS5B. This cell line was used to determine compound potency using the luciferase activity readout as a measurement of compound inhibition of replicon levels.

Cells were grown at 37° C. in a 5% CO₂ humidified incubator in DMEM (Invitrogen) with 10% FBS (HyClone), 1×NEAA (Invitrogen), 1× Pen-Strep (Invitrogen), and 500 μg/mL G418 (Invitrogen). On day 1 of the assay, cells were plated at 10,000 cells/well in white 96-well tissue culture plates (Costar) in 200 μL media lacking G418. Four hours later, once the cells have adhered, the media was removed and replaced with media (no G418) containing dose-responses of test compounds. Compounds were initially diluted in DMSO and then diluted another 200× in media to bring the final DMSO concentration down to 0.5%. The cells were incubated with test compounds for 48 hours. At the end of the incubation period, media and compound were removed from the plates and the luciferase activity was determined using Promega Renilla-Glo reagents.

To analyze the data, the luciferase activity was plotted vs. the compound concentration, and EC₅₀ values were determined from a 4-parameter robust fit model with the GraphPad Prism software package (GraphPad Software, Inc., San Diego, Calif.). Results are expressed as the negative decadic logarithm of the $EC_{50}$ value, $pEC_{50}$.

Test compounds having a higher $pEC_{50}$ value in this assay show greater inhibition of HCV genotype 1b replication. Compounds of the invention tested in this assay typically exhibited $pEC_{50}$ values between about 7 and about 12.

Assay 2: HCV Genotype 1a Replicon Assay

The HCV genotype 1a replicon cell line was obtained from Apath LLC (APC89; Huh7.5 cell background). This subgenomic replicon contains the N-terminus of the HCV core protein fused to the neomycin-resistance selectable marker. The EMCV IRES lies downstream and drives expression of the non-structural proteins NS3-NS5B. Compound potencies were determined using the NS3-specific protease activity in lysates as a measurement of compound inhibition of replicon levels.

Cells were grown at 37° C. in a 5% $CO_2$ humidified incubator in DMEM (Invitrogen) with 10% FBS (HyClone), 1×NEAA (Invitrogen), 1× Pen-Strep (Invitrogen), and 850 μg/mL G418 (Invitrogen). On day 1 of the assay, cells were plated at 15,000 cells/well in black 96-well tissue culture plates (Costar) in 200 μL media lacking G418. Four hours later, once the cells had adhered, the media was removed and replaced with media (no G418) containing dose-responses of test compounds. Compounds were initially diluted in DMSO and then diluted another 200× in media to bring the final DMSO concentration down to 0.5%. The cells were incubated with test compounds for 48 or 72 hours. At the end of the incubation period, media and compound were removed from the plates.

To determine the NS3-specific protease activity in lysates, the cells were lysed at room temperature in 50 μL/well of 50 mM Hepes pH 7.5, 150 mM NaCl, 15% Glycerol, 0.15% Triton X-100, 10 mM DTT for 20 minutes with shaking. 50 μL of an NS3/4a protease-specific FRET substrate (Anaspec RET S1 Cat#22991) was then added to the wells at a final concentration of 15 μM. The plates were incubated at 37° C. for 20 minutes, which corresponds to a timepoint at which the protease activity is still in the linear phase. Protease activity was determined by measuring fluorescence (Excitation: 340 nm; Emission: 509 nm).

To analyze the data, the fluorescence was plotted vs. the compound concentration, and EC50 values were determined from a 4-parameter robust fit model using GraphPad Prism software. Compounds of the invention tested in this assay typically exhibited $pEC_{50}$ values between about 7 and about 11.5.

Assay 3: Replicon Assays Against Resistant Mutants

To create replicon cells with resistant mutations of interest, the mutation was first introduced into the parental plasmid by site-directed mutagenesis. Mutations in genotype 1b included L31V, Y93H, and the L31V/Y93H double mutant. Mutations in genotype 1a included Q30R and L31V. The replicon plasmid was then linearized and in vitro transcribed to RNA. The RNA was used to stably transfect Huh7 cells by electroporation, and new cell lines were selected with 500 μg/mL G418. Potencies of test compounds against these mutant cell lines were determined as previously described above for the HCV Genotype 1b and 1a replicon assays.

Potencies of test compounds against additional mutations of interest were determined using transient transfection assays. These mutants included and genotype 1a Y93C, Y93H, M28T, Q30E, Q30K. The mutation was first introduced into the parental plasmid by site-directed mutagenesis. The replicon plasmid was then linearized and in vitro transcribed to RNA. The RNA was used to transiently transfect Huh-LUNET cells (obtained from ReBLikon GmbH, Schriesheim, Germany) by electroporation, and the potencies of test compounds against the mutants were determined as previously described.

Assay 4: Colony Formation Assay

Colony formation assays were used to assess overall genetic barrier of resistance of test compounds. Replicon cells were plated in tissue culture flasks and treated with various concentrations of test compound(s) (or DMSO control) in the presence of G418 (500-850 μg/mL) for 3-4 weeks. The media was replaced with fresh media containing compound and G418 twice per week. Cells were split as necessary. During this time, many cells died, and resistant colonies emerged. The colonies were then fixed and stained with crystal violet/methanol. The combination of a compound of the invention and danoprevir (an NS3 protease inhibitor) was able to significantly suppress the emergence of resistant mutants to a greater degree than either single compound alone.

Assay 5: Replicon Assays of Combinations of Agents

Combinations of a compound of the invention and another therapeutic agent were tested as described for the HCV genotype 1b and 1a replicon assays. Cells were incubated with various combinations (in a checkerboard matrix) of test compounds for 48 hours. Potencies of either compound alone were determined as described above, and MacSynergy II software was used to determine if the combination of test compounds exhibited synergy vs additivity vs antagonism. The combination of a compound of the invention and danoprevir (an NS3 protease inhibitor) showed an additive antiviral effect. Similarly, the combination of a compound of the invention and interferon alpha2b showed an additive antiviral effect.

Assay Results

All of the compounds of Examples 1 to 77 and Tables 1 to 33 were tested in one or more of the assays described above. For example, the following results were obtained in the HCV genotype 1b and 1a replicon assays where A represents a $pEC_{50}$ value between 7 and 8 ($EC_{50}$ between 100 nM and 10 nM), B represents $pEC_{50}$ between 8 and 9 ($EC_{50}$ between 1 and 10 nM), C represents $pEC_{50}$ between and 9 and about 10, ($EC_{50}$ between 1 nM and 0.1 nM), and D represents $pEC_{50}>10$ ($EC_{50}<0.1$ nM).

| Example No. | Genotype 1b | Genotype 1a |
| --- | --- | --- |
| 1 | D | B |
| 2 | D | B* |
| 3 | D | B* |
| 4 | D | A* |
| 5 | D | B |
| 6 | D | A* |
| 7 | D | B* |
| 8 | D | B |
| 9 | D | C* |
| 10 | D | C* |
| 11 | D | C* |
| 12 | D | C |
| 13 | D | D |
| 14 | D | D |
| 15 | D | D |
| 16 | D | D |
| 17 | D | C |
| 18 | D | C |
| 19 | D | C |
| 20 |  | B |
| 21 | D | D |
| 22 | D | D |

| Example No. | Genotype 1b | Genotype 1a |
|---|---|---|
| 23 | | C |
| 24 | | C |
| 25 | D | D |
| 26 | D | D |
| 27 | D | D |
| 28 | D | C |
| 29 | D | D |
| 30 | D | D |
| 31 | D | D |
| 32 | D | D |
| 33 | D | D |
| 34 | D | D |
| 35 | D | C |
| 36 | D | C |
| 37 | D | C |
| 38 | D | D |
| 39 | D | D |
| 40 | D | C |
| 41 | D | D |
| 42 | D | C |
| 43 | D | C |
| 44 | D | C |
| 45 | D | D |
| 46 | D | C |
| 47 | D | C |
| 48 | D | C |
| 49 | D | D |
| 50 | D | D |
| 51 | D | D |
| 52 | D | D |
| 53 | D | D |
| 54 | D | D |
| 55 | D | D |
| 56 | D | C |
| 57 | D | D |
| 58 | D | D |
| 59 | D | D |
| 60 | D | D |
| 61 | D | D |
| 62 | D | D |
| 63 | D | D |
| 64 | D | D |
| 65 | D | D |
| 66 | D | D |
| 67 | | C |
| 68 | D | C |
| 69 | D | C |
| 70 | | C |
| 71 | D | C |
| 72 | C | B |
| 73 | | B |
| 74 | | B |
| 75 | | B |
| 76 | | C |
| 77 | D | D |
| 27-1 | | D |
| 27-2 | | C |
| 27-3 | | C |
| 27-4 | | C |
| 27-5 | D | D |
| 27-6 | | C |
| 27-7 | D | D |
| 27-8 | | D |
| 27-9 | | B |
| 27-10 | D | D |
| 27-11 | | C |
| 27-12 | D | D |
| 27-13 | | C |
| 27-14 | | D |
| 27-15 | D | D |
| 27-16 | D | D |
| 27-17 | D | D |
| 27-18 | D | D |
| 27-19 | | D |
| 27-20 | D | D |
| 27-21 | D | D |
| 27-22 | D | D |
| 27-23 | D | D |
| 27-24 | | C |
| 27-25 | | B |
| 27-26 | | C |
| 27-27 | | B |
| 27-28 | D | D |
| 27-29 | | C |
| 27-30 | | D |
| 27-31 | D | D |
| 27-32 | | C |
| 27-33 | D | D |
| 27-34 | D | D |
| 27-35 | | C |
| 27-36 | D | D |
| 27-37 | D | D |
| 27-38 | D | D |
| 27-39 | | C |
| 27-40 | | C |
| 27-41 | | C |
| 27-42 | D | D |
| 27-43 | D | D |
| 27-44 | D | D |
| 27-45 | D | D |
| 27-46 | D | D |
| 27-47 | D | D |
| 27-48 | D | D |
| 27-49 | | D |
| 27-50 | D | D |
| 27-51 | | C |
| 27-52 | D | D |
| 27-53 | | C |
| 27-54 | | C |
| 27-55 | | D |
| 27-56 | | C |
| 27-57 | | B |
| 27-58 | | D |
| 27-59 | | D |
| 27-60 | | D |
| 27-61 | | C |
| 27-62 | | C |
| 27-63 | | C |
| 27-64 | | D |
| 27-65 | | C |
| 27-66 | | D |
| 27-67 | D | C |
| 27-68 | D | D |
| 27-69 | D | D |
| 27-70 | | C |
| 27-71 | | D |
| 27-72 | D | D |
| 27-73 | D | D |
| 27-74 | | D |
| 27-75 | | D |
| 27-76 | | D |
| 28-1 | D | D |
| 28-2 | D | D |
| 28-3 | | C |
| 28-4 | | D |
| 28-5 | D | D |
| 28-6 | | C |
| 28-7 | | D |
| 28-8 | D | D |
| 28-9 | | C |
| 28-10 | | C |
| 28-11 | | C |
| 28-12 | | C |
| 28-13 | | D |
| 28-14 | D | D |
| 28-15 | D | D |
| 28-16 | D | D |
| 28-17 | D | D |
| 28-18 | D | D |
| 28-19 | D | D |
| 28-20 | D | D |
| 28-21 | | C |

-continued

| Example No. | Genotype 1b | Genotype 1a |
|---|---|---|
| 28-22 | D | D |
| 28-23 | D | D |
| 28-24 | D | D |
| 28-25 | D | D |
| 28-26 | D | D |
| 27-27 | | B |
| 28-28 | | B |
| 28-29 | D | D |
| 28-30 | | B |
| 28-31 | | C |
| 28-32 | | D |
| 28-32 | | D |
| 28-34 | | D |
| 28-35 | | C |
| 28-36 | D | D |
| 28-37 | | D |
| 28-38 | D | D |
| 28-39 | D | D |
| 28-40 | D | D |
| 28-41 | | D |
| 28-42 | | D |
| 28-43 | | D |

*Compounds incubated for 48 hours; all other Genotype 1a results for 72 hour incubation While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. Additionally, all publications, patents, and patent documents cited hereinabove are incorporated by reference herein in full, as though individually incorporated by reference.

What is claimed is:
1. A compound of formula (I):

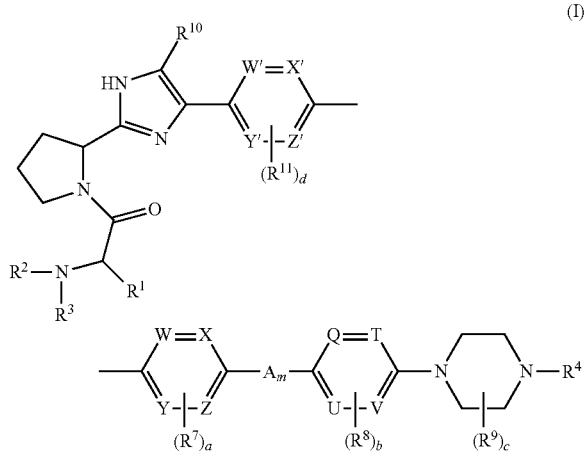

wherein:
$R^1$ is selected from $C_{1-6}$alkyl, phenyl, $C_{3-6}$cycloalkyl, heteroaryl, and heterocycle; wherein $C_{1-6}$alkyl is optionally substituted with $-OR^q$, wherein $R^q$ is hydrogen or $C_{1-3}$alkyl;

$R^2$ is selected from hydrogen and $C_{1-6}$alkyl;
$R^3$ is selected from hydrogen, $C_{1-6}$alkyl, $-C(O)OC_{1-6}$alkyl, $-C(O)OC_{3-6}$cycloalkyl, $-C(O)NR^aR^b$, $-C(O)C_{1-6}$alkyl, $-C(O)C_{3-6}$cycloalkyl, and $-S(O)_2C_{1-3}$alkyl;
wherein
$R^a$ and $R^b$ are independently hydrogen or $C_{1-6}$alkyl;
$R^4$ is $-C(O)R^5$ or $-S(O)_2R^6$;
$R^5$ is selected from $C_{1-6}$alkyl, $C_{3-6}$cycloalkyl, $C_{1-6}$alkoxy, $-C(R^kR^d)NR^eR^f$, $-NR^gR^h$, heteroaryl, heterocycle, $-CH_2$-heteroaryl, and phenyl;
wherein
$C_{1-6}$alkyl is optionally substituted with one or two substituents independently selected from $-OR^c$, $-S(O)_2C_{1-3}$alkyl, $-NHC(O)C_{1-3}$alkyl, and $-NHC(O)OC_{1-3}$alkyl;
$C_{1-6}$alkoxy is optionally substituted with $-OR^d$;
$C_{3-6}$cycloalkyl is optionally substituted with one, two, or three substituents independently selected from $C_{1-3}$alkyl, $NR^jR^m$, $-OR^n$, and halo;
any heterocycle is optionally substituted with one, two, or three substituents independently selected from $C_{1-3}$alkyl, halo, $-C(O)OC_{1-3}$alkyl, $-C(O)C_{1-6}$alkyl, $-C(O)C_{3-6}$cycloalkyl, $-C(O)NHC_{1-6}$alkyl, $-C(O)NHC_{3-6}$cycloalkyl, and $-S(O)_2C_{1-3}$alkyl;
wherein any $-C(O)C_{1-6}$alkyl is optionally substituted with $-NHC(O)OC_{1-3}$alkyl, $-OR^n$, $-NR^dR^e$, or heterocycle,
any $-C(O)C_{3-6}$cycloalkyl is optionally substituted with one or two $C_{1-3}$alkyl, and
any $-C(O)NHC_{1-6}$alkyl is optionally substituted with $-OR^n$ or $C_{3-6}$cycloalkyl;
any heteroaryl is optionally substituted with $C_{1-6}$alkyl or halo;
$R^c$ is independently selected from hydrogen, $C_{1-6}$alkyl, and phenyl;
$R^d$ is independently hydrogen or $C_{1-6}$alkyl;
$R^e$ is independently hydrogen or $C_{1-6}$alkyl;
$R^f$ is independently selected from hydrogen, $C_{1-6}$alkyl, $-C(O)OC_{1-6}$alkyl, and $-C(O)C_{1-6}$alkyl;
$R^n$ is independently hydrogen or $C_{1-3}$alkyl;
$R^k$ is independently selected from hydrogen, $C_{1-6}$alkyl, $C_{3-6}$cycloalkyl, phenyl, and $-CH_2OR^n$;
$R^g$ is independently hydrogen or $C_{1-6}$alkyl;
$R^h$ is independently selected from hydrogen, $C_{1-6}$alkyl, $C_{3-6}$cycloalkyl, and $-S(O)_2C_{1-3}$alkyl, wherein $C_{1-6}$alkyl is optionally substituted with $-OR^d$;
$R^j$ is independently hydrogen or $C_{1-6}$alkyl;
$R^m$ is independently selected from hydrogen, $C_{1-6}$alkyl, $-C(O)OC_{1-6}$alkyl, and $-C(O)C_{1-6}$alkyl;
$R^6$ is selected from $C_{1-6}$alkyl, $C_{3-6}$cycloalkyl, phenyl, and a heteroaryl ring;
$R^7$, $R^8$, and $R^{11}$ are independently selected from halo, $C_{1-6}$alkyl, $C_{1-6}$alkoxy, $-C(O)OR^n$, $-CH_2NR^aR^b$, and $-CN$, wherein $C_{1-6}$alkyl and $C_{1-6}$alkoxy are optionally substituted with one, two, three, four, or five halo, and wherein $C_{1-6}$alkoxy is optionally substituted with $-OR^d$;
$R^9$ is independently selected from $C_{1-6}$alkyl, $-CH_2OR^n$, $-C(O)NR^nR^p$, and $C(O)OR^n$, wherein $C_{1-6}$alkyl is optionally substituted with $-S(O)_2C_{1-3}$alkyl or with $-SC_{1-3}$alkyl;
$R^p$ is independently hydrogen or $C_{1-3}$alkyl;
$R^{10}$ is selected from hydrogen, halo, $C_{1-6}$alkyl, $-C(O)OR^c$, $-C(O)NR^aR^b$, $-CH_2NR^aR^b$, $C_{3-6}$cycloalkyl, and $-CN$;

W', X', Y', and Z' are each carbon wherein each carbon atom is bonded to hydrogen or to $R^{11}$;

W, X, Y, and Z are each carbon wherein each carbon atom is bonded to hydrogen or to $R^7$;

$A_m$ is —NHC(O);

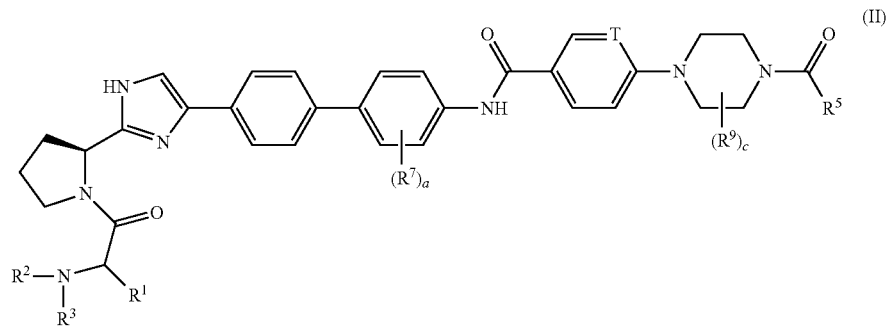

Q, U, and V are each carbon wherein each carbon atom is bonded to hydrogen or to $R^8$, T is nitrogen; and a, b, c, and d are independently 0, 1, or 2;

or a pharmaceutically-acceptable salt or stereoisomer thereof.

2. The compound of claim 1 wherein:

$R^5$ is selected from $C_{1-6}$alkyl, $C_{3-6}$cycloalkyl, $C_{1-6}$alkoxy, —C($R^k R^d$)$NR^e R^f$, —$NR^g R^h$, heteroaryl, heterocycle, —$CH_2$-heteroaryl, and phenyl;

wherein $C_{1-6}$alkyl is optionally substituted with —$OR^c$ or —$S(O)_2 C_{1-3}$alkyl;

$C_{3-6}$cycloalkyl is optionally substituted with one or two $C_{1-3}$alkyl, or with $NR^j R^m$ or —$OR^n$;

any heterocycle is optionally substituted with one or two substituents selected from $C_{1-3}$alkyl, halo, —C(O)O$C_{1-3}$alkyl, —C(O)$C_{1-6}$alkyl, and —C(O)$C_{3-6}$cycloalkyl, wherein —C(O)$C_{1-6}$alkyl is optionally substituted with —NHC(O)O$C_{1-3}$alkyl, and —C(O)$C_{3-6}$cycloalkyl is optionally substituted with one or two $C_{1-3}$alkyl;

any heteroaryl is optionally substituted with $C_{1-6}$alkyl;

$R^h$ is selected from hydrogen, $C_{1-6}$alkyl, $C_{3-6}$cycloalkyl, and —$S(O)_2 C_{1-3}$alkyl;

$R^6$ is selected from $C_{1-6}$alkyl, $C_{3-6}$cycloalkyl, and a heteroaryl ring; and $R^7$, $R^8$, and $R^{11}$ are independently selected from halo, $C_{1-6}$alkyl, $C_{1-6}$alkoxy, —C(O)$OR^n$, —$CH_2 NR^a R^b$, and —CN, wherein $C_{1-6}$alkyl and $C_{1-6}$alkoxy are optionally substituted with one, two, or three halo.

3. The compound of claim 2 wherein:

$R^1$ is selected from $C_{1-6}$alkyl, phenyl, and $C_{3-6}$cycloalkyl, wherein $C_{1-6}$alkyl is optionally substituted with —$OR^q$;

$R^3$ is selected from hydrogen, $C_{1-6}$alkyl, —C(O)O$C_{1-6}$alkyl, —C(O)$NR^a R^b$, —C(O)$C_{3-6}$cycloalkyl, and —$S(O)_2 C_{1-3}$alkyl; and $R^{10}$ is selected from hydrogen, halo, and $C_{1-6}$alkyl.

4. The compound of claim 3 wherein the compound is a compound of formula (II):

wherein $C_{1-3}$alkyl;

$R^5$ is selected from $C_{1-6}$alkyl, $C_{3-6}$cycloalkyl, $C_{1-6}$alkoxy, —C($R^k R^d$)$NR^e R^f$, —$NR^g R^h$, heteroaryl, heterocycle, and —$CH_2$-heteroaryl;

wherein any heteroaryl or heterocycle has five or six ring atoms;

$C_{3-6}$cycloalkyl is optionally substituted with one or two $C_{1-3}$alkyl;

any heterocycle is optionally substituted with one or two substituents selected from $C_{1-3}$alkyl, halo, —C(O)O$C_{1-3}$alkyl, —C(O)$C_{1-6}$alkyl, and —C(O)$C_{3-6}$cycloalkyl, wherein —C(O)$C_{1-6}$alkyl is optionally substituted with —NHC(O)O$C_{1-3}$alkyl, and —C(O)$C_{3-6}$cycloakyl is optionally substituted with one or two $R^k$, $R^d$, $R^e$, $R^g$, and $R^h$ are each independently hydrogen or $C_{1-3}$alkyl;

$R^f$ is selected from hydrogen and —C(O)$C_{1-3}$alkyl;

$R^7$ is selected from halo, $C_{1-6}$alkyl, and $C_{1-6}$alkoxy wherein $C_{1-6}$alkyl and $C_{1-6}$alkoxy are optionally substituted with one, two, or three halo;

$R^9$ is $C_{1-3}$alkyl or —$CH_2 OR^n$; and

T is N.

5. The compound of claim 4 wherein T is N.

6. The compound of claim 4 wherein $R^1$ is isopropyl; $R^2$ is hydrogen; and $R^3$ is —C(O)O$CH_3$.

7. The compound of claim 4 wherein $R^5$ is selected from, —O-tert-butyl, cyclopropyl, tert-butyl, —$NHCH_3$, 2,2-dimethylcyclopropyl, pyrimidinyl, pyrazolyl, imidazolyl, —$CH_2$-pyrazolyl, 1-acetylpyrrolidinyl.

8. The compound of claim 1 wherein the compound of formula (I) is a compound of formula (III):

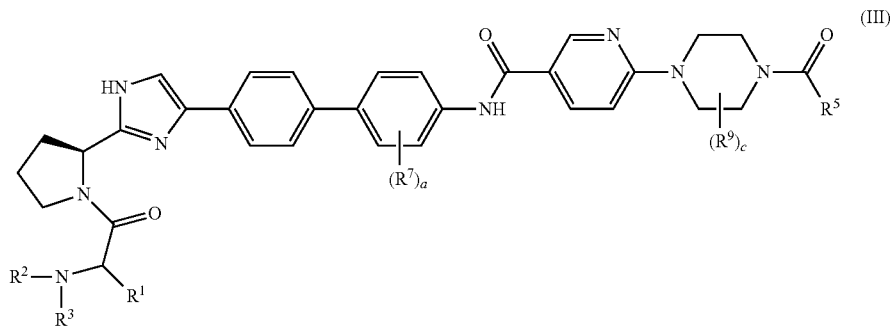

wherein
R¹ is selected from $C_{1-6}$alkyl, phenyl, and $C_{3-6}$cycloalkyl, wherein $C_{1-6}$alkyl is optionally substituted with —OR$^q$;
R³ is selected from hydrogen, $C_{1-6}$alkyl, —C(O)OC$_{1-6}$alkyl, —C(O)NR$^a$R$^b$, —C(O)C$_{3-6}$cycloallyl, and —S(O)$_2$C$_{1-3}$alkyl;
R⁵ is selected from $C_{1-6}$alkyl, $C_{3-6}$cycloalkyl, $C_{1-6}$alkoxy, —C(R$^k$R$^d$)NR$^e$R$^f$, —NR$^g$R$^h$, heteroaryl, heterocycle, and —CH$_2$-heteroaryl;
wherein:
any heteroaryl or heterocycle has 5 or 6 ring atoms;
$C_{1-6}$alkyl is optionally substituted with one or two substituents independently selected from —OR$^c$, —NHC(O)C$_{1-3}$alkyl, and —NHC(O)OC$_{1-3}$alkyl;
$C_{1-6}$alkoxy is optionally substituted with —OR$^d$;
$C_{3-6}$cycloalkyl is optionally substituted with one or two substituents independently selected from $C_{1-3}$alkyl and halo;
any heterocycle is optionally substituted with one, two, or three substituents independently selected from $C_{1-3}$alkyl, halo, —C(O)OC$_{1-3}$alkyl, —C(O)C$_{1-6}$alkyl, —C(O)C$_{3-6}$cycloalkyl, —C(O)NHC$_{1-6}$alkyl, and —C(O)NHC$_{3-6}$cycloalkyl;
wherein any —C(O)C$_{1-6}$alkyl is optionally substituted with —NHC(O)OC$_{1-3}$alkyl, —OR$^n$, —NR$^d$R$^e$, or heterocycle,
any —C(O)C$_{3-6}$cycloalkyl is optionally substituted with one or two $C_{1-3}$alkyl, and
any —C(O)NHC$_{1-6}$alkyl is optionally substituted with —OR$^n$ or $C_{3-6}$cycloalkyl;
any heteroaryl is optionally substituted with $C_{1-3}$alkyl;
R$^k$, R$^d$, R$^e$, R$^g$, and R$^h$ are each independently hydrogen or $C_{1-3}$alkyl;
R$^f$ is selected from hydrogen and —C(O)C$_{1-3}$alkyl;
R⁷ is selected from halo, $C_{1-3}$alkyl, and $C_{1-3}$alkoxy wherein $C_{1-3}$alkyl, and $C_{1-3}$alkoxy are optionally substituted with one, two, or three halo; and
R⁹ is $C_{1-3}$alkyl;
a is 1 or 2; and
c is 1 or 2.

9. The compound of claim 8 wherein R⁵ is selected from $C_{3-4}$cycloalkyl, —CH$_2$NR$^e$R$^f$, —NR$^g$R$^h$, imidazolyl, pyrazolyl, pyrimidinyl, and pyrrolidinyl;
wherein:
$C_{3-4}$cycloalkyl is optionally substituted with one or two $C_{1-3}$alkyl;
pyrrolidinyl is substituted with methyl and a substituent selected from —C(O)OC$_{1-3}$alkyl, —C(O)C$_{1-6}$alkyl, and —C(O)NHC$_{1-6}$alkyl, wherein —C(O)C$_{1-6}$alkyl is substituted with —NHC(O) OC$_{1-3}$ alkyl, —OR$^n$, —NR$^d$R$^e$, or heterocycle.

10. The compound of claim 8, wherein R⁵ is selected from —NHCH$_3$, 2,2-dimethylcyclopropyl,

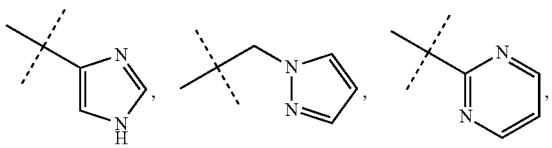

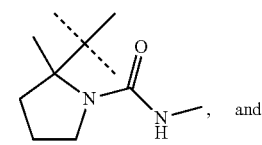

and

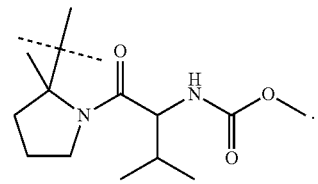

11. The compound of claim 8 wherein R¹ is $C_{1-6}$alkyl, R² is hydrogen; and R³ is —C(O)OC$_{1-6}$alkyl.

12. The compound of claim 8 wherein R⁷ is selected from fluoro, chloro, —CF$_3$, and —OCF$_3$, and R⁹ is methyl.

13. The compound of claim 8 wherein:
R¹ is isopropyl, R² is hydrogen; and R³ is —C(O)OCH$_3$;
R⁷ is selected from fluoro, chloro, —CF$_3$, and —OCF$_3$, and R⁹ is methyl; and
R⁵ is selected from —NHCH$_3$, 2,2-dimethylcyclopropyl, and

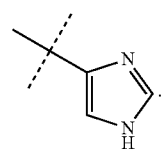

14. The compound of claim 8 wherein the compound is selected from:
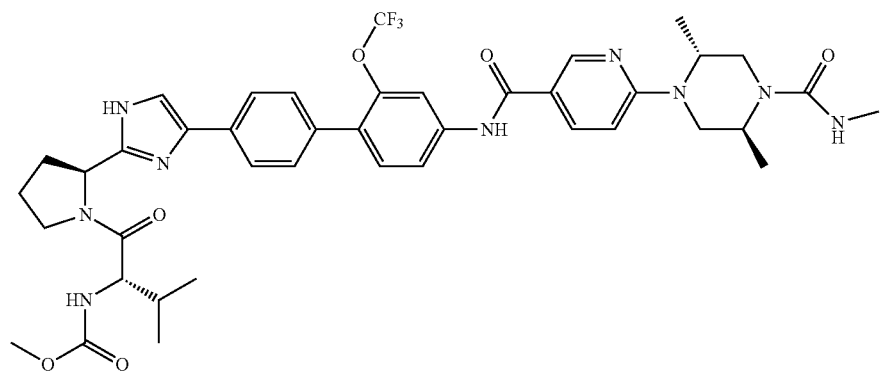
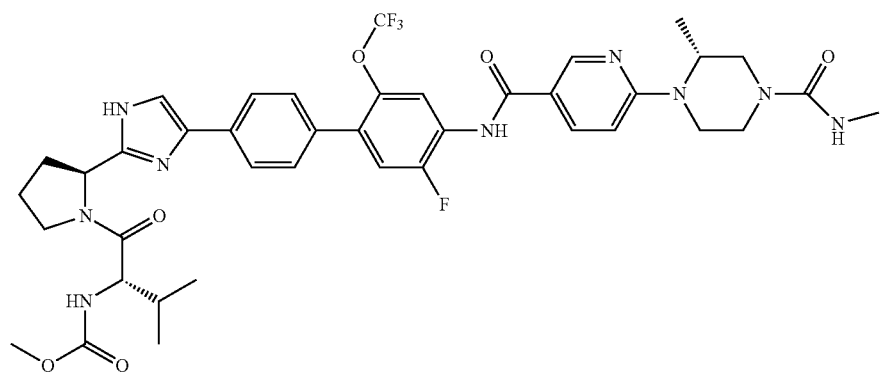
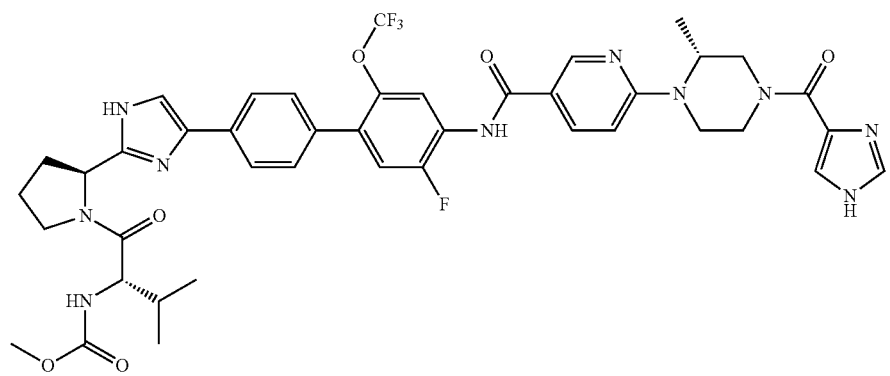
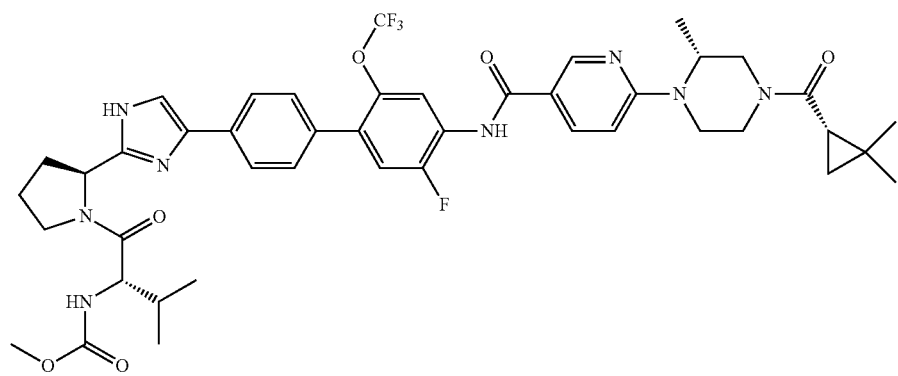

-continued
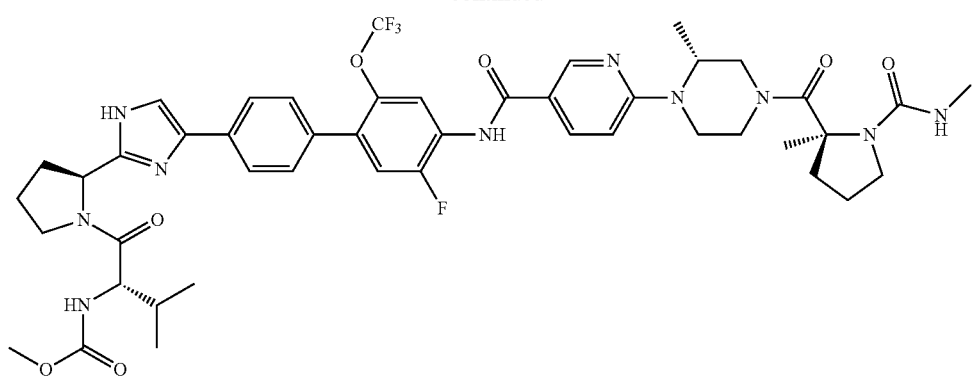
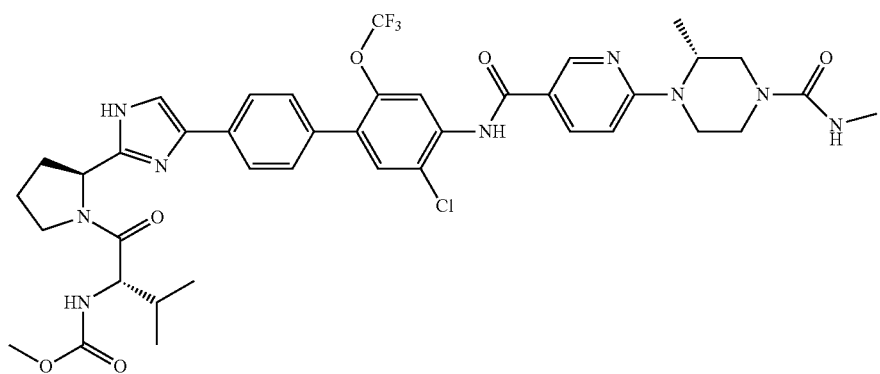
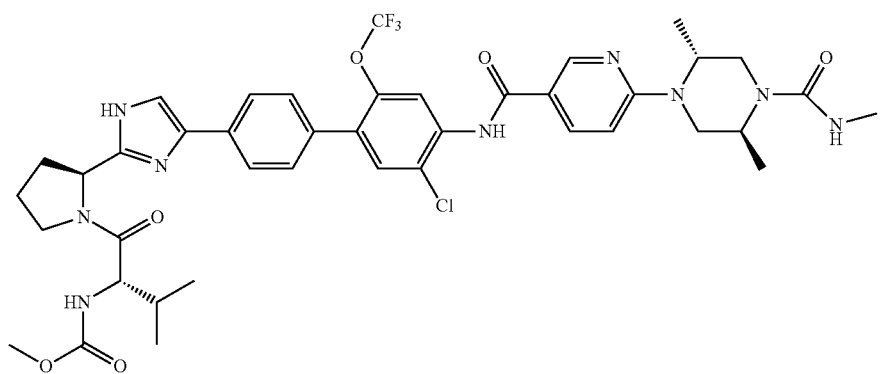
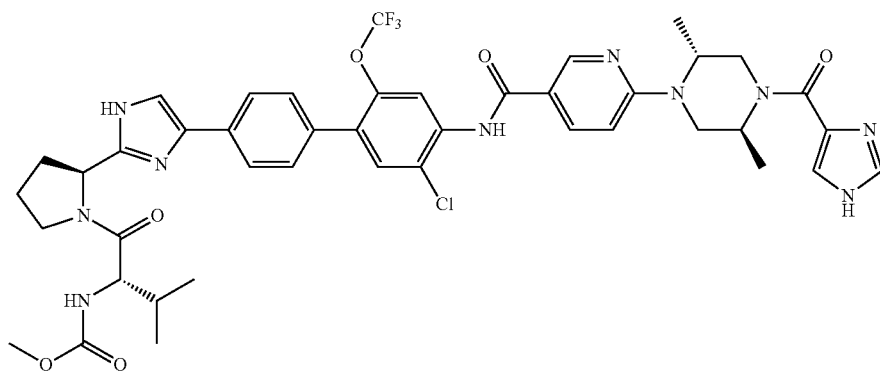

-continued
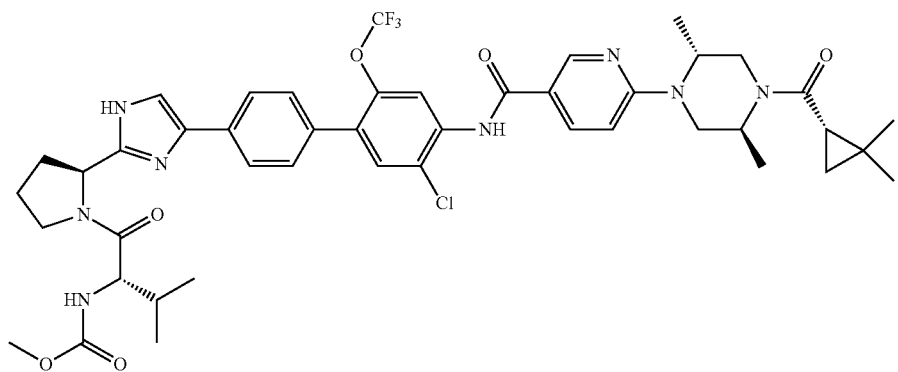
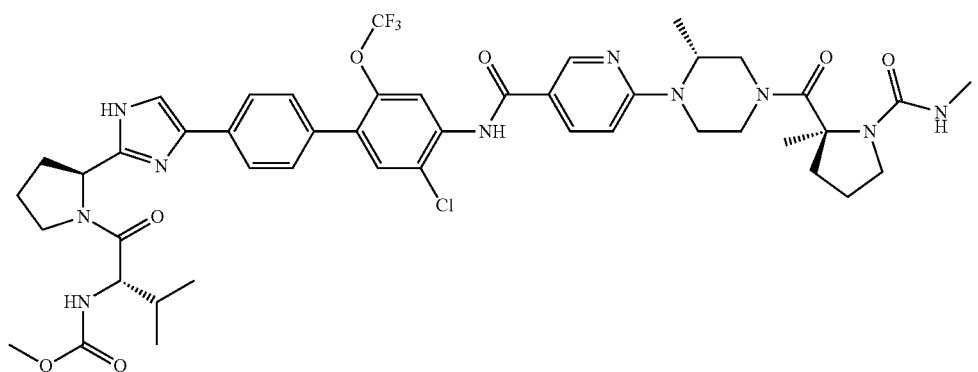
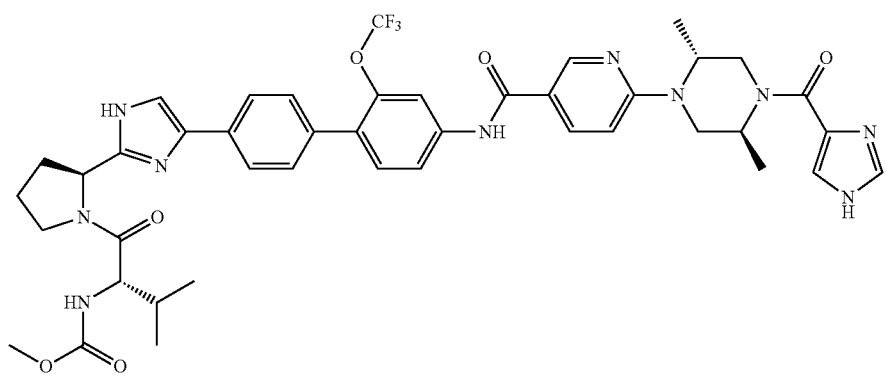
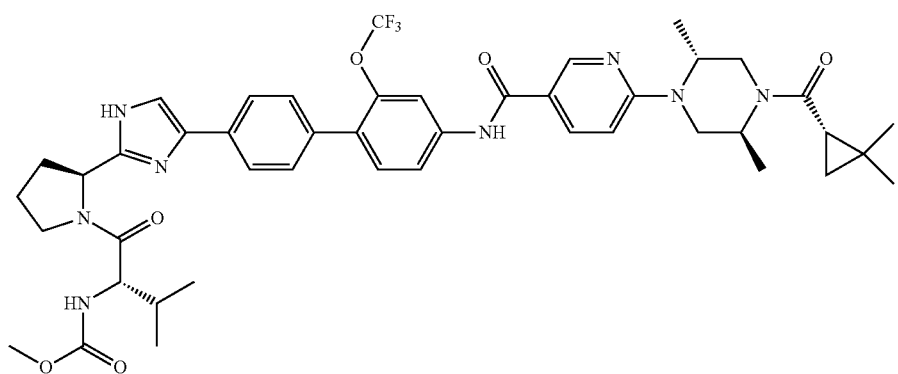

-continued
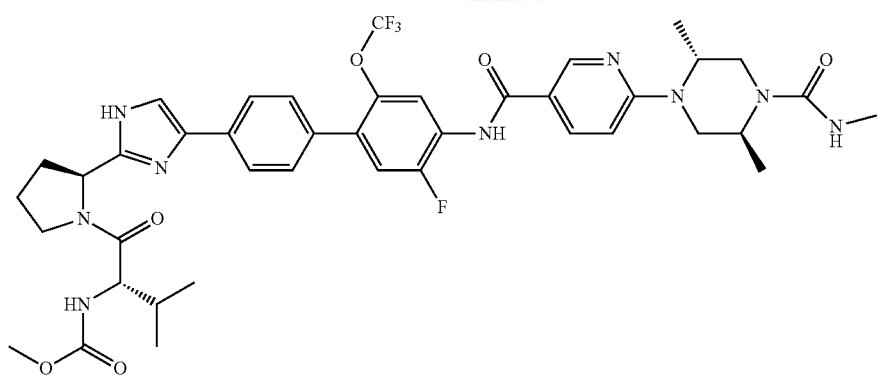
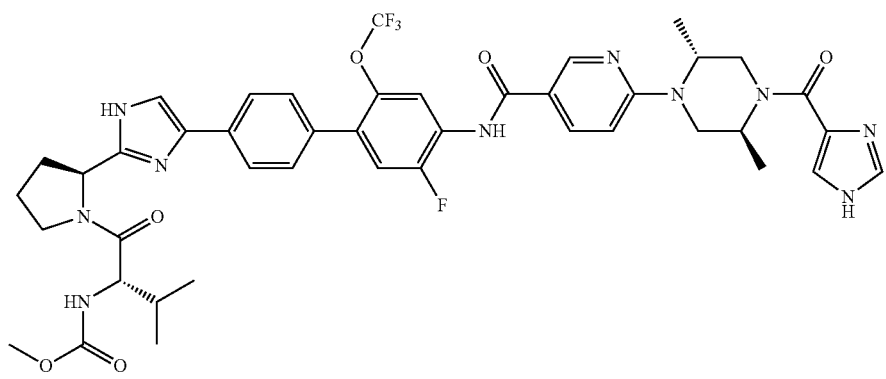
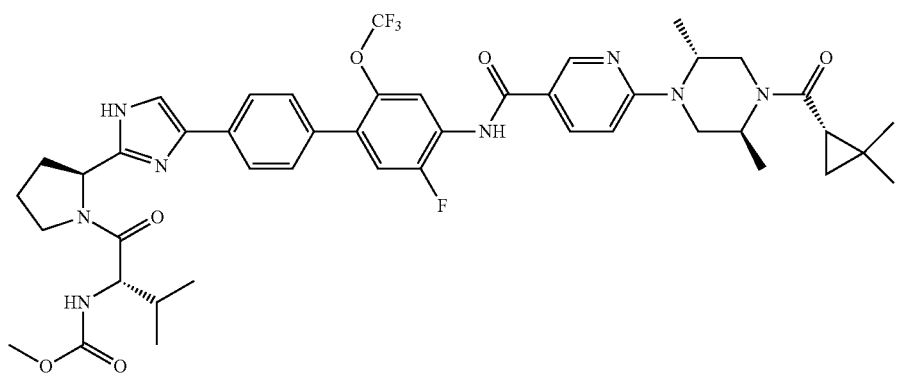
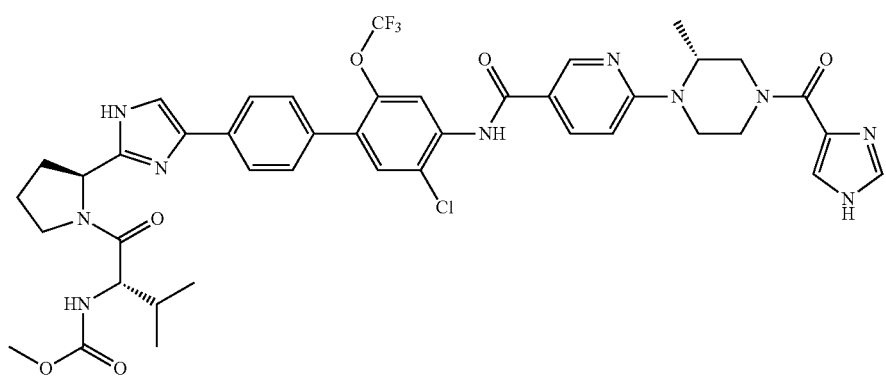

-continued
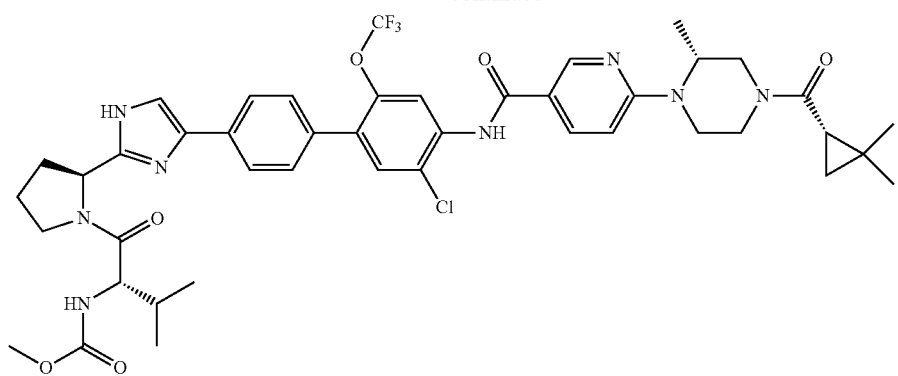
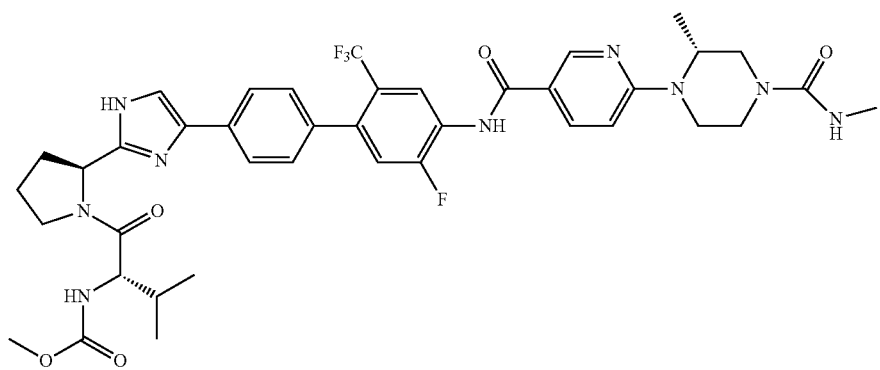
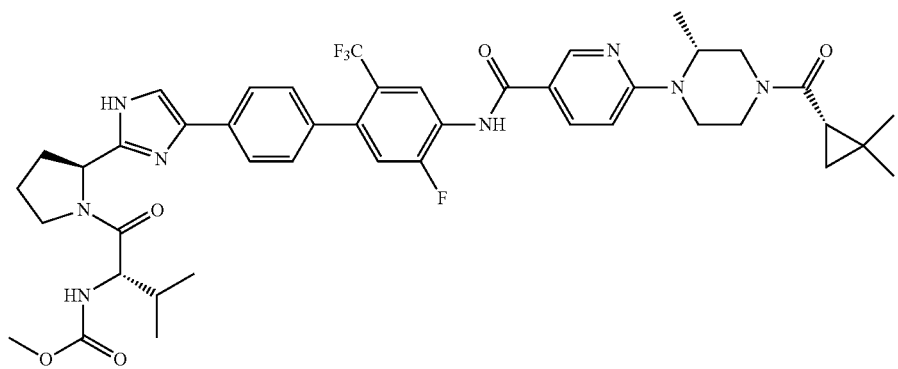
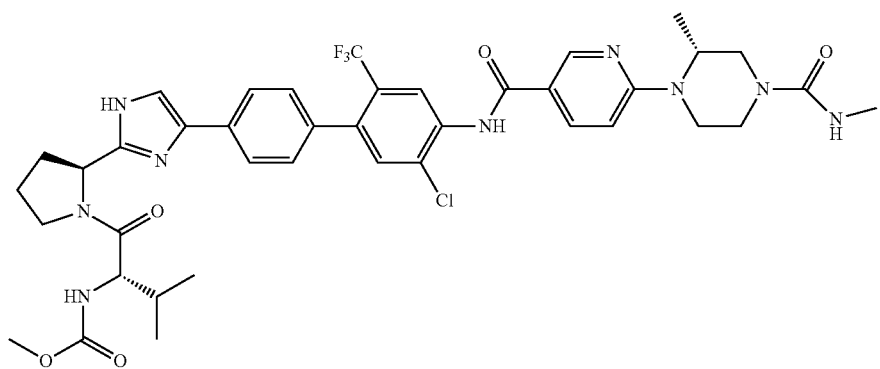

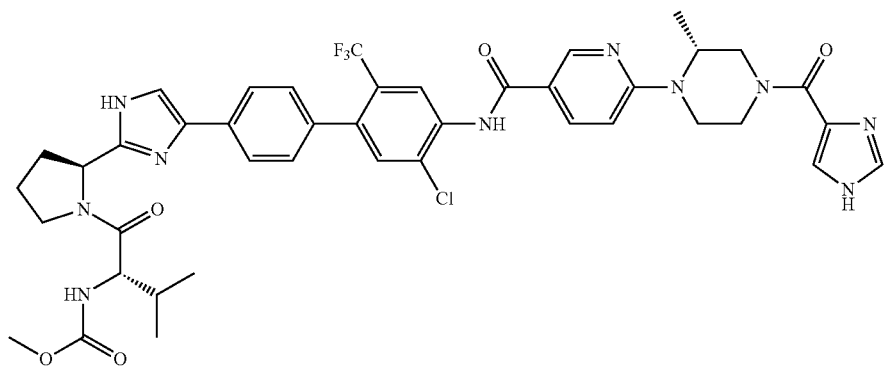 [SMILES: COC(=O)N[C@H](C(=O)N1CCC[C@H]1c1nc(-c2ccc(-c3cc(Cl)c(NC(=O)c4ccc(N5CCN(C(=O)c6c[nH]cn6)C[C@H]5C)nc4)cc3C(F)(F)F)cc2)c[nH]1)C(C)C]
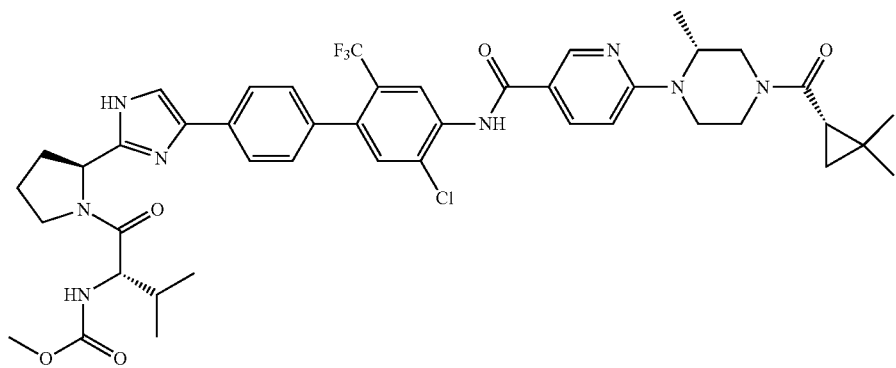
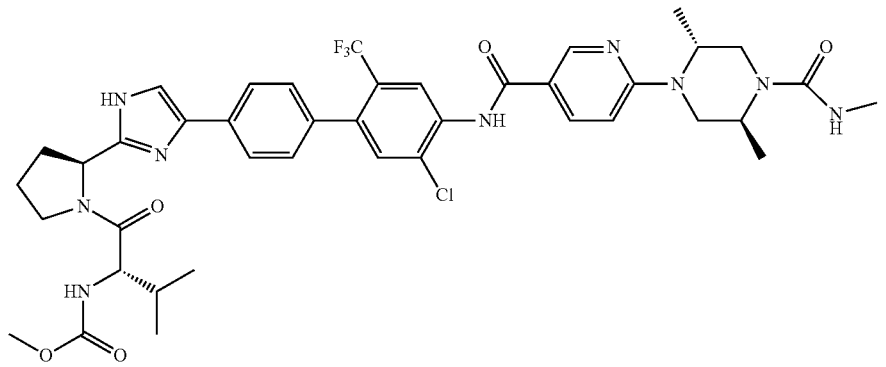
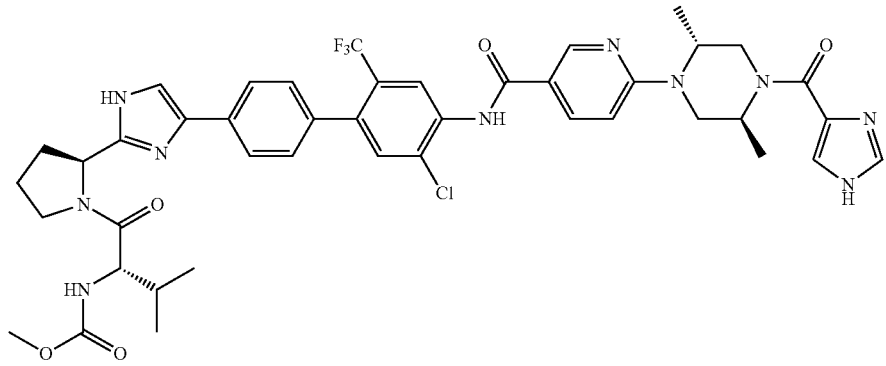

-continued
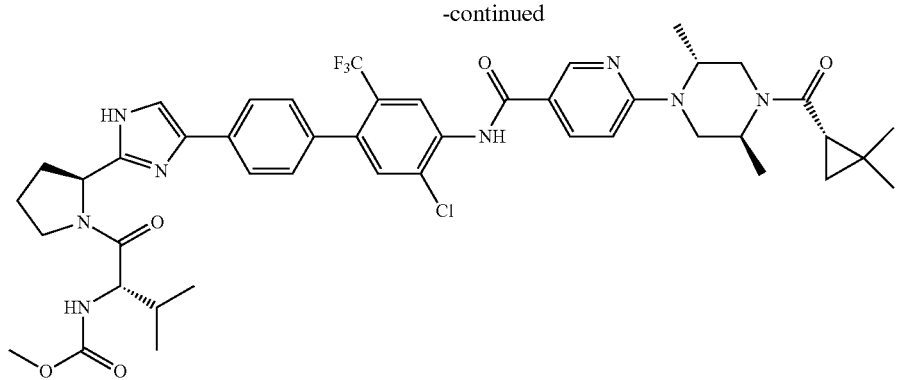
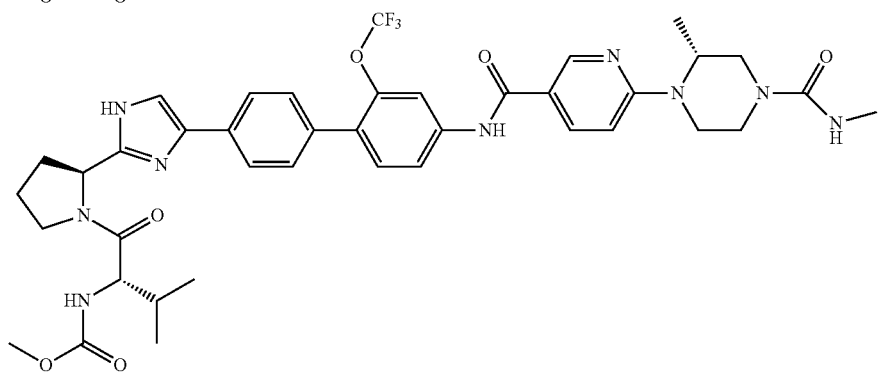
and pharmaceutically-acceptable salts thereof.
15. The compound of claim 8 wherein the compound is selected from:
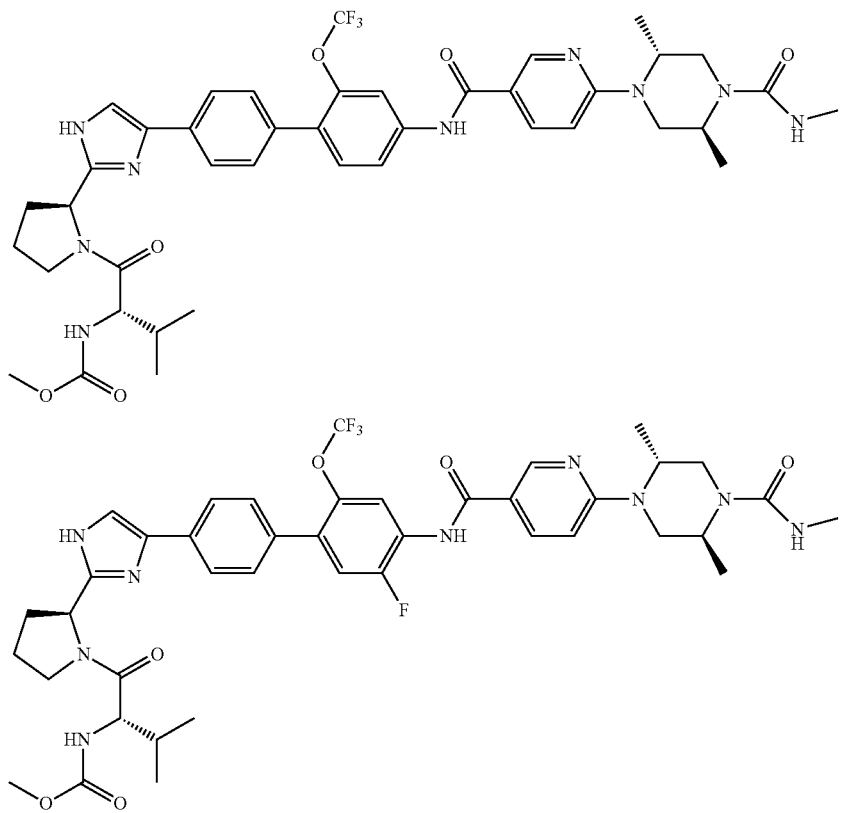

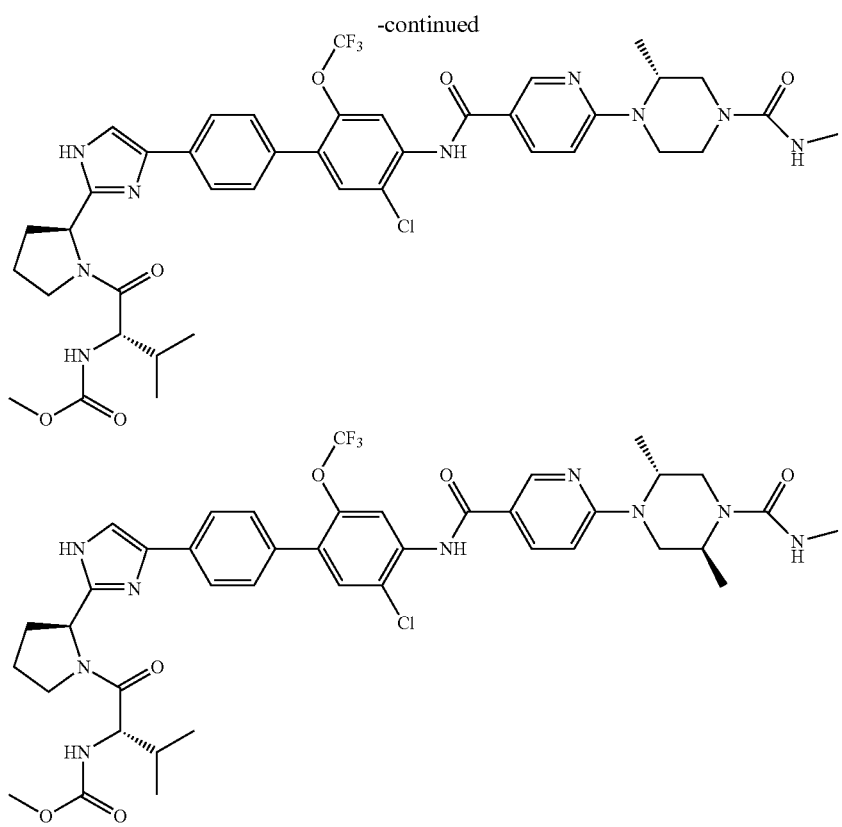

and pharmaceutically-acceptable salts thereof.

16. A pharmaceutical composition comprising a compound of claim 1 and a pharmaceutically-acceptable carrier.

17. The pharmaceutical composition of claim 16 further comprising one or more other therapeutic agents useful for treating hepatitis C viral infections.

18. The pharmaceutical composition of claim 17 wherein the one or more other therapeutic agents is selected from HCV NS3 protease inhibitors, HCV NS5B nucleoside and non-nucleoside polymerase inhibitors, interferons and pegylated interferons, and ribavirin and nucleoside analogs related to ribavirin.

* * * * *

UNITED STATES PATENT AND TRADEMARK OFFICE
CERTIFICATE OF CORRECTION

PATENT NO. : 8,921,372 B2  
APPLICATION NO. : 13/288216  
DATED : December 30, 2014  
INVENTOR(S) : Robert Murray McKinnell et al.

It is certified that error appears in the above-identified patent and that said Letters Patent is hereby corrected as shown below:

On the Title page, item (54),
"INHIBITORS OF HEPATITIS C VIRUS" should be
"NOVEL INHIBITORS OF HEPATITIS C VIRUS".

In the Claims
At Column 310, line 34,
delete "$C_{1-3}$alkyl;".
At Column 310, line 50,
insert --$C_{1-3}$alkyl;-- after "one or two".
At Column 310, line 59,
delete Claim 5.

Signed and Sealed this
Twenty-second Day of September, 2015

Michelle K. Lee
*Director of the United States Patent and Trademark Office*